(12) United States Patent
Maine et al.

(10) Patent No.: US 7,094,879 B2
(45) Date of Patent: Aug. 22, 2006

(54) GENETICALLY ENGINEERED P30 ANTIGEN, IMPROVED ANTIGEN COCKTAIL, AND USES THEREOF

(75) Inventors: Gregory T. Maine, Gurnee, IL (US); Chandu B. Patel, Libertyville, IL (US); Sanford R. Ginsburg, Palatine, IL (US); Timothy R. Bliese, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 206 days.

(21) Appl. No.: 10/263,153

(22) Filed: Oct. 2, 2002

(65) Prior Publication Data
US 2004/0067239 A1    Apr. 8, 2004

(51) Int. Cl.
C07K 1/00    (2006.01)
C07K 14/00   (2006.01)
C07K 17/00   (2006.01)
G01N 33/53   (2006.01)

(52) U.S. Cl. ...................... 530/350; 435/7.22; 435/975

(58) Field of Classification Search ............. 424/185.1, 424/190.1, 192.1; 530/350, 300; 536/23.2, 536/23.7; 435/975, 7.1, 7.92
See application file for complete search history.

(56) References Cited

U.S. PATENT DOCUMENTS 6,329,157 B1  12/2001  Maine et al.
6,372,443 B1   4/2002  Jacobs et al.

FOREIGN PATENT DOCUMENTS

WO           99/61906    * 12/1999

OTHER PUBLICATIONS

Gerhold et al.[BioEssays, vol. 18, No. 12, pp. 973-981 (1996)].*
Wells et al.Journal of Leukocyte Biology, vol. 61, No. 5, pp. 545-550 (1997).*
Russell et al.Journal of Molecular Biology, vol. 244, pp. 332-350 (1994).*
Remington, J.S., et al., *Infectious Diseases of the Fetus and Newborn Infant, Fourth Edition*, "Toxoplasmosis", J.S. Remington and J.O. Klein, Eds., pp. 140-267, Saunders, Philadelphia (1995).
Sabin, A.B. et al., *Science*, "Dyes as Microchemical Indicators of a New Immunity Phenomenon Affecting a Protozoon parasiste (Toxoplasma)", vol. 108, pp. 660-663 (1948).
Jacobs, L., et al., *J. Parasitol*, "A Hemagglutination Test for Toxoplasmosis", vol. 43, pp. 308-314 (1957).
Walton, B.C. et al., *Am. J. Trop. Med. Hyg.* , "Comparison of the Indirect Fluorescent Antibody Test and Methylene Blue Dye Test for Detection of Antibodies to Toxoplasma Gondii", vol. 15, pp. 149-152 (1966).

Naot, Y. et al., *J. Infect. Dis.* , An Enzyme-Linked Immunosorbent Assay for Detection of IgM Antibodies to Toxoplasma Gondii: Use for Diagnosis of Acute Acquired Toxoplasmosis, 142, pp. 757-766 (1980).
Prince, et al., *Mol. Biochem. Parasito*, "Cloning Expression, and cDNA Sequence of Surface Antigen P22 from Toxoplasma Gondii", vol. 43, pp. 97-106 (1990).
Cesbron-Delauw, et al., *Proc. Nat. Acad. Sci.* , "Molecular characterization of a 23-Kilodalton Major Antigen Secreted by Toxoplasma Gondii", vol. 86, pp. 7537-7541 (1989).
Johnson, et al., *Gene*, "Cloning of Toxoplasma Gondii Gene Fragments Encoding Diagnostic Antigens", vol. 99, pp. 127-132 (1991).
Prince, et al., *Mol. Biochem. Parasiotol*, "Cloning of cDNAs Encloding a 28 Kilodalton Antigen of Toxoplasma Gondii", vol. 34, pp. 3-13 (1989).
Bonhomme, et al., *J. Histochem. Cytochem*, "Quantitative Immunolocalization of a P29 Protein (GRA7), a New Antigen of Toxoplasma Gondii", vol. 46, pp. 1411-1421 (1998).
Burg, et al., *J. Immunol.*, "Molecular Analysis of the Gen Encoding the major Surave Antigen of Toxoplasma Gondii", vol. 141, pp. 3584-3591 (1998).
Mevelec, et al., *Mol. Biochem. Parasitol.*, "Molecular Cloning of GRA4, a Toxoplasma Gondii Dense Granule Protein, Recongnized by Mucosal IgA Antibodies", vol. 56, pp. 227-238 (1992).
Saavedra, et al., *J. Immunol.* , "Human T Cell Clone Identifies A Potentially Protective 54-kDa Protein Antigen of Toxoplasma Gondii Cloned and Expressed in *Excherichia coli*", vol. 147, pp. 1975-1982 (1991).
Safford, et al., *J. Clin. Pathol.* , "Automated Microparticle Enzyme Immunoassays for IgG and IgM Antibodies to Toxoplasma Gondii", 44:238-242 (1991).
Kapust and Waugh, *Protein Science*, "*Escherichia coli* Maltose-Binding Protein is Uncommonly Effective at Promoting the Solubility of Polypeptides To Which It Is Fused", 8, 1668-1674 (1991).
Robinson, et al., *J. Clin. Microbiol.*, "Analysis of the Humoral Response to the Flagellin Protein of Borrelia Burgdorferi: Cloning of Regions Capable of Differentiating Lyme Disease from Syphilis", 31:629-635 (1993).

(Continued)

*Primary Examiner*—Patricia A. Duffy
(74) *Attorney, Agent, or Firm*—Cheryl L. Becker

(57) ABSTRACT

The present invention relates to a genetically engineered P30 antigen and a combination or mixture of antigens (e.g., the genetically engineered P30 antigen and P35) that may be used in the detection of IgM and/or IgG antibodies to *Toxoplasma gondii*. Furthermore, the present invention also relates to methods of using this genetically engineered P30 antigen and combination of antigens, antibodies raised against this genetically engineered P30 antigen and combination of antigens, as well as kits and vaccines containing the genetically engineered P30 antigen and antigens present in the combination.

11 Claims, 84 Drawing Sheets

OTHER PUBLICATIONS

Velge-Roussel, et al., *Molec. Biochem. Parasitol*, "Epitopic Anlaysis of the Toxoplasma Gondii Major Surface Antigen SAG1", 66:31-38 (1994).

Desomonts, G. and Remington, J.S., *J. Clin. Microbiol.*, "Direct Agglutination Test for Diagnosis of Toxoplasma Infection: Method for Increasing Sensitivity and Specificity", 11:562-568 (1980).

Pouletty, et al. *J. Immunol. Methods*, "An Anti-human γ Chain Monoclonal Antibody: Use for Detection of IgM Antibodies to Toxoplasma Gondii by Reverse Immunosorbent Assay", 76:289-298 (1985).

Zweig, HM, *Clin. Chem.*, "Receiver-Operating Characteristic (ROC) Plots: A Fundamental Evaluation Tool in Clinical Medicine", 39:561-577 (1993).

New England Biolabs, Inc. 1998/1999 Catalog, pp. 136-137.

* cited by examiner

FIGURE 2 pMBP-c2X-ToxoP30(52-336aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCCG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                    Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 2 pMBP-c2X-ToxoP30(52-336aa)

```
1756  TTGGCTGAA  ATCACCCCG  GACAAAGCG  TTCCAGGAC  AAGCTGTAT
      ProPheThr  TrpAspAla  ValArgTyr  AsnGlyLys  LeuIleAla
1801  CCGTTTACC  TGGGATGCC  GTACGTTAC  AACGGCAAG  CTGATTGCT
      TyrProIle  AlaValGlu  AlaLeuSer  LeuIleTyr  AsnLysAsp
1846  TACCCGATC  GCTGTTGAA  GCGTTATCG  CTGATTTAT  AACAAAGAT
      LeuLeuPro  AsnProPro  LysThrTrp  GluGluIle  ProAlaLeu
1891  CTGCTGCCG  AACCCGCCA  AAAACCTGG  GAAGAGATC  CCGGCGCTG
      AspLysGlu  LeuLysAla  LysGlyLys  SerAlaLeu  MetPheAsn
1936  GATAAAGAA  CTGAAAGCG  AAAGGTAAG  AGCGCGCTG  ATGTTCAAC
      LeuGlnGlu  ProTyrPhe  ThrTrpPro  LeuIleAla  AlaAspGly
1981  CTGCAAGAA  CCGTACTTC  ACCTGGCCG  CTGATTGCT  GCTGACGGG
      GlyTyrAla  PheLysTyr  GluAsnGly  LysTyrAsp  IleLysAsp
2026  GGTTATGCG  TTCAAGTAT  GAAAACGGC  AAGTACGAC  ATTAAAGAC
      ValGlyVal  AspAsnAla  GlyAlaLys  AlaGlyLeu  ThrPheLeu
2071  GTGGGCGTG  GATAACGCT  GGCGCGAAA  GCGGGTCTG  ACCTTCCTG
      ValAspLeu  IleLysAsn  LysHisMet  AsnAlaAsp  ThrAspTyr
2116  GTTGACCTG  ATTAAAAAC  AAACACATG  AATGCAGAC  ACCGATTAC
      SerIleAla  GluAlaAla  PheAsnLys  GlyGluThr  AlaMetThr
2161  TCCATCGCA  GAAGCTGCC  TTTAATAAA  GGCGAAACA  GCGATGACC
      IleAsnGly  ProTrpAla  TrpSerAsn  IleAspThr  SerLysVal
2206  ATCAACGGC  CCGTGGGCA  TGGTCCAAC  ATCGACACC  AGCAAAGTG
      AsnTyrGly  ValThrVal  LeuProThr  PheLysGly  GlnProSer
2251  AATTATGGT  GTAACGGTA  CTGCCGACC  TTCAAGGGT  CAACCATCC
      LysProPhe  ValGlyVal  LeuSerAla  GlyIleAsn  AlaAlaSer
2296  AAACCGTTC  GTTGGCGTG  CTGAGCGCA  GGTATTAAC  GCCGCCAGT
      ProAsnLys  GluLeuAla  LysGluPhe  LeuGluAsn  TyrLeuLeu
2341  CCGAACAAA  GAGCTGGCA  AAAGAGTTC  CTCGAAAAC  TATCTGCTG
      ThrAspGlu  GlyLeuGlu  AlaValAsn  LysAspLys  ProLeuGly
2386  ACTGATGAA  GGTCTGGAA  GCGGTTAAT  AAAGACAAA  CCGCTGGGT
      AlaValAla  LeuLysSer  TyrGluGlu  GluLeuAla  LysAspPro
2431  GCCGTAGCG  CTGAAGTCT  TACGAGGAA  GAGTTGGCG  AAAGATCCA
      ArgIleAla  AlaThrMet  GluAsnAla  GlnLysGly  GluIleMet
2476  CGTATTGCC  GCCACTATG  GAAAACGCC  CAGAAAGGT  GAAATCATG
      ProAsnIle  ProGlnMet  SerAlaPhe  TrpTyrAla  ValArgThr
2521  CCGAACATC  CCGCAGATG  TCCGCTTTC  TGGTATGCC  GTGCGTACT
      AlaValIle  AsnAlaAla  SerGlyArg  GlnThrVal  AspGluAla
2566  GCGGTGATC  AACGCCGCC  AGCGGTCGT  CAGACTGTC  GATGAAGCC
      LeuLysAsp  AlaGlnThr  AsnSerSer  SerAsnAsn  AsnAsnAsn
2611  CTGAAAGAC  GCGCAGACT  AATTCGAGC  TCGAACAAC  AACAACAAT
      AsnAsnAsn  AsnAsnLeu  GlyIleGlu  GlyArgIle  SerGluPhe
2656  AACAATAAC  AACAACCTC  GGGATCGAG  GGAAGGATT  TCAGAATTC
      LeuValAla  AsnGlnVal  ValThrCys  ProAspLys  LysSerThr
2701  CTTGTTGCC  AATCAAGTT  GTCACCTGC  CCAGATAAA  AAATCGACA
      AlaAlaVal  IleLeuThr  ProThrGlu  AsnHisPhe  ThrLeuLys
2746  GCCGCGGTC  ATTCTCACA  CCGACGGAG  AACCACTTC  ACTCTCAAG
      CysProLys  ThrAlaLeu  ThrGluPro  ProThrLeu  AlaTyrSer
```

FIGURE 2 pMBP-c2X-ToxoP30(52-336aa)

```
2791  TGCCCTAAA  ACAGCGCTC  ACAGAGCCT  CCCACTCTT  GCGTACTCA
      ProAsnArg  GlnIleCys  ProAlaGly  ThrThrSer  SerCysThr
2836  CCCAACAGG  CAAATCTGC  CCAGCGGGT  ACTACAAGT  AGCTGTACA
      SerLysAla  ValThrLeu  SerSerLeu  IleProGlu  AlaGluAsp
2881  TCAAAGGCT  GTAACATTG  AGCTCCTTG  ATTCCTGAA  GCAGAAGAT
      SerTrpTrp  ThrGlyAsp  SerAlaSer  LeuAspThr  AlaGlyIle
2926  AGCTGGTGG  ACGGGGGAT  TCTGCTAGT  CTCGACACG  GCAGGCATC
      LysLeuThr  ValProIle  GluLysPhe  ProValThr  ThrGlnThr
2971  AAACTCACG  GTTCCAATC  GAGAAGTTC  CCCGTGACA  ACGCAGACG
      PheValVal  GlyCysIle  LysGlyAsp  AspAlaGln  SerCysMet
3016  TTTGTGGTC  GGTTGCATC  AAGGGAGAC  GACGCACAG  AGTTGTATG
      ValThrVal  ThrValGln  AlaArgAla  SerSerVal  ValAsnAsn
3061  GTCACAGTG  ACAGTACAA  GCCAGAGCC  TCATCGGTC  GTCAATAAT
      ValAlaArg  CysSerTyr  GlyAlaAsp  SerThrLeu  GlyProVal
3106  GTCGCAAGG  TGCTCCTAC  GGTGCAGAC  AGCACTCTT  GGTCCTGTC
      LysLeuSer  AlaGluGly  ProThrThr  MetThrLeu  ValCysGly
3151  AAGTTGTCT  GCGGAAGGA  CCCACTACA  ATGACCCTC  GTGTGCGGG
      LysAspGly  ValLysVal  ProGlnAsp  AsnAsnGln  TyrCysSer
3196  AAAGATGGA  GTCAAAGTT  CCTCAAGAC  AACAATCAG  TACTGTTCC
      GlyThrThr  LeuThrGly  CysAsnGlu  LysSerPhe  LysAspIle
3241  GGGACGACG  CTGACTGGT  TGCAACGAG  AAATCGTTC  AAAGATATT
      LeuProLys  LeuThrGlu  AsnProTrp  GlnGlyAsn  AlaSerSer
3286  TTGCCAAAA  TTAACTGAG  AACCCGTGG  CAGGGTAAC  GCTTCGAGT
      AspLysGly  AlaThrLeu  ThrIleLys  LysGluAla  PheProAla
3331  GATAAGGGT  GCCACGCTA  ACGATCAAG  AAGGAAGCA  TTTCCAGCC
      GluSerLys  SerValIle  IleGlyCys  ThrGlyGly  SerProGlu
3376  GAGTCAAAA  AGCGTCATT  ATTGGATGC  ACAGGGGGA  TCGCCTGAG
      LysHisHis  CysThrVal  LysLeuGlu  PheAlaGly  AlaAlaGly
3421  AAGCATCAC  TGTACCGTG  AAACTGGAG  TTTGCCGGG  GCTGCAGGG
      SerAlaLys  SerAlaAla  GlyThrAla  SerHisVal  SerIlePhe
3466  TCAGCAAAA  TCGGCTGCG  GGAACAGCC  AGTCACGTT  TCCATTTTT
      AlaMetVal  IleGlyLeu  IleGlySer  IleAlaAla  CysValAla
3511  GCCATGGTG  ATCGGACTT  ATTGGCTCT  ATCGCAGCT  TGTGTCGCG
3556  TGAAAGCTT  GGCACTGGC  CGTCGTTTT  ACAACGTCG  TGACTGGGA
3601  AAACCCTGG  CGTTACCCA  ACTTAATCG  CCTTGCAGC  ACATCCCCC
3646  TTTCGCCAG  CTGGCGTAA  TAGCGAAGA  GGCCCGCAC  CGATCGCCC
3691  TTCCCAACA  GTTGCGCAG  CCTGAATGG  CGAATGGCA  GCTTGGCTG
3736  TTTTGGCGG  ATGAGATAA  GATTTTCAG  CCTGATACA  GATTAAATC
3781  AGAACGCAG  AAGCGGTCT  GATAAAACA  GAATTTGCC  TGGCGGCAG
3826  TAGCGCGGT  GGTCCCACC  TGACCCCAT  GCCGAACTC  AGAAGTGAA
3871  ACGCCGTAG  CGCCGATGG  TAGTGTGGG  GTCTCCCCA  TGCGAGAGT
3916  AGGGAACTG  CCAGGCATC  AAATAAAAC  GAAAGGCTC  AGTCGAAAG
3961  ACTGGGCCT  TCGTTTTA  TCTGTTGTT  TGTCGGTGA  ACGCTCTCC
4006  TGAGTAGGA  CAAATCCGC  CGGGAGCGG  ATTTGAACG  TTGCGAAGC
4051  AACGGCCCG  GAGGGTGGC  GGGCAGGAC  GCCCGCCAT  AAACTGCCA
4096  GGCATCAAA  TTAAGCAGA  AGGCCATCC  TGACGGATG  GCCTTTTTG
```

FIGURE 2 pMBP-c2X-ToxoP30(52-336aa)

```
4141  CGTTTCTAC AAACTCTTT TTGTTTATT TTCTAAAT ACATTCAAA
4186  TATGTATCC GCTCATGAG ACAATAACC CTGATAAAT GCTTCAATA
4231  ATATTGAAA AAGGAAGAG TATGAGTAT TCAACATTT CCGTGTCGC
4276  CCTTATTCC CTTTTTTGC GGCATTTTG CCTTCCTGT TTTTGCTCA
4321  CCCAGAAAC GCTGGTGAA AGTAAAAGA TGCTGAAGA TCAGTTGGG
4366  TGCACGAGT GGGTTACAT CGAACTGGA TCTCAACAG CGGTAAGAT
4411  CCTTGAGAG TTTTCGCCC CGAAGAACG TTCTCCAAT GATGAGCAC
4456  TTTTAAAGT TCTGCTATG TGGCGCGGT ATTATCCCG TGTTGACGC
4501  CGGGCAAGA GCAACTCGG TCGCCGCAT ACACTATTC TCAGAATGA
4546  CTTGGTTGA GTACTCACC AGTCACAGA AAAGCATCT TACGGATGG
4591  CATGACAGT AAGAGAATT ATGCAGTGC TGCCATAAC CATGAGTGA
4636  TAACACTGC GGCCAACTT ACTTCTGAC AACGATCGG AGGACCGAA
4681  GGAGCTAAC CGCTTTTTT GCACAACAT GGGGGATCA TGTAACTCG
4726  CCTTGATCG TTGGGAACC GGAGCTGAA TGAAGCCAT ACCAAACGA
4771  CGAGCGTGA CACCACGAT GCCTGTAGC AATGGCAAC AACGTTGCG
4816  CAAACTATT AACTGGCGA ACTACTTAC TCTAGCTTC CCGGCAACA
4861  ATTAATAGA CTGGATGGA GGCGGATAA AGTTGCAGG ACCACTTCT
4906  GCGCTCGGC CCTTCCGGC TGGCTGGTT TATTGCTGA TAAATCTGG
4951  AGCCGGTGA GCGTGGGTC TCGCGGTAT CATTGCAGC ACTGGGGCC
4996  AGATGGTAA GCCCTCCCG TATCGTAGT TATCTACAC GACGGGGAG
5041  TCAGGCAAC TATGGATGA ACGAAATAG ACAGATCGC TGAGATAGG
5086  TGCCTCACT GATTAAGCA TTGGTAACT GTCAGACCA AGTTTACTC
5131  ATATATACT TTAGATTGA TTTACCCCG GTTGATAAT CAGAAAAGC
5176  CCCAAAAAC AGGAAGATT GTATAAGCA ATATTTAA ATTGTAAAC
5221  GTTAATATT TTGTTAAAA TTCGCGTTA AATTTTTGT TAAATCAGC
5266  TCATTTTTT AACCAATAG GCCGAAATC GGCAAAATC CCTTATAAA
5311  TCAAAAGAA TAGACCGAG ATAGGGTTG AGTGTTGTT CCAGTTTGG
5356  AACAAGAGT CCACTATTA AGAACGTG GACTCCAAC GTCAAAGGG
5401  CGAAAAACC GTCTATCAG GGCGATGGC CCACTACGT GAACCATCA
5446  CCCAAATCA AGTTTTTTG GGGTCGAGG TGCCGTAAA GCACTAAAT
5491  CGGAACCCT AAAGGGAGC CCCCGATTT AGAGCTTGA CGGGGAAAG
5536  CCGGCGAAC GTGGCGAGA AAGGAAGGG AAGAAAGCG AAAGGAGCG
5581  GGCGCTAGG GCGCTGGCA AGTGTAGCG GTCACGCTG CGCGTAACC
5626  ACCACACCC GCCGCGCTT AATGCGCCG CTACAGGGC GCGTAAAAG
5671  GATCTAGGT GAAGATCCT TTTTGATAA TCTCATGAC CAAAATCCC
5716  TTAACGTGA GTTTTCGTT CCACTGAGC GTCAGACCC CGTAGAAAA
5761  GATCAAAGG ATCTTCTTG AGATCCTTT TTTTCTGCG CGTAATCTG
5806  CTGCTTGCA AACAAAAAA ACCACCGCT ACCAGCGGT GGTTTGTTT
5851  GCCGGATCA AGAGCTACC AACTCTTTT TCCGAAGGT AACTGGCTT
5896  CAGCAGAGC GCAGATACC AAATACTGT CCTTCTAGT GTAGCCGTA
5941  GTTAGGCCA CCACTTCAA GAACTCTGT AGCACCGCC TACATACCT
5986  CGCTCTGCT AATCCTGTT ACCAGTGGC TGCTGCCAG TGGCGATAA
6031  GTCGTGTCT TACCGGGTT GGACTCAAG ACGATAGTT ACCGGATAA
6076  GGCGCAGCG GTCGGGCTG AACGGGGGG TTCGTGCAC ACAGCCCAG
6121  CTTGGAGCG AACGACCTA CACCGAACT GAGATACCT ACAGCGTGA
6166  GCTATGAGA AAGCGCCAC GCTTCCCGA AGGGAGAAA GGCGGACAG
```

FIGURE 2 pMBP-c2X-ToxoP30(52-336aa)

```
6211  GTATCCGGT  AAGCGGCAG  GGTCGGAAC  AGGAGAGCG  CACGAGGGA
6256  GCTTCCAGG  GGGAAACGC  CTGGTATCT  TTATAGTCC  TGTCGGGTT
6301  TCGCCACCT  CTGACTTGA  GCGTCGATT  TTTGTGATG  CTCGTCAGG
6346  GGGGCGGAG  CCTATGGAA  AAACGCCAG  CAACGCGGC  CTTTTTACG
6391  GTTCCTGGC  CTTTTGCTG  GCCTTTTGC  TCACATGTT  CTTTCCTGC
6436  GTTATCCCC  TGATTCTGT  GGATAACCG  TATTACCGC  CTTTGAGTG
6481  AGCTGATAC  CGCTCGCCG  CAGCCGAAC  GACCGAGCG  CAGCGAGTC
6526  AGTGAGCGA  GGAAGCGGA  AGAGCGCCT  GATGCGGTA  TTTTCTCCT
6571  TACGCATCT  GTGCGGTAT  TTCACACCG  CATATATGG  TGCACTCTC
6616  AGTACAATC  TGCTCTGAT  GCCGCATAG  TTAAGCCAG  TATACACTC
6661  CGCTATCGC  TACGTGACT  GGGTCATGG  CTGCGCCCC  GACACCCGC
6706  CAACACCCG  CTGACGCGC  CCTGACGGG  CTTGTCTGC  TCCCGGCAT
6751  CCGCTTACA  GACAAGCTG  TGACCGTCT  CCGGGAGCT  GCATGTGTC
6796  AGAGGTTTT  CACCGTCAT  CACCGAAAC  GCGCGAGGC  AGCTGCGGT
6841  AAAGCTCAT  CAGCGTGGT  CGTGCAGCG  ATTCACAGA  TGTCTGCCT
6886  GTTCATCCG  CGTCCAGCT  CGTTGAGTT  CTCCAGAA  GCGTTAATG
6931  TCTGGCTTC  TGATAAAGC  GGGCCATGT  AAGGGCGG  TTTTTTCCT
6976  GTTTGGTCA  CTGATGCCT  CCGTGTAAG  GGGGATTTC  TGTTCATGG
7021  GGGTAATGA  TACCGATGA  AACGAGAGA  GGATGCTCA  CGATACGGG
7066  TTACTGATG  ATGAACATG  CCCGGTTAC  TGGAACGTT  GTGAGGGTA
7111  AACAACTGG  CGGTATGGA  TGCGGCGGG  ACCAGAGAA  AAATCACTC
7156  AGGGTCAAT  GCCAGCGCT  TCGTTAATA  CAGATGTAG  GTGTTCCAC
7201  AGGGTAGCC  AGCAGCATC  CTGCGATGC  AGATCCGGA  ACATAATGG
7246  TGCAGGGCG  CTGACTTCC  GCGTTTCCA  GACTTTACG  AAACACGGA
7291  AACCGAAGA  CCATTCATG  TTGTTGCTC  AGGTCGCAG  ACGTTTGC
7336  AGCAGCAGT  CGCTTCACG  TTCGCTCGC  GTATCGGTG  ATTCATTCT
7381  GCTAACCAG  TAAGGCAAC  CCCGCCAGC  CTAGCCGGG  TCCTCAACG
7426  ACAGGAGCA  CGATCATGC  GCACCCGTG  GCCAGGACC  AACGCTGC
7471  CCGAAATT
```

FIGURE 3  ToxoP30(52-336aa)

```
         LeuValAla  AsnGlnVal  ValThrCys  ProAspLys  LysSerThr
   1     CTTGTTGCC  AATCAAGTT  GTCACCTGC  CCAGATAAA  AAATCGACA
         AlaAlaVal  IleLeuThr  ProThrGlu  AsnHisPhe  ThrLeuLys
  46     GCCGCGGTC  ATTCTCACA  CCGACGGAG  AACCACTTC  ACTCTCAAG
         CysProLys  ThrAlaLeu  ThrGluPro  ProThrLeu  AlaTyrSer
  91     TGCCCTAAA  ACAGCGCTC  ACAGAGCCT  CCCACTCTT  GCGTACTCA
         ProAsnArg  GlnIleCys  ProAlaGly  ThrThrSer  SerCysThr
 136     CCCAACAGG  CAAATCTGC  CCAGCGGGT  ACTACAAGT  AGCTGTACA
         SerLysAla  ValThrLeu  SerSerLeu  IleProGlu  AlaGluAsp
 181     TCAAAGGCT  GTAACATTG  AGCTCCTTG  ATTCCTGAA  GCAGAAGAT
         SerTrpTrp  ThrGlyAsp  SerAlaSer  LeuAspThr  AlaGlyIle
 226     AGCTGGTGG  ACGGGGGAT  TCTGCTAGT  CTCGACACG  GCAGGCATC
         LysLeuThr  ValProIle  GluLysPhe  ProValThr  ThrGlnThr
 271     AAACTCACG  GTTCCAATC  GAGAAGTTC  CCCGTGACA  ACGCAGACG
         PheValVal  GlyCysIle  LysGlyAsp  AspAlaGln  SerCysMet
 316     TTTGTGGTC  GGTTGCATC  AAGGGAGAC  GACGCACAG  AGTTGTATG
         ValThrVal  ThrValGln  AlaArgAla  SerSerVal  ValAsnAsn
 361     GTCACAGTG  ACAGTACAA  GCCAGAGCC  TCATCGGTC  GTCAATAAT
         ValAlaArg  CysSerTyr  GlyAlaAsp  SerThrLeu  GlyProVal
 406     GTCGCAAGG  TGCTCCTAC  GGTGCAGAC  AGCACTCTT  GGTCCTGTC
         LysLeuSer  AlaGluGly  ProThrThr  MetThrLeu  ValCysGly
 451     AAGTTGTCT  GCGGAAGGA  CCCACTACA  ATGACCCTC  GTGTGCGGG
         LysAspGly  ValLysVal  ProGlnAsp  AsnAsnGln  TyrCysSer
 496     AAAGATGGA  GTCAAAGTT  CCTCAAGAC  AACAATCAG  TACTGTTCC
         GlyThrThr  LeuThrGly  CysAsnGlu  LysSerPhe  LysAspIle
 541     GGGACGACG  CTGACTGGT  TGCAACGAG  AAATCGTTC  AAAGATATT
         LeuProLys  LeuThrGlu  AsnProTrp  GlnGlyAsn  AlaSerSer
 586     TTGCCAAAA  TTAACTGAG  AACCCGTGG  CAGGGTAAC  GCTTCGAGT
         AspLysGly  AlaThrLeu  ThrIleLys  LysGluAla  PheProAla
 631     GATAAGGGT  GCCACGCTA  ACGATCAAG  AAGGAAGCA  TTTCCAGCC
         GluSerLys  SerValIle  IleGlyCys  ThrGlyGly  SerProGlu
 676     GAGTCAAAA  AGCGTCATT  ATTGGATGC  ACAGGGGGA  TCGCCTGAG
         LysHisHis  CysThrVal  LysLeuGlu  PheAlaGly  AlaAlaGly
 721     AAGCATCAC  TGTACCGTG  AAACTGGAG  TTTGCCGGG  GCTGCAGGG
         SerAlaLys  SerAlaAla  GlyThrAla  SerHisVal  SerIlePhe
 766     TCAGCAAAA  TCGGCTGCG  GGAACAGCC  AGTCACGTT  TCCATTTTT
         AlaMetVal  IleGlyLeu  IleGlySer  IleAlaAla  CysValAla
 811     GCCATGGTG  ATCGGACTT  ATTGGCTCT  ATCGCAGCT  TGTGTCGCG
```

FIGURE 5   pMBP-p2X-ToxoP30(52-336aa)

```
   1   CCGACACCA TCGAATGGT GCAAAACCT TTCGCGGTA TGGCATGAT
  46   AGCGCCCGG AAGAGAGTC AATTCAGGG TGGTGAATG TGAAACCAG
  91   TAACGTTAT ACGATGTCG CAGAGTATG CCGGTGTCT CTTATCAGA
 136   CCGTTTCCC GCGTGGTGA ACCAGGCCA GCCACGTTT CTGCGAAAA
 181   CGCGGGAAA AAGTGGAAG CGGCGATGG CGGAGCTGA ATTACATTC
 226   CCAACCGCG TGGCACAAC AACTGGCGG GCAAACAGT CGTTGCTGA
 271   TTGGCGTTG CCACCTCCA GTCTGGCCC TGCACGCGC CGTCGCAAA
 316   TTGTCGCGG CGATTAAAT CTCGCGCCG ATCAACTGG GTGCCAGCG
 361   TGGTGGTGT CGATGGTAG AACGAAGCG GCGTCGAAG CCTGTAAAG
 406   CGGCGGTGC ACAATCTTC TCGCGCAAC GCGTCAGTG GGCTGATCA
 451   TTAACTATC CGCTGGATG ACCAGGATG CCATTGCTG TGGAAGCTG
 496   CCTGCACTA ATGTTCCGG CGTTATTTC TTGATGTCT CTGACCAGA
 541   CACCCATCA ACAGTATTA TTTTCTCCC ATGAAGACG GTACGCGAC
 586   TGGGCGTGG AGCATCTGG TCGCATTGG GTCACCAGC AAATCGCGC
 631   TGTTAGCGG GCCCATTAA GTTCTGTCT CGGCGCGTC TGCGTCTGG
 676   CTGGCTGGC ATAAATATC TCACTCGCA ATCAAATTC AGCCGATAG
 721   CGGAACGGG AAGGCGACT GGAGTGCCA TGTCCGGTT TTCAACAAA
 766   CCATGCAAA TGCTGAATG AGGGCATCG TTCCCACTG CGATGCTGG
 811   TTGCCAACG ATCAGATGG CGCTGGGCG CAATGCGCG CCATTACCG
 856   AGTCCGGGC TGCGCGTTG GTGCGGATA TCTCGGTAG TGGGATACG
 901   ACGATACCG AAGACAGCT CATGTTATA TCCCGCCGT TAACCACCA
 946   TCAAACAGG ATTTTCGCC TGCTGGGGC AAACCAGCG TGGACCGCT
 991   TGCTGCAAC TCTCTCAGG GCCAGGCGG TGAAGGGCA ATCAGCTGT
1036   TGCCCGTCT CACTGGTGA AAGAAAAA CCACCCTGG CGCCCAATA
1081   CGCAAACCG CCTCTCCCC GCGCGTTGG CCGATTCAT TAATGCAGC
1126   TGGCACGAC AGGTTTCCC GACTGGAAA GCGGGCAGT GAGCGCAAC
1171   GCAATTAAT GTAAGTTAG CTCACTCAT TAGGCACAA TTCTCATGT
1216   TTGACAGCT TATCATCGA CTGCACGGT GCACCAATG CTTCTGGCG
1261   TCAGGCAGC CATCGGAAG CTGTGGTAT GGCTGTGCA GGTCGTAAA
1306   TCACTGCAT AATTCGTGT CGCTCAAGG CGCACTCCC GTTCTGGAT
1351   AATGTTTTT TGCGCCGAC ATCATAACG GTTCTGGCA AATATTCTG
1396   AAATGAGCT GTTGACAAT TAATCATCG GCTCGTATA ATGTGTGGA
1441   ATTGTGAGC GGATAACAA TTTCACACA GGAAACAGC CAGTCCGTT
                                                                        Met
1486   TAGGTGTTT TCACGAGCA CTTCACCAA CAAGGACCA TAGCATATG
       LysIleLys  ThrGlyAla  ArgIleLeu  AlaLeuSer  AlaLeuThr
1531   AAAATAAAA ACAGGTGCA CGCATCCTC GCATTATCC GCATTAACG
       ThrMetMet  PheSerAla  SerAlaLeu  AlaLysIle  GluGluGly
1576   ACGATGATG TTTTCCGCC TCGGCTCTC GCCAAAATC GAAGAAGGT
       LysLeuVal  IleTrpIle  AsnGlyAsp  LysGlyTyr  AsnGlyLeu
1621   AAACTGGTA ATCTGGATT AACGGCGAT AAAGGCTAT AACGGTCTC
       AlaGluVal  GlyLysLys  PheGluLys  AspThrGly  IleLysVal
1666   GCTGAAGTC GGTAAGAAA TTCGAGAAA GATACCGGA ATTAAAGTC
       ThrValGlu  HisProAsp  LysLeuGlu  GluLysPhe  ProGlnVal
1711   ACCGTTGAG CATCCGGAT AAACTGGAA GAGAAATTC CCACAGGTT
       AlaAlaThr  GlyAspGly  ProAspIle  IlePheTrp  AlaHisAsp
```

FIGURE 5  pMBP-p2X-ToxoP30(52-336aa)

```
1756 GCGGCAACT GGCGATGGC CCTGACATT ATCTTCTGG GCACACGAC
     ArgPheGly GlyTyrAla GlnSerGly LeuLeuAla GluIleThr
1801 CGCTTTGGT GGCTACGCT CAATCTGGC CTGTTGGCT GAAATCACC
     ProAspLys AlaPheGln AspLysLeu TyrProPhe ThrTrpAsp
1846 CCGGACAAA GCGTTCCAG GACAAGCTG TATCCGTTT ACCTGGGAT
     AlaValArg TyrAsnGly LysLeuIle AlaTyrPro IleAlaVal
1891 GCCGTACGT TACAACGGC AAGCTGATT GCTTACCCG ATCGCTGTT
     GluAlaLeu SerLeuIle TyrAsnLys AspLeuLeu ProAsnPro
1936 GAAGCGTTA TCGCTGATT TATAACAAA GATCTGCTG CCGAACCCG
     ProLysThr TrpGluGlu IleProAla LeuAspLys GluLeuLys
1981 CCAAAAACC TGGGAAGAG ATCCCGGCG CTGGATAAA GAACTGAAA
     AlaLysGly LysSerAla LeuMetPhe AsnLeuGln GluProTyr
2026 GCGAAAGGT AAGAGCGCG CTGATGTTC AACCTGCAA GAACCGTAC
     PheThrTrp ProLeuIle AlaAlaAsp GlyGlyTyr AlaPheLys
2071 TTCACCTGG CCGCTGATT GCTGCTGAC GGGGGTTAT GCGTTCAAG
     TyrGluAsn GlyLysTyr AspIleLys AspValGly ValAspAsn
2116 TATGAAAAC GGCAAGTAC GACATTAAA GACGTGGGC GTGGATAAC
     AlaGlyAla LysAlaGly LeuThrPhe LeuValAsp LeuIleLys
2161 GCTGGCGCG AAAGCGGGT CTGACCTTC CTGGTTGAC CTGATTAAA
     AsnLysHis MetAsnAla AspThrAsp TyrSerIle AlaGluAla
2206 AACAAACAC ATGAATGCA GACACCGAT TACTCCATC GCAGAAGCT
     AlaPheAsn LysGlyGlu ThrAlaMet ThrIleAsn GlyProTrp
2251 GCCTTTAAT AAAGGCGAA ACAGCGATG ACCATCAAC GGCCCGTGG
     AlaTrpSer AsnIleAsp ThrSerLys ValAsnTyr GlyValThr
2296 GCATGGTCC AACATCGAC ACCAGCAAA GTGAATTAT GGTGTAACG
     ValLeuPro ThrPheLys GlyGlnPro SerLysPro PheValGly
2341 GTACTGCCG ACCTTCAAG GGTCAACCA TCCAAACCG TTCGTTGGC
     ValLeuSer AlaGlyIle AsnAlaAla SerProAsn LysGluLeu
2386 GTGCTGAGC GCAGGTATT AACGCCGCC AGTCCGAAC AAAGAGCTG
     AlaLysGlu PheLeuGlu AsnTyrLeu LeuThrAsp GluGlyLeu
2431 GCAAAAGAG TTCCTCGAA AACTATCTG CTGACTGAT GAAGGTCTG
     GluAlaVal AsnLysAsp LysProLeu GlyAlaVal AlaLeuLys
2476 GAAGCGGTT AATAAAGAC AAACCGCTG GGTGCCGTA GCGCTGAAG
     SerTyrGlu GluGluLeu AlaLysAsp ProArgIle AlaAlaThr
2521 TCTTACGAG GAAGAGTTG GCGAAAGAT CCACGTATT GCCGCCACT
     MetGluAsn AlaGlnLys GlyGluIle MetProAsn IleProGln
2566 ATGGAAAAC GCCCAGAAA GGTGAAATC ATGCCGAAC ATCCCGCAG
     MetSerAla PheTrpTyr AlaValArg ThrAlaVal IleAsnAla
2611 ATGTCCGCT TTCTGGTAT GCCGTGCGT ACTGCGGTG ATCAACGCC
     AlaSerGly ArgGlnThr ValAspGlu AlaLeuLys AspAlaGln
2656 GCCAGCGGT CGTCAGACT GTCGATGAA GCCCTGAAA GACGCGCAG
     ThrAsnSer SerSerAsn AsnAsnAsn AsnAsnAsn AsnAsnAsn
2701 ACTAATTCG AGCTCGAAC AACAACAAC AATAACAAT AACAACAAC
     LeuGlyIle GluGlyArg IleSerGlu PheLeuVal AlaAsnGln
2746 CTCGGGATC GAGGGAAGG ATTTCAGAA TTCCTTGTT GCCAATCAA
     ValValThr CysProAsp LysLysSer ThrAlaAla ValIleLeu
```

FIGURE 5  pMBP-p2X-ToxoP30(52-336aa)

```
2791  GTTGTCACC  TGCCCAGAT  AAAAAATCG  ACAGCCGCG  GTCATTCTC
      ThrProThr  GluAsnHis  PheThrLeu  LysCysPro  LysThrAla
2836  ACACCGACG  GAGAACCAC  TTCACTCTC  AAGTGCCCT  AAAACAGCG
      LeuThrGlu  ProProThr  LeuAlaTyr  SerProAsn  ArgGlnIle
2881  CTCACAGAG  CCTCCCACT  CTTGCGTAC  TCACCCAAC  AGGCAAATC
      CysProAla  GlyThrThr  SerSerCys  ThrSerLys  AlaValThr
2926  TGCCCAGCG  GGTACTACA  AGTAGCTGT  ACATCAAAG  GCTGTAACA
      LeuSerSer  LeuIlePro  GluAlaGlu  AspSerTrp  TrpThrGly
2971  TTGAGCTCC  TTGATTCCT  GAAGCAGAA  GATAGCTGG  TGGACGGGG
      AspSerAla  SerLeuAsp  ThrAlaGly  IleLysLeu  ThrValPro
3016  GATTCTGCT  AGTCTCGAC  ACGGCAGGC  ATCAAACTC  ACAGTTCCA
      IleGluLys  PheProVal  ThrThrGln  ThrPheVal  ValGlyCys
3061  ATCGAGAAG  TTCCCCGTG  ACAACGCAG  ACGTTTGTG  GTCGGTTGC
      IleLysGly  AspAspAla  GlnSerCys  MetValThr  ValThrVal
3106  ATCAAGGGA  GACGACGCA  CAGAGTTGT  ATGGTCACA  GTGACAGTA
      GlnAlaArg  AlaSerSer  ValValAsn  AsnValAla  ArgCysSer
3151  CAAGCCAGA  GCCTCATCG  GTCGTCAAT  AATGTCGCA  AGGTGCTCC
      TyrGlyAla  AspSerThr  LeuGlyPro  ValLysLeu  SerAlaGlu
3196  TACGGTGCA  GACAGCACT  CTTGGTCCT  GTCAAGTTG  TCTGCGGAA
      GlyProThr  ThrMetThr  LeuValCys  GlyLysAsp  GlyValLys
3241  GGACCCACT  ACAATGACC  CTCGTGTGC  GGGAAAGAT  GGAGTCAAA
      ValProGln  AspAsnAsn  GlnTyrCys  SerGlyThr  ThrLeuThr
3286  GTTCCTCAA  GACAACAAT  CAGTACTGT  TCCGGGACG  ACGCTGACT
      GlyCysAsn  GluLysSer  PheLysAsp  IleLeuPro  LysLeuThr
3331  GGTTGCAAC  GAGAAATCG  TTCAAAGAT  ATTTTGCCA  AAATTAACT
      GluAsnPro  TrpGlnGly  AsnAlaSer  SerAspLys  GlyAlaThr
3376  GAGAACCCG  TGGCAGGGT  AACGCTTCG  AGTGATAAG  GGTGCCACG
      LeuThrIle  LysLysGlu  AlaPhePro  AlaGluSer  LysSerVal
3421  CTAACGATC  AAGAAGGAA  GCATTTCCA  GCCGAGTCA  AAAAGCGTC
      IleIleGly  CysThrGly  GlySerPro  GluLysHis  HisCysThr
3466  ATTATTGGA  TGCACAGGG  GGATCGCCT  GAGAAGCAT  CACTGTACC
      ValLysLeu  GluPheAla  GlyAlaAla  GlySerAla  LysSerAla
3511  GTGAAACTG  GAGTTTGCC  GGGGCTGCA  GGGTCAGCA  AAATCGGCT
      AlaGlyThr  AlaSerHis  ValSerIle  PheAlaMet  ValIleGly
3556  GCGGGAACA  GCCAGTCAC  GTTTCCATT  TTTGCCATG  GTGATCGGA
      LeuIleGly  SerIleAla  AlaCysVal  Ala
3601  CTTATTGGC  TCTATCGCA  GCTTGTGTC  GCGTGAAAG  CTTGGCACT
3646  GGCCGTCGT  TTTACAACG  TCGTGACTG  GGAAAACCC  TGGCGTTAC
3691  CCAACTTAA  TCGCCTTGC  AGCACATCC  CCCTTTCGC  CAGCTGGCG
3736  TAATAGCGA  AGAGGCCCG  CACCGATCG  CCCTTCCCA  ACAGTTGCG
3781  CAGCCTGAA  TGGCGAATG  GCAGCTTGG  CTGTTTTGG  CGGATGAGA
3826  TAAGATTTT  CAGCCTGAT  ACAGATTAA  ATCAGAACG  CAGAAGCGG
3871  TCTGATAAA  ACAGAATTT  GCCTGGCGG  CAGTAGCGC  GGTGGTCCC
3916  ACCTGACCC  CATGCCGAA  CTCAGAAGT  GAAACGCCG  TAGCGCCGA
3961  TGGTAGTGT  GGGGTCTCC  CCATGCGAG  AGTAGGGAA  CTGCCAGGC
4006  ATCAAATAA  AACGAAAGG  CTCAGTCGA  AAGACTGGG  CCTTTCGTT
```

FIGURE 5 pMBP-p2X-ToxoP30(52-336aa)

```
4051 TTATCTGTT GTTTGTCGG TGAACGCTC TCCTGAGTA GGACAAATC
4096 CGCCGGGAG CGGATTTGA ACGTTGCGA AGCAACGGC CCGGAGGGT
4141 GGCGGGCAG GACGCCCGC CATAAACTG CCAGGCATC AAATTAAGC
4186 AGAAGGCCA TCCTGACGG ATGGCCTTT TTGCGTTTC TACAAACTC
4231 TTTTTGTTT ATTTTTCTA AATACATTC AAATATGTA TCCGCTCAT
4276 GAGACAATA ACCCTGATA AATGCTTCA ATAATATTG AAAAGGAA
4321 GAGTATGAG TATTCAACA TTTCCGTGT CGCCCTTAT TCCCTTTTT
4366 TGCGGCATT TTGCCTTCC TGTTTTTGC TCACCCAGA AACGCTGGT
4411 GAAAGTAAA AGATGCTGA AGATCAGTT GGGTGCACG AGTGGGTTA
4456 CATCGAACT GGATCTCAA CAGCGGTAA GATCCTTGA GAGTTTTCG
4501 CCCCGAAGA ACGTTCTCC AATGATGAG CACTTTTAA AGTTCTGCT
4546 ATGTGGCGC GGTATTATC CCGTGTTGA CGCCGGGCA AGAGCAACT
4591 CGGTCGCCG CATACACTA TTCTCAGAA TGACTTGGT TGAGTACTC
4636 ACCAGTCAC AGAAAAGCA TCTTACGGA TGGCATGAC AGTAAGAGA
4681 ATTATGCAG TGCTGCCAT AACCATGAG TGATAACAC TGCGGCCAA
4726 CTTACTTCT GACAACGAT CGGAGGACC GAAGGAGCT AACCGCTTT
4771 TTTGCACAA CATGGGGGA TCATGTAAC TCGCCTTGA TCGTTGGGA
4816 ACCGGAGCT GAATGAAGC CATACCAAA CGACGAGCG TGACACCAC
4861 GATGCCTGT AGCAATGGC AACAACGTT GCGCAAACT ATTAACTGG
4906 CGAACTACT TACTCTAGC TTCCCGGCA ACAATTAAT AGACTGGAT
4951 GGAGGCGGA TAAAGTTGC AGGACCACT TCTGCGCTC GGCCCTTCC
4996 GGCTGGCTG GTTTATTGC TGATAAATC TGGAGCCGG TGAGCGTGG
5041 GTCTCGCGG TATCATTGC AGCACTGGG GCCAGATGG TAAGCCCTC
5086 CCGTATCGT AGTTATCTA CACGACGGG GAGTCAGGC AACTATGGA
5131 TGAACGAAA TAGACAGAT CGCTGAGAT AGGTGCCTC ACTGATTAA
5176 GCATTGGTA ACTGTCAGA CCAAGTTTA CTCATATAT ACTTTAGAT
5221 TGATTTACC CCGGTTGAT AATCAGAAA AGCCCCAAA AACAGGAAG
5266 ATTGTATAA GCAAATATT TAAATTGTA AACGTTAAT ATTTTGTTA
5311 AAATTCGCG TTAAATTTT TGTTAAATC AGCTCATTT TTTAACCAA
5356 TAGGCCGAA ATCGGCAAA ATCCCTTAT AAATCAAAA GAATAGACC
5401 GAGATAGGG TTGAGTGTT GTTCCAGTT TGGAACAAG AGTCCACTA
5446 TTAAAGAAC GTGGACTCC AACGTCAAA GGGCGAAAA ACCGTCTAT
5491 CAGGGCGAT GGCCCACTA CGTGAACCA TCACCCAAA TCAAGTTTT
5536 TTGGGGTCG AGGTGCCGT AAAGCACTA AATCGGAAC CCTAAAGGG
5581 AGCCCCCGA TTTAGAGCT TGACGGGGA AAGCCGGCG AACGTGGCG
5626 AGAAAGGAA GGGAAGAAA GCGAAAGGA GCGGGCGCT AGGGCGCTG
5671 GCAAGTGTA GCGGTCACG CTGCGCGTA ACCACCACA CCCGCCGCG
5716 CTTAATGCG CCGCTACAG GGCGCGTAA AAGGATCTA GGTGAAGAT
5761 CCTTTTTGA TAATCTCAT GACCAAAAT CCCTTAACG TGAGTTTTC
5806 GTTCCACTG AGCGTCAGA CCCCGTAGA AAGATCAA AGGATCTTC
5851 TTGAGATCC TTTTTTTCT GCGCGTAAT CTGCTGCTT GCAAACAAA
5896 AAACCACC GCTACCAGC GGTGGTTTG TTTGCCGGA TCAAGAGCT
5941 ACCAACTCT TTTCCGAA GGTAACTGG CTTCAGCAG AGCGCAGAT
5986 ACCAAATAC TGTCCTTCT AGTGTAGCC GTAGTTAGG CCACCACTT
6031 CAAGAACTC TGTAGCACC GCCTACATA CCTCGCTCT GCTAATCCT
6076 GTTACCAGT GGCTGCTGC CAGTGGCGA TAAGTCGTG TCTTACCGG
```

FIGURE 5   pMBP-p2X-ToxoP30(52-336aa)

```
6121 GTTGGACTC AAGACGATA GTTACCGGA TAAGGCGCA GCGGTCGGG
6166 CTGAACGGG GGGTTCGTG CACACAGCC CAGCTTGGA GCGAACGAC
6211 CTACACCGA ACTGAGATA CCTACAGCG TGAGCTATG AGAAAGCGC
6256 CACGCTTCC CGAAGGGAG AAAGGCGGA CAGGTATCC GGTAAGCGG
6301 CAGGGTCGG AACAGGAGA GCGCACGAG GGAGCTTCC AGGGGGAAA
6346 CGCCTGGTA TCTTTATAG TCCTGTCGG GTTTCGCCA CCTCTGACT
6391 TGAGCGTCG ATTTTTGTG ATGCTCGTC AGGGGGGCG GAGCCTATG
6436 GAAAAACGC CAGCAACGC GGCCTTTTT ACGGTTCCT GGCCTTTTG
6481 CTGGCCTTT TGCTCACAT GTTCTTTCC TGCGTTATC CCTGATTC
6526 TGTGGATAA CCGTATTAC CGCCTTTGA GTGAGCTGA TACCGCTCG
6571 CCGCAGCCG AACGACCGA GCGCAGCGA GTCAGTGAG CGAGGAAGC
6616 GGAAGAGCG CCTGATGCG GTATTTTCT CCTTACGCA TCTGTGCGG
6661 TATTTCACA CCGCATATA TGGTGCACT CTCAGTACA ATCTGCTCT
6706 GATGCCGCA TAGTTAAGC CAGTATACA CTCCGCTAT CGCTACGTG
6751 ACTGGGTCA TGGCTGCGC CCCGACACC CGCCAACAC CCGCTGACG
6796 CGCCCTGAC GGGCTTGTC TGCTCCCGG CATCCGCTT ACAGACAAG
6841 CTGTGACCG TCTCCGGGA GCTGCATGT GTCAGAGGT TTTCACCGT
6886 CATCACCGA AACGCGCGA GGCAGCTGC GGTAAAGCT CATCAGCGT
6931 GGTCGTGCA GCGATTCAC AGATGTCTG CCTGTTCAT CCGCGTCCA
6976 GCTCGTTGA GTTTCTCCA GAAGCGTTA ATGTCTGGC TTCTGATAA
7021 AGCGGGCCA TGTTAAGGG CGGTTTTTT CCTGTTTGG TCACTGATG
7066 CCTCCGTGT AAGGGGGAT TTCTGTTCA TGGGGGTAA TGATACCGA
7111 TGAAACGAG AGAGGATGC TCACGATAC GGGTTACTG ATGATGAAC
7156 ATGCCCGGT TACTGGAAC GTTGTGAGG GTAAACAAC TGGCGGTAT
7201 GGATGCGGC GGGACCAGA GAAAAATCA CTCAGGGTC AATGCCAGC
7246 GCTTCGTTA ATACAGATG TAGGTGTTC CACAGGGTA GCCAGCAGC
7291 ATCCTGCGA TGCAGATCC GGAACATAA TGGTGCAGG GCGCTGACT
7336 TCCGCGTTT CCAGACTTT ACGAAACAC GGAAACCGA AGACCATTC
7381 ATGTTGTTG CTCAGGTCG CAGACGTTT TGCAGCAGC AGTCGCTTC
7426 ACGTTCGCT CGCGTATCG GTGATTCAT TCTGCTAAC CAGTAAGGC
7471 AACCCCGCC AGCCTAGCC GGGTCCTCA ACGACAGGA GCACGATCA
7516 TGCGCACCC GTGGCCAGG ACCAACGC TGCCCGAAA TT
```

FIGURE 8  pMBP-c2X-ToxoP30del1C(52-324aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCCGTT TCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA AATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 8    pMBP-c2X-ToxoP30del1C(52-324aa)

```
1756  TTGGCTGAA ATCACCCCG GACAAAGCG TTCCAGGAC AAGCTGTAT
      ProPheThr TrpAspAla ValArgTyr AsnGlyLys LeuIleAla
1801  CCGTTTACC TGGGATGCC GTACGTTAC AACGGCAAG CTGATTGCT
      TyrProIle AlaValGlu AlaLeuSer LeuIleTyr AsnLysAsp
1846  TACCCGATC GCTGTTGAA GCGTTATCG CTGATTTAT AACAAAGAT
      LeuLeuPro AsnProPro LysThrTrp GluGluIle ProAlaLeu
1891  CTGCTGCCG AACCCGCCA AAAACCTGG AAGAGATC CCGGCGCTG
      AspLysGlu LeuLysAla LysGlyLys SerAlaLeu MetPheAsn
1936  GATAAAGAA CTGAAAGCG AAAGGTAAG AGCGCGCTG ATGTTCAAC
      LeuGlnGlu ProTyrPhe ThrTrpPro LeuIleAla AlaAspGly
1981  CTGCAAGAA CCGTACTTC ACCTGGCCG CTGATTGCT GCTGACGGG
      GlyTyrAla PheLysTyr GluAsnGly LysTyrAsp IleLysAsp
2026  GGTTATGCG TTCAAGTAT GAAAACGGC AAGTACGAC ATTAAGAC
      ValGlyVal AspAsnAla GlyAlaLys AlaGlyLeu ThrPheLeu
2071  GTGGGCGTG GATAACGCT GGCGCGAAA GCGGGTCTG ACCTTCCTG
      ValAspLeu IleLysAsn LysHisMet AsnAlaAsp ThrAspTyr
2116  GTTGACCTG ATTAAAAAC AAACACATG AATGCAGAC ACCGATTAC
      SerIleAla GluAlaAla PheAsnLys GlyGluThr AlaMetThr
2161  TCCATCGCA GAAGCTGCC TTTAATAAA GGCGAAACA GCGATGACC
      IleAsnGly ProTrpAla TrpSerAsn IleAspThr SerLysVal
2206  ATCAACGGC CCGTGGGCA TGGTCCAAC ATCGACACC AGCAAAGTG
      AsnTyrGly ValThrVal LeuProThr PheLysGly GlnProSer
2251  AATTATGGT GTAACGGTA CTGCCGACC TTCAAGGGT CAACCATCC
      LysProPhe ValGlyVal LeuSerAla GlyIleAsn AlaAlaSer
2296  AAACCGTTC GTTGGCGTG CTGAGCGCA GGTATTAAC GCCGCCAGT
      ProAsnLys GluLeuAla LysGluPhe LeuGluAsn TyrLeuLeu
2341  CCGAACAAA GAGCTGGCA AAAGAGTTC CTCGAAAAC TATCTGCTG
      ThrAspGlu GlyLeuGlu AlaValAsn LysAspLys ProLeuGly
2386  ACTGATGAA GGTCTGGAA GCGGTTAAT AAAGACAAA CCGCTGGGT
      AlaValAla LeuLysSer TyrGluGlu GluLeuAla LysAspPro
2431  GCCGTAGCG CTGAAGTCT TACGAGGAA GAGTTGGCG AAAGATCCA
      ArgIleAla AlaThrMet GluAsnAla GlnLysGly GluIleMet
2476  CGTATTGCC GCCACTATG GAAAACGCC CAGAAAGGT GAAATCATG
      ProAsnIle ProGlnMet SerAlaPhe TrpTyrAla ValArgThr
2521  CCGAACATC CCGCAGATG TCCGCTTTC TGGTATGCC GTGCGTACT
      AlaValIle AsnAlaAla SerGlyArg GlnThrVal AspGluAla
2566  GCGGTGATC AACGCCGCC AGCGGTCGT CAGACTGTC GATGAAGCC
      LeuLysAsp AlaGlnThr AsnSerSer SerAsnAsn AsnAsnAsn
2611  CTGAAAGAC GCGCAGACT AATTCGAGC TCGAACAAC AACAACAAT
      AsnAsnAsn AsnAsnLeu GlyIleGlu GlyArgIle SerGluPhe
2656  AACAATAAC AACAACCTC GGGATCGAG GGAAGGATT TCAGAATTC
      LeuValAla AsnGlnVal ValThrCys ProAspLys LysSerThr
2701  CTTGTTGCC AATCAAGTT GTCACCTGC CCAGATAAA AAATCGACA
      AlaAlaVal IleLeuThr ProThrGlu AsnHisPhe ThrLeuLys
2746  GCCGCGGTC ATTCTCACA CCGACGGAG AACCACTTC ACTCTCAAG
      CysProLys ThrAlaLeu ThrGluPro ProThrLeu AlaTyrSer
```

FIGURE 8  pMBP-c2X-ToxoP30del1C(52-324aa)

```
2791  TGCCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCTCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACAGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGluGly ProThrThr MetThrLeu ValCysGly
3151  AAGTTGTCT GCGGAAGGA CCCACTACA ATGACCCTC GTGTGCGGG
      LysAspGly ValLysVal ProGlnAsp AsnAsnGln TyrCysSer
3196  AAAGATGGA GTCAAAGTT CCTCAAGAC AACAATCAG TACTGTTCC
      GlyThrThr LeuThrGly CysAsnGlu LysSerPhe LysAspIle
3241  GGGACGACG CTGACTGGT TGCAACGAG AAATCGTTC AAAGATATT
      LeuProLys LeuThrGlu AsnProTrp GlnGlyAsn AlaSerSer
3286  TTGCCAAAA TTAACTGAG AACCCGTGG CAGGGTAAC GCTTCGAGT
      AspLysGly AlaThrLeu ThrIleLys LysGluAla PheProAla
3331  GATAAGGGT GCCACGCTA ACGATCAAG AAGGAAGCA TTTCCAGCC
      GluSerLys SerValIle IleGlyCys ThrGlyGly SerProGlu
3376  GAGTCAAAA AGCGTCATT ATTGGATGC ACAGGGGGA TCGCCTGAG
      LysHisHis CysThrVal LysLeuGlu PheAlaGly AlaAlaGly
3421  AAGCATCAC TGTACCGTG AAACTGGAG TTTGCCGGG GCTGCAGGG
      SerAlaLys SerAlaAla GlyThrAla SerHisVal SerIlePhe
3466  TCAGCAAAA TCGGCTGCG GGAACAGCC AGTACGTT TCCATTTTT
      AlaMetVal
3511  GCCATGGTG TGAAAGCTT GGCACTGGC CGTCGTTTT ACAACGTCG
3556  TGACTGGGA AAACCCTGG CGTTACCCA ACTTAATCG CCTTGCAGC
3601  ACATCCCCC TTTCGCCAG CTGGCGTAA TAGCGAAGA GGCCCGCAC
3646  CGATCGCCC TTCCCAACA GTTGCGCAG CCTGAATGG CGAATGGCA
3691  GCTTGGCTG TTTTGGCGG ATGAGATAA GATTTTCAG CCTGATACA
3736  GATTAAATC AGAACGCAG AAGCGGTCT GATAAAACA GAATTTGCC
3781  TGGCGGCAG TAGCGCGGT GGTCCCACC TGACCCCAT GCCGAACTC
3826  AGAAGTGAA ACGCCGTAG CGCCGATGG TAGTGTGGG GTCTCCCCA
3871  TGCGAGAGT AGGGAACTG CCAGGCATC AAATAAAAC GAAAGGCTC
3916  AGTCGAAAG ACTGGGCCT TCGTTTTA TCTGTTGTT TGTCGGTGA
3961  ACGCTCTCC TGAGTAGGA CAAATCCGC CGGGAGCGG ATTTGAACG
4006  TTGCGAAGC AACGGCCCG GAGGGTGGC GGGCAGGAC GCCCGCCAT
4051  AAACTGCCA GGCATCAAA TTAAGCAGA AGGCCATCC TGACGGATG
4096  GCCTTTTTG CGTTTCTAC AAACTCTTT TTGTTTATT TTTCTAAAT
```

FIGURE 8 pMBP-c2X-ToxoP30del1C(52-324aa)

```
4141  ACATTCAAA TATGTATCC GCTCATGAG ACAATAACC CTGATAAAT
4186  GCTTCAATA ATATTGAAA AAGGAAGAG TATGAGTAT TCAACATTT
4231  CCGTGTCGC CCTTATTCC CTTTTTTGC GGCATTTTG CCTTCCTGT
4276  TTTTGCTCA CCCAGAAAC GCTGGTGAA AGTAAAAGA TGCTGAAGA
4321  TCAGTTGGG TGCACGAGT GGGTTACAT CGAACTGGA TCTCAACAG
4366  CGGTAAGAT CCTTGAGAG TTTTCGCCC CGAAGAACG TTCTCCAAT
4411  GATGAGCAC TTTTAAAGT TCTGCTATG TGGCGCGGT ATTATCCCG
4456  TGTTGACGC CGGGCAAGA GCAACTCGG TCGCCGCAT ACACTATTC
4501  TCAGAATGA CTTGGTTGA GTACTCACC AGTCACAGA AAAGCATCT
4546  TACGGATGG CATGACAGT AAGAGAATT ATGCAGTGC TGCCATAAC
4591  CATGAGTGA TAACACTGC GGCCAACTT ACTTCTGAC AACGATCGG
4636  AGGACCGAA GGAGCTAAC CGCTTTTTT GCACAACAT GGGGGATCA
4681  TGTAACTCG CCTTGATCG TTGGGAACC GGAGCTGAA TGAAGCCAT
4726  ACCAAACGA CGAGCGTGA CACCACGAT GCCTGTAGC AATGGCAAC
4771  AACGTTGCG CAAACTATT AACTGGCGA ACTACTTAC TCTAGCTTC
4816  CCGGCAACA ATTAATAGA CTGGATGGA GGCGGATAA AGTTGCAGG
4861  ACCACTTCT GCGCTCGGC CCTTCCGGC TGGCTGGTT TATTGCTGA
4906  TAAATCTGG AGCCGGTGA GCGTGGGTC TCGCGGTAT CATTGCAGC
4951  ACTGGGGCC AGATGGTAA GCCCTCCCG TATCGTAGT TATCTACAC
4996  GACGGGGAG TCAGGCAAC TATGGATGA ACGAAATAG ACAGATCGC
5041  TGAGATAGG TGCCTCACT GATTAAGCA TTGGTAACT GTCAGACCA
5086  AGTTTACTC ATATATACT TTAGATTGA TTTACCCCG GTTGATAAT
5131  CAGAAAAGC CCCAAAAAC AGGAAGATT GTATAAGCA AATATTTAA
5176  ATTGTAAAC GTTAATATT TTGTTAAAA TTCGCGTTA AATTTTTGT
5221  TAAATCAGC TCATTTTTT AACCAATAG GCCGAAATC GGCAAAATC
5266  CCTTATAAA TCAAAAGAA TAGACCGAG ATAGGGTTG AGTGTTGTT
5311  CCAGTTTGG AACAAGAGT CCACTATTA AAGAACGTG GACTCCAAC
5356  GTCAAAGGG CGAAAAACC GTCTATCAG GGCGATGGC CCACTACGT
5401  GAACCATCA CCCAAATCA AGTTTTTTG GGGTCGAGG TGCCGTAAA
5446  GCACTAAAT CGGAACCCT AAAGGGAGC CCCCGATTT AGAGCTTGA
5491  CGGGGAAAG CCGGCGAAC GTGGCGAGA AAGGAAGGG AAGAAAGCG
5536  AAAGGAGCG GGCGCTAGG GCGCTGGCA AGTGTAGCG GTCACGCTG
5581  CGCGTAACC ACCACACCC GCCGCGCTT AATGCGCCG CTACAGGGC
5626  GCGTAAAAG GATCTAGGT GAAGATCCT TTTTGATAA TCTCATGAC
5671  CAAAATCCC TTAACGTGA GTTTTCGTT CCACTGAGC GTCAGACCC
5716  CGTAGAAAA GATCAAAGG ATCTTCTTG AGATCCTTT TTTTCTGCG
5761  CGTAATCTG CTGCTTGCA AACAAAAAA ACCACCGCT ACCAGCGGT
5806  GGTTTGTTT GCCGGATCA AGAGCTACC AACTCTTTT TCCGAAGGT
5851  AACTGGCTT CAGCAGAGC GCAGATACC AAATACTGT CCTTCTAGT
5896  GTAGCCGTA GTTAGGCCA CCACTTCAA GAACTCTGT AGCACCGCC
5941  TACATACCT CGCTCTGCT AATCCTGTT ACCAGTGGC TGCTGCCAG
5986  TGGCGATAA GTCGTGTCT TACCGGGTT GGACTCAAG ACGATAGTT
6031  ACCGGATAA GGCGCAGCG GTCGGGCTG AACGGGGGG TTCGTGCAC
6076  ACAGCCCAG CTTGGAGCG AACGACCTA CACCGAACT GAGATACCT
6121  ACAGCGTGA GCTATGAGA AAGCGCCAC GCTTCCCGA AGGGAGAAA
6166  GGCGGACAG GTATCCGGT AAGCGGCAG GGTCGGAAC AGGAGAGCG
```

FIGURE 8  pMBP-c2X-ToxoP30del1C(52-324aa)

```
6211 CACGAGGGA GCTTCCAGG GGGAAACGC CTGGTATCT TTATAGTCC
6256 TGTCGGGTT TCGCCACCT CTGACTTGA GCGTCGATT TTTGTGATG
6301 CTCGTCAGG GGGGCGGAG CCTATGGAA AAACGCCAG CAACGCGGC
6346 CTTTTTACG GTTCCTGGC CTTTTGCTG GCCTTTTGC TCACATGTT
6391 CTTTCCTGC GTTATCCCC TGATTCTGT GGATAACCG TATTACCGC
6436 CTTTGAGTG AGCTGATAC CGCTCGCCG CAGCCGAAC GACCGAGCG
6481 CAGCGAGTC AGTGAGCGA GGAAGCGGA AGAGCGCCT GATGCGGTA
6526 TTTTCTCCT TACGCATCT GTGCGGTAT TCACACCG CATATATGG
6571 TGCACTCTC AGTACAATC TGCTCTGAT GCCGCATAG TTAAGCCAG
6616 TATACACTC CGCTATCGC TACGTGACT GGGTCATGG CTGCGCCCC
6661 GACACCCGC CAACACCCG CTGACGCGC CCTGACGGG CTTGTCTGC
6706 TCCCGGCAT CCGCTTACA GACAAGCTG TGACCGTCT CCGGGAGCT
6751 GCATGTGTC AGAGGTTTT CACCGTCAT CACCGAAAC GCGCGAGGC
6796 AGCTGCGGT AAAGCTCAT CAGCGTGGT CGTGCAGCG ATTCACAGA
6841 TGTCTGCCT GTTCATCCG CGTCCAGCT CGTTGAGTT CTCCAGAA
6886 GCGTTAATG TCTGGCTTC TGATAAAGC GGGCCATGT TAAGGGCGG
6931 TTTTTTCCT GTTTGGTCA CTGATGCCT CCGTGTAAG GGGGATTTC
6976 TGTTCATGG GGGTAATGA TACCGATGA AACGAGAGA GGATGCTCA
7021 CGATACGGG TTACTGATG ATGAACATG CCCGGTTAC TGGAACGTT
7066 GTGAGGGTA AACAACTGG CGGTATGGA TGCGGCGGG ACCAGAGAA
7111 AAATCACTC AGGGTCAAT GCCAGCGCT TCGTTAATA CAGATGTAG
7156 GTGTTCCAC AGGGTAGCC AGCAGCATC CTGCGATGC AGATCCGGA
7201 ACATAATGG TGCAGGGCG CTGACTTCC GCGTTTCCA GACTTTACG
7246 AAACACGGA AACCGAAGA CCATTCATG TTGTTGCTC AGGTCGCAG
7291 ACGTTTTGC AGCAGCAGT CGCTTCACG TTCGCTCGC GTATCGGTG
7336 ATTCATTCT GCTAACCAG TAAGGCAAC CCCGCCAGC CTAGCCGGG
7381 TCCTCAACG ACAGGAGCA CGATCATGC GCACCCGTG GCCAGGACC
7426 CAACGCTGC CCGAAATT
```

FIGURE 9  ToxoP30del1C(52-324aa)

```
        LeuValAla  AsnGlnVal  ValThrCys  ProAspLys  LysSerThr
  1     CTTGTTGCC  AATCAAGTT  GTCACCTGC  CCAGATAAA  AAATCGACA
        AlaAlaVal  IleLeuThr  ProThrGlu  AsnHisPhe  ThrLeuLys
 46     GCCGCGGTC  ATTCTCACA  CCGACGGAG  AACCACTTC  ACTCTCAAG
        CysProLys  ThrAlaLeu  ThrGluPro  ProThrLeu  AlaTyrSer
 91     TGCCCTAAA  ACAGCGCTC  ACAGAGCCT  CCCACTCTT  GCGTACTCA
        ProAsnArg  GlnIleCys  ProAlaGly  ThrThrSer  SerCysThr
136     CCCAACAGG  CAAATCTGC  CCAGCGGGT  ACTACAAGT  AGCTGTACA
        SerLysAla  ValThrLeu  SerSerLeu  IleProGlu  AlaGluAsp
181     TCAAAGGCT  GTAACATTG  AGCTCCTTG  ATTCCTGAA  GCAGAAGAT
        SerTrpTrp  ThrGlyAsp  SerAlaSer  LeuAspThr  AlaGlyIle
226     AGCTGGTGG  ACGGGGGAT  TCTGCTAGT  CTCGACACG  GCAGGCATC
        LysLeuThr  ValProIle  GluLysPhe  ProValThr  ThrGlnThr
271     AAACTCACA  GTTCCAATC  GAGAAGTTC  CCCGTGACA  ACGCAGACG
        PheValVal  GlyCysIle  LysGlyAsp  AspAlaGln  SerCysMet
316     TTTGTGGTC  GGTTGCATC  AAGGGAGAC  GACGCACAG  AGTTGTATG
        ValThrVal  ThrValGln  AlaArgAla  SerSerVal  ValAsnAsn
361     GTCACAGTG  ACAGTACAA  GCCAGAGCC  TCATCGGTC  GTCAATAAT
        ValAlaArg  CysSerTyr  GlyAlaAsp  SerThrLeu  GlyProVal
406     GTCGCAAGG  TGCTCCTAC  GGTGCAGAC  AGCACTCTT  GGTCCTGTC
        LysLeuSer  AlaGluGly  ProThrThr  MetThrLeu  ValCysGly
451     AAGTTGTCT  GCGGAAGGA  CCCACTACA  ATGACCCTC  GTGTGCGGG
        LysAspGly  ValLysVal  ProGlnAsp  AsnAsnGln  TyrCysSer
496     AAAGATGGA  GTCAAAGTT  CCTCAAGAC  AACAATCAG  TACTGTTCC
        GlyThrThr  LeuThrGly  CysAsnGlu  LysSerPhe  LysAspIle
541     GGGACGACG  CTGACTGGT  TGCAACGAG  AAATCGTTC  AAAGATATT
        LeuProLys  LeuThrGlu  AsnProTrp  GlnGlyAsn  AlaSerSer
586     TTGCCAAAA  TTAACTGAG  AACCCGTGG  CAGGGTAAC  GCTTCGAGT
        AspLysGly  AlaThrLeu  ThrIleLys  LysGluAla  PheProAla
631     GATAAGGGT  GCCACGCTA  ACGATCAAG  AAGGAAGCA  TTTCCAGCC
        GluSerLys  SerValIle  IleGlyCys  ThrGlyGly  SerProGlu
676     GAGTCAAAA  AGCGTCATT  ATTGGATGC  ACAGGGGGA  TCGCCTGAG
        LysHisHis  CysThrVal  LysLeuGlu  PheAlaGly  AlaAlaGly
721     AAGCATCAC  TGTACCGTG  AAACTGGAG  TTTGCCGGG  GCTGCAGGG
        SerAlaLys  SerAlaAla  GlyThrAla  SerHisVal  SerIlePhe
766     TCAGCAAAA  TCGGCTGCG  GGAACAGCC  AGTCACGTT  TCCATTTTT
        AlaMetVal
811     GCCATGGTG
```

FIGURE 11  pMBP-c2X-ToxoP30del2(52-311aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA ATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                       Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 11  pMBP-c2X-ToxoP30del2(52-311aa)

```
1756  TTGGCTGAA  ATCACCCCG  GACAAAGCG  TTCCAGGAC  AAGCTGTAT
      ProPheThr  TrpAspAla  ValArgTyr  AsnGlyLys  LeuIleAla
1801  CCGTTTACC  TGGGATGCC  GTACGTTAC  AACGGCAAG  CTGATTGCT
      TyrProIle  AlaValGlu  AlaLeuSer  LeuIleTyr  AsnLysAsp
1846  TACCCGATC  GCTGTTGAA  GCGTTATCG  CTGATTTAT  AACAAAGAT
      LeuLeuPro  AsnProPro  LysThrTrp  GluGluIle  ProAlaLeu
1891  CTGCTGCCG  AACCCGCCA  AAACCTGG   GAAGAGATC  CCGGCGCTG
      AspLysGlu  LeuLysAla  LysGlyLys  SerAlaLeu  MetPheAsn
1936  GATAAAGAA  CTGAAAGCG  AAAGGTAAG  AGCGCGCTG  ATGTTCAAC
      LeuGlnGlu  ProTyrPhe  ThrTrpPro  LeuIleAla  AlaAspGly
1981  CTGCAAGAA  CCGTACTTC  ACCTGGCCG  CTGATTGCT  GCTGACGGG
      GlyTyrAla  PheLysTyr  GluAsnGly  LysTyrAsp  IleLysAsp
2026  GGTTATGCG  TTCAAGTAT  GAAAACGGC  AAGTACGAC  ATTAAAGAC
      ValGlyVal  AspAsnAla  GlyAlaLys  AlaGlyLeu  ThrPheLeu
2071  GTGGGCGTG  GATAACGCT  GGCGCGAAA  GCGGGTCTG  ACCTTCCTG
      ValAspLeu  IleLysAsn  LysHisMet  AsnAlaAsp  ThrAspTyr
2116  GTTGACCTG  ATTAAAAAC  AAACACATG  AATGCAGAC  ACCGATTAC
      SerIleAla  GluAlaAla  PheAsnLys  GlyGluThr  AlaMetThr
2161  TCCATCGCA  GAAGCTGCC  TTTAATAAA  GGCGAAACA  GCGATGACC
      IleAsnGly  ProTrpAla  TrpSerAsn  IleAspThr  SerLysVal
2206  ATCAACGGC  CCGTGGGCA  TGGTCCAAC  ATCGACACC  AGCAAAGTG
      AsnTyrGly  ValThrVal  LeuProThr  PheLysGly  GlnProSer
2251  AATTATGGT  GTAACGGTA  CTGCCGACC  TTCAAGGGT  CAACCATCC
      LysProPhe  ValGlyVal  LeuSerAla  GlyIleAsn  AlaAlaSer
2296  AAACCGTTC  GTTGGCGTG  CTGAGCGCA  GGTATTAAC  GCCGCCAGT
      ProAsnLys  GluLeuAla  LysGluPhe  LeuGluAsn  TyrLeuLeu
2341  CCGAACAAA  GAGCTGGCA  AAAGAGTTC  CTCGAAAAC  TATCTGCTG
      ThrAspGlu  GlyLeuGlu  AlaValAsn  LysAspLys  ProLeuGly
2386  ACTGATGAA  GGTCTGGAA  GCGGTTAAT  AAAGACAAA  CCGCTGGGT
      AlaValAla  LeuLysSer  TyrGluGlu  GluLeuAla  LysAspPro
2431  GCCGTAGCG  CTGAAGTCT  TACGAGGAA  GAGTTGGCG  AAAGATCCA
      ArgIleAla  AlaThrMet  GluAsnAla  GlnLysGly  GluIleMet
2476  CGTATTGCC  GCCACTATG  GAAAACGCC  CAGAAAGGT  GAAATCATG
      ProAsnIle  ProGlnMet  SerAlaPhe  TrpTyrAla  ValArgThr
2521  CCGAACATC  CCGCAGATG  TCCGCTTTC  TGGTATGCC  GTGCGTACT
      AlaValIle  AsnAlaAla  SerGlyArg  GlnThrVal  AspGluAla
2566  GCGGTGATC  AACGCCGCC  AGCGGTCGT  CAGACTGTC  GATGAAGCC
      LeuLysAsp  AlaGlnThr  AsnSerSer  SerAsnAsn  AsnAsnAsn
2611  CTGAAAGAC  GCGCAGACT  AATTCGAGC  TCGAACAAC  AACAACAAT
      AsnAsnAsn  AsnAsnLeu  GlyIleGlu  GlyArgIle  SerGluPhe
2656  AACAATAAC  AACAACCTC  GGGATCGAG  GGAAGGATT  TCAGAATTC
      LeuValAla  AsnGlnVal  ValThrCys  ProAspLys  LysSerThr
2701  CTTGTTGCC  AATCAAGTT  GTCACCTGC  CCAGATAAA  AAATCGACA
      AlaAlaVal  IleLeuThr  ProThrGlu  AsnHisPhe  ThrLeuLys
2746  GCCGCGGTC  ATTCTCACA  CCGACGGAG  AACCACTTC  ACTCTCAAG
      CysProLys  ThrAlaLeu  ThrGluPro  ProThrLeu  AlaTyrSer
```

FIGURE 11  pMBP-c2X-ToxoP30del2(52-311aa)

```
2791  TGCCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCTCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACAGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGluGly ProThrThr MetThrLeu ValCysGly
3151  AAGTTGTCT GCGGAAGGA CCCACTACA ATGACCCTC GTGTGCGGG
      LysAspGly ValLysVal ProGlnAsp AsnAsnGln TyrCysSer
3196  AAAGATGGA GTCAAAGTT CCTCAAGAC AACAATCAG TACTGTTCC
      GlyThrThr LeuThrGly CysAsnGlu LysSerPhe LysAspIle
3241  GGGACGACG CTGACTGGT TGCAACGAG AAATCGTTC AAAGATATT
      LeuProLys LeuThrGlu AsnProTrp GlnGlyAsn AlaSerSer
3286  TTGCCAAAA TTAACTGAG AACCCGTGG CAGGGTAAC GCTTCGAGT
      AspLysGly AlaThrLeu ThrIleLys LysGluAla PheProAla
3331  GATAAGGGT GCCACGCTA ACGATCAAG AAGGAAGCA TTTCCAGCC
      GluSerLys SerValIle IleGlyCys ThrGlyGly SerProGlu
3376  GAGTCAAAA AGCGTCATT ATTGGATGC ACAGGGGGA TCGCCTGAG
      LysHisHis CysThrVal LysLeuGlu PheAlaGly AlaAlaGly
3421  AAGCATCAC TGTACCGTG AAACTGGAG TTTGCCGGG GCTGCAGGG
      SerAlaLys SerAla
3466  TCAGCAAAA TCGGCTTGA AAGCTTGGC ACTGGCCGT CGTTTTACA
3511  ACGTCGTGA CTGGGAAAA CCCTGGCGT TACCCAACT TAATCGCCT
3556  TGCAGCACA TCCCCCTTT CGCCAGCTG GCGTAATAG CGAAGAGGC
3601  CCGCACCGA TCGCCCTTC CAACAGTT GCGCAGCCT GAATGGCGA
3646  ATGGCAGCT TGGCTGTTT TGGCGGATG AGATAAGAT TTTCAGCCT
3691  GATACAGAT TAAATCAGA ACGCAGAAG CGGTCTGAT AAAACAGAA
3736  TTTGCCTGG CGGCAGTAG CGCGGTGGT CCCACCTGA CCCCATGCC
3781  GAACTCAGA AGTGAAACG CCGTAGCGC CGATGGTAG TGTGGGGTC
3826  TCCCCATGC GAGAGTAGG GAACTGCCA GGCATCAAA TAAAACGAA
3871  AGGCTCAGT CGAAAGACT GGGCCTTTC GTTTTATCT GTTGTTTGT
3916  CGGTGAACG CTCTCCTGA GTAGGACAA ATCCGCCGG GAGCGGATT
3961  TGAACGTTG CAAGCAAC GGCCCGGAG GGTGGCGGG CAGGACGCC
4006  CGCCATAAA CTGCCAGGC ATCAAATTA AGCAGAAGG CCATCCTGA
4051  CGGATGGCC TTTTTGCGT TTCTACAAA CTCTTTTTG TTTATTTTT
4096  CTAAATACA TTCAAATAT GTATCCGCT CATGAGACA ATAACCCTG
4141  ATAAATGCT TCAATAATA TTGAAAAAG GAAGAGTAT GAGTATTCA
```

FIGURE 11 pMBP-c2X-ToxoP30del2(52-311aa)

```
4186  ACATTTCCG TGTCGCCCT TATTCCCTT TTTTGCGGC ATTTTGCCT
4231  TCCTGTTTT TGCTCACCC AGAAACGCT GGTGAAAGT AAAAGATGC
4276  TGAAGATCA GTTGGGTGC ACGAGTGGG TTACATCGA ACTGGATCT
4321  CAACAGCGG TAAGATCCT TGAGAGTTT TCGCCCCGA AGAACGTTC
4366  TCCAATGAT GAGCACTTT TAAAGTTCT GCTATGTGG CGCGGTATT
4411  ATCCCGTGT TGACGCCGG GCAAGAGCA ACTCGGTCG CCGCATACA
4456  CTATTCTCA GAATGACTT GGTTGAGTA CTCACCAGT CACAGAAAA
4501  GCATCTTAC GGATGGCAT GACAGTAAG AGAATTATG CAGTGCTGC
4546  CATAACCAT GAGTGATAA CACTGCGGC CAACTTACT TCTGACAAC
4591  GATCGGAGG ACCGAAGGA GCTAACCGC TTTTTTGCA CAACATGGG
4636  GGATCATGT AACTCGCCT TGATCGTTG GGAACCGGA GCTGAATGA
4681  AGCCATACC AAACGACGA GCGTGACAC CACGATGCC TGTAGCAAT
4726  GGCAACAAC GTTGCGCAA ACTATTAAC TGGCGAACT ACTTACTCT
4771  AGCTTCCCG GCAACAATT AATAGACTG GATGGAGGC GGATAAAGT
4816  TGCAGGACC ACTTCTGCG CTCGGCCCT TCCGGCTGG CTGGTTTAT
4861  TGCTGATAA ATCTGGAGC CGGTGAGCG TGGGTCTCG CGGTATCAT
4906  TGCAGCACT GGGGCCAGA TGGTAAGCC CTCCCGTAT CGTAGTTAT
4951  CTACACGAC GGGGAGTCA GGCAACTAT GGATGAACG AAATAGACA
4996  GATCGCTGA GATAGGTGC CTCACTGAT TAAGCATTG GTAACTGTC
5041  AGACCAAGT TTACTCATA TATACTTTA GATTGATTT ACCCCGGTT
5086  GATAATCAG AAAAGCCCC AAAAACAGG AAGATTGTA TAAGCAAAT
5131  ATTTAAATT GTAAACGTT AATATTTTG TTAAAATTC GCGTTAAAT
5176  TTTTGTTAA ATCAGCTCA TTTTTTAAC CAATAGGCC GAAATCGGC
5221  AAAATCCCT TATAAATCA AAAGAATAG ACCGAGATA GGGTTGAGT
5266  GTTGTTCCA GTTTGGAAC AAGAGTCCA CTATTAAAG AACGTGGAC
5311  TCCAACGTC AAAGGGCGA AAAACCGTC TATCAGGGC GATGGCCCA
5356  CTACGTGAA CCATCACCC AAATCAAGT TTTTTGGGG TCGAGGTGC
5401  CGTAAAGCA CTAAATCGG AACCCTAAA GGGAGCCCC CGATTTAGA
5446  GCTTGACGG GGAAAGCCG GCGAACGTG GCGAGAAAG GAAGGGAAG
5491  AAAGCGAAA GGAGCGGGC GCTAGGGCG CTGGCAAGT GTAGCGGTC
5536  ACGCTGCGC GTAACCACC ACACCCGCC GCGCTTAAT GCGCCGCTA
5581  CAGGGCGCG TAAAAGGAT CTAGGTGAA GATCCTTTT TGATAATCT
5626  CATGACCAA AATCCCTTA ACGTGAGTT TTCGTTCCA CTGAGCGTC
5671  AGACCCCGT AGAAAAGAT CAAAGGATC TTCTTGAGA TCCTTTTTT
5716  TCTGCGCGT AATCTGCTG CTTGCAAAC AAAAAAACC ACCGCTACC
5761  AGCGGTGGT TTGTTTGCC GGATCAAGA GCTACCAAC TCTTTTTCC
5806  GAAGGTAAC TGGCTTCAG CAGAGCGCA GATACCAAA TACTGTCCT
5851  TCTAGTGTA GCCGTAGTT AGGCCACCA CTTCAAGAA CTCTGTAGC
5896  ACCGCCTAC ATACCTCGC TCTGCTAAT CCTGTTACC AGTGGCTGC
5941  TGCCAGTGG CGATAAGTC GTGTCTTAC CGGGTTGGA CTCAAGACG
5986  ATAGTTACC GGATAAGGC GCAGCGGTC GGGCTGAAC GGGGGGTTC
6031  GTGCACACA GCCCAGCTT GGAGCGAAC GACCTACAC CGAACTGAG
6076  ATACCTACA GCGTGAGCT ATGAGAAAG CGCCACGCT TCCCGAAGG
6121  GAGAAAGGC GGACAGGTA TCCGGTAAG CGGCAGGGT CGGAACAGG
6166  AGAGCGCAC GAGGGAGCT TCCAGGGGG AAACGCCTG GTATCTTTA
6211  TAGTCCTGT CGGGTTTCG CCACCTCTG ACTTGAGCG TCGATTTTT
```

FIGURE 11   pMBP-c2X-ToxoP30del2(52-311aa)

```
6256  GTGATGCTC GTCAGGGGG GCGGAGCCT ATGGAAAAA CGCCAGCAA
6301  CGCGGCCTT TTTACGGTT CCTGGCCTT TTGCTGGCC TTTTGCTCA
6346  CATGTTCTT TCCTGCGTT ATCCCCTGA TTCTGTGGA TAACCGTAT
6391  TACCGCCTT TGAGTGAGC TGATACCGC TCGCCGCAG CCGAACGAC
6436  CGAGCGCAG CGAGTCAGT GAGCGAGGA AGCGGAAGA GCGCCTGAT
6481  GCGGTATTT TCTCCTTAC GCATCTGTG CGGTATTTC ACACCGCAT
6526  ATATGGTGC ACTCTCAGT ACAATCTGC TCTGATGCC GCATAGTTA
6571  AGCCAGTAT ACACTCCGC TATCGCTAC GTGACTGGG TCATGGCTG
6616  CGCCCCGAC ACCCGCCAA CACCCGCTG ACGCGCCCT GACGGGCTT
6661  GTCTGCTCC CGGCATCCG CTTACAGAC AAGCTGTGA CCGTCTCCG
6706  GGAGCTGCA TGTGTCAGA GGTTTTCAC CGTCATCAC CGAAACGCG
6751  CGAGGCAGC TGCGGTAAA GCTCATCAG CGTGGTCGT GCAGCGATT
6796  CACAGATGT CTGCCTGTT CATCCGCGT CCAGCTCGT TGAGTTTCT
6841  CCAGAAGCG TTAATGTCT GGCTTCTGA TAAAGCGGG CCATGTTAA
6886  GGGCGGTTT TTTCCTGTT TGGTCACTG ATGCCTCCG TGTAAGGGG
6931  GATTTCTGT TCATGGGGG TAATGATAC CGATGAAAC GAGAGAGGA
6976  TGCTCACGA TACGGGTTA CTGATGATG AACATGCCC GGTTACTGG
7021  AACGTTGTG AGGGTAAAC AACTGGCGG TATGGATGC GGCGGGACC
7066  AGAGAAAAA TCACTCAGG GTCAATGCC AGCGCTTCG TTAATACAG
7111  ATGTAGGTG TTCCACAGG GTAGCCAGC AGCATCCTG CGATGCAGA
7156  TCCGGAACA TAATGGTGC AGGGCGCTG ACTTCCGCG TTTCCAGAC
7201  TTTACGAAA CACGGAAAC CGAAGACCA TTCATGTTG TTGCTCAGG
7246  TCGCAGACG TTTTGCAGC AGCAGTCGC TTCACGTTC GCTCGCGTA
7291  TCGGTGATT CATTCTGCT AACCAGTAA GGCAACCCC GCCAGCCTA
7336  GCCGGGTCC TCAACGACA GGAGCACGA TCATGCGCA CCCGTGGCC
7381  AGGACCCAA CGCTGCCCG AAATT
```

FIGURE 12  ToxoP30del2(52-311aa)

```
        LeuValAla  AsnGlnVal  ValThrCys  ProAspLys  LysSerThr
  1     CTTGTTGCC  AATCAAGTT  GTCACCTGC  CCAGATAAA  AAATCGACA
        AlaAlaVal  IleLeuThr  ProThrGlu  AsnHisPhe  ThrLeuLys
 46     GCCGCGGTC  ATTCTCACA  CCGACGGAG  AACCACTTC  ACTCTCAAG
        CysProLys  ThrAlaLeu  ThrGluPro  ProThrLeu  AlaTyrSer
 91     TGCCCTAAA  ACAGCGCTC  ACAGAGCCT  CCCACTCTT  GCGTACTCA
        ProAsnArg  GlnIleCys  ProAlaGly  ThrThrSer  SerCysThr
136     CCCAACAGG  CAAATCTGC  CCAGCGGGT  ACTACAAGT  AGCTGTACA
        SerLysAla  ValThrLeu  SerSerLeu  IleProGlu  AlaGluAsp
181     TCAAAGGCT  GTAACATTG  AGCTCCTTG  ATTCCTGAA  GCAGAAGAT
        SerTrpTrp  ThrGlyAsp  SerAlaSer  LeuAspThr  AlaGlyIle
226     AGCTGGTGG  ACGGGGGAT  TCTGCTAGT  CTCGACACG  GCAGGCATC
        LysLeuThr  ValProIle  GluLysPhe  ProValThr  ThrGlnThr
271     AAACTCACA  GTTCCAATC  GAGAAGTTC  CCCGTGACA  ACGCAGACG
        PheValVal  GlyCysIle  LysGlyAsp  AspAlaGln  SerCysMet
316     TTTGTGGTC  GGTTGCATC  AAGGGAGAC  GACGCACAG  AGTTGTATG
        ValThrVal  ThrValGln  AlaArgAla  SerSerVal  ValAsnAsn
361     GTCACAGTG  ACAGTACAA  GCCAGAGCC  TCATCGGTC  GTCAATAAT
        ValAlaArg  CysSerTyr  GlyAlaAsp  SerThrLeu  GlyProVal
406     GTCGCAAGG  TGCTCCTAC  GGTGCAGAC  AGCACTCTT  GGTCCTGTC
        LysLeuSer  AlaGluGly  ProThrThr  MetThrLeu  ValCysGly
451     AAGTTGTCT  GCGGAAGGA  CCCACTACA  ATGACCCTC  GTGTGCGGG
        LysAspGly  ValLysVal  ProGlnAsp  AsnAsnGln  TyrCysSer
496     AAAGATGGA  GTCAAAGTT  CCTCAAGAC  AACAATCAG  TACTGTTCC
        GlyThrThr  LeuThrGly  CysAsnGlu  LysSerPhe  LysAspIle
541     GGGACGACG  CTGACTGGT  TGCAACGAG  AAATCGTTC  AAAGATATT
        LeuProLys  LeuThrGlu  AsnProTrp  GlnGlyAsn  AlaSerSer
586     TTGCCAAAA  TTAACTGAG  AACCCGTGG  CAGGGTAAC  GCTTCGAGT
        AspLysGly  AlaThrLeu  ThrIleLys  LysGluAla  PheProAla
631     GATAAGGGT  GCCACGCTA  ACGATCAAG  AAGGAAGCA  TTTCCAGCC
        GluSerLys  SerValIle  IleGlyCys  ThrGlyGly  SerProGlu
676     GAGTCAAAA  AGCGTCATT  ATTGGATGC  ACAGGGGGA  TCGCCTGAG
        LysHisHis  CysThrVal  LysLeuGlu  PheAlaGly  AlaAlaGly
721     AAGCATCAC  TGTACCGTG  AAACTGGAG  TTTGCCGGG  GCTGCAGGG
        SerAlaLys  SerAla
766     TCAGCAAAA  TCGGCT
```

FIGURE 15  pMBP-c2X-ToxoP30del3C(52-300aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA ATATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                          Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 15    pMBP-c2X-ToxoP30del3C(52-300aa)

```
1756  TTGGCTGAA ATCACCCCG GACAAAGCG TTCCAGGAC AAGCTGTAT
      ProPheThr TrpAspAla ValArgTyr AsnGlyLys LeuIleAla
1801  CCGTTTACC TGGGATGCC GTACGTTAC AACGGCAAG CTGATTGCT
      TyrProIle AlaValGlu AlaLeuSer LeuIleTyr AsnLysAsp
1846  TACCCGATC GCTGTTGAA GCGTTATCG CTGATTTAT AACAAAGAT
      LeuLeuPro AsnProPro LysThrTrp GluGluIle ProAlaLeu
1891  CTGCTGCCG AACCCGCCA AAACCTGG GAAGAGATC CCGGCGCTG
      AspLysGlu LeuLysAla LysGlyLys SerAlaLeu MetPheAsn
1936  GATAAAGAA CTGAAAGCG AAAGGTAAG AGCGCGCTG ATGTTCAAC
      LeuGlnGlu ProTyrPhe ThrTrpPro LeuIleAla AlaAspGly
1981  CTGCAAGAA CCGTACTTC ACCTGGCCG CTGATTGCT GCTGACGGG
      GlyTyrAla PheLysTyr GluAsnGly LysTyrAsp IleLysAsp
2026  GGTTATGCG TTCAAGTAT GAAAACGGC AAGTACGAC ATTAAAGAC
      ValGlyVal AspAsnAla GlyAlaLys AlaGlyLeu ThrPheLeu
2071  GTGGGCGTG GATAACGCT GGCGCGAAA GCGGGTCTG ACCTTCCTG
      ValAspLeu IleLysAsn LysHisMet AsnAlaAsp ThrAspTyr
2116  GTTGACCTG ATTAAAAAC AAACACATG AATGCAGAC ACCGATTAC
      SerIleAla GluAlaAla PheAsnLys GlyGluThr AlaMetThr
2161  TCCATCGCA GAAGCTGCC TTTAATAAA GGCGAAACA GCGATGACC
      IleAsnGly ProTrpAla TrpSerAsn IleAspThr SerLysVal
2206  ATCAACGGC CCGTGGGCA TGGTCCAAC ATCGACACC AGCAAAGTG
      AsnTyrGly ValThrVal LeuProThr PheLysGly GlnProSer
2251  AATTATGGT GTAACGGTA CTGCCGACC TTCAAGGGT CAACCATCC
      LysProPhe ValGlyVal LeuSerAla GlyIleAsn AlaAlaSer
2296  AAACCGTTC GTTGGCGTG CTGAGCGCA GGTATTAAC GCCGCCAGT
      ProAsnLys GluLeuAla LysGluPhe LeuGluAsn TyrLeuLeu
2341  CCGAACAAA GAGCTGGCA AAAGAGTTC CTCGAAAAC TATCTGCTG
      ThrAspGlu GlyLeuGlu AlaValAsn LysAspLys ProLeuGly
2386  ACTGATGAA GGTCTGGAA GCGGTTAAT AAAGACAAA CCGCTGGGT
      AlaValAla LeuLysSer TyrGluGlu GluLeuAla LysAspPro
2431  GCCGTAGCG CTGAAGTCT TACGAGGAA GAGTTGGCG AAAGATCCA
      ArgIleAla AlaThrMet GluAsnAla GlnLysGly GluIleMet
2476  CGTATTGCC GCCACTATG GAAACGCC CAGAAAGGT GAAATCATG
      ProAsnIle ProGlnMet SerAlaPhe TrpTyrAla ValArgThr
2521  CCGAACATC CCGCAGATG TCCGCTTTC TGGTATGCC GTGCGTACT
      AlaValIle AsnAlaAla SerGlyArg GlnThrVal AspGluAla
2566  GCGGTGATC AACGCCGCC AGCGGTCGT CAGACTGTC GATGAAGCC
      LeuLysAsp AlaGlnThr AsnSerSer SerAsnAsn AsnAsnAsn
2611  CTGAAAGAC GCGCAGACT AATTCGAGC TCGAACAAC AACAACAAT
      AsnAsnAsn AsnAsnLeu GlyIleGlu GlyArgIle SerGluPhe
2656  AACAATAAC AACAACCTC GGGATCGAG GGAAGGATT TCAGAATTC
      LeuValAla AsnGlnVal ValThrCys ProAspLys LysSerThr
2701  CTTGTTGCC AATCAAGTT GTCACCTGC CCAGATAAA AAATCGACA
      AlaAlaVal IleLeuThr ProThrGlu AsnHisPhe ThrLeuLys
2746  GCCGCGGTC ATTCTCACA CCGACGGAG AACCACTTC ACTCTCAAG
      CysProLys ThrAlaLeu ThrGluPro ProThrLeu AlaTyrSer
```

FIGURE 15  pMBP-c2X-ToxoP30del3C(52-300aa)

```
2791  TGCCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCTCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACAGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGluGly ProThrThr MetThrLeu ValCysGly
3151  AAGTTGTCT GCGGAAGGA CCCACTACA ATGACCCTC GTGTGCGGG
      LysAspGly ValLysVal ProGlnAsp AsnAsnGln TyrCysSer
3196  AAAGATGGA GTCAAAGTT CCTCAAGAC AACAATCAG TACTGTTCC
      GlyThrThr LeuThrGly CysAsnGlu LysSerPhe LysAspIle
3241  GGGACGACG CTGACTGGT TGCAACGAG AAATCGTTC AAAGATATT
      LeuProLys LeuThrGlu AsnProTrp GlnGlyAsn AlaSerSer
3286  TTGCCAAAA TTAACTGAG AACCCGTGG CAGGGTAAC GCTTCGAGT
      AspLysGly AlaThrLeu ThrIleLys LysGluAla PheProAla
3331  GATAAGGGT GCCACGCTA ACGATCAAG AAGGAAGCA TTTCCAGCC
      GluSerLys SerValIle IleGlyCys ThrGlyGly SerProGlu
3376  GAGTCAAAA AGCGTCATT ATTGGATGC ACAGGGGGA TCGCCTGAG
      LysHisHis CysThrVal LysLeuGlu
3421  AAGCATCAC TGTACCGTG AAACTGGAG TGAAAGCTT GGCACTGGC
3466  CGTCGTTTT ACAACGTCG TGACTGGGA AAACCCTGG CGTTACCCA
3511  ACTTAATCG CCTTGCAGC ACATCCCCC TTTCGCCAG CTGGCGTAA
3556  TAGCGAAGA GGCCCGCAC CGATCGCCC TTCCCAACA GTTGCGCAG
3601  CCTGAATGG CGAATGGCA GCTTGGCTG TTTTGGCGG ATGAGATAA
3646  GATTTTCAG CCTGATACA GATTAAATC AGAACGCAG AAGCGGTCT
3691  GATAAAACA GAATTTGCC TGGCGGCAG TAGCGCGGT GGTCCCACC
3736  TGACCCCAT GCCGAACTC AGAAGTGAA ACGCCGTAG CGCCGATGG
3781  TAGTGTGGG GTCTCCCCA TGCGAGAGT AGGGAACTG CCAGGCATC
3826  AAATAAAAC GAAAGGCTC AGTCGAAAG ACTGGGCCT TTCGTTTTA
3871  TCTGTTGTT TGTCGGTGA ACGCTCTCC TGAGTAGGA CAAATCCGC
3916  CGGGAGCGG ATTTGAACG TTGCGAAGC AACGGCCCG GAGGGTGGC
3961  GGGCAGGAC GCCCGCCAT AAACTGCCA GGCATCAAA TTAAGCAGA
4006  AGGCCATCC TGACGGATG CCTTTTTG CGTTCTAC AAACTCTTT
4051  TTGTTTATT TTTCTAAAT ACATTCAAA TATGTATCC GCTCATGAG
4096  ACAATAACC CTGATAAAT GCTTCAATA ATATTGAAA AAGGAAGAG
4141  TATGAGTAT TCAACATTT CCGTGTCGC CCTTATTCC CTTTTTTGC
4186  GGCATTTTG CCTTCCTGT TTTTGCTCA CCCAGAAAC GCTGGTGAA
```

FIGURE 15  pMBP-c2X-ToxoP30del3C(52-300aa)

```
6301  GCCTTTTGC  TCACATGTT  CTTTCCTGC  GTTATCCCC  TGATTCTGT
6346  GGATAACCG  TATTACCGC  CTTTGAGTG  AGCTGATAC  CGCTCGCCG
6391  CAGCCGAAC  GACCGAGCG  CAGCGAGTC  AGTGAGCGA  GGAAGCGGA
6436  AGAGCGCCT  GATGCGGTA  TTTTCTCCT  TACGCATCT  GTGCGGTAT
6481  TTCACACCG  CATATATGG  TGCACTCTC  AGTACAATC  TGCTCTGAT
6526  GCCGCATAG  TTAAGCCAG  TATACACTC  CGCTATCGC  TACGTGACT
6571  GGGTCATGG  CTGCGCCCC  GACACCCGC  CAACACCCG  CTGACGCGC
6616  CCTGACGGG  CTTGTCTGC  TCCCGGCAT  CCGCTTACA  GACAAGCTG
6661  TGACCGTCT  CCGGGAGCT  GCATGTGTC  AGAGGTTTT  CACCGTCAT
6706  CACCGAAAC  GCGCGAGGC  AGCTGCGGT  AAAGCTCAT  CAGCGTGGT
6751  CGTGCAGCG  ATTCACAGA  TGTCTGCCT  GTTCATCCG  CGTCCAGCT
6796  CGTTGAGTT  CTCCAGAA   GCGTTAATG  TCTGGCTTC  TGATAAAGC
6841  GGGCCATGT  TAAGGGCGG  TTTTTTCCT  GTTTGGTCA  CTGATGCCT
6886  CCGTGTAAG  GGGGATTTC  TGTTCATGG  GGGTAATGA  TACCGATGA
6931  AACGAGAGA  GGATGCTCA  CGATACGGG  TTACTGATG  ATGAACATG
6976  CCCGGTTAC  TGGAACGTT  GTGAGGGTA  AACAACTGG  CGGTATGGA
7021  TGCGGCGGG  ACCAGAGAA  AAATCACTC  AGGGTCAAT  GCCAGCGCT
7066  TCGTTAATA  CAGATGTAG  GTGTTCCAC  AGGGTAGCC  AGCAGCATC
7111  CTGCGATGC  AGATCCGGA  ACATAATGG  TGCAGGGCG  CTGACTTCC
7156  GCGTTTCCA  GACTTTACG  AAACACGGA  AACCGAAGA  CCATTCATG
7201  TTGTTGCTC  AGGTCGCAG  ACGTTTTGC  AGCAGCAGT  CGCTTCACG
7246  TTCGCTCGC  GTATCGGTG  ATTCATTCT  GCTAACCAG  TAAGGCAAC
7291  CCCGCCAGC  CTAGCCGGG  TCCTCAACG  ACAGGAGCA  CGATCATGC
7336  GCACCCGTG  GCCAGGACC  CAACGCTGC  CCGAAATT
```

FIGURE 15 pMBP-c2X-ToxoP30del3C(52-300aa)

```
4231  AGTAAAAGA TGCTGAAGA TCAGTTGGG TGCACGAGT GGGTTACAT
4276  CGAACTGGA TCTCAACAG CGGTAAGAT CCTTGAGAG TTTTCGCCC
4321  CGAAGAACG TTCTCCAAT GATGAGCAC TTTTAAAGT TCTGCTATG
4366  TGGCGCGGT ATTATCCCG TGTTGACGC CGGGCAAGA GCAACTCGG
4411  TCGCCGCAT ACACTATTC TCAGAATGA CTTGGTTGA GTACTCACC
4456  AGTCACAGA AAAGCATCT TACGGATGG CATGACAGT AAGAGAATT
4501  ATGCAGTGC TGCCATAAC CATGAGTGA TAACACTGC GGCCAACTT
4546  ACTTCTGAC AACGATCGG AGGACCGAA GGAGCTAAC CGCTTTTTT
4591  GCACAACAT GGGGGATCA TGTAACTCG CCTTGATCG TTGGGAACC
4636  GGAGCTGAA TGAAGCCAT ACCAAACGA CGAGCGTGA CACCACGAT
4681  GCCTGTAGC AATGGCAAC AACGTTGCG CAAACTATT AACTGGCGA
4726  ACTACTTAC TCTAGCTTC CCGGCAACA ATTAATAGA CTGGATGGA
4771  GGCGGATAA AGTTGCAGG ACCACTTCT GCGCTCGGC CCTTCCGGC
4816  TGGCTGGTT TATTGCTGA TAAATCTGG AGCCGGTGA GCGTGGGTC
4861  TCGCGGTAT CATTGCAGC ACTGGGGCC AGATGGTAA GCCCTCCCG
4906  TATCGTAGT TATCTACAC GACGGGGAG TCAGGCAAC TATGGATGA
4951  ACGAAATAG ACAGATCGC TGAGATAGG TGCCTCACT GATTAAGCA
4996  TTGGTAACT GTCAGACCA AGTTTACTC ATATATACT TTAGATTGA
5041  TTTACCCCG GTTGATAAT CAGAAAAGC CCCAAAAAC AGGAAGATT
5086  GTATAAGCA AATATTTAA ATTGTAAAC GTTAATATT TTGTTAAAA
5131  TTCGCGTTA AATTTTTGT TAAATCAGC TCATTTTTT AACCAATAG
5176  GCCGAAATC GGCAAAATC CCTTATAAA TCAAAAGAA TAGACCGAG
5221  ATAGGGTTG AGTGTTGTT CCAGTTTGG AACAAGAGT CCACTATTA
5266  AAGAACGTG GACTCCAAC GTCAAAGGG CGAAAAACC GTCTATCAG
5311  GGCGATGGC CCACTACGT GAACCATCA CCCAAATCA AGTTTTTTG
5356  GGGTCGAGG TGCCGTAAA GCACTAAAT CGGAACCCT AAAGGGAGC
5401  CCCCGATTT AGAGCTTGA CGGGGAAAG CCGGCGAAC GTGGCGAGA
5446  AAGGAAGGG AAGAAAGCG AAAGGAGCG GGCGCTAGG GCGCTGGCA
5491  AGTGTAGCG GTCACGCTG CGCGTAACC ACCACACCC GCCGCGCTT
5536  AATGCGCCG CTACAGGGC GCGTAAAAG GATCTAGGT GAAGATCCT
5581  TTTTGATAA TCTCATGAC CAAAATCCC TTAACGTGA GTTTTCGTT
5626  CCACTGAGC GTCAGACCC CGTAGAAAA GATCAAAGG ATCTTCTTG
5671  AGATCCTTT TTTTCTGCG CGTAATCTG CTGCTTGCA AACAAAAAA
5716  ACCACCGCT ACCAGCGGT GGTTTGTTT GCCGGATCA AGAGCTACC
5761  AACTCTTTT TCCGAAGGT AACTGGCTT CAGCAGAGC GCAGATACC
5806  AAATACTGT CCTTCTAGT GTAGCCGTA GTTAGGCCA CCACTTCAA
5851  GAACTCTGT AGCACCGCC TACATACCT CGCTCTGCT AATCCTGTT
5896  ACCAGTGGC TGCTGCCAG TGGCGATAA GTCGTGTCT TACCGGGTT
5941  GGACTCAAG ACGATAGTT ACCGGATAA GGCGCAGCG GTCGGGCTG
5986  AACGGGGGG TTCGTGCAC ACAGCCCAG CTTGGAGCG AACGACCTA
6031  CACCGAACT GAGATACCT ACAGCGTGA GCTATGAGA AAGCGCCAC
6076  GCTTCCCGA AGGGAGAAA GGCGGACAG GTATCCGGT AAGCGGCAG
6121  GGTCGGAAC AGGAGAGCG CACGAGGGA GCTTCCAGG GGGAAACGC
6166  CTGGTATCT TTATAGTCC TGTCGGGTT TCGCCACCT CTGACTTGA
6211  GCGTCGATT TTTGTGATG CTCGTCAGG GGGGCGGAG CCTATGGAA
6256  AAACGCCAG CAACGCGGC CTTTTTACG GTTCCTGGC CTTTTGCTG
```

FIGURE 16 ToxoP30del3C(52-300aa)

```
    LeuValAla AsnGlnVal ValThrCys ProAspLys LysSerThr
  1 CTTGTTGCC AATCAAGTT GTCACCTGC CCAGATAAA AAATCGACA
    AlaAlaVal IleLeuThr ProThrGlu AsnHisPhe ThrLeuLys
 46 GCCGCGGTC ATTCTCACA CCGACGGAG AACCACTTC ACTCTCAAG
    CysProLys ThrAlaLeu ThrGluPro ProThrLeu AlaTyrSer
 91 TGCCCTAAA ACAGCGCTC ACAGAGCCT CCCACTCTT GCGTACTCA
    ProAsnArg GlnIleCys ProAlaGly ThrThrSer SerCysThr
136 CCCAACAGG CAAATCTGC CCAGCGGGT ACTACAAGT AGCTGTACA
    SerLysAla ValThrLeu SerSerLeu IleProGlu AlaGluAsp
181 TCAAAGGCT GTAACATTG AGCTCCTTG ATTCCTGAA GCAGAAGAT
    SerTrpTrp ThrGlyAsp SerAlaSer LeuAspThr AlaGlyIle
226 AGCTGGTGG ACGGGGGAT TCTGCTAGT CTCGACACG GCAGGCATC
    LysLeuThr ValProIle GluLysPhe ProValThr ThrGlnThr
271 AAACTCACA GTTCCAATC GAGAAGTTC CCCGTGACA ACGCAGACG
    PheValVal GlyCysIle LysGlyAsp AspAlaGln SerCysMet
316 TTTGTGGTC GGTTGCATC AAGGGAGAC GACGCACAG AGTTGTATG
    ValThrVal ThrValGln AlaArgAla SerSerVal ValAsnAsn
361 GTCACAGTG ACAGTACAA GCCAGAGCC TCATCGGTC GTCAATAAT
    ValAlaArg CysSerTyr GlyAlaAsp SerThrLeu GlyProVal
406 GTCGCAAGG TGCTCCTAC GGTGCAGAC AGCACTCTT GGTCCTGTC
    LysLeuSer AlaGluGly ProThrThr MetThrLeu ValCysGly
451 AAGTTGTCT GCGGAAGGA CCCACTACA ATGACCCTC GTGTGCGGG
    LysAspGly ValLysVal ProGlnAsp AsnAsnGln TyrCysSer
496 AAAGATGGA GTCAAAGTT CCTCAAGAC AACAATCAG TACTGTTCC
    GlyThrThr LeuThrGly CysAsnGlu LysSerPhe LysAspIle
541 GGGACGACG CTGACTGGT TGCAACGAG AAATCGTTC AAAGATATT
    LeuProLys LeuThrGlu AsnProTrp GlnGlyAsn AlaSerSer
586 TTGCCAAAA TTAACTGAG AACCCGTGG CAGGGTAAC GCTTCGAGT
    AspLysGly AlaThrLeu ThrIleLys LysGluAla PheProAla
631 GATAAGGGT GCCACGCTA ACGATCAAG AAGGAAGCA TTTCCAGCC
    GluSerLys SerValIle IleGlyCys ThrGlyGly SerProGlu
676 GAGTCAAAA AGCGTCATT ATTGGATGC ACAGGGGGA TCGCCTGAG
    LysHisHis CysThrVal LysLeuGlu
721 AAGCATCAC TGTACCGTG AAACTGGAG
```

FIGURE 19    pMBP-c2X-ToxoP30del4C(52-294aa)

```
   1   CCGACACCA TCGAATGGT GCAAAACCT TTCGCGGTA TGGCATGAT
  46   AGCGCCCGG AAGAGAGTC AATTCAGGG TGGTGAATG TGAAACCAG
  91   TAACGTTAT ACGATGTCG CAGAGTATG CCGGTGTCT CTTATCAGA
 136   CCGTTTCCC GCGTGGTGA ACCAGGCCA GCCACGTTT CTGCGAAAA
 181   CGCGGGAAA AAGTGGAAG CGGCGATGG CGGAGCTGA ATTACATTC
 226   CCAACCGCG TGGCACAAC AACTGGCGG GCAAACAGT CGTTGCTGA
 271   TTGGCGTTG CCACCTCCA GTCTGGCCC TGCACGCGC CGTCGCAAA
 316   TTGTCGCGG CGATTAAAT CTCGCGCCG ATCAACTGG GTGCCAGCG
 361   TGGTGGTGT CGATGGTAG AACGAAGCG GCGTCGAAG CCTGTAAAG
 406   CGGCGGTGC ACAATCTTC TCGCGCAAC GCGTCAGTG GGCTGATCA
 451   TTAACTATC CGCTGGATG ACCAGGATG CCATTGCTG TGGAAGCTG
 496   CCTGCACTA ATGTTCCGG CGTTATTTC TTGATGTCT CTGACCAGA
 541   CACCCATCA ACAGTATTA TTTTCTCCC ATGAAGACG GTACGCGAC
 586   TGGGCGTGG AGCATCTGG TCGCATTGG GTCACCAGC AAATCGCGC
 631   TGTTAGCGG GCCCATTAA GTTCTGTCT CGGCGCGTC TGCGTCTGG
 676   CTGGCTGGC ATAAATATC TCACTCGCA ATCAAATTC AGCCGATAG
 721   CGGAACGGG AAGGCGACT GGAGTGCCA TGTCCGGTT TTCAACAAA
 766   CCATGCAAA TGCTGAATG AGGGCATCG TTCCCACTG CGATGCTGG
 811   TTGCCAACG ATCAGATGG CGCTGGGCG CAATGCGCG CCATTACCG
 856   AGTCCGGGC TGCGCGTTG GTGCGGATA TCTCGGTAG TGGGATACG
 901   ACGATACCG AAGACAGCT CATGTTATA TCCCGCCGT TAACCACCA
 946   TCAAACAGG ATTTTCGCC TGCTGGGGC AAACCAGCG TGGACCGCT
 991   TGCTGCAAC TCTCTCAGG GCCAGGCGG TGAAGGGCA ATCAGCTGT
1036   TGCCCGTCT CACTGGTGA AAAGAAAAA CCACCCTGG CGCCCAATA
1081   CGCAAACCG CCTCTCCCC GCGCGTTGG CCGATTCAT TAATGCAGC
1126   TGGCACGAC AGGTTTCCC GACTGGAAA GCGGGCAGT GAGCGCAAC
1171   GCAATTAAT GTAAGTTAG CTCACTCAT TAGGCACAA TTCTCATGT
1216   TTGACAGCT TATCATCGA CTGCACGGT GCACCAATG CTTCTGGCG
1261   TCAGGCAGC CATCGGAAG CTGTGGTAT GGCTGTGCA GGTCGTAAA
1306   TCACTGCAT AATTCGTGT CGCTCAAGG CGCACTCCC GTTCTGGAT
1351   AATGTTTTT TGCGCCGAC ATCATAACG GTTCTGGCA AATATTCTG
1396   AAATGAGCT GTTGACAAT TAATCATCG GCTCGTATA ATGTGTGGA
1441   ATTGTGAGC GGATAACAA TTTCACACA GGAAACAGC CAGTCCGTT
                                                      Met
1486   TAGGTGTTT TCACGAGCA CTTCACCAA CAAGGACCA TAGCATATG
       LysIleGlu GluGlyLys LeuValIle TrpIleAsn GlyAspLys
1531   AAAATCGAA GAAGGTAAA CTGGTAATC TGGATTAAC GGCGATAAA
       GlyTyrAsn GlyLeuAla GluValGly LysLysPhe GluLysAsp
1576   GGCTATAAC GGTCTCGCT GAAGTCGGT AAGAAATTC GAGAAAGAT
       ThrGlyIle LysValThr ValGluHis ProAspLys LeuGluGlu
1621   ACCGGAATT AAAGTCACC GTTGAGCAT CCGGATAAA CTGGAAGAG
       LysPhePro GlnValAla AlaThrGly AspGlyPro AspIleIle
1666   AAATTCCCA CAGGTTGCG GCAACTGGC GATGGCCCT GACATTATC
       PheTrpAla HisAspArg PheGlyGly TyrAlaGln SerGlyLeu
1711   TTCTGGGCA CACGACCGC TTTGGTGGC TACGCTCAA TCTGGCCTG
       LeuAlaGlu IleThrPro AspLysAla PheGlnAsp LysLeuTyr
```

FIGURE 19  pMBP-c2X-ToxoP30del4C(52-294aa)

```
1756  TTGGCTGAA  ATCACCCCG  GACAAAGCG  TTCCAGGAC  AAGCTGTAT
      ProPheThr  TrpAspAla  ValArgTyr  AsnGlyLys  LeuIleAla
1801  CCGTTTACC  TGGGATGCC  GTACGTTAC  AACGGCAAG  CTGATTGCT
      TyrProIle  AlaValGlu  AlaLeuSer  LeuIleTyr  AsnLysAsp
1846  TACCCGATC  GCTGTTGAA  GCGTTATCG  CTGATTTAT  AACAAAGAT
      LeuLeuPro  AsnProPro  LysThrTrp  GluGluIle  ProAlaLeu
1891  CTGCTGCCG  AACCCGCCA  AAAACCTGG  GAAGAGATC  CCGGCGCTG
      AspLysGlu  LeuLysAla  LysGlyLys  SerAlaLeu  MetPheAsn
1936  GATAAAGAA  CTGAAAGCG  AAAGGTAAG  AGCGCGCTG  ATGTTCAAC
      LeuGlnGlu  ProTyrPhe  ThrTrpPro  LeuIleAla  AlaAspGly
1981  CTGCAAGAA  CCGTACTTC  ACCTGGCCG  CTGATTGCT  GCTGACGGG
      GlyTyrAla  PheLysTyr  GluAsnGly  LysTyrAsp  IleLysAsp
2026  GGTTATGCG  TTCAAGTAT  GAAAACGGC  AAGTACGAC  ATTAAAGAC
      ValGlyVal  AspAsnAla  GlyAlaLys  AlaGlyLeu  ThrPheLeu
2071  GTGGGCGTG  GATAACGCT  GGCGCGAAA  GCGGGTCTG  ACCTTCCTG
      ValAspLeu  IleLysAsn  LysHisMet  AsnAlaAsp  ThrAspTyr
2116  GTTGACCTG  ATTAAAAAC  AAACACATG  AATGCAGAC  ACCGATTAC
      SerIleAla  GluAlaAla  PheAsnLys  GlyGluThr  AlaMetThr
2161  TCCATCGCA  GAAGCTGCC  TTTAATAAA  GGCGAAACA  GCGATGACC
      IleAsnGly  ProTrpAla  TrpSerAsn  IleAspThr  SerLysVal
2206  ATCAACGGC  CCGTGGGCA  TGGTCCAAC  ATCGACACC  AGCAAAGTG
      AsnTyrGly  ValThrVal  LeuProThr  PheLysGly  GlnProSer
2251  AATTATGGT  GTAACGGTA  CTGCCGACC  TTCAAGGGT  CAACCATCC
      LysProPhe  ValGlyVal  LeuSerAla  GlyIleAsn  AlaAlaSer
2296  AAACCGTTC  GTTGGCGTG  CTGAGCGCA  GGTATTAAC  GCCGCCAGT
      ProAsnLys  GluLeuAla  LysGluPhe  LeuGluAsn  TyrLeuLeu
2341  CCGAACAAA  GAGCTGGCA  AAAGAGTTC  CTCGAAAAC  TATCTGCTG
      ThrAspGlu  GlyLeuGlu  AlaValAsn  LysAspLys  ProLeuGly
2386  ACTGATGAA  GGTCTGGAA  GCGGTTAAT  AAAGACAAA  CCGCTGGGT
      AlaValAla  LeuLysSer  TyrGluGlu  GluLeuAla  LysAspPro
2431  GCCGTAGCG  CTGAAGTCT  TACGAGGAA  GAGTTGGCG  AAAGATCCA
      ArgIleAla  AlaThrMet  GluAsnAla  GlnLysGly  GluIleMet
2476  CGTATTGCC  GCCACTATG  GAAAACGCC  CAGAAAGGT  GAAATCATG
      ProAsnIle  ProGlnMet  SerAlaPhe  TrpTyrAla  ValArgThr
2521  CCGAACATC  CCGCAGATG  TCCGCTTTC  TGGTATGCC  GTGCGTACT
      AlaValIle  AsnAlaAla  SerGlyArg  GlnThrVal  AspGluAla
2566  GCGGTGATC  AACGCCGCC  AGCGGTCGT  CAGACTGTC  GATGAAGCC
      LeuLysAsp  AlaGlnThr  AsnSerSer  SerAsnAsn  AsnAsnAsn
2611  CTGAAAGAC  GCGCAGACT  AATTCGAGC  TCGAACAAC  AACAACAAT
      AsnAsnAsn  AsnAsnLeu  GlyIleGlu  GlyArgIle  SerGluPhe
2656  AACAATAAC  AACAACCTC  GGGATCGAG  GGAAGGATT  TCAGAATTC
      LeuValAla  AsnGlnVal  ValThrCys  ProAspLys  LysSerThr
2701  CTTGTTGCC  AATCAAGTT  GTCACCTGC  CCAGATAAA  AAATCGACA
      AlaAlaVal  IleLeuThr  ProThrGlu  AsnHisPhe  ThrLeuLys
2746  GCCGCGGTC  ATTCTCACA  CCGACGGAG  AACCACTTC  ACTCTCAAG
      CysProLys  ThrAlaLeu  ThrGluPro  ProThrLeu  AlaTyrSer
```

FIGURE 19   pMBP-c2X-ToxoP30del4C(52-294aa)

```
2791  TGCCCTAAA  ACAGCGCTC  ACAGAGCCT  CCCACTCTT  GCGTACTCA
      ProAsnArg  GlnIleCys  ProAlaGly  ThrThrSer  SerCysThr
2836  CCCAACAGG  CAAATCTGC  CCAGCGGGT  ACTACAAGT  AGCTGTACA
      SerLysAla  ValThrLeu  SerSerLeu  IleProGlu  AlaGluAsp
2881  TCAAAGGCT  GTAACATTG  AGCTCCTTG  ATTCCTGAA  GCAGAAGAT
      SerTrpTrp  ThrGlyAsp  SerAlaSer  LeuAspThr  AlaGlyIle
2926  AGCTGGTGG  ACGGGGAT   TCTGCTAGT  CTCGACACG  GCAGGCATC
      LysLeuThr  ValProIle  GluLysPhe  ProValThr  ThrGlnThr
2971  AAACTCACA  GTTCCAATC  GAGAAGTTC  CCCGTGACA  ACGCAGACG
      PheValVal  GlyCysIle  LysGlyAsp  AspAlaGln  SerCysMet
3016  TTTGTGGTC  GGTTGCATC  AAGGGAGAC  GACGCACAG  AGTTGTATG
      ValThrVal  ThrValGln  AlaArgAla  SerSerVal  ValAsnAsn
3061  GTCACAGTG  ACAGTACAA  GCCAGAGCC  TCATCGGTC  GTCAATAAT
      ValAlaArg  CysSerTyr  GlyAlaAsp  SerThrLeu  GlyProVal
3106  GTCGCAAGG  TGCTCCTAC  GGTGCAGAC  AGCACTCTT  GGTCCTGTC
      LysLeuSer  AlaGluGly  ProThrThr  MetThrLeu  ValCysGly
3151  AAGTTGTCT  GCGGAAGGA  CCCACTACA  ATGACCCTC  GTGTGCGGG
      LysAspGly  ValLysVal  ProGlnAsp  AsnAsnGln  TyrCysSer
3196  AAAGATGGA  GTCAAAGTT  CCTCAAGAC  AACAATCAG  TACTGTTCC
      GlyThrThr  LeuThrGly  CysAsnGlu  LysSerPhe  LysAspIle
3241  GGGACGACG  CTGACTGGT  TGCAACGAG  AAATCGTTC  AAAGATATT
      LeuProLys  LeuThrGlu  AsnProTrp  GlnGlyAsn  AlaSerSer
3286  TTGCCAAAA  TTAACTGAG  AACCCGTGG  CAGGGTAAC  GCTTCGAGT
      AspLysGly  AlaThrLeu  ThrIleLys  LysGluAla  PheProAla
3331  GATAAGGGT  GCCACGCTA  ACGATCAAG  AAGGAAGCA  TTTCCAGCC
      GluSerLys  SerValIle  IleGlyCys  ThrGlyGly  SerProGlu
3376  GAGTCAAAA  AGCGTCATT  ATTGGATGC  ACAGGGGGA  TCGCCTGAG
      LysHisHis
3421  AAGCATCAC  TGAAAGCTT  GGCACTGGC  CGTCGTTTT  ACAACGTCG
3466  TGACTGGGA  AAACCCTGG  CGTTACCCA  ACTTAATCG  CCTTGCAGC
3511  ACATCCCCC  TTTCGCCAG  CTGGCGTAA  TAGCGAAGA  GGCCCGCAC
3556  CGATCGCCC  TTCCCAACA  GTTGCGCAG  CCTGAATGG  CGAATGGCA
3601  GCTTGGCTG  TTTTGGCGG  ATGAGATAA  GATTTTCAG  CCTGATACA
3646  GATTAAATC  AGAACGCAG  AAGCGGTCT  GATAAAACA  GAATTTGCC
3691  TGGCGGCAG  TAGCGCGGT  GGTCCCACC  TGACCCCAT  GCCGAACTC
3736  AGAAGTGAA  ACGCCGTAG  CGCCGATGG  TAGTGTGGG  GTCTCCCCA
3781  TGCGAGAGT  AGGGAACTG  CCAGGCATC  AAATAAAAC  GAAAGGCTC
3826  AGTCGAAAG  ACTGGGCCT  TCGTTTTA   TCTGTTGTT  TGTCGGTGA
3871  ACGCTCTCC  TGAGTAGGA  CAAATCCGC  CGGGAGCGG  ATTTGAACG
3916  TTGCGAAGC  AACGGCCCG  GAGGGTGGC  GGGCAGGAC  GCCCGCCAT
3961  AAACTGCCA  GGCATCAAA  TTAAGCAGA  AGGCCATCC  TGACGGATG
4006  GCCTTTTTG  CGTTTCTAC  AAACTCTTT  TTGTTTATT  TTTCTAAAT
4051  ACATTCAAA  TATGTATCC  GCTCATGAG  ACAATAACC  CTGATAAAT
4096  GCTTCAATA  ATATTGAAA  AAGGAAGAG  TATGAGTAT  TCAACATTT
4141  CCGTGTCGC  CCTTATTCC  CTTTTTTGC  GGCATTTTG  CCTTCCTGT
4186  TTTTGCTCA  CCCAGAAAC  GCTGGTGAA  AGTAAAAGA  TGCTGAAGA
```

FIGURE 19  pMBP-c2X-ToxoP30del4C(52-294aa)

```
4231  TCAGTTGGG TGCACGAGT GGGTTACAT CGAACTGGA TCTCAACAG
4276  CGGTAAGAT CCTTGAGAG TTTTCGCCC CGAAGAACG TTCTCCAAT
4321  GATGAGCAC TTTTAAAGT TCTGCTATG TGGCGCGGT ATTATCCCG
4366  TGTTGACGC CGGGCAAGA GCAACTCGG TCGCCGCAT ACACTATTC
4411  TCAGAATGA CTTGGTTGA GTACTCACC AGTCACAGA AAAGCATCT
4456  TACGGATGG CATGACAGT AAGAGAATT ATGCAGTGC TGCCATAAC
4501  CATGAGTGA TAACACTGC GGCCAACTT ACTTCTGAC AACGATCGG
4546  AGGACCGAA GGAGCTAAC CGCTTTTTT GCACAACAT GGGGGATCA
4591  TGTAACTCG CCTTGATCG TTGGGAACC GGAGCTGAA TGAAGCCAT
4636  ACCAAACGA CGAGCGTGA CACCACGAT GCCTGTAGC AATGGCAAC
4681  AACGTTGCG CAAACTATT AACTGGCGA ACTACTTAC TCTAGCTTC
4726  CCGGCAACA ATTAATAGA CTGGATGGA GGCGGATAA AGTTGCAGG
4771  ACCACTTCT GCGCTCGGC CCTTCCGGC TGGCTGGTT TATTGCTGA
4816  TAAATCTGG AGCCGGTGA GCGTGGGTC TCGCGGTAT CATTGCAGC
4861  ACTGGGGCC AGATGGTAA GCCCTCCCG TATCGTAGT TATCTACAC
4906  GACGGGGAG TCAGGCAAC TATGGATGA ACGAAATAG ACAGATCGC
4951  TGAGATAGG TGCCTCACT GATTAAGCA TTGGTAACT GTCAGACCA
4996  AGTTTACTC ATATATACT TTAGATTGA TTTACCCCG GTTGATAAT
5041  CAGAAAAGC CCCAAAAAC AGGAAGATT GTATAAGCA AATATTTAA
5086  ATTGTAAAC GTTAATATT TTGTTAAAA TTCGCGTTA AATTTTTGT
5131  TAAATCAGC TCATTTTTT AACCAATAG GCCGAAATC GGCAAAATC
5176  CCTTATAAA TCAAAGAA TAGACCGAG ATAGGGTTG AGTGTTGTT
5221  CCAGTTTGG AACAAGAGT CCACTATTA AGAACGTG GACTCCAAC
5266  GTCAAAGGG CGAAAAACC GTCTATCAG GGCGATGGC CCACTACGT
5311  GAACCATCA CCCAAATCA AGTTTTTTG GGGTCGAGG TGCCGTAAA
5356  GCACTAAAT CGGAACCCT AAAGGGAGC CCCCGATTT AGAGCTTGA
5401  CGGGGAAAG CCGGCGAAC GTGGCGAGA AAGGAAGGG AAGAAAGCG
5446  AAAGGAGCG GGCGCTAGG GCGCTGGCA AGTGTAGCG GTCACGCTG
5491  CGCGTAACC ACCACACCC GCCGCGCTT AATGCGCCG CTACAGGGC
5536  GCGTAAAAG GATCTAGGT GAAGATCCT TTTTGATAA TCTCATGAC
5581  CAAAATCCC TTAACGTGA GTTTTCGTT CCACTGAGC GTCAGACCC
5626  CGTAGAAAA GATCAAAGG ATCTTCTTG AGATCCTTT TTTTCTGCG
5671  CGTAATCTG CTGCTTGCA AACAAAAAA ACCACCGCT ACCAGCGGT
5716  GGTTTGTTT GCCGGATCA AGAGCTACC AACTCTTTT TCCGAAGGT
5761  AACTGGCTT CAGCAGAGC GCAGATACC AAATACTGT CCTTCTAGT
5806  GTAGCCGTA GTTAGGCCA CCACTTCAA GAACTCTGT AGCACCGCC
5851  TACATACCT CGCTCTGCT AATCCTGTT ACCAGTGGC TGCTGCCAG
5896  TGGCGATAA GTCGTGTCT TACCGGGTT GGACTCAAG ACGATAGTT
5941  ACCGGATAA GGCGCAGCG GTCGGGCTG AACGGGGGG TTCGTGCAC
5986  ACAGCCCAG CTTGGAGCG AACGACCTA CACCGAACT GAGATACCT
6031  ACAGCGTGA GCTATGAGA AAGCGCCAC GCTTCCCGA AGGGAGAAA
6076  GGCGGACAG GTATCCGGT AAGCGGCAG GGTCGGAAC AGGAGAGCG
6121  CACGAGGGA GCTTCCAGG GGGAAACGC CTGGTATCT TTATAGTCC
6166  TGTCGGGTT TCGCCACCT CTGACTTGA GCGTCGATT TTTGTGATG
6211  CTCGTCAGG GGGGCGGAG CCTATGGAA AAACGCCAG CAACGCGGC
6256  CTTTTTACG GTTCCTGGC CTTTTGCTG GCCTTTTGC TCACATGTT
```

FIGURE 19   pMBP-c2X-ToxoP30del4C(52-294aa)

```
6301  CTTTCCTGC  GTTATCCCC  TGATTCTGT  GGATAACCG  TATTACCGC
6346  CTTTGAGTG  AGCTGATAC  CGCTCGCCG  CAGCCGAAC  GACCGAGCG
6391  CAGCGAGTC  AGTGAGCGA  GGAAGCGGA  AGAGCGCCT  GATGCGGTA
6436  TTTTCTCCT  TACGCATCT  GTGCGGTAT  TTCACACCG  CATATATGG
6481  TGCACTCTC  AGTACAATC  TGCTCTGAT  GCCGCATAG  TTAAGCCAG
6526  TATACACTC  CGCTATCGC  TACGTGACT  GGGTCATGG  CTGCGCCCC
6571  GACACCCGC  CAACACCCG  CTGACGCGC  CCTGACGGG  CTTGTCTGC
6616  TCCCGGCAT  CCGCTTACA  GACAAGCTG  TGACCGTCT  CCGGGAGCT
6661  GCATGTGTC  AGAGGTTTT  CACCGTCAT  CACCGAAAC  GCGCGAGGC
6706  AGCTGCGGT  AAAGCTCAT  CAGCGTGGT  CGTGCAGCG  ATTCACAGA
6751  TGTCTGCCT  GTTCATCCG  CGTCCAGCT  CGTTGAGTT  CTCCAGAA
6796  GCGTTAATG  TCTGGCTTC  TGATAAAGC  GGGCCATGT  TAAGGGCGG
6841  TTTTTTCCT  GTTTGGTCA  CTGATGCCT  CCGTGTAAG  GGGGATTTC
6886  TGTTCATGG  GGGTAATGA  TACCGATGA  AACGAGAGA  GGATGCTCA
6931  CGATACGGG  TTACTGATG  ATGAACATG  CCCGGTTAC  TGGAACGTT
6976  GTGAGGGTA  AACAACTGG  CGGTATGGA  TGCGGCGGG  ACCAGAGAA
7021  AAATCACTC  AGGGTCAAT  GCCAGCGCT  TCGTTAATA  CAGATGTAG
7066  GTGTTCCAC  AGGGTAGCC  AGCAGCATC  CTGCGATGC  AGATCCGGA
7111  ACATAATGG  TGCAGGGCG  CTGACTTCC  GCGTTTCCA  GACTTTACG
7156  AAACACGGA  AACCGAAGA  CCATTCATG  TTGTTGCTC  AGGTCGCAG
7201  ACGTTTTGC  AGCAGCAGT  CGCTTCACG  TTCGCTCGC  GTATCGGTG
7246  ATTCATTCT  GCTAACCAG  TAAGGCAAC  CCCGCCAGC  CTAGCCGGG
7291  TCCTCAACG  ACAGGAGCA  CGATCATGC  GCACCCGTG  GCCAGGACC
7336  CAACGCTGC  CCGAAATT
```

FIGURE 20    ToxoP30del4C(52-294aa)

```
      LeuValAla AsnGlnVal ValThrCys ProAspLys LysSerThr
  1   CTTGTTGCC AATCAAGTT GTCACCTGC CCAGATAAA AAATCGACA
      AlaAlaVal IleLeuThr ProThrGlu AsnHisPhe ThrLeuLys
 46   GCCGCGGTC ATTCTCACA CCGACGGAG AACCACTTC ACTCTCAAG
      CysProLys ThrAlaLeu ThrGluPro ProThrLeu AlaTyrSer
 91   TGCCCTAAA ACAGCGCTC ACAGAGCCT CCCACTCTT GCGTACTCA
      ProAsnArg GlnIleCys ProAlaGly ThrThrSer SerCysThr
136   CCCAACAGG CAAATCTGC CCAGCGGGT ACTACAAGT AGCTGTACA
      SerLysAla ValThrLeu SerSerLeu IleProGlu AlaGluAsp
181   TCAAAGGCT GTAACATTG AGCTCCTTG ATTCCTGAA GCAGAAGAT
      SerTrpTrp ThrGlyAsp SerAlaSer LeuAspThr AlaGlyIle
226   AGCTGGTGG ACGGGGGAT TCTGCTAGT CTCGACACG GCAGGCATC
      LysLeuThr ValProIle GluLysPhe ProValThr ThrGlnThr
271   AAACTCACA GTTCCAATC GAGAAGTTC CCCGTGACA ACGCAGACG
      PheValVal GlyCysIle LysGlyAsp AspAlaGln SerCysMet
316   TTTGTGGTC GGTTGCATC AAGGGAGAC GACGCACAG AGTTGTATG
      ValThrVal ThrValGln AlaArgAla SerSerVal ValAsnAsn
361   GTCACAGTG ACAGTACAA GCCAGAGCC TCATCGGTC GTCAATAAT
      ValAlaArg CysSerTyr GlyAlaAsp SerThrLeu GlyProVal
406   GTCGCAAGG TGCTCCTAC GGTGCAGAC AGCACTCTT GGTCCTGTC
      LysLeuSer AlaGluGly ProThrThr MetThrLeu ValCysGly
451   AAGTTGTCT GCGGAAGGA CCCACTACA ATGACCCTC GTGTGCGGG
      LysAspGly ValLysVal ProGlnAsp AsnAsnGln TyrCysSer
496   AAAGATGGA GTCAAAGTT CCTCAAGAC AACAATCAG TACTGTTCC
      GlyThrThr LeuThrGly CysAsnGlu LysSerPhe LysAspIle
541   GGGACGACG CTGACTGGT TGCAACGAG AAATCGTTC AAAGATATT
      LeuProLys LeuThrGlu AsnProTrp GlnGlyAsn AlaSerSer
586   TTGCCAAAA TTAACTGAG AACCCGTGG CAGGGTAAC GCTTCGAGT
      AspLysGly AlaThrLeu ThrIleLys LysGluAla PheProAla
631   GATAAGGGT GCCACGCTA ACGATCAAG AAGGAAGCA TTTCCAGCC
      GluSerLys SerValIle IleGlyCys ThrGlyGly SerProGlu
676   GAGTCAAAA AGCGTCATT ATTGGATGC ACAGGGGGA TCGCCTGAG
      LysHisHis
721   AAGCATCAC
```

FIGURE 22  pMBP-c2X-ToxoP30del4del8(83-294aa)

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA ATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                     Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 22 pMBP-c2X-ToxoP30del4del8(83-294aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     ProLysThr AlaLeuThr GluProPro ThrLeuAla TyrSerPro
2701 CCTAAAACA GCGCTCACA GAGCCTCCC ACTCTTGCG TACTCACCC
     AsnArgGln IleCysPro AlaGlyThr ThrSerSer CysThrSer
2746 AACAGGCAA ATCTGCCCA GCGGGTACT ACAAGTAGC TGTACATCA
     LysAlaVal ThrLeuSer SerLeuIle ProGluAla GluAspSer
```

FIGURE 22 pMBP-c2X-ToxoP30del4del8(83-294aa)

```
2791  AAGGCTGTA ACATTGAGC TCCTTGATT CCTGAAGCA GAAGATAGC
      TrpTrpThr GlyAspSer AlaSerLeu AspThrAla GlyIleLys
2836  TGGTGGACG GGGGATTCT GCTAGTCTC GACACGGCA GGCATCAAA
      LeuThrVal ProIleGlu LysPhePro ValThrThr GlnThrPhe
2881  CTCACAGTT CCAATCGAG AAGTTCCCC GTGACAACG CAGACGTTT
      ValValGly CysIleLys GlyAspAsp AlaGlnSer CysMetVal
2926  GTGGTCGGT TGCATCAAG GGAGACGAC GCACAGAGT TGTATGGTC
      ThrValThr ValGlnAla ArgAlaSer SerValVal AsnAsnVal
2971  ACAGTGACA GTACAAGCC AGAGCCTCA TCGGTCGTC AATAATGTC
      AlaArgCys SerTyrGly AlaAspSer ThrLeuGly ProValLys
3016  GCAAGGTGC TCCTACGGT GCAGACAGC ACTCTTGGT CCTGTCAAG
      LeuSerAla GluGlyPro ThrThrMet ThrLeuVal CysGlyLys
3061  TTGTCTGCG GAAGGACCC ACTACAATG ACCCTCGTG TGCGGGAAA
      AspGlyVal LysValPro GlnAspAsn AsnGlnTyr CysSerGly
3106  GATGGAGTC AAAGTTCCT CAAGACAAC AATCAGTAC TGTTCCGGG
      ThrThrLeu ThrGlyCys AsnGluLys SerPheLys AspIleLeu
3151  ACGACGCTG ACTGGTTGC AACGAGAAA TCGTTCAAA GATATTTTG
      ProLysLeu ThrGluAsn ProTrpGln GlyAsnAla SerSerAsp
3196  CCAAAATTA ACTGAGAAC CCGTGGCAG GGTAACGCT TCGAGTGAT
      LysGlyAla ThrLeuThr IleLysLys GluAlaPhe ProAlaGlu
3241  AAGGGTGCC ACGCTAACG ATCAAGAAG GAAGCATTT CCAGCCGAG
      SerLysSer ValIleIle GlyCysThr GlyGlySer ProGluLys
3286  TCAAAAAGC GTCATTATT GGATGCACA GGGGGATCG CCTGAGAAG
      HisHis
3331  CATCACTGA AAGCTTGGC ACTGGCCGT CGTTTTACA ACGTCGTGA
3376  CTGGGAAAA CCCTGGCGT TACCCAACT TAATCGCCT TGCAGCACA
3421  TCCCCCTTT CGCCAGCTG GCGTAATAG CGAAGAGGC CCGCACCGA
3466  TCGCCCTTC CCAACAGTT GCGCAGCCT GAATGGCGA ATGGCAGCT
3511  TGGCTGTTT TGGCGGATG AGATAAGAT TTTCAGCCT GATACAGAT
3556  TAAATCAGA ACGCAGAAG CGGTCTGAT AAAACAGAA TTTGCCTGG
3601  CGGCAGTAG CGCGGTGGT CCCACCTGA CCCCATGCC GAACTCAGA
3646  AGTGAAACG CCGTAGCGC CGATGGTAG TGTGGGGTC TCCCCATGC
3691  GAGAGTAGG GAACTGCCA GGCATCAAA TAAAACGAA AGGCTCAGT
3736  CGAAAGACT GGGCCTTTC GTTTTATCT GTTGTTTGT CGGTGAACG
3781  CTCTCCTGA GTAGGACAA ATCCGCCGG GAGCGGATT TGAACGTTG
3826  CGAAGCAAC GGCCCGGAG GGTGGCGGG CAGGACGCC CGCCATAAA
3871  CTGCCAGGC ATCAAATTA AGCAGAAGG CCATCCTGA CGGATGGCC
3916  TTTTTGCGT TTCTACAAA CTCTTTTTG TTTATTTTT CTAAATACA
3961  TTCAAATAT GTATCCGCT CATGAGACA ATAACCCTG ATAAATGCT
4006  TCAATAATA TTGAAAAAG GAAGAGTAT GAGTATTCA ACATTTCCG
4051  TGTCGCCCT TATTCCCTT TTTTGCGGC ATTTTGCCT TCCTGTTTT
4096  TGCTCACCC AGAAACGCT GGTGAAAGT AAAAGATGC TGAAGATCA
4141  GTTGGGTGC ACGAGTGGG TTACATCGA ACTGGATCT CAACAGCGG
4186  TAAGATCCT TGAGAGTTT TCGCCCCGA AGAACGTTC TCCAATGAT
4231  GAGCACTTT TAAAGTTCT GCTATGTGG CGCGGTATT ATCCCGTGT
4276  TGACGCCGG GCAAGAGCA ACTCGGTCG CCGCATACA CTATTCTCA
```

FIGURE 22    pMBP-c2X-ToxoP30del4del8(83-294aa)

```
4321   GAATGACTT GGTTGAGTA CTCACCAGT CACAGAAAA GCATCTTAC
4366   GGATGGCAT GACAGTAAG AGAATTATG CAGTGCTGC CATAACCAT
4411   GAGTGATAA CACTGCGGC CAACTTACT TCTGACAAC GATCGGAGG
4456   ACCGAAGGA GCTAACCGC TTTTTTGCA CAACATGGG GGATCATGT
4501   AACTCGCCT TGATCGTTG GGAACCGGA GCTGAATGA AGCCATACC
4546   AAACGACGA GCGTGACAC CACGATGCC TGTAGCAAT GGCAACAAC
4591   GTTGCGCAA ACTATTAAC TGGCGAACT ACTTACTCT AGCTTCCCG
4636   GCAACAATT AATAGACTG GATGGAGGC GGATAAAGT TGCAGGACC
4681   ACTTCTGCG CTCGGCCCT TCCGGCTGG CTGGTTTAT TGCTGATAA
4726   ATCTGGAGC CGGTGAGCG TGGGTCTCG CGGTATCAT TGCAGCACT
4771   GGGGCCAGA TGGTAAGCC CTCCCGTAT CGTAGTTAT CTACACGAC
4816   GGGGAGTCA GGCAACTAT GGATGAACG AAATAGACA GATCGCTGA
4861   GATAGGTGC CTCACTGAT TAAGCATTG GTAACTGTC AGACCAAGT
4906   TTACTCATA TATACTTTA GATTGATTT ACCCCGGTT GATAATCAG
4951   AAAAGCCCC AAAAACAGG AAGATTGTA TAAGCAAAT ATTTAAATT
4996   GTAAACGTT AATATTTTG TTAAAATTC GCGTTAAAT TTTTGTTAA
5041   ATCAGCTCA TTTTTTAAC CAATAGGCC GAAATCGGC AAAATCCCT
5086   TATAAATCA AAGAATAG ACCGAGATA GGGTTGAGT GTTGTTCCA
5131   GTTTGGAAC AAGAGTCCA CTATTAAAG AACGTGGAC TCCAACGTC
5176   AAAGGGCGA AAAACCGTC TATCAGGGC GATGGCCCA CTACGTGAA
5221   CCATCACCC AAATCAAGT TTTTTGGGG TCGAGGTGC CGTAAAGCA
5266   CTAAATCGG AACCCTAAA GGGAGCCCC CGATTTAGA GCTTGACGG
5311   GGAAAGCCG GCGAACGTG GCGAGAAAG GAAGGGAAG AAAGCGAAA
5356   GGAGCGGGC GCTAGGGCG CTGGCAAGT GTAGCGGTC ACGCTGCGC
5401   GTAACCACC ACACCCGCC GCGCTTAAT GCCGCGCTA CAGGGCGCG
5446   TAAAAGGAT CTAGGTGAA GATCCTTTT TGATAATCT CATGACCAA
5491   AATCCCTTA ACGTGAGTT TTCGTTCCA CTGAGCGTC AGACCCCGT
5536   AGAAAAGAT CAAAGGATC TTCTTGAGA TCCTTTTTT TCTGCGCGT
5581   AATCTGCTG CTTGCAAAC AAAAAAACC ACCGCTACC AGCGGTGGT
5626   TTGTTTGCC GGATCAAGA GCTACCAAC TCTTTTTCC GAAGGTAAC
5671   TGGCTTCAG CAGAGCGCA GATACCAAA TACTGTCCT TCTAGTGTA
5716   GCCGTAGTT AGGCCACCA CTTCAAGAA CTCTGTAGC ACCGCCTAC
5761   ATACCTCGC TCTGCTAAT CCTGTTACC AGTGGCTGC TGCCAGTGG
5806   CGATAAGTC GTGTCTTAC CGGGTTGGA CTCAAGACG ATAGTTACC
5851   GGATAAGGC GCAGCGGTC GGGCTGAAC GGGGGGTTC GTGCACACA
5896   GCCCAGCTT GGAGCGAAC GACCTACAC CGAACTGAG ATACCTACA
5941   GCGTGAGCT ATGAGAAAG CGCCACGCT TCCCGAAGG AGAAAGGC
5986   GGACAGGTA TCCGGTAAG CGGCAGGGT CGGAACAGG AGAGCGCAC
6031   GAGGGAGCT TCCAGGGGG AAACGCCTG GTATCTTTA TAGTCCTGT
6076   CGGGTTTCG CCACCTCTG ACTTGAGCG TCGATTTTT GTGATGCTC
6121   GTCAGGGGG GCGGAGCCT ATGGAAAAA CGCCAGCAA CGCGGCCTT
6166   TTTACGGTT CCTGGCCTT TTGCTGGCC TTTTGCTCA CATGTTCTT
6211   TCCTGCGTT ATCCCCTGA TTCTGTGGA TAACCGTAT TACCGCCTT
6256   TGAGTGAGC TGATACCGC TCGCCGCAG CCGAACGAC CGAGCGCAG
6301   CGAGTCAGT GAGCGAGGA AGCGGAAGA GCGCCTGAT GCGGTATTT
6346   TCTCCTTAC GCATCTGTG CGGTATTTC ACACCGCAT ATATGGTGC
```

FIGURE 22    pMBP-c2X-ToxoP30del4del8(83-294aa)

```
6391 ACTCTCAGT ACAATCTGC TCTGATGCC GCATAGTTA AGCCAGTAT
6436 ACACTCCGC TATCGCTAC GTGACTGGG TCATGGCTG CGCCCCGAC
6481 ACCCGCCAA CACCCGCTG ACGCGCCCT GACGGGCTT GTCTGCTCC
6526 CGGCATCCG CTTACAGAC AAGCTGTGA CCGTCTCCG GGAGCTGCA
6571 TGTGTCAGA GGTTTTCAC CGTCATCAC CGAAACGCG CGAGGCAGC
6616 TGCGGTAAA GCTCATCAG CGTGGTCGT GCAGCGATT CACAGATGT
6661 CTGCCTGTT CATCCGCGT CCAGCTCGT TGAGTTTCT CCAGAAGCG
6706 TTAATGTCT GGCTTCTGA TAAAGCGGG CCATGTTAA GGGCGGTTT
6751 TTTCCTGTT TGGTCACTG ATGCCTCCG TGTAAGGGG GATTTCTGT
6796 TCATGGGGG TAATGATAC CGATGAAAC GAGAGAGGA TGCTCACGA
6841 TACGGGTTA CTGATGATG AACATGCCC GGTTACTGG AACGTTGTG
6886 AGGGTAAAC AACTGGCGG TATGGATGC GGCGGGACC AGAGAAAAA
6931 TCACTCAGG GTCAATGCC AGCGCTTCG TTAATACAG ATGTAGGTG
6976 TTCCACAGG GTAGCCAGC AGCATCCTG CGATGCAGA TCCGGAACA
7021 TAATGGTGC AGGGCGCTG ACTTCCGCG TTTCCAGAC TTTACGAAA
7066 CACGGAAAC CGAAGACCA TTCATGTTG TTGCTCAGG TCGCAGACG
7111 TTTTGCAGC AGCAGTCGC TTCACGTTC GCTCGCGTA TCGGTGATT
7156 CATTCTGCT AACCAGTAA GGCAACCCC GCCAGCCTA GCCGGGTCC
7201 TCAACGACA GGAGCACGA TCATGCGCA CCCGTGGCC AGGACCCAA
7246 CGCTGCCCG AAATT
```

FIGURE 23  ToxoP30del4del8(83-294aa)

```
      ProLysThr AlaLeuThr GluProPro ThrLeuAla TyrSerPro
  1   CCTAAAACA GCGCTCACA GAGCCTCCC ACTCTTGCG TACTCACCC
      AsnArgGln IleCysPro AlaGlyThr ThrSerSer CysThrSer
 46   AACAGGCAA ATCTGCCCA GCGGGTACT ACAAGTAGC TGTACATCA
      LysAlaVal ThrLeuSer SerLeuIle ProGluAla GluAspSer
 91   AAGGCTGTA ACATTGAGC TCCTTGATT CCTGAAGCA GAAGATAGC
      TrpTrpThr GlyAspSer AlaSerLeu AspThrAla GlyIleLys
136   TGGTGGACG GGGGATTCT GCTAGTCTC GACACGGCA GGCATCAAA
      LeuThrVal ProIleGlu LysPhePro ValThrThr GlnThrPhe
181   CTCACAGTT CCAATCGAG AAGTTCCCC GTGACAACG CAGACGTTT
      ValValGly CysIleLys GlyAspAsp AlaGlnSer CysMetVal
226   GTGGTCGGT TGCATCAAG GGAGACGAC GCACAGAGT TGTATGGTC
      ThrValThr ValGlnAla ArgAlaSer SerValVal AsnAsnVal
271   ACAGTGACA GTACAAGCC AGAGCCTCA TCGGTCGTC AATAATGTC
      AlaArgCys SerTyrGly AlaAspSer ThrLeuGly ProValLys
316   GCAAGGTGC TCCTACGGT GCAGACAGC ACTCTTGGT CCTGTCAAG
      LeuSerAla GluGlyPro ThrThrMet ThrLeuVal CysGlyLys
361   TTGTCTGCG GAAGGACCC ACTACAATG ACCCTCGTG TGCGGGAAA
      AspGlyVal LysValPro GlnAspAsn AsnGlnTyr CysSerGly
406   GATGGAGTC AAAGTTCCT CAAGACAAC AATCAGTAC TGTTCCGGG
      ThrThrLeu ThrGlyCys AsnGluLys SerPheLys AspIleLeu
451   ACGACGCTG ACTGGTTGC AACGAGAAA TCGTTCAAA GATATTTTG
      ProLysLeu ThrGluAsn ProTrpGln GlyAsnAla SerSerAsp
496   CCAAAATTA ACTGAGAAC CCGTGGCAG GGTAACGCT TCGAGTGAT
      LysGlyAla ThrLeuThr IleLysLys GluAlaPhe ProAlaGlu
541   AAGGGTGCC ACGCTAACG ATCAAGAAG GAAGCATTT CCAGCCGAG
      SerLysSer ValIleIle GlyCysThr GlyGlySer ProGluLys
586   TCAAAAAGC GTCATTATT GGATGCACA GGGGATCG CCTGAGAAG
      HisHis
631   CATCAC
```

FIGURE 25   pMBP-c2X-ToxoP30del10(52-284aa)

```
   1  CCGACACCA TCGAATGGT GCAAAACCT TTCGCGGTA TGGCATGAT
  46  AGCGCCCGG AAGAGAGTC AATTCAGGG TGGTGAATG TGAAACCAG
  91  TAACGTTAT ACGATGTCG CAGAGTATG CCGGTGTCT CTTATCAGA
 136  CCGTTTCCC GCGTGGTGA ACCAGGCCA GCCACGTTT CTGCGAAAA
 181  CGCGGGAAA AAGTGGAAG CGGCGATGG CGGAGCTGA ATTACATTC
 226  CCAACCGCG TGGCACAAC AACTGGCGG GCAAACACT CGTTGCTGA
 271  TTGGCGTTG CCACCTCCA GTCTGGCCC TGCACGCGC CGTCGCAAA
 316  TTGTCGCGG CGATTAAAT CTCGCGCCG ATCAACTGG GTGCCAGCG
 361  TGGTGGTGT CGATGGTAG AACGAAGCG GCGTCGAAG CCTGTAAAG
 406  CGGCGGTGC ACAATCTTC TCGCGCAAC GCGTCAGTG GCTGATCA
 451  TTAACTATC CGCTGGATG ACCAGGATG CCATTGCTG TGGAAGCTG
 496  CCTGCACTA ATGTTCCGG CGTTATTTC TTGATGTCT CTGACCAGA
 541  CACCCATCA ACAGTATTA TTTTCTCCC ATGAAGACG GTACGCGAC
 586  TGGGCGTGG AGCATCTGG TCGCATTGG GTCACCAGC AAATCGCGC
 631  TGTTAGCGG GCCCATTAA GTTCTGTCT CGGCGCGTC TGCGTCTGG
 676  CTGGCTGGC ATAAATATC TCACTCGCA ATCAAATTC AGCCGATAG
 721  CGGAACGGG AAGGCGACT GGAGTGCCA TGTCCGGTT TCAACAAA
 766  CCATGCAAA TGCTGAATG AGGGCATCG TTCCCACTG CGATGCTGG
 811  TTGCCAACG ATCAGATGG CGCTGGGCG CAATGCGCG CCATTACCG
 856  AGTCCGGGC TGCGCGTTG GTGCGGATA TCTCGGTAG TGGGATACG
 901  ACGATACCG AAGACAGCT CATGTTATA TCCCGCCGT TAACCACCA
 946  TCAAACAGG ATTTTCGCC TGCTGGGGC AAACCAGCG TGGACCGCT
 991  TGCTGCAAC TCTCTCAGG GCCAGGCGG TGAAGGGCA ATCAGCTGT
1036  TGCCCGTCT CACTGGTGA AAAGAAAAA CCACCCTGG CGCCCAATA
1081  CGCAAACCG CCTCTCCCC GCGCGTTGG CCGATTCAT TAATGCAGC
1126  TGGCACGAC AGGTTTCCC GACTGGAAA GCGGGCAGT GAGCGCAAC
1171  GCAATTAAT GTAAGTTAG CTCACTCAT TAGGCACAA TTCTCATGT
1216  TTGACAGCT TATCATCGA CTGCACGGT GCACCAATG CTTCTGGCG
1261  TCAGGCAGC CATCGGAAG CTGTGGTAT GGCTGTGCA GGTCGTAAA
1306  TCACTGCAT AATTCGTGT CGCTCAAGG CGCACTCCC GTTCTGGAT
1351  AATGTTTTT TGCGCCGAC ATCATAACG GTTCTGGCA AATATTCTG
1396  AAATGAGCT GTTGACAAT TAATCATCG GCTCGTATA ATGTGTGGA
1441  ATTGTGAGC GGATAACAA TTTCACACA GGAAACAGC CAGTCCGTT
                                                      Met
1486  TAGGTGTTT TCACGAGCA CTTCACCAA CAAGGACCA TAGCATATG
      LysIleGlu GluGlyLys LeuValIle TrpIleAsn GlyAspLys
1531  AAAATCGAA GAAGGTAAA CTGGTAATC TGGATTAAC GGCGATAAA
      GlyTyrAsn GlyLeuAla GluValGly LysLysPhe GluLysAsp
1576  GGCTATAAC GGTCTCGCT GAAGTCGGT AAGAAATTC GAGAAAGAT
      ThrGlyIle LysValThr ValGluHis ProAspLys LeuGluGlu
1621  ACCGGAATT AAAGTCACC GTTGAGCAT CCGGATAAA CTGGAAGAG
      LysPhePro GlnValAla AlaThrGly AspGlyPro AspIleIle
1666  AAATTCCCA CAGGTTGCG GCAACTGGC GATGGCCCT GACATTATC
      PheTrpAla HisAspArg PheGlyGly TyrAlaGln SerGlyLeu
1711  TTCTGGGCA CACGACCGC TTTGGTGGC TACGCTCAA TCTGGCCTG
      LeuAlaGlu IleThrPro AspLysAla PheGlnAsp LysLeuTyr
```

FIGURE 25  pMBP-c2X-ToxoP30del10(52-284aa)

```
1756  TTGGCTGAA ATCACCCCG GACAAAGCG TTCCAGGAC AAGCTGTAT
      ProPheThr TrpAspAla ValArgTyr AsnGlyLys LeuIleAla
1801  CCGTTTACC TGGGATGCC GTACGTTAC AACGGCAAG CTGATTGCT
      TyrProIle AlaValGlu AlaLeuSer LeuIleTyr AsnLysAsp
1846  TACCCGATC GCTGTTGAA GCGTTATCG CTGATTTAT AACAAAGAT
      LeuLeuPro AsnProPro LysThrTrp GluGluIle ProAlaLeu
1891  CTGCTGCCG AACCCGCCA AAACCTGG GAAGAGATC CCGGCGCTG
      AspLysGlu LeuLysAla LysGlyLys SerAlaLeu MetPheAsn
1936  GATAAAGAA CTGAAAGCG AAAGGTAAG AGCGCGCTG ATGTTCAAC
      LeuGlnGlu ProTyrPhe ThrTrpPro LeuIleAla AlaAspGly
1981  CTGCAAGAA CCGTACTTC ACCTGGCCG CTGATTGCT GCTGACGGG
      GlyTyrAla PheLysTyr GluAsnGly LysTyrAsp IleLysAsp
2026  GGTTATGCG TTCAAGTAT GAAAACGGC AAGTACGAC ATTAAAGAC
      ValGlyVal AspAsnAla GlyAlaLys AlaGlyLeu ThrPheLeu
2071  GTGGGCGTG GATAACGCT GGCGCGAAA GCGGGTCTG ACCTTCCTG
      ValAspLeu IleLysAsn LysHisMet AsnAlaAsp ThrAspTyr
2116  GTTGACCTG ATTAAAAAC AAACACATG AATGCAGAC ACCGATTAC
      SerIleAla GluAlaAla PheAsnLys GlyGluThr AlaMetThr
2161  TCCATCGCA GAAGCTGCC TTTAATAAA GGCGAAACA GCGATGACC
      IleAsnGly ProTrpAla TrpSerAsn IleAspThr SerLysVal
2206  ATCAACGGC CCGTGGGCA TGGTCCAAC ATCGACACC AGCAAAGTG
      AsnTyrGly ValThrVal LeuProThr PheLysGly GlnProSer
2251  AATTATGGT GTAACGGTA CTGCCGACC TTCAAGGGT CAACCATCC
      LysProPhe ValGlyVal LeuSerAla GlyIleAsn AlaAlaSer
2296  AAACCGTTC GTTGGCGTG CTGAGCGCA GGTATTAAC GCCGCCAGT
      ProAsnLys GluLeuAla LysGluPhe LeuGluAsn TyrLeuLeu
2341  CCGAACAAA GAGCTGGCA AAAGAGTTC CTCGAAAAC TATCTGCTG
      ThrAspGlu GlyLeuGlu AlaValAsn LysAspLys ProLeuGly
2386  ACTGATGAA GGTCTGGAA GCGGTTAAT AAAGACAAA CCGCTGGGT
      AlaValAla LeuLysSer TyrGluGlu GluLeuAla LysAspPro
2431  GCCGTAGCG CTGAAGTCT TACGAGGAA GAGTTGGCG AAAGATCCA
      ArgIleAla AlaThrMet GluAsnAla GlnLysGly GluIleMet
2476  CGTATTGCC GCCACTATG GAAAACGCC CAGAAAGGT GAAATCATG
      ProAsnIle ProGlnMet SerAlaPhe TrpTyrAla ValArgThr
2521  CCGAACATC CCGCAGATG TCCGCTTTC TGGTATGCC GTGCGTACT
      AlaValIle AsnAlaAla SerGlyArg GlnThrVal AspGluAla
2566  GCGGTGATC AACGCCGCC AGCGGTCGT CAGACTGTC GATGAAGCC
      LeuLysAsp AlaGlnThr AsnSerSer SerAsnAsn AsnAsnAsn
2611  CTGAAAGAC GCGCAGACT AATTCGAGC TCGAACAAC AACAACAAT
      AsnAsnAsn AsnAsnLeu GlyIleGlu GlyArgIle SerGluPhe
2656  AACAATAAC AACAACCTC GGGATCGAG GGAAGGATT TCAGAATTC
      LeuValAla AsnGlnVal ValThrCys ProAspLys LysSerThr
2701  CTTGTTGCC AATCAAGTT GTCACCTGC CCAGATAAA AAATCGACA
      AlaAlaVal IleLeuThr ProThrGlu AsnHisPhe ThrLeuLys
2746  GCCGCGGTC ATTCTCACA CCGACGGAG AACCACTTC ACTCTCAAG
      CysProLys ThrAlaLeu ThrGluPro ProThrLeu AlaTyrSer
```

FIGURE 25  pMBP-c2X-ToxoP30del10(52-284aa)

```
2791  TGCCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACAGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGlyGly ProThrThr MetThrLeu ValCysGly
3151  AAGTTGTCT GCGGGAGGA CCCACTACA ATGACCCTC GTGTGCGGG
      LysAspGly ValLysVal ProGlnAsp AsnAsnGln TyrCysSer
3196  AAAGATGGA GTCAAAGTT CCTCAAGAC AACAATCAG TACTGTTCC
      GlyThrThr LeuThrGly CysAsnGlu LysSerPhe LysAspIle
3241  GGGACGACG CTGACTGGT TGCAACGAG AAATCGTTC AAAGATATT
      LeuProLys LeuThrGlu AsnProTrp GlnGlyAsn AlaSerSer
3286  TTGCCAAAA TTAACTGAG AACCCGTGG CAGGGTAAC GCTTCGAGT
      AspLysGly AlaThrLeu ThrIleLys LysGluAla PheProAla
3331  GATAAGGGT GCCACGCTA ACGATCAAG AAGGAAGCA TTTCCAGCC
      GluSerLys SerValIle IleGly
3376  GAGTCAAAA AGCGTCATT ATTGGATGA AAGCTTGGC ACTGGCCGT
3421  CGTTTTACA ACGTCGTGA CTGGGAAAA CCCTGGCGT TACCCAACT
3466  TAATCGCCT TGCAGCACA TCCCCCTTT CGCCAGCTG GCGTAATAG
3511  CGAAGAGGC CCGCACCGA TCGCCCTTC CAACAGTT GCGCAGCCT
3556  GAATGGCGA ATGGCAGCT TGGCTGTTT TGGCGGATG AGATAAGAT
3601  TTTCAGCCT GATACAGAT TAAATCAGA ACGCAGAAG CGGTCTGAT
3646  AAAACAGAA TTTGCCTGG CGGCAGTAG CGCGGTGGT CCCACCTGA
3691  CCCCATGCC GAACTCAGA AGTGAAACG CCGTAGCGC CGATGGTAG
3736  TGTGGGGTC TCCCCATGC GAGAGTAGG GAACTGCCA GGCATCAAA
3781  TAAAACGAA AGGCTCAGT CGAAAGACT GGGCCTTTC GTTTTATCT
3826  GTTGTTTGT CGGTGAACG CTCTCCTGA GTAGGACAA ATCCGCCGG
3871  GAGCGGATT TGAACGTTG CGAAGCAAC GGCCCGGAG GGTGGCGGG
3916  CAGGACGCC CGCCATAAA CTGCCAGGC ATCAAATTA AGCAGAAGG
3961  CCATCCTGA CGGATGGCC TTTTTGCGT TTCTACAAA CTCTTTTTG
4006  TTTATTTTT CTAAATACA TTCAAATAT GTATCCGCT CATGAGACA
4051  ATAACCCTG ATAAATGCT TCAATAATA TTGAAAAAG GAAGAGTAT
4096  GAGTATTCA ACATTTCCG TGTCGCCCT TATTCCCTT TTTTGCGGC
4141  ATTTTGCCT TCCTGTTTT TGCTCACCC AGAAACGCT GGTGAAAGT
4186  AAAAGATGC TGAAGATCA GTTGGGTGC ACGAGTGGG TTACATCGA
4231  ACTGGATCT CAACAGCGG TAAGATCCT TGAGAGTTT CGCCCCGA
```

FIGURE 25   pMBP-c2X-ToxoP30del10(52-284aa)

```
4276  AGAACGTTC TCCAATGAT GAGCACTTT TAAAGTTCT GCTATGTGG
4321  CGCGGTATT ATCCCGTGT TGACGCCGG GCAAGAGCA ACTCGGTCG
4366  CCGCATACA CTATTCTCA GAATGACTT GGTTGAGTA CTCACCAGT
4411  CACAGAAAA GCATCTTAC GGATGGCAT GACAGTAAG AGAATTATG
4456  CAGTGCTGC CATAACCAT GAGTGATAA CACTGCGGC CAACTTACT
4501  TCTGACAAC GATCGGAGG ACCGAAGGA GCTAACCGC TTTTTTGCA
4546  CAACATGGG GGATCATGT AACTCGCCT TGATCGTTG GGAACCGGA
4591  GCTGAATGA AGCCATACC AAACGACGA GCGTGACAC CACGATGCC
4636  TGTAGCAAT GGCAACAAC GTTGCGCAA ACTATTAAC TGGCGAACT
4681  ACTTACTCT AGCTTCCCG GCAACAATT AATAGACTG GATGGAGGC
4726  GGATAAAGT TGCAGGACC ACTTCTGCG CTCGGCCCT TCCGGCTGG
4771  CTGGTTTAT TGCTGATAA ATCTGGAGC CGGTGAGCG TGGGTCTCG
4816  CGGTATCAT TGCAGCACT GGGGCCAGA TGGTAAGCC CTCCCGTAT
4861  CGTAGTTAT CTACACGAC GGGGAGTCA GGCAACTAT GGATGAACG
4906  AAATAGACA GATCGCTGA GATAGGTGC CTCACTGAT TAAGCATTG
4951  GTAACTGTC AGACCAAGT TTACTCATA TATACTTTA GATTGATTT
4996  ACCCCGGTT GATAATCAG AAAAGCCCC AAAAACAGG AAGATTGTA
5041  TAAGCAAAT ATTTAAATT GTAACGTT AATATTTTG TTAAAATTC
5086  GCGTTAAAT TTTTGTTAA ATCAGCTCA TTTTTTAAC CAATAGGCC
5131  GAAATCGGC AAAATCCCT TATAAATCA AAAGAATAG ACCGAGATA
5176  GGGTTGAGT GTTGTTCCA GTTTGGAAC AAGAGTCCA CTATTAAAG
5221  AACGTGGAC TCCAACGTC AAAGGGCGA AAAACCGTC TATCAGGGC
5266  GATGGCCCA CTACGTGAA CCATCACCC AAATCAAGT TTTTTGGGG
5311  TCGAGGTGC CGTAAAGCA CTAAATCGG AACCCTAAA GGGAGCCCC
5356  CGATTTAGA GCTTGACGG GGAAAGCCG GCGAACGTG GCGAGAAAG
5401  GAAGGGAAG AAAGCGAAA GGAGCGGGC GCTAGGGCG CTGGCAAGT
5446  GTAGCGGTC ACGCTGCGC GTAACCACC ACACCCGCC GCGCTTAAT
5491  GCGCCGCTA CAGGGCGCG TAAAAGGAT CTAGGTGAA GATCCTTTT
5536  TGATAATCT CATGACCAA AATCCCTTA ACGTGAGTT TTCGTTCCA
5581  CTGAGCGTC AGACCCCGT AGAAAAGAT CAAAGGATC TTCTTGAGA
5626  TCCTTTTTT TCTGCGCGT AATCTGCTG CTTGCAAAC AAAAAAACC
5671  ACCGCTACC AGCGGTGGT TTGTTTGCC GGATCAAGA GCTACCAAC
5716  TCTTTTTCC GAAGGTAAC TGGCTTCAG CAGAGCGCA GATACCAAA
5761  TACTGTCCT TCTAGTGTA GCCGTAGTT AGGCCACCA CTTCAAGAA
5806  CTCTGTAGC ACCGCCTAC ATACCTCGC TCTGCTAAT CCTGTTACC
5851  AGTGGCTGC TGCCAGTGG CGATAAGTC GTGTCTTAC CGGGTTGGA
5896  CTCAAGACG ATAGTTACC GGATAAGGC GCAGCGGTC GGGCTGAAC
5941  GGGGGGTTC GTGCACACA GCCCAGCTT GGAGCGAAC GACCTACAC
5986  CGAACTGAG ATACCTACA GCGTGAGCT ATGAGAAAG CGCCACGCT
6031  TCCCGAAGG GAGAAAGGC GGACAGGTA TCCGGTAAG CGGCAGGGT
6076  CGGAACAGG AGAGCGCAC GAGGGAGCT TCCAGGGGG AAACGCCTG
6121  GTATCTTTA TAGTCCTGT CGGGTTTCG CCACCTCTG ACTTGAGCG
6166  TCGATTTTT GTGATGCTC GTCAGGGGG GCGGAGCCT ATGGAAAAA
6211  CGCCAGCAA CGCGGCCTT TTTACGGTT CCTGGCCTT TTGCTGGCC
6256  TTTTGCTCA CATGTTCTT TCCTGCGTT ATCCCCTGA TTCTGTGGA
6301  TAACCGTAT TACCGCCTT TGAGTGAGC TGATACCGC TCGCCGCAG
```

FIGURE 25 pMBP-c2X-ToxoP30del10(52-284aa)

```
6346  CCGAACGAC  CGAGCGCAG  CGAGTCAGT  GAGCGAGGA  AGCGGAAGA
6391  GCGCCTGAT  GCGGTATTT  TCTCCTTAC  GCATCTGTG  CGGTATTTC
6436  ACACCGCAT  ATATGGTGC  ACTCTCAGT  ACAATCTGC  TCTGATGCC
6481  GCATAGTTA  AGCCAGTAT  ACACTCCGC  TATCGCTAC  GTGACTGGG
6526  TCATGGCTG  CGCCCCGAC  ACCCGCCAA  CACCCGCTG  ACGCGCCCT
6571  GACGGGCTT  GTCTGCTCC  CGGCATCCG  CTTACAGAC  AAGCTGTGA
6616  CCGTCTCCG  GGAGCTGCA  TGTGTCAGA  GGTTTTCAC  CGTCATCAC
6661  CGAAACGCG  CGAGGCAGC  TGCGGTAAA  GCTCATCAG  CGTGGTCGT
6706  GCAGCGATT  CACAGATGT  CTGCCTGTT  CATCCGCGT  CCAGCTCGT
6751  TGAGTTTCT  CCAGAAGCG  TTAATGTCT  GGCTTCTGA  TAAAGCGGG
6796  CCATGTTAA  GGGCGGTTT  TTTCCTGTT  TGGTCACTG  ATGCCTCCG
6841  TGTAAGGGG  GATTTCTGT  TCATGGGGG  TAATGATAC  CGATGAAAC
6886  GAGAGAGGA  TGCTCACGA  TACGGGTTA  CTGATGATG  AACATGCCC
6931  GGTTACTGG  AACGTTGTG  AGGGTAAAC  AACTGGCGG  TATGGATGC
6976  GGCGGGACC  AGAGAAAAA  TCACTCAGG  GTCAATGCC  AGCGCTTCG
7021  TTAATACAG  ATGTAGGTG  TTCCACAGG  GTAGCCAGC  AGCATCCTG
7066  CGATGCAGA  TCCGGAACA  TAATGGTGC  AGGGCGCTG  ACTTCCGCG
7111  TTTCCAGAC  TTTACGAAA  CACGGAAAC  CGAAGACCA  TTCATGTTG
7156  TTGCTCAGG  TCGCAGACG  TTTTGCAGC  AGCAGTCGC  TTCACGTTC
7201  GCTCGCGTA  TCGGTGATT  CATTCTGCT  AACCAGTAA  GGCAACCCC
7246  GCCAGCCTA  GCCGGGTCC  TCAACGACA  GGAGCACGA  TCATGCGCA
7291  CCCGTGGCC  AGGACCCAA  CGCTGCCCG  AAATT
```

FIGURE 26  ToxoP30del10(52-284aa)

```
         LeuValAla AsnGlnVal ValThrCys ProAspLys LysSerThr
  1      CTTGTTGCC AATCAAGTT GTCACCTGC CCAGATAAA AAATCGACA
         AlaAlaVal IleLeuThr ProThrGlu AsnHisPhe ThrLeuLys
 46      GCCGCGGTC ATTCTCACA CCGACGGAG AACCACTTC ACTCTCAAG
         CysProLys ThrAlaLeu ThrGluPro ProThrLeu AlaTyrSer
 91      TGCCCTAAA ACAGCGCTC ACAGAGCCT CCCACTCTT GCGTACTCA
         ProAsnArg GlnIleCys ProAlaGly ThrThrSer SerCysThr
136      CCCAACAGG CAAATCTGC CCAGCGGGT ACTACAAGT AGCTGTACA
         SerLysAla ValThrLeu SerSerLeu IleProGlu AlaGluAsp
181      TCAAAGGCT GTAACATTG AGCTCCTTG ATTCCTGAA GCAGAAGAT
         SerTrpTrp ThrGlyAsp SerAlaSer LeuAspThr AlaGlyIle
226      AGCTGGTGG ACGGGGGAT TCTGCTAGT CTCGACACG GCAGGCATC
         LysLeuThr ValProIle GluLysPhe ProValThr ThrGlnThr
271      AAACTCACA GTTCCAATC GAGAAGTTC CCCGTGACA ACGCAGACG
         PheValVal GlyCysIle LysGlyAsp AspAlaGln SerCysMet
316      TTTGTGGTC GGTTGCATC AAGGGAGAC GACGCACAG AGTTGTATG
         ValThrVal ThrValGln AlaArgAla SerSerVal ValAsnAsn
361      GTCACAGTG ACAGTACAA GCCAGAGCC TCATCGGTC GTCAATAAT
         ValAlaArg CysSerTyr GlyAlaAsp SerThrLeu GlyProVal
406      GTCGCAAGG TGCTCCTAC GGTGCAGAC AGCACTCTT GGTCCTGTC
         LysLeuSer AlaGlyGly ProThrThr MetThrLeu ValCysGly
451      AAGTTGTCT GCGGGAGGA CCCACTACA ATGACCCTC GTGTGCGGG
         LysAspGly ValLysVal ProGlnAsp AsnAsnGln TyrCysSer
496      AAAGATGGA GTCAAAGTT CCTCAAGAC AACAATCAG TACTGTTCC
         GlyThrThr LeuThrGly CysAsnGlu LysSerPhe LysAspIle
541      GGGACGACG CTGACTGGT TGCAACGAG AAATCGTTC AAAGATATT
         LeuProLys LeuThrGlu AsnProTrp GlnGlyAsn AlaSerSer
586      TTGCCAAAA TTAACTGAG AACCCGTGG CAGGGTAAC GCTTCGAGT
         AspLysGly AlaThrLeu ThrIleLys LysGluAla PheProAla
631      GATAAGGGT GCCACGCTA ACGATCAAG AAGGAAGCA TTTCCAGCC
         GluSerLys SerValIle IleGly
676      GAGTCAAAA AGCGTCATT ATTGGA
```

FIGURE 28  pMBP-c2X-ToxoP30del11(52-214aa)

```
   1  CCGACACCA TCGAATGGT GCAAAACCT TTCGCGGTA TGGCATGAT
  46  AGCGCCCGG AAGAGAGTC AATTCAGGG TGGTGAATG TGAAACCAG
  91  TAACGTTAT ACGATGTCG CAGAGTATG CCGGTGTCT CTTATCAGA
 136  CCGTTTCCC GCGTGGTGA ACCAGGCCA GCCACGTTT CTGCGAAAA
 181  CGCGGGAAA AAGTGGAAG CGGCGATGG CGGAGCTGA ATTACATTC
 226  CCAACCGCG TGGCACAAC AACTGGCGG GCAAACAGT CGTTGCTGA
 271  TTGGCGTTG CCACCTCCA GTCTGGCCC TGCACGCGC CGTCGCAAA
 316  TTGTCGCGG CGATTAAAT CTCGCGCCG ATCAACTGG GTGCCAGCG
 361  TGGTGGTGT CGATGGTAG AACGAAGCG CGTCGAAG CCTGTAAAG
 406  CGGCGGTGC ACAATCTTC TCGCGCAAC GCGTCAGTG GCTGATCA
 451  TTAACTATC CGCTGGATG ACCAGGATG CCATTGCTG TGGAAGCTG
 496  CCTGCACTA ATGTTCCGG CGTTATTTC TTGATGTCT CTGACCAGA
 541  CACCCATCA ACAGTATTA TTTTCTCCC ATGAAGACG GTACGCGAC
 586  TGGGCGTGG AGCATCTGG TCGCATTGG GTCACCAGC AAATCGCGC
 631  TGTTAGCGG GCCCATTAA GTTCTGTCT CGGCGCGTC TGCGTCTGG
 676  CTGGCTGGC ATAAATATC TCACTCGCA ATCAAATTC AGCCGATAG
 721  CGGAACGGG AAGGCGACT GGAGTGCCA TGTCCGGTT TCAACAAA
 766  CCATGCAAA TGCTGAATG AGGGCATCG TTCCCACTG CGATGCTGG
 811  TTGCCAACG ATCAGATGG CGCTGGGCG CAATGCGCG CCATTACCG
 856  AGTCCGGGC TGCGCGTTG GTGCGGATA TCTCGGTAG TGGGATACG
 901  ACGATACCG AAGACAGCT CATGTTATA TCCCGCCGT TAACCACCA
 946  TCAAACAGG ATTTTCGCC TGCTGGGGC AAACCAGCG TGGACCGCT
 991  TGCTGCAAC TCTCTCAGG GCCAGGCGG TGAAGGGCA ATCAGCTGT
1036  TGCCCGTCT CACTGGTGA AAAGAAAAA CCACCCTGG CGCCCAATA
1081  CGCAAACCG CCTCTCCCC GCGCGTTGG CCGATTCAT TAATGCAGC
1126  TGGCACGAC AGGTTTCCC GACTGGAAA GCGGGCAGT GAGCGCAAC
1171  GCAATTAAT GTAAGTTAG CTCACTCAT TAGGCACAA TTCTCATGT
1216  TTGACAGCT TATCATCGA CTGCACGGT GCACCAATG CTTCTGGCG
1261  TCAGGCAGC CATCGGAAG CTGTGGTAT GGCTGTGCA GGTCGTAAA
1306  TCACTGCAT AATTCGTGT CGCTCAAGG CGCACTCCC GTTCTGGAT
1351  AATGTTTTT TGCGCCGAC ATCATAACG GTTCTGGCA AATATTCTG
1396  AAATGAGCT GTTGACAAT TAATCATCG GCTCGTATA ATGTGTGGA
1441  ATTGTGAGC GGATAACAA TTTCACACA GGAAACAGC CAGTCCGTT
                                                            Met
1486  TAGGTGTTT TCACGAGCA CTTCACCAA CAAGGACCA TAGCATATG
      LysIleGlu GluGlyLys LeuValIle TrpIleAsn GlyAspLys
1531  AAAATCGAA GAAGGTAAA CTGGTAATC TGGATTAAC GGCGATAAA
      GlyTyrAsn GlyLeuAla GluValGly LysLysPhe GluLysAsp
1576  GGCTATAAC GGTCTCGCT GAAGTCGGT AAGAAATTC GAGAAAGAT
      ThrGlyIle LysValThr ValGluHis ProAspLys LeuGluGlu
1621  ACCGGAATT AAAGTCACC GTTGAGCAT CCGGATAAA CTGGAAGAG
      LysPhePro GlnValAla AlaThrGly AspGlyPro AspIleIle
1666  AAATTCCCA CAGGTTGCG GCAACTGGC GATGGCCCT GACATTATC
      PheTrpAla HisAspArg PheGlyGly TyrAlaGln SerGlyLeu
1711  TTCTGGGCA CACGACCGC TTTGGTGGC TACGCTCAA TCTGGCCTG
      LeuAlaGlu IleThrPro AspLysAla PheGlnAsp LysLeuTyr
```

FIGURE 28  pMBP-c2X-ToxoP30del11(52-214aa)

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAACCTGG GAAGAGATC CCGGCGCTG
     AspLysGlu LeuLysAla LysGlyLys SerAlaLeu MetPheAsn
1936 GATAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     CysProLys ThrAlaLeu ThrGluPro ProThrLeu AlaTyrSer
```

FIGURE 28   pMBP-c2X-ToxoP30del11(52-214aa)

```
2791  TGCCCTAAA ACAGCGCTC ACAGAGCCT CCCACTCTT GCGTACTCA
      ProAsnArg GlnIleCys ProAlaGly ThrThrSer SerCysThr
2836  CCCAACAGG CAAATCTGC CCAGCGGGT ACTACAAGT AGCTGTACA
      SerLysAla ValThrLeu SerSerLeu IleProGlu AlaGluAsp
2881  TCAAAGGCT GTAACATTG AGCTCCTTG ATTCCTGAA GCAGAAGAT
      SerTrpTrp ThrGlyAsp SerAlaSer LeuAspThr AlaGlyIle
2926  AGCTGGTGG ACGGGGGAT TCTGCTAGT CTCGACACG GCAGGCATC
      LysLeuThr ValProIle GluLysPhe ProValThr ThrGlnThr
2971  AAACTCACA GTTCCAATC GAGAAGTTC CCCGTGACA ACGCAGACG
      PheValVal GlyCysIle LysGlyAsp AspAlaGln SerCysMet
3016  TTTGTGGTC GGTTGCATC AAGGGAGAC GACGCACAG AGTTGTATG
      ValThrVal ThrValGln AlaArgAla SerSerVal ValAsnAsn
3061  GTCACAGTG ACAGTACAA GCCAGAGCC TCATCGGTC GTCAATAAT
      ValAlaArg CysSerTyr GlyAlaAsp SerThrLeu GlyProVal
3106  GTCGCAAGG TGCTCCTAC GGTGCAGAC AGCACTCTT GGTCCTGTC
      LysLeuSer AlaGluGly ProThrThr MetThrLeu Val
3151  AAGTTGTCT GCGGAAGGA CCCACTACA ATGACCCTC GTGTGAAAG
3196  CTTGGCACT GGCCGTCGT TTTACAACG TCGTGACTG GGAAAACCC
3241  TGGCGTTAC CCAACTTAA TCGCCTTGC AGCACATCC CCCTTTCGC
3286  CAGCTGGCG TAATAGCGA AGAGGCCCG CACCGATCG CCCTTCCCA
3331  ACAGTTGCG CAGCCTGAA TGGCGAATG GCAGCTTGG CTGTTTTGG
3376  CGGATGAGA TAAGATTTT CAGCCTGAT ACAGATTAA ATCAGAACG
3421  CAGAAGCGG TCTGATAAA ACAGAATTT GCCTGGCGG CAGTAGCGC
3466  GGTGGTCCC ACCTGACCC CATGCCGAA CTCAGAAGT GAAACGCCG
3511  TAGCGCCGA TGGTAGTGT GGGGTCTCC CCATGCGAG AGTAGGGAA
3556  CTGCCAGGC ATCAAATAA AACGAAAGG CTCAGTCGA AAGACTGGG
3601  CCTTTCGTT TTATCTGTT GTTTGTCGG TGAACGCTC TCCTGAGTA
3646  GGACAAATC CGCCGGGAG CGGATTTGA ACGTTGCGA AGCAACGGC
3691  CCGGAGGGT GGCGGGCAG GACGCCCGC CATAAACTG CCAGGCATC
3736  AAATTAAGC AGAAGGCCA TCCTGACGG ATGGCCTTT TTGCGTTTC
3781  TACAAACTC TTTTTGTTT ATTTTTCTA AATACATTC AAATATGTA
3826  TCCGCTCAT GAGACAATA ACCCTGATA AATGCTTCA ATAATATTG
3871  AAAAAGGAA GAGTATGAG TATTCAACA TTTCCGTGT CGCCCTTAT
3916  TCCCTTTTT TGCGGCATT TTGCCTTCC TGTTTTTGC TCACCCAGA
3961  AACGCTGGT GAAAGTAAA AGATGCTGA AGATCAGTT GGGTGCACG
4006  AGTGGGTTA CATCGAACT GGATCTCAA CAGCGGTAA GATCCTTGA
4051  GAGTTTTCG CCCCAAGAA CGTTCTCC AATGATGAG CACTTTTAA
4096  AGTTCTGCT ATGTGGCGC GGTATTATC CCGTGTTGA CGCCGGGCA
4141  AGAGCAACT CGGTCGCCG CATACACTA TTCTCAGAA TGACTTGGT
4186  TGAGTACTC ACCAGTCAC AGAAAAGCA TCTTACGGA TGGCATGAC
4231  AGTAAGAGA ATTATGCAG TGCTGCCAT AACCATGAG TGATAACAC
4276  TGCGGCCAA CTTACTTCT GACAACGAT CGGAGGACC GAAGGAGCT
4321  AACCGCTTT TTTGCACAA CATGGGGGA TCATGTAAC TCGCCTTGA
4366  TCGTTGGGA ACCGGAGCT GAATGAAGC CATACCAAA CGACGAGCG
4411  TGACACCAC GATGCCTGT AGCAATGGC AACAACGTT GCGCAAACT
4456  ATTAACTGG CGAACTACT TACTCTAGC TTCCCGGCA ACAATTAAT
```

FIGURE 28  pMBP-c2X-ToxoP30del11(52-214aa)

```
4501  AGACTGGAT GGAGGCGGA TAAAGTTGC AGGACCACT TCTGCGCTC
4546  GGCCCTTCC GGCTGGCTG GTTTATTGC TGATAAATC TGGAGCCGG
4591  TGAGCGTGG GTCTCGCGG TATCATTGC AGCACTGGG GCCAGATGG
4636  TAAGCCCTC CCGTATCGT AGTTATCTA CACGACGGG GAGTCAGGC
4681  AACTATGGA TGAACGAAA TAGACAGAT CGCTGAGAT AGGTGCCTC
4726  ACTGATTAA GCATTGGTA ACTGTCAGA CCAAGTTTA CTCATATAT
4771  ACTTTAGAT TGATTTACC CCGGTTGAT AATCAGAAA AGCCCCAAA
4816  AACAGGAAG ATTGTATAA GCAAATATT TAAATTGTA AACGTTAAT
4861  ATTTTGTTA AAATTCGCG TTAAATTTT TGTTAAATC AGCTCATTT
4906  TTTAACCAA TAGGCCGAA ATCGGCAAA ATCCCTTAT AAATCAAAA
4951  GAATAGACC GAGATAGGG TTGAGTGTT GTTCCAGTT TGGAACAAG
4996  AGTCCACTA TTAAAGAAC GTGGACTCC AACGTCAAA GGGCGAAAA
5041  ACCGTCTAT CAGGGCGAT GGCCCACTA CGTGAACCA TCACCCAAA
5086  TCAAGTTTT TTGGGGTCG AGGTGCCGT AAAGCACTA AATCGGAAC
5131  CCTAAAGGG AGCCCCCGA TTTAGAGCT TGACGGGGA AAGCCGGCG
5176  AACGTGGCG AGAAAGGAA GGGAAGAAA GCGAAAGGA GCGGGCGCT
5221  AGGGCGCTG GCAAGTGTA GCGGTCACG CTGCGCGTA ACCACCACA
5266  CCCGCCGCG CTTAATGCG CCGCTACAG GGCGCGTAA AAGGATCTA
5311  GGTGAAGAT CCTTTTTGA TAATCTCAT GACCAAAAT CCCTTAACG
5356  TGAGTTTTC GTTCCACTG AGCGTCAGA CCCCGTAGA AAAGATCAA
5401  AGGATCTTC TTGAGATCC TTTTTTTCT GCGCGTAAT CTGCTGCTT
5446  GCAAACAAA AAAACCACC GCTACCAGC GGTGGTTTG TTTGCCGGA
5491  TCAAGAGCT ACCAACTCT TTTTCCGAA GGTAACTGG CTTCAGCAG
5536  AGCGCAGAT ACCAAATAC TGTCCTTCT AGTGTAGCC GTAGTTAGG
5581  CCACCACTT CAAGAACTC TGTAGCACC GCCTACATA CCTCGCTCT
5626  GCTAATCCT GTTACCAGT GGCTGCTGC CAGTGGCGA TAAGTCGTG
5671  TCTTACCGG GTTGGACTC AAGACGATA GTTACCGGA TAAGGCGCA
5716  GCGGTCGGG CTGAACGGG GGGTTCGTG CACACAGCC CAGCTTGGA
5761  GCGAACGAC CTACACCGA ACTGAGATA CCTACAGCG TGAGCTATG
5806  AGAAAGCGC CACGCTTCC CGAAGGGAG AAAGGCGGA CAGGTATCC
5851  GGTAAGCGG CAGGGTCGG AACAGGAGA GCGCACGAG GGAGCTTCC
5896  AGGGGGAAA CGCCTGGTA TCTTTATAG TCCTGTCGG GTTTCGCCA
5941  CCTCTGACT TGAGCGTCG ATTTTGTG ATGCTCGTC AGGGGGGCG
5986  GAGCCTATG GAAAAACGC CAGCAACGC GGCCTTTTT ACGGTTCCT
6031  GGCCTTTTG CTGGCCTTT TGCTCACAT GTTCTTTCC TGCGTTATC
6076  CCCTGATTC TGTGGATAA CCGTATTAC CGCCTTTGA GTGAGCTGA
6121  TACCGCTCG CCGCAGCCG AACGACCGA GCGCAGCGA GTCAGTGAG
6166  CGAGGAAGC GGAAGAGCG CCTGATGCG GTATTTCT CCTTACGCA
6211  TCTGTGCGG TATTTCACA CCGCATATA TGGTGCACT CTCAGTACA
6256  ATCTGCTCT GATGCCGCA TAGTTAAGC CAGTATACA CTCCGCTAT
6301  CGCTACGTG ACTGGGTCA TGGCTGCGC CCCGACACC CGCCAACAC
6346  CCGCTGACG CGCCCTGAC GGGCTTGTC TGCTCCCGG CATCCGCTT
6391  ACAGACAAG CTGTGACCG TCTCCGGGA GCTGCATGT GTCAGAGGT
6436  TTTCACCGT CATCACCGA AACGCGCGA GGCAGCTGC GGTAAAGCT
6481  CATCAGCGT GGTCGTGCA GCGATTCAC AGATGTCTG CCTGTTCAT
6526  CCGCGTCCA GCTCGTTGA GTTTCTCCA GAAGCGTTA ATGTCTGGC
```

FIGURE 28   pMBP-c2X-ToxoP30del11(52-214aa)

```
6571  TTCTGATAA  AGCGGGCCA  TGTTAAGGG  CGGTTTTTT  CCTGTTTGG
6616  TCACTGATG  CCTCCGTGT  AAGGGGGAT  TTCTGTTCA  TGGGGGTAA
6661  TGATACCGA  TGAAACGAG  AGAGGATGC  TCACGATAC  GGGTTACTG
6706  ATGATGAAC  ATGCCCGGT  TACTGGAAC  GTTGTGAGG  GTAAACAAC
6751  TGGCGGTAT  GGATGCGGC  GGGACCAGA  GAAAAATCA  CTCAGGGTC
6796  AATGCCAGC  GCTTCGTTA  ATACAGATG  TAGGTGTTC  CACAGGGTA
6841  GCCAGCAGC  ATCCTGCGA  TGCAGATCC  GGAACATAA  TGGTGCAGG
6886  GCGCTGACT  TCCGCGTTT  CCAGACTTT  ACGAAACAC  GGAAACCGA
6931  AGACCATTC  ATGTTGTTG  CTCAGGTCG  CAGACGTTT  TGCAGCAGC
6976  AGTCGCTTC  ACGTTCGCT  CGCGTATCG  GTGATTCAT  TCTGCTAAC
7021  CAGTAAGGC  AACCCCGCC  AGCCTAGCC  GGGTCCTCA  ACGACAGGA
7066  GCACGATCA  TGCGCACCC  GTGGCCAGG  ACCCAACGC  TGCCCGAAA
7111  TT
```

FIGURE 29  ToxoP30del11(52-214aa)

```
        LeuValAla AsnGlnVal ValThrCys ProAspLys LysSerThr
    1   CTTGTTGCC AATCAAGTT GTCACCTGC CCAGATAAA AAATCGACA
        AlaAlaVal IleLeuThr ProThrGlu AsnHisPhe ThrLeuLys
   46   GCCGCGGTC ATTCTCACA CCGACGGAG AACCACTTC ACTCTCAAG
        CysProLys ThrAlaLeu ThrGluPro ProThrLeu AlaTyrSer
   91   TGCCCTAAA ACAGCGCTC ACAGAGCCT CCCACTCTT GCGTACTCA
        ProAsnArg GlnIleCys ProAlaGly ThrThrSer SerCysThr
  136   CCCAACAGG CAAATCTGC CCAGCGGGT ACTACAAGT AGCTGTACA
        SerLysAla ValThrLeu SerSerLeu IleProGlu AlaGluAsp
  181   TCAAAGGCT GTAACATTG AGCTCCTTG ATTCCTGAA GCAGAAGAT
        SerTrpTrp ThrGlyAsp SerAlaSer LeuAspThr AlaGlyIle
  226   AGCTGGTGG ACGGGGGAT TCTGCTAGT CTCGACACG GCAGGCATC
        LysLeuThr ValProIle GluLysPhe ProValThr ThrGlnThr
  271   AAACTCACA GTTCCAATC GAGAAGTTC CCCGTGACA ACGCAGACG
        PheValVal GlyCysIle LysGlyAsp AspAlaGln SerCysMet
  316   TTTGTGGTC GGTTGCATC AAGGGAGAC GACGCACAG AGTTGTATG
        ValThrVal ThrValGln AlaArgAla SerSerVal ValAsnAsn
  361   GTCACAGTG ACAGTACAA GCCAGAGCC TCATCGGTC GTCAATAAT
        ValAlaArg CysSerTyr GlyAlaAsp SerThrLeu GlyProVal
  406   GTCGCAAGG TGCTCCTAC GGTGCAGAC AGCACTCTT GGTCCTGTC
        LysLeuSer AlaGluGly ProThrThr MetThrLeu Val
  451   AAGTTGTCT GCGGAAGGA CCCACTACA ATGACCCTC GTG
```

FIGURE 31    pMBP-c2X-ToxoP30MIX1

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TTCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA ATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                                Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 31    pMBP-c2X-ToxoP30MIX1

```
1756  TTGGCTGAA  ATCACCCCG  GACAAAGCG  TTCCAGGAC  AAGCTGTAT
      ProPheThr  TrpAspAla  ValArgTyr  AsnGlyLys  LeuIleAla
1801  CCGTTTACC  TGGGATGCC  GTACGTTAC  AACGGCAAG  CTGATTGCT
      TyrProIle  AlaValGlu  AlaLeuSer  LeuIleTyr  AsnLysAsp
1846  TACCCGATC  GCTGTTGAA  GCGTTATCG  CTGATTTAT  AACAAAGAT
      LeuLeuPro  AsnProPro  LysThrTrp  GluGluIle  ProAlaLeu
1891  CTGCTGCCG  AACCCGCCA  AAAACCTGG  GAAGAGATC  CCGGCGCTG
      AspLysGlu  LeuLysAla  LysGlyLys  SerAlaLeu  MetPheAsn
1936  GATAAAGAA  CTGAAAGCG  AAAGGTAAG  AGCGCGCTG  ATGTTCAAC
      LeuGlnGlu  ProTyrPhe  ThrTrpPro  LeuIleAla  AlaAspGly
1981  CTGCAAGAA  CCGTACTTC  ACCTGGCCG  CTGATTGCT  GCTGACGGG
      GlyTyrAla  PheLysTyr  GluAsnGly  LysTyrAsp  IleLysAsp
2026  GGTTATGCG  TTCAAGTAT  GAAAACGGC  AAGTACGAC  ATTAAAGAC
      ValGlyVal  AspAsnAla  GlyAlaLys  AlaGlyLeu  ThrPheLeu
2071  GTGGGCGTG  GATAACGCT  GGCGCGAAA  GCGGGTCTG  ACCTTCCTG
      ValAspLeu  IleLysAsn  LysHisMet  AsnAlaAsp  ThrAspTyr
2116  GTTGACCTG  ATTAAAAAC  AAACACATG  AATGCAGAC  ACCGATTAC
      SerIleAla  GluAlaAla  PheAsnLys  GlyGluThr  AlaMetThr
2161  TCCATCGCA  GAAGCTGCC  TTTAATAAA  GGCGAAACA  GCGATGACC
      IleAsnGly  ProTrpAla  TrpSerAsn  IleAspThr  SerLysVal
2206  ATCAACGGC  CCGTGGGCA  TGGTCCAAC  ATCGACACC  AGCAAAGTG
      AsnTyrGly  ValThrVal  LeuProThr  PheLysGly  GlnProSer
2251  AATTATGGT  GTAACGGTA  CTGCCGACC  TTCAAGGGT  CAACCATCC
      LysProPhe  ValGlyVal  LeuSerAla  GlyIleAsn  AlaAlaSer
2296  AAACCGTTC  GTTGGCGTG  CTGAGCGCA  GGTATTAAC  GCCGCCAGT
      ProAsnLys  GluLeuAla  LysGluPhe  LeuGluAsn  TyrLeuLeu
2341  CCGAACAAA  GAGCTGGCA  AAAGAGTTC  CTCGAAAAC  TATCTGCTG
      ThrAspGlu  GlyLeuGlu  AlaValAsn  LysAspLys  ProLeuGly
2386  ACTGATGAA  GGTCTGGAA  GCGGTTAAT  AAAGACAAA  CCGCTGGGT
      AlaValAla  LeuLysSer  TyrGluGlu  GluLeuAla  LysAspPro
2431  GCCGTAGCG  CTGAAGTCT  TACGAGGAA  GAGTTGGCG  AAAGATCCA
      ArgIleAla  AlaThrMet  GluAsnAla  GlnLysGly  GluIleMet
2476  CGTATTGCC  GCCACTATG  GAAAACGCC  CAGAAAGGT  GAAATCATG
      ProAsnIle  ProGlnMet  SerAlaPhe  TrpTyrAla  ValArgThr
2521  CCGAACATC  CCGCAGATG  TCCGCTTTC  TGGTATGCC  GTGCGTACT
      AlaValIle  AsnAlaAla  SerGlyArg  GlnThrVal  AspGluAla
2566  GCGGTGATC  AACGCCGCC  AGCGGTCGT  CAGACTGTC  GATGAAGCC
      LeuLysAsp  AlaGlnThr  AsnSerSer  SerAsnAsn  AsnAsnAsn
2611  CTGAAAGAC  GCGCAGACT  AATTCGAGC  TCGAACAAC  AACAACAAT
      AsnAsnAsn  AsnAsnLeu  GlyIleGlu  GlyArgIle  SerGluPhe
2656  AACAATAAC  AACAACCTC  GGGATCGAG  GGAAGGATT  TCAGAATTC
      LeuValAla  AsnGlnVal  ValThrCys  ProAspLys  LysSerThr
2701  CTTGTTGCC  AATCAAGTT  GTCACCTGC  CCAGATAAA  AAATCGACA
      AlaAlaVal  IleLeuThr  ProThrGlu  AsnHisPhe  ThrLeuLys
2746  GCCGCGGTC  ATTCTCACA  CCGACGGAG  AACCACTTC  ACTCTCAAG
      CysProLys  ThrAlaLeu  ThrGluPro  ProThrLeu  AlaTyrSer
```

FIGURE 31   pMBP-c2X-ToxoP30MIX1

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACGGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValAlaGly
3151 AAGTTGTCT GCGGAAGGA CCCACTACA ATGACCCTC GTGGCTGGG
     LysAspGly ValLysVal ProGlnAsp AsnAsnGln TyrAlaSer
3196 AAAGATGGA GTCAAAGTT CCTCAAGAC AATAATCAG TACGCTTCC
     GlyThrThr LeuThrGly AlaAsnGlu LysSerPhe LysAspIle
3241 GGGACGACG CTGACTGGT GCTAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyAla ThrGlyGly SerProGlu
3376 GAGTCAAAA AGCGTCATT ATTGGAGCT ACAGGGGGA TCGCCTGAG
     LysHisHis AlaThrVal LysLeuGlu
3421 AAGCATCAC GCTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTTGGCGG ATGAGATAA
3646 GATTTTCAG CCTGATACA GATTAAATC AGAACGCAG AAGCGGTCT
3691 GATAAAACA GAATTTGCC TGGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG CCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AAGGAAGAG
4141 TATGAGTAT TCAACATTT CCGTGTCGC CCTTATTCC CTTTTTTGC
4186 GGCATTTTG CCTTCCTGT TTTTGCTCA CCCAGAAAC GCTGGTGAA
```

FIGURE 31  pMBP-c2X-ToxoP30MIX1

```
4231  AGTAAAAGA TGCTGAAGA TCAGTTGGG TGCACGAGT GGGTTACAT
4276  CGAACTGGA TCTCAACAG CGGTAAGAT CCTTGAGAG TTTTCGCCC
4321  CGAAGAACG TTCTCCAAT GATGAGCAC TTTTAAAGT CTGCTATG
4366  TGGCGCGGT ATTATCCCG TGTTGACGC CGGGCAAGA GCAACTCGG
4411  TCGCCGCAT ACACTATTC TCAGAATGA CTTGGTTGA GTACTCACC
4456  AGTCACAGA AAAGCATCT TACGGATGG CATGACAGT AAGAGAATT
4501  ATGCAGTGC TGCCATAAC CATGAGTGA TAACACTGC GGCCAACTT
4546  ACTTCTGAC AACGATCGG AGGACCGAA GGAGCTAAC CGCTTTTTT
4591  GCACAACAT GGGGGATCA TGTAACTCG CCTTGATCG TTGGGAACC
4636  GGAGCTGAA TGAAGCCAT ACCAAACGA CGAGCGTGA CACCACGAT
4681  GCCTGTAGC AATGGCAAC AACGTTGCG CAAACTATT AACTGGCGA
4726  ACTACTTAC TCTAGCTTC CCGGCAACA ATTAATAGA CTGGATGGA
4771  GGCGGATAA AGTTGCAGG ACCACTTCT GCGCTCGGC CCTTCCGGC
4816  TGGCTGGTT TATTGCTGA TAAATCTGG AGCCGGTGA GCGTGGGTC
4861  TCGCGGTAT CATTGCAGC ACTGGGGCC AGATGGTAA GCCCTCCCG
4906  TATCGTAGT TATCTACAC GACGGGGAG TCAGGCAAC TATGGATGA
4951  ACGAAATAG ACAGATCGC TGAGATAGG TGCCTCACT GATTAAGCA
4996  TTGGTAACT GTCAGACCA AGTTTACTC ATATATACT TTAGATTGA
5041  TTTACCCCG GTTGATAAT CAGAAAAGC CCCAAAAAC AGGAAGATT
5086  GTATAAGCA AATATTTAA ATTGTAAAC GTTAATATT TTGTTAAAA
5131  TTCGCGTTA AATTTTGT TAAATCAGC TCATTTTTT AACCAATAG
5176  GCCGAAATC GGCAAAATC CCTTATAAA TCAAAAGAA TAGACCGAG
5221  ATAGGGTTG AGTGTTGTT CCAGTTTGG AACAAGAGT CCACTATTA
5266  AAGAACGTG GACTCCAAC GTCAAAGGG CGAAAAACC GTCTATCAG
5311  GGCGATGGC CCACTACGT GAACCATCA CCCAAATCA GTTTTTTG
5356  GGGTCGAGG TGCCGTAAA GCACTAAAT CGGAACCCT AAAGGGAGC
5401  CCCCGATTT AGAGCTTGA CGGGGAAAG CCGGCGAAC GTGGCGAGA
5446  AAGGAAGGG AAGAAAGCG AAAGGAGCG GGCGCTAGG GCGCTGGCA
5491  AGTGTAGCG GTCACGCTG CGCGTAACC ACCACACCC GCCGCGCTT
5536  AATGCGCCG CTACAGGGC GCGTAAAAG GATCTAGGT GAAGATCCT
5581  TTTTGATAA TCTCATGAC CAAAATCCC TTAACGTGA GTTTTCGTT
5626  CCACTGAGC GTCAGACCC CGTAGAAAA GATCAAAGG ATCTTCTTG
5671  AGATCCTTT TTTTCTGCG CGTAATCTG CTGCTTGCA AACAAAAAA
5716  ACCACCGCT ACCAGCGGT GGTTTGTTT GCCGGATCA AGAGCTACC
5761  AACTCTTTT TCCGAAGGT AACTGGCTT CAGCAGAGC GCAGATACC
5806  AAATACTGT CCTTCTAGT GTAGCCGTA GTTAGGCCA CCACTTCAA
5851  GAACTCTGT AGCACCGCC TACATACCT CGCTCTGCT AATCCTGTT
5896  ACCAGTGGC TGCTGCCAG TGGCGATAA GTCGTGTCT TACCGGGTT
5941  GGACTCAAG ACGATAGTT ACCGGATAA GGCGCAGCG GTCGGGCTG
5986  AACGGGGGG TTCGTGCAC ACAGCCCAG CTTGGAGCG AACGACCTA
6031  CACCGAACT GAGATACCT ACAGCGTGA GCTATGAGA AAGCGCCAC
6076  GCTTCCCGA AGGGAGAAA GGCGGACAG GTATCCGGT AAGCGGCAG
6121  GGTCGGAAC AGGAGAGCG CACGAGGGA GCTTCCAGG GGGAAACGC
6166  CTGGTATCT TTATAGTCC TGTCGGGTT TCGCCACCT CTGACTTGA
6211  GCGTCGATT TTTGTGATG CTCGTCAGG GGGCGGAG CCTATGGAA
6256  AAACGCCAG CAACGCGGC CTTTTTACG GTTCCTGGC CTTTTGCTG
```

FIGURE 31 pMBP-c2X-ToxoP30MIX1

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT TCTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIGURE 32   ToxoP30MIX1

```
      LeuValAla AsnGlnVal ValThrCys ProAspLys LysSerThr
  1   CTTGTTGCC AATCAAGTT GTCACCTGC CCAGATAAA AAATCGACA
      AlaAlaVal IleLeuThr ProThrGlu AsnHisPhe ThrLeuLys
 46   GCCGCGGTC ATTCTCACA CCGACGGAG AACCACTTC ACTCTCAAG
      CysProLys ThrAlaLeu ThrGluPro ProThrLeu AlaTyrSer
 91   TGCCCTAAA ACAGCGCTC ACAGAGCCT CCCACTCTT GCGTACTCA
      ProAsnArg GlnIleCys ProAlaGly ThrThrSer SerCysThr
136   CCCAACAGG CAAATCTGC CCAGCGGGT ACTACAAGT AGCTGTACA
      SerLysAla ValThrLeu SerSerLeu IleProGlu AlaGluAsp
181   TCAAAGGCT GTAACATTG AGCTCCTTG ATTCCTGAA GCAGAAGAT
      SerTrpTrp ThrGlyAsp SerAlaSer LeuAspThr AlaGlyIle
226   AGCTGGTGG ACGGGGGAT TCTGCTAGT CTCGACACG GCAGGCATC
      LysLeuThr ValProIle GluLysPhe ProValThr ThrGlnThr
271   AAACTCACA GTTCCAATC GAGAAGTTC CCCGTGACA ACGCAGACG
      PheValVal GlyCysIle LysGlyAsp AspAlaGln SerCysMet
316   TTTGTGGTC GGTTGCATC AAGGGAGAC GACGCACAG AGTTGTATG
      ValThrVal ThrValGln AlaArgAla SerSerVal ValAsnAsn
361   GTCACGGTG ACAGTACAA GCCAGAGCC TCATCGGTC GTCAATAAT
      ValAlaArg CysSerTyr GlyAlaAsp SerThrLeu GlyProVal
406   GTCGCAAGG TGCTCCTAC GGTGCAGAC AGCACTCTT GGTCCTGTC
      LysLeuSer AlaGluGly ProThrThr MetThrLeu ValAlaGly
451   AAGTTGTCT GCGGAAGGA CCCACTACA ATGACCCTC GTGGCTGGG
      LysAspGly ValLysVal ProGlnAsp AsnAsnGln TyrAlaSer
496   AAAGATGGA GTCAAAGTT CCTCAAGAC AATAATCAG TACGCTTCC
      GlyThrThr LeuThrGly AlaAsnGlu LysSerPhe LysAspIle
541   GGGACGACG CTGACTGGT GCTAACGAG AAATCGTTC AAAGATATT
      LeuProLys LeuThrGlu AsnProTrp GlnGlyAsn AlaSerSer
586   TTGCCAAAA TTAACTGAG AACCCGTGG CAGGGTAAC GCTTCGAGT
      AspLysGly AlaThrLeu ThrIleLys LysGluAla PheProAla
631   GATAAGGGT GCCACGCTA ACGATCAAG AAGGAAGCA TTTCCAGCC
      GluSerLys SerValIle IleGlyAla ThrGlyGly SerProGlu
676   GAGTCAAAA AGCGTCATT ATTGGAGCT ACAGGGGGA TCGCCTGAG
      LysHisHis AlaThrVal LysLeuGlu
721   AAGCATCAC GCTACCGTG AAACTGGAG
```

FIGURE 33  pMBP-c2X-ToxoP30MIX3

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA ATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                    Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 33   pMBP-c2X-ToxoP30MIX3

```
1756  TTGGCTGAA  ATCACCCCG  GACAAAGCG  TTCCAGGAC  AAGCTGTAT
      ProPheThr  TrpAspAla  ValArgTyr  AsnGlyLys  LeuIleAla
1801  CCGTTTACC  TGGGATGCC  GTACGTTAC  AACGGCAAG  CTGATTGCT
      TyrProIle  AlaValGlu  AlaLeuSer  LeuIleTyr  AsnLysAsp
1846  TACCCGATC  GCTGTTGAA  GCGTTATCG  CTGATTTAT  AACAAAGAT
      LeuLeuPro  AsnProPro  LysThrTrp  GluGluIle  ProAlaLeu
1891  CTGCTGCCG  AACCCGCCA  AAAACCTGG  AAGAGATC   CCGGCGCTG
      AspLysGlu  LeuLysAla  LysGlyLys  SerAlaLeu  MetPheAsn
1936  GATAAAGAA  CTGAAAGCG  AAAGGTAAG  AGCGCGCTG  ATGTTCAAC
      LeuGlnGlu  ProTyrPhe  ThrTrpPro  LeuIleAla  AlaAspGly
1981  CTGCAAGAA  CCGTACTTC  ACCTGGCCG  CTGATTGCT  GCTGACGGG
      GlyTyrAla  PheLysTyr  GluAsnGly  LysTyrAsp  IleLysAsp
2026  GGTTATGCG  TTCAAGTAT  GAAAACGGC  AAGTACGAC  ATTAAAGAC
      ValGlyVal  AspAsnAla  GlyAlaLys  AlaGlyLeu  ThrPheLeu
2071  GTGGGCGTG  GATAACGCT  GGCGCGAAA  GCGGGTCTG  ACCTTCCTG
      ValAspLeu  IleLysAsn  LysHisMet  AsnAlaAsp  ThrAspTyr
2116  GTTGACCTG  ATTAAAAAC  AAACACATG  AATGCAGAC  ACCGATTAC
      SerIleAla  GluAlaAla  PheAsnLys  GlyGluThr  AlaMetThr
2161  TCCATCGCA  GAAGCTGCC  TTTAATAAA  GGCGAAACA  GCGATGACC
      IleAsnGly  ProTrpAla  TrpSerAsn  IleAspThr  SerLysVal
2206  ATCAACGGC  CCGTGGGCA  TGGTCCAAC  ATCGACACC  AGCAAAGTG
      AsnTyrGly  ValThrVal  LeuProThr  PheLysGly  GlnProSer
2251  AATTATGGT  GTAACGGTA  CTGCCGACC  TTCAAGGGT  CAACCATCC
      LysProPhe  ValGlyVal  LeuSerAla  GlyIleAsn  AlaAlaSer
2296  AAACCGTTC  GTTGGCGTG  CTGAGCGCA  GGTATTAAC  GCCGCCAGT
      ProAsnLys  GluLeuAla  LysGluPhe  LeuGluAsn  TyrLeuLeu
2341  CCGAACAAA  GAGCTGGCA  AAAGAGTTC  CTCGAAAAC  TATCTGCTG
      ThrAspGlu  GlyLeuGlu  AlaValAsn  LysAspLys  ProLeuGly
2386  ACTGATGAA  GGTCTGGAA  GCGGTTAAT  AAAGACAAA  CCGCTGGGT
      AlaValAla  LeuLysSer  TyrGluGlu  GluLeuAla  LysAspPro
2431  GCCGTAGCG  CTGAAGTCT  TACGAGGAA  GAGTTGGCG  AAAGATCCA
      ArgIleAla  AlaThrMet  GluAsnAla  GlnLysGly  GluIleMet
2476  CGTATTGCC  GCCACTATG  GAAAACGCC  CAGAAAGGT  GAAATCATG
      ProAsnIle  ProGlnMet  SerAlaPhe  TrpTyrAla  ValArgThr
2521  CCGAACATC  CCGCAGATG  TCCGCTTTC  TGGTATGCC  GTGCGTACT
      AlaValIle  AsnAlaAla  SerGlyArg  GlnThrVal  AspGluAla
2566  GCGGTGATC  AACGCCGCC  AGCGGTCGT  CAGACTGTC  GATGAAGCC
      LeuLysAsp  AlaGlnThr  AsnSerSer  SerAsnAsn  AsnAsnAsn
2611  CTGAAAGAC  GCGCAGACT  AATTCGAGC  TCGAACAAC  AACAACAAT
      AsnAsnAsn  AsnAsnLeu  GlyIleGlu  GlyArgIle  SerGluPhe
2656  AACAATAAC  AACAACCTC  GGGATCGAG  GGAAGGATT  TCAGAATTC
      LeuValAla  AsnGlnVal  ValThrCys  ProAspLys  LysSerThr
2701  CTTGTTGCC  AATCAAGTT  GTCACCTGC  CCAGATAAA  AAATCGACA
      AlaAlaVal  IleLeuThr  ProThrGlu  AsnHisPhe  ThrLeuLys
2746  GCCGCGGTC  ATTCTCACA  CCGACGGAG  AACCACTTC  ACTCTCAAG
      CysProLys  ThrAlaLeu  ThrGluPro  ProThrLeu  AlaTyrSer
```

FIGURE 33  pMBP-c2X-ToxoP30MIX3

```
2791 TGCCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACGGTG ACAGTACAA GCCAGAGCC TCATCGGTC GTCAATAAT
     ValAlaArg AlaSerTyr GlyAlaAsp SerThrLeu GlyProVal
3106 GTCGCAAGG GCTTCCTAC GGTGCAGAC AGCACTCTT GGTCCTGTC
     LysLeuSer AlaGluGly ProThrThr MetThrLeu ValAlaGly
3151 AAGTTGTCT GCGGAAGGA CCCACTACA ATGACCCTC GTGGCTGGG
     LysAspGly ValLysVal ProGlnAsp AsnAsnGln TyrAlaSer
3196 AAAGATGGA GTCAAAGTT CCTCAAGAC AACAATCAG TACGCTTCC
     GlyThrThr LeuThrGly AlaAsnGlu LysSerPhe LysAspIle
3241 GGGACGACG CTGACTGGT GCTAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyAla ThrGlyGly SerProGlu
3376 GAGTCAAAA AGCGTCATT ATTGGAGCT ACAGGGGGA TCGCCTGAG
     LysHisHis AlaThrVal LysLeuGlu
3421 AAGCATCAC GCTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTTGGCGG ATGAGATAA
3646 GATTTTCAG CCTGATACA GATTAAATC AGAACGCAG AAGCGGTCT
3691 GATAAAACA GAATTTGCC TGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TTCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG CCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AGGAAGAG
4141 TATGAGTAT TCAACATTT CCGTGTCGC CCTTATTCC CTTTTTTGC
4186 GGCATTTTG CCTTCCTGT TTTTGCTCA CCCAGAAAC GCTGGTGAA
```

FIGURE 33  pMBP-c2X-ToxoP30MIX3

```
4231 AGTAAAAGA TGCTGAAGA TCAGTTGGG TGCACGAGT GGGTTACAT
4276 CGAACTGGA TCTCAACAG CGGTAAGAT CCTTGAGAG TTTTCGCCC
4321 CGAAGAACG TTCTCCAAT GATGAGCAC TTTTAAAGT TCTGCTATG
4366 TGGCGCGGT ATTATCCCG TGTTGACGC CGGGCAAGA GCAACTCGG
4411 TCGCCGCAT ACACTATTC TCAGAATGA CTTGGTTGA GTACTCACC
4456 AGTCACAGA AAAGCATCT TACGGATGG CATGACAGT AAGAGAATT
4501 ATGCAGTGC TGCCATAAC CATGAGTGA TAACACTGC GGCCAACTT
4546 ACTTCTGAC AACGATCGG AGGACCGAA GGAGCTAAC CGCTTTTTT
4591 GCACAACAT GGGGGATCA TGTAACTCG CCTTGATCG TTGGGAACC
4636 GGAGCTGAA TGAAGCCAT ACCAAACGA CGAGCGTGA CACCACGAT
4681 GCCTGTAGC AATGGCAAC AACGTTGCG CAAACTATT AACTGGCGA
4726 ACTACTTAC TCTAGCTTC CCGGCAACA ATTAATAGA CTGGATGGA
4771 GGCGGATAA AGTTGCAGG ACCACTTCT GCGCTCGGC CCTTCCGGC
4816 TGGCTGGTT TATTGCTGA TAAATCTGG AGCCGGTGA GCGTGGGTC
4861 TCGCGGTAT CATTGCAGC ACTGGGGCC AGATGGTAA GCCCTCCCG
4906 TATCGTAGT TATCTACAC GACGGGGAG TCAGGCAAC TATGGATGA
4951 ACGAAATAG ACAGATCGC TGAGATAGG TGCCTCACT GATTAAGCA
4996 TTGGTAACT GTCAGACCA AGTTTACTC ATATATACT TTAGATTGA
5041 TTTACCCCG GTTGATAAT CAGAAAAGC CCCAAAAAC AGGAAGATT
5086 GTATAAGCA AATATTTAA ATTGTAAAC GTTAATATT TTGTTAAAA
5131 TTCGCGTTA AATTTTTGT TAAATCAGC TCATTTTTT AACCAATAG
5176 GCCGAAATC GGCAAAATC CCTTATAAA TCAAAAGAA TAGACCGAG
5221 ATAGGGTTG AGTGTTGTT CCAGTTTGG AACAAGAGT CCACTATTA
5266 AAGAACGTG GACTCCAAC GTCAAAGGG CGAAAAACC GTCTATCAG
5311 GGCGATGGC CCACTACGT GAACCATCA CCCAAATCA AGTTTTTTG
5356 GGGTCGAGG TGCCGTAAA GCACTAAAT CGGAACCCT AAAGGGAGC
5401 CCCCGATTT AGAGCTTGA CGGGGAAAG CCGGCGAAC GTGGCGAGA
5446 AAGGAAGGG AAGAAAGCG AAAGGAGCG GCGCTAGG GCGCTGGCA
5491 AGTGTAGCG GTCACGCTG CGCGTAACC ACCACACCC GCCGCGCTT
5536 AATGCGCCG CTACAGGGC GCGTAAAAG GATCTAGGT GAAGATCCT
5581 TTTTGATAA TCTCATGAC CAAAATCCC TTAACGTGA GTTTTCGTT
5626 CCACTGAGC GTCAGACCC CGTAGAAAA GATCAAAGG ATCTTCTTG
5671 AGATCCTTT TTTTCTGCG CGTAATCTG CTGCTTGCA AACAAAAAA
5716 ACCACCGCT ACCAGCGGT GGTTTGTTT GCCGGATCA AGAGCTACC
5761 AACTCTTTT TCCGAAGGT AACTGGCTT CAGCAGAGC GCAGATACC
5806 AAATACTGT CCTTCTAGT GTAGCCGTA GTTAGGCCA CCACTTCAA
5851 GAACTCTGT AGCACCGCC TACATACCT CGCTCTGCT AATCCTGTT
5896 ACCAGTGGC TGCTGCCAG TGGCGATAA GTCGTGTCT TACCGGGTT
5941 GGACTCAAG ACGATAGTT ACCGGATAA GGCGCAGCG GTCGGGCTG
5986 AACGGGGGG TTCGTGCAC ACAGCCCAG CTTGGAGCG AACGACCTA
6031 CACCGAACT GAGATACCT ACAGCGTGA GCTATGAGA AAGCGCCAC
6076 GCTTCCCGA AGGGAGAAA GGCGGACAG GTATCCGGT AAGCGGCAG
6121 GGTCGGAAC AGGAGAGCG CACGAGGGA GCTTCCAGG GGGAAACGC
6166 CTGGTATCT TTATAGTCC TGTCGGGTT TCGCCACCT CTGACTTGA
6211 GCGTCGATT TTTGTGATG CTCGTCAGG GGGCGGAG CCTATGGAA
6256 AAACGCCAG CAACGCGGC CTTTTTACG GTTCCTGGC CTTTTGCTG
```

FIGURE 33    pMBP-c2X-ToxoP30MIX3

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT CTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA ACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIGURE 34  ToxoP30MIX3

```
         LeuValAla AsnGlnVal ValThrCys ProAspLys LysSerThr
    1    CTTGTTGCC AATCAAGTT GTCACCTGC CCAGATAAA AAATCGACA
         AlaAlaVal IleLeuThr ProThrGlu AsnHisPhe ThrLeuLys
   46    GCCGCGGTC ATTCTCACA CCGACGGAG AACCACTTC ACTCTCAAG
         CysProLys ThrAlaLeu ThrGluPro ProThrLeu AlaTyrSer
   91    TGCCCTAAA ACAGCGCTC ACAGAGCCT CCCACTCTT GCGTACTCA
         ProAsnArg GlnIleCys ProAlaGly ThrThrSer SerCysThr
  136    CCCAACAGG CAAATCTGC CCAGCGGGT ACTACAAGT AGCTGTACA
         SerLysAla ValThrLeu SerSerLeu IleProGlu AlaGluAsp
  181    TCAAAGGCT GTAACATTG AGCTCCTTG ATTCCTGAA GCAGAAGAT
         SerTrpTrp ThrGlyAsp SerAlaSer LeuAspThr AlaGlyIle
  226    AGCTGGTGG ACGGGGGAT TCTGCTAGT CTCGACACG GCAGGCATC
         LysLeuThr ValProIle GluLysPhe ProValThr ThrGlnThr
  271    AAACTCACA GTTCCAATC GAGAAGTTC CCCGTGACA ACGCAGACG
         PheValVal GlyCysIle LysGlyAsp AspAlaGln SerCysMet
  316    TTTGTGGTC GGTTGCATC AAGGGAGAC GACGCACAG AGTTGTATG
         ValThrVal ThrValGln AlaArgAla SerSerVal ValAsnAsn
  361    GTCACGGTG ACAGTACAA GCCAGAGCC TCATCGGTC GTCAATAAT
         ValAlaArg AlaSerTyr GlyAlaAsp SerThrLeu GlyProVal
  406    GTCGCAAGG GCTTCCTAC GGTGCAGAC AGCACTCTT GGTCCTGTC
         LysLeuSer AlaGluGly ProThrThr MetThrLeu ValAlaGly
  451    AAGTTGTCT GCGGAAGGA CCCACTACA ATGACCCTC GTGGCTGGG
         LysAspGly ValLysVal ProGlnAsp AsnAsnGln TyrAlaSer
  496    AAAGATGGA GTCAAAGTT CCTCAAGAC AACAATCAG TACGCTTCC
         GlyThrThr LeuThrGly AlaAsnGlu LysSerPhe LysAspIle
  541    GGGACGACG CTGACTGGT GCTAACGAG AAATCGTTC AAAGATATT
         LeuProLys LeuThrGlu AsnProTrp GlnGlyAsn AlaSerSer
  586    TTGCCAAAA TTAACTGAG AACCCGTGG CAGGGTAAC GCTTCGAGT
         AspLysGly AlaThrLeu ThrIleLys LysGluAla PheProAla
  631    GATAAGGGT GCCACGCTA ACGATCAAG AAGGAAGCA TTTCCAGCC
         GluSerLys SerValIle IleGlyAla ThrGlyGly SerProGlu
  676    GAGTCAAAA AGCGTCATT ATTGGAGCT ACAGGGGGA TCGCCTGAG
         LysHisHis AlaThrVal LysLeuGlu
  721    AAGCATCAC GCTACCGTG AAACTGGAG
```

FIGURE 35   pMBP-c2X-ToxoP30MIX5

```
   1 CCGACACCA TCGAATGGT GCAAAACCT TTCGCGGTA TGGCATGAT
  46 AGCGCCCGG AAGAGAGTC AATTCAGGG TGGTGAATG TGAAACCAG
  91 TAACGTTAT ACGATGTCG CAGAGTATG CCGGTGTCT CTTATCAGA
 136 CCGTTTCCC GCGTGGTGA ACCAGGCCA GCCACGTTT CTGCGAAAA
 181 CGCGGGAAA AAGTGGAAG CGGCGATGG CGGAGCTGA ATTACATTC
 226 CCAACCGCG TGGCACAAC AACTGGCGG GCAAACAGT CGTTGCTGA
 271 TTGGCGTTG CCACCTCCA GTCTGGCCC TGCACGCGC CGTCGCAAA
 316 TTGTCGCGG CGATTAAAT CTCGCGCCG ATCAACTGG GTGCCAGCG
 361 TGGTGGTGT CGATGGTAG AACGAAGCG GCGTCGAAG CCTGTAAAG
 406 CGGCGGTGC ACAATCTTC TCGCGCAAC GCGTCAGTG GGCTGATCA
 451 TTAACTATC CGCTGGATG ACCAGGATG CCATTGCTG TGGAAGCTG
 496 CCTGCACTA ATGTTCCGG CGTTATTTC TTGATGTCT CTGACCAGA
 541 CACCCATCA ACAGTATTA TTTTCTCCC ATGAAGACG GTACGCGAC
 586 TGGGCGTGG AGCATCTGG TCGCATTGG GTCACCAGC AAATCGCGC
 631 TGTTAGCGG GCCCATTAA GTTCTGTCT CGGCGCGTC TGCGTCTGG
 676 CTGGCTGGC ATAAATATC TCACTCGCA ATCAAATTC AGCCGATAG
 721 CGGAACGGG AAGGCGACT GGAGTGCCA TGTCCGGTT TCAACAAA
 766 CCATGCAAA TGCTGAATG AGGGCATCG TTCCCACTG CGATGCTGG
 811 TTGCCAACG ATCAGATGG CGCTGGGCG CAATGCGCG CCATTACCG
 856 AGTCCGGGC TGCGCGTTG GTGCGGATA TCTCGGTAG TGGGATACG
 901 ACGATACCG AAGACAGCT CATGTTATA TCCCGCCGT TAACCACCA
 946 TCAAACAGG ATTTTCGCC TGCTGGGGC AAACCAGCG TGGACCGCT
 991 TGCTGCAAC TCTCTCAGG GCCAGGCGG TGAAGGGCA ATCAGCTGT
1036 TGCCCGTCT CACTGGTGA AAAGAAAAA CCACCCTGG CGCCCAATA
1081 CGCAAACCG CCTCTCCCC GCGCGTTGG CCGATTCAT TAATGCAGC
1126 TGGCACGAC AGGTTTCCC GACTGGAAA GCGGGCAGT GAGCGCAAC
1171 GCAATTAAT GTAAGTTAG CTCACTCAT TAGGCACAA TTCTCATGT
1216 TTGACAGCT TATCATCGA CTGCACGGT GCACCAATG CTTCTGGCG
1261 TCAGGCAGC CATCGGAAG CTGTGGTAT GGCTGTGCA GGTCGTAAA
1306 TCACTGCAT AATTCGTGT CGCTCAAGG CGCACTCCC GTTCTGGAT
1351 AATGTTTTT TGCGCCGAC ATCATAACG GTTCTGGCA ATATTCTG
1396 AAATGAGCT GTTGACAAT TAATCATCG GCTCGTATA ATGTGTGGA
1441 ATTGTGAGC GGATAACAA TTTCACACA GGAAACAGC CAGTCCGTT
                                                                Met
1486 TAGGTGTTT TCACGAGCA CTTCACCAA CAAGGACCA TAGCATATG
     LysIleGlu GluGlyLys LeuValIle TrpIleAsn GlyAspLys
1531 AAAATCGAA GAAGGTAAA CTGGTAATC TGGATTAAC GGCGATAAA
     GlyTyrAsn GlyLeuAla GluValGly LysLysPhe GluLysAsp
1576 GGCTATAAC GGTCTCGCT GAAGTCGGT AAGAAATTC GAGAAAGAT
     ThrGlyIle LysValThr ValGluHis ProAspLys LeuGluGlu
1621 ACCGGAATT AAAGTCACC GTTGAGCAT CCGGATAAA CTGGAAGAG
     LysPhePro GlnValAla AlaThrGly AspGlyPro AspIleIle
1666 AAATTCCCA CAGGTTGCG GCAACTGGC GATGGCCCT GACATTATC
     PheTrpAla HisAspArg PheGlyGly TyrAlaGln SerGlyLeu
1711 TTCTGGGCA CACGACCGC TTTGGTGGC TACGCTCAA TCTGGCCTG
     LeuAlaGlu IleThrPro AspLysAla PheGlnAsp LysLeuTyr
```

FIGURE 35  pMBP-c2X-ToxoP30MIX5

```
1756 TTGGCTGAA ATCACCCCG GACAAAGCG TTCCAGGAC AAGCTGTAT
     ProPheThr TrpAspAla ValArgTyr AsnGlyLys LeuIleAla
1801 CCGTTTACC TGGGATGCC GTACGTTAC AACGGCAAG CTGATTGCT
     TyrProIle AlaValGlu AlaLeuSer LeuIleTyr AsnLysAsp
1846 TACCCGATC GCTGTTGAA GCGTTATCG CTGATTTAT AACAAAGAT
     LeuLeuPro AsnProPro LysThrTrp GluGluIle ProAlaLeu
1891 CTGCTGCCG AACCCGCCA AAACCTGG GAAGAGATC CCGGCGCTG
     AspLysGlu LeuLysAla LysGlyLys SerAlaLeu MetPheAsn
1936 GATAAAGAA CTGAAAGCG AAAGGTAAG AGCGCGCTG ATGTTCAAC
     LeuGlnGlu ProTyrPhe ThrTrpPro LeuIleAla AlaAspGly
1981 CTGCAAGAA CCGTACTTC ACCTGGCCG CTGATTGCT GCTGACGGG
     GlyTyrAla PheLysTyr GluAsnGly LysTyrAsp IleLysAsp
2026 GGTTATGCG TTCAAGTAT GAAAACGGC AAGTACGAC ATTAAAGAC
     ValGlyVal AspAsnAla GlyAlaLys AlaGlyLeu ThrPheLeu
2071 GTGGGCGTG GATAACGCT GGCGCGAAA GCGGGTCTG ACCTTCCTG
     ValAspLeu IleLysAsn LysHisMet AsnAlaAsp ThrAspTyr
2116 GTTGACCTG ATTAAAAAC AAACACATG AATGCAGAC ACCGATTAC
     SerIleAla GluAlaAla PheAsnLys GlyGluThr AlaMetThr
2161 TCCATCGCA GAAGCTGCC TTTAATAAA GGCGAAACA GCGATGACC
     IleAsnGly ProTrpAla TrpSerAsn IleAspThr SerLysVal
2206 ATCAACGGC CCGTGGGCA TGGTCCAAC ATCGACACC AGCAAAGTG
     AsnTyrGly ValThrVal LeuProThr PheLysGly GlnProSer
2251 AATTATGGT GTAACGGTA CTGCCGACC TTCAAGGGT CAACCATCC
     LysProPhe ValGlyVal LeuSerAla GlyIleAsn AlaAlaSer
2296 AAACCGTTC GTTGGCGTG CTGAGCGCA GGTATTAAC GCCGCCAGT
     ProAsnLys GluLeuAla LysGluPhe LeuGluAsn TyrLeuLeu
2341 CCGAACAAA GAGCTGGCA AAAGAGTTC CTCGAAAAC TATCTGCTG
     ThrAspGlu GlyLeuGlu AlaValAsn LysAspLys ProLeuGly
2386 ACTGATGAA GGTCTGGAA GCGGTTAAT AAAGACAAA CCGCTGGGT
     AlaValAla LeuLysSer TyrGluGlu GluLeuAla LysAspPro
2431 GCCGTAGCG CTGAAGTCT TACGAGGAA GAGTTGGCG AAAGATCCA
     ArgIleAla AlaThrMet GluAsnAla GlnLysGly GluIleMet
2476 CGTATTGCC GCCACTATG GAAAACGCC CAGAAAGGT GAAATCATG
     ProAsnIle ProGlnMet SerAlaPhe TrpTyrAla ValArgThr
2521 CCGAACATC CCGCAGATG TCCGCTTTC TGGTATGCC GTGCGTACT
     AlaValIle AsnAlaAla SerGlyArg GlnThrVal AspGluAla
2566 GCGGTGATC AACGCCGCC AGCGGTCGT CAGACTGTC GATGAAGCC
     LeuLysAsp AlaGlnThr AsnSerSer SerAsnAsn AsnAsnAsn
2611 CTGAAAGAC GCGCAGACT AATTCGAGC TCGAACAAC AACAACAAT
     AsnAsnAsn AsnAsnLeu GlyIleGlu GlyArgIle SerGluPhe
2656 AACAATAAC AACAACCTC GGGATCGAG GGAAGGATT TCAGAATTC
     LeuValAla AsnGlnVal ValThrCys ProAspLys LysSerThr
2701 CTTGTTGCC AATCAAGTT GTCACCTGC CCAGATAAA AAATCGACA
     AlaAlaVal IleLeuThr ProThrGlu AsnHisPhe ThrLeuLys
2746 GCCGCGGTC ATTCTCACA CCGACGGAG AACCACTTC ACTCTCAAG
     AlaProLys ThrAlaLeu ThrGluPro ProThrLeu AlaTyrSer
```

FIGURE 35  pMBP-c2X-ToxoP30MIX5

```
2791 GCTCCTAAA ACAGCGCTC ACAGAGCCT CCCACTCTT GCGTACTCA
     ProAsnArg GlnIleCys ProAlaGly ThrThrSer SerCysThr
2836 CCCAACAGG CAAATCTGC CCAGCGGGT ACTACAAGT AGCTGTACA
     SerLysAla ValThrLeu SerSerLeu IleProGlu AlaGluAsp
2881 TCAAAGGCT GTAACATTG AGCTCCTTG ATTCCTGAA GCAGAAGAT
     SerTrpTrp ThrGlyAsp SerAlaSer LeuAspThr AlaGlyIle
2926 AGCTGGTGG ACGGGGGAT TCTGCTAGT CTCGACACG GCAGGCATC
     LysLeuThr ValProIle GluLysPhe ProValThr ThrGlnThr
2971 AAACTCACA GTTCCAATC GAGAAGTTC CCCGTGACA ACGCAGACG
     PheValVal GlyCysIle LysGlyAsp AspAlaGln SerCysMet
3016 TTTGTGGTC GGTTGCATC AAGGGAGAC GACGCACAG AGTTGTATG
     ValThrVal ThrValGln AlaArgAla SerSerVal ValAsnAsn
3061 GTCACGGTG ACAGTACAA GCCAGAGCC TCATCGGTC GTCAATAAT
     ValAlaArg CysSerTyr GlyAlaAsp SerThrLeu GlyProVal
3106 GTCGCAAGG TGCTCCTAC GGTGCAGAC AGCACTCTT GGTCCTGTC
     LysLeuSer AlaGluGly ProThrThr MetThrLeu ValAlaGly
3151 AAGTTGTCT GCGGAAGGA CCCACTACA ATGACCCTC GTGGCTGGG
     LysAspGly ValLysVal ProGlnAsp AsnAsnGln TyrAlaSer
3196 AAAGATGGA GTCAAAGTT CCTCAAGAC AACAATCAG TACGCTTCC
     GlyThrThr LeuThrGly AlaAsnGlu LysSerPhe LysAspIle
3241 GGGACGACG CTGACTGGT GCTAACGAG AAATCGTTC AAAGATATT
     LeuProLys LeuThrGlu AsnProTrp GlnGlyAsn AlaSerSer
3286 TTGCCAAAA TTAACTGAG AACCCGTGG CAGGGTAAC GCTTCGAGT
     AspLysGly AlaThrLeu ThrIleLys LysGluAla PheProAla
3331 GATAAGGGT GCCACGCTA ACGATCAAG AAGGAAGCA TTTCCAGCC
     GluSerLys SerValIle IleGlyAla ThrGlyGly SerProGlu
3376 GAGTCAAAA AGCGTCATT ATTGGAGCT ACAGGGGGA TCGCCTGAG
     LysHisHis AlaThrVal LysLeuGlu
3421 AAGCATCAC GCTACCGTG AAACTGGAG TGAAAGCTT GGCACTGGC
3466 CGTCGTTTT ACAACGTCG TGACTGGGA AAACCCTGG CGTTACCCA
3511 ACTTAATCG CCTTGCAGC ACATCCCCC TTTCGCCAG CTGGCGTAA
3556 TAGCGAAGA GGCCCGCAC CGATCGCCC TTCCCAACA GTTGCGCAG
3601 CCTGAATGG CGAATGGCA GCTTGGCTG TTTTGGCGG ATGAGATAA
3646 GATTTTCAG CCTGATACA GATTAAATC AGAACGCAG AAGCGGTCT
3691 GATAAAACA GAATTTGCC TGGCGGCAG TAGCGCGGT GGTCCCACC
3736 TGACCCCAT GCCGAACTC AGAAGTGAA ACGCCGTAG CGCCGATGG
3781 TAGTGTGGG GTCTCCCCA TGCGAGAGT AGGGAACTG CCAGGCATC
3826 AAATAAAAC GAAAGGCTC AGTCGAAAG ACTGGGCCT TCGTTTTA
3871 TCTGTTGTT TGTCGGTGA ACGCTCTCC TGAGTAGGA CAAATCCGC
3916 CGGGAGCGG ATTTGAACG TTGCGAAGC AACGGCCCG GAGGGTGGC
3961 GGGCAGGAC GCCCGCCAT AAACTGCCA GGCATCAAA TTAAGCAGA
4006 AGGCCATCC TGACGGATG GCCTTTTTG CGTTTCTAC AAACTCTTT
4051 TTGTTTATT TTTCTAAAT ACATTCAAA TATGTATCC GCTCATGAG
4096 ACAATAACC CTGATAAAT GCTTCAATA ATATTGAAA AAGGAAGAG
4141 TATGAGTAT TCAACATTT CCGTGTCGC CCTTATTCC CTTTTTTGC
4186 GGCATTTTG CCTTCCTGT TTTTGCTCA CCCAGAAAC GCTGGTGAA
```

FIGURE 35  pMBP-c2X-ToxoP30MIX5

```
4231 AGTAAAAGA TGCTGAAGA TCAGTTGGG TGCACGAGT GGGTTACAT
4276 CGAACTGGA TCTCAACAG CGGTAAGAT CCTTGAGAG TTTTCGCCC
4321 CGAAGAACG TTCTCCAAT GATGAGCAC TTTTAAAGT TCTGCTATG
4366 TGGCGCGGT ATTATCCCG TGTTGACGC CGGGCAAGA GCAACTCGG
4411 TCGCCGCAT ACACTATTC TCAGAATGA CTTGGTTGA GTACTCACC
4456 AGTCACAGA AAAGCATCT TACGGATGG CATGACAGT AAGAGAATT
4501 ATGCAGTGC TGCCATAAC CATGAGTGA TAACACTGC GGCCAACTT
4546 ACTTCTGAC AACGATCGG AGGACCGAA GGAGCTAAC CGCTTTTTT
4591 GCACAACAT GGGGGATCA TGTAACTCG CCTTGATCG TTGGGAACC
4636 GGAGCTGAA TGAAGCCAT ACCAAACGA CGAGCGTGA CACCACGAT
4681 GCCTGTAGC AATGGCAAC AACGTTGCG CAAACTATT AACTGGCGA
4726 ACTACTTAC TCTAGCTTC CCGGCAACA ATTAATAGA CTGGATGGA
4771 GGCGGATAA AGTTGCAGG ACCACTTCT GCGCTCGGC CCTTCCGGC
4816 TGGCTGGTT TATTGCTGA TAAATCTGG AGCCGGTGA GCGTGGGTC
4861 TCGCGGTAT CATTGCAGC ACTGGGGCC AGATGGTAA GCCCTCCCG
4906 TATCGTAGT TATCTACAC GACGGGGAG TCAGGCAAC TATGGATGA
4951 ACGAAATAG ACAGATCGC TGAGATAGG TGCCTCACT GATTAAGCA
4996 TTGGTAACT GTCAGACCA AGTTTACTC ATATATACT TTAGATTGA
5041 TTTACCCCG GTTGATAAT CAGAAAAGC CCCAAAAAC AGGAAGATT
5086 GTATAAGCA AATATTTAA ATTGTAAAC GTTAATATT TTGTTAAAA
5131 TTCGCGTTA AATTTTGT TAAATCAGC TCATTTTTT AACCAATAG
5176 GCCGAAATC GGCAAAATC CCTTATAAA TCAAAAGAA TAGACCGAG
5221 ATAGGGTTG AGTGTTGTT CCAGTTTGG AACAAGAGT CCACTATTA
5266 AAGAACGTG GACTCCAAC GTCAAAGGG CGAAAAACC GTCTATCAG
5311 GGCGATGGC CCACTACGT GAACCATCA CCCAAATCA AGTTTTTTG
5356 GGGTCGAGG TGCCGTAAA GCACTAAAT CGGAACCCT AAAGGGAGC
5401 CCCCGATTT AGAGCTTGA CGGGGAAAG CCGGCGAAC GTGGCGAGA
5446 AAGGAAGGG AAGAAAGCG AAAGGAGCG GCGCTAGG GCGCTGGCA
5491 AGTGTAGCG GTCACGCTG CGCGTAACC ACCACACCC GCCGCGCTT
5536 AATGCGCCG CTACAGGGC GCGTAAAAG GATCTAGGT GAAGATCCT
5581 TTTTGATAA TCTCATGAC CAAAATCCC TTAACGTGA GTTTTCGTT
5626 CCACTGAGC GTCAGACCC CGTAGAAAA GATCAAAGG ATCTTCTTG
5671 AGATCCTTT TTTTCTGCG CGTAATCTG CTGCTTGCA ACAAAAAA
5716 ACCACCGCT ACCAGCGGT GGTTTGTTT GCCGGATCA AGAGCTACC
5761 AACTCTTTT TCCGAAGGT AACTGGCTT CAGCAGAGC GCAGATACC
5806 AAATACTGT CCTTCTAGT GTAGCCGTA GTTAGGCCA CCACTTCAA
5851 GAACTCTGT AGCACCGCC TACATACCT CGCTCTGCT AATCCTGTT
5896 ACCAGTGGC TGCTGCCAG TGGCGATAA GTCGTGTCT TACCGGGTT
5941 GGACTCAAG ACGATAGTT ACCGGATAA GGCGCAGCG GTCGGGCTG
5986 AACGGGGGG TTCGTGCAC ACAGCCCAG CTTGGAGCG AACGACCTA
6031 CACCGAACT GAGATACCT ACAGCGTGA GCTATGAGA AAGCGCCAC
6076 GCTTCCCGA AGGGAGAAA GGCGGACAG GTATCCGGT AAGCGGCAG
6121 GGTCGGAAC AGGAGAGCG CACGAGGGA GCTTCCAGG GGGAAACGC
6166 CTGGTATCT TTATAGTCC TGTCGGGTT TCGCCACCT CTGACTTGA
6211 GCGTCGATT TTTGTGATG CTCGTCAGG GGGCGGAG CCTATGGAA
6256 AAACGCCAG CAACGCGGC CTTTTTACG GTTCCTGGC CTTTTGCTG
```

FIGURE 35 pMBP-c2X-ToxoP30MIX5

```
6301  GCCTTTTGC TCACATGTT CTTTCCTGC GTTATCCCC TGATTCTGT
6346  GGATAACCG TATTACCGC CTTTGAGTG AGCTGATAC CGCTCGCCG
6391  CAGCCGAAC GACCGAGCG CAGCGAGTC AGTGAGCGA GGAAGCGGA
6436  AGAGCGCCT GATGCGGTA TTTTCTCCT TACGCATCT GTGCGGTAT
6481  TTCACACCG CATATATGG TGCACTCTC AGTACAATC TGCTCTGAT
6526  GCCGCATAG TTAAGCCAG TATACACTC CGCTATCGC TACGTGACT
6571  GGGTCATGG CTGCGCCCC GACACCCGC CAACACCCG CTGACGCGC
6616  CCTGACGGG CTTGTCTGC TCCCGGCAT CCGCTTACA GACAAGCTG
6661  TGACCGTCT CCGGGAGCT GCATGTGTC AGAGGTTTT CACCGTCAT
6706  CACCGAAAC GCGCGAGGC AGCTGCGGT AAAGCTCAT CAGCGTGGT
6751  CGTGCAGCG ATTCACAGA TGTCTGCCT GTTCATCCG CGTCCAGCT
6796  CGTTGAGTT TCTCCAGAA GCGTTAATG TCTGGCTTC TGATAAAGC
6841  GGGCCATGT TAAGGGCGG TTTTTTCCT GTTTGGTCA CTGATGCCT
6886  CCGTGTAAG GGGGATTTC TGTTCATGG GGGTAATGA TACCGATGA
6931  AACGAGAGA GGATGCTCA CGATACGGG TTACTGATG ATGAACATG
6976  CCCGGTTAC TGGAACGTT GTGAGGGTA AACAACTGG CGGTATGGA
7021  TGCGGCGGG ACCAGAGAA AAATCACTC AGGGTCAAT GCCAGCGCT
7066  TCGTTAATA CAGATGTAG GTGTTCCAC AGGGTAGCC AGCAGCATC
7111  CTGCGATGC AGATCCGGA ACATAATGG TGCAGGGCG CTGACTTCC
7156  GCGTTTCCA GACTTTACG AAACACGGA AACCGAAGA CCATTCATG
7201  TTGTTGCTC AGGTCGCAG ACGTTTTGC AGCAGCAGT CGCTTCACG
7246  TTCGCTCGC GTATCGGTG ATTCATTCT GCTAACCAG TAAGGCAAC
7291  CCCGCCAGC CTAGCCGGG TCCTCAACG ACAGGAGCA CGATCATGC
7336  GCACCCGTG GCCAGGACC CAACGCTGC CCGAAATT
```

FIGURE 36  ToxoP30MIX5

```
        LeuValAla AsnGlnVal ValThrCys ProAspLys LysSerThr
  1     CTTGTTGCC AATCAAGTT GTCACCTGC CCAGATAAA AAATCGACA
        AlaAlaVal IleLeuThr ProThrGlu AsnHisPhe ThrLeuLys
 46     GCCGCGGTC ATTCTCACA CCGACGGAG AACCACTTC ACTCTCAAG
        AlaProLys ThrAlaLeu ThrGluPro ProThrLeu AlaTyrSer
 91     GCTCCTAAA ACAGCGCTC ACAGAGCCT CCCACTCTT GCGTACTCA
        ProAsnArg GlnIleCys ProAlaGly ThrThrSer SerCysThr
136     CCCAACAGG CAAATCTGC CCAGCGGGT ACTACAAGT AGCTGTACA
        SerLysAla ValThrLeu SerSerLeu IleProGlu AlaGluAsp
181     TCAAAGGCT GTAACATTG AGCTCCTTG ATTCCTGAA GCAGAAGAT
        SerTrpTrp ThrGlyAsp SerAlaSer LeuAspThr AlaGlyIle
226     AGCTGGTGG ACGGGGGAT TCTGCTAGT CTCGACACG GCAGGCATC
        LysLeuThr ValProIle GluLysPhe ProValThr ThrGlnThr
271     AAACTCACA GTTCCAATC GAGAAGTTC CCCGTGACA ACGCAGACG
        PheValVal GlyCysIle LysGlyAsp AspAlaGln SerCysMet
316     TTTGTGGTC GGTTGCATC AAGGGAGAC GACGCACAG AGTTGTATG
        ValThrVal ThrValGln AlaArgAla SerSerVal ValAsnAsn
361     GTCACGGTG ACAGTACAA GCCAGAGCC TCATCGGTC GTCAATAAT
        ValAlaArg CysSerTyr GlyAlaAsp SerThrLeu GlyProVal
406     GTCGCAAGG TGCTCCTAC GGTGCAGAC AGCACTCTT GGTCCTGTC
        LysLeuSer AlaGluGly ProThrThr MetThrLeu ValAlaGly
451     AAGTTGTCT GCGGAAGGA CCCACTACA ATGACCCTC GTGGCTGGG
        LysAspGly ValLysVal ProGlnAsp AsnAsnGln TyrAlaSer
496     AAAGATGGA GTCAAAGTT CCTCAAGAC AACAATCAG TACGCTTCC
        GlyThrThr LeuThrGly AlaAsnGlu LysSerPhe LysAspIle
541     GGGACGACG CTGACTGGT GCTAACGAG AAATCGTTC AAAGATATT
        LeuProLys LeuThrGlu AsnProTrp GlnGlyAsn AlaSerSer
586     TTGCCAAAA TTAACTGAG AACCCGTGG CAGGGTAAC GCTTCGAGT
        AspLysGly AlaThrLeu ThrIleLys LysGluAla PheProAla
631     GATAAGGGT GCCACGCTA ACGATCAAG AAGGAAGCA TTTCCAGCC
        GluSerLys SerValIle IleGlyAla ThrGlyGly SerProGlu
676     GAGTCAAAA AGCGTCATT ATTGGAGCT ACAGGGGGA TCGCCTGAG
        LysHisHis AlaThrVal LysLeuGlu
721     AAGCATCAC GCTACCGTG AAACTGGAG
```

GENETICALLY ENGINEERED P30 ANTIGEN, IMPROVED ANTIGEN COCKTAIL, AND USES THEREOF

BACKGROUND OF THE INVENTION

1. Technical Field

The present invention relates to a genetically engineered P30 antigen as well as a combination or mixture of antigens which may be used in the detection of IgM and/or IgG antibodies to *Toxoplasma gondii*. Furthermore, the present invention also relates to methods of using this genetically engineered P30 antigen and combination of antigens, antibodies raised against this genetically engineered P30 antigen and combination of antigens, as well as kits and vaccines containing the genetically engineered P30 antigen and antigens present in the combination.

2. Background Information

*Toxoplasma gondii* is an obligate intracellular parasite which is classified among the Coccidia. This parasite has relatively broad host range infecting both mammals and birds. The organism is ubiquitous in nature and exists in three forms: tachyzoite, cyst, and oocyst (Remington, J. S., McLeod, R., Desmonds, G., Infectious Diseases of the Fetus and Newborn Infant (J. S. Remington and J. O. Klein, Eds.), pp. 140–267, Saunders, Philadelphia (1995)). Tachyzoites, found during acute infection, are the invasive form capable of invading all nucleated mammalian cells. After the acute stage of infection, tissue cysts called bradyzoites are formed within host cells and persist within the host organism for the life of the host. Cysts are important in transmission of infection, especially in humans, as the ingestion of raw or undercooked meat can result in the ingestion of bradyzoites which can infect the individual resulting in an acute infection. Oocysts represent a stage of sexual reproduction which occurs only in the intestinal lining of the cat family from which they are excreted in the feces.

A *T. gondii* infection acquired through contaminated meat or cat feces in a healthy adult is often asymptomatic. In pregnant women and immunosuppressed patients, the clinical outcome can be very serious. An acute infection with *T. gondii* acquired during pregnancy, especially during the first trimester, can result in intrauterine transmission to the unborn fetus resulting in severe fetal and neonatal complications, including mental retardation and fetal death. Recrudescence of a previous *T. gondii* infection or an acute infection in an immunosuppressed individual can be pathogenic. Toxoplasmic encephalitis is a major cause of morbidity and mortality in AIDS patients. Toxoplasma infection has also been shown to be a significant cause of chorioretinitis in children and adults.

Diagnosis of infection with *T. gondii* may be established by the isolation of *T. gondii* from blood or body fluids, demonstration of the presence of the organism in the placenta or tissues of the fetus, demonstration of the presence of antigen by detection of specific nucleic acid sequences (e.g., DNA probes), or detection of *T. gondii* specific immunoglobulins synthesized by the host in response to infection using serologic tests.

The detection of *T. gondii* specific antibodies and determination of antibody titer are important tools used in the diagnosis of toxoplasmosis. The most widely used serologic tests for the diagnosis of toxoplasmosis are the Sabin-Feldman dye test (Sabin, A. B. and Feldman, H. A. (1948) Science 108, 660–663), the indirect hemagglutination (IHA) test (Jacobs, L. and Lunde, M. (1957) J. Parasitol. 43, 308–314), the IFA test (Walton, B. C. et al. (1966) Am. J. Trop. Med. Hyg. 15, 149–152), the agglutination test (Fondation Mérieux, Sérologie de l'Infection Toxoplasmique en Particulier à Son Début: Méthodes et Interprétation des Résultants, Lyon, 182 pp. (1975)) and the ELISA (Naot, Y. and Remington, J. S. (1980) J. Infect. Dis. 142, 757–766). The ELISA test is one the easiest tests to perform, and many automated serologic tests for the detection of Toxoplasma specific IgM and IgG are commercially available.

The current tests for the detection of IgM and IgG antibodies in infected individuals can vary widely in their ability to detect serum antibody. Hence, there is significant inter-assay variation seen among the commercially available kits. The differences observed between the different commercial kits are caused primarily by the preparation of the antigen used for the serologic test. Most kits use either whole or sonicated tachyzoites grown in tissue culture or in mice which contain a high proportion of extra-parasitic material, for example, mammalian cells, tissue culture components, etc. Due to the lack of a purified, standardized antigen or standard method for preparing the tachyzoite antigen, it is not surprising that inter-assay variability exists resulting in different assays having different performance characteristics in terms of assay sensitivity and specificity.

Given the limitations of serologic tests employing the tachyzoite antigen, as described above, as well as the persistent problems regarding determination of onset of infection, purified recombinant antigens obtained by molecular biology are an attractive alternative in that they can be purified and standardized. In the literature, a number of Toxo genes have been cloned and expressed in a suitable host to produce immunoreactive, recombinant Toxo antigens. For example, the Toxo P22 (SAG2), P24 (GRA1), P25, P28 (GRA2), P29 (GRA7), P30 (SAG1), P35, P41 (GRA4), P54 (ROP2), P66 (ROP1), and the Toxo P68 antigens have been described (Prince et al. (1990) Mol. Biochem. Parasitol 43, 97–106; Cesbron-Delauw et al. (1989) Proc. Nat. Acad. Sci. 86, 7537–7541; Johnson et al. (1991) Gene 99, 127–132; Prince et al. (1989) Mol. Biochem. Parasitol. 34, 3–13; Bonhomme et al. (1998) J. Histochem. Cytochem. 46, 1411–1421; Burg et al. (1988) J. Immunol. 141, 3584–3591; Knapp et al. (1989) EPA 431541A2; Mevelec et al. (1992) Mol. Biochem. Parasitol. 56, 227–238; Saavedra et al. (1991) J. Immunol. 147, 1975–1982); EPA 751 147).

It is plausible that no single Toxo antigen can replace the tachyzoite in an initial screening immunoassay for the detection of Toxo-specific immunoglobulins. This may be due to several reasons. First, the antibodies produced during infection vary with the stage of infection, i.e., the antibodies produced by an infected individual vary over time reacting with different epitopes. Secondly, the epitopes present in a recombinant antigen may be different or less reactive than native antigen prepared from the tachyzoite depending on the host used for expression and the purification scheme employed. Thirdly, different recombinant antigens may be needed to detect the different classes of immunoglobulins produced in response to an infection, e.g., IgM, IgG, IgA and IgE.

In order to overcome the limitations of the tachyzoite antigen in terms of assay specificity and sensitivity, a search was done for Toxo antigens which could be used in combination in order to configure new assays for the detection of Toxo-specific immunoglobulins. Maine et al. (in U.S. Pat. No. 6,329,157 B1) disclose recombinant Toxo antigen cocktails for the detection of Toxo-specific IgG and IgM. It was determined that the above mentioned Toxo antigen cocktails could be improved and enhanced by expression of Toxo P30 in *E. coli* as a soluble protein with genetically engineered modifications. This genetically engineered P30 antigen and improved antigen cocktail will be described in further detail below.

SUMMARY OF THE INVENTION

The present invention includes a genetically engineered *Toxoplasma gondii* P30 antigen as well as a composition comprising both *Toxoplasma gondii* genetically engineered P30 antigen and P35 antigen. This genetically engineered antigen and composition may be used as diagnostic reagents, and the genetically engineered antigen and the antigens within this composition may be produced either recombinantly or synthetically.

In particular, the present invention includes an isolated nucleotide sequence or fragment thereof comprising or complementary to a nucleotide sequence having at least 70% nucleotide sequence identity to a nucleotide sequence selected from the group consisting of SEQ ID NO:22, SEQ ID NO:27 and SEQ ID NO:63. The present invention also includes an isolated nucleotide sequence or fragment thereof encoding a polypeptide, wherein the polypeptide has at least 70% amino acid sequence identity to an amino acid sequence selected from the group consisting of SEQ ID NO:23, SEQ ID NO:28 and SEQ ID NO:64. The present invention also includes a purified polypeptide encoded by any of the nucleotide sequences presented above.

Additionally, the present invention includes a purified polypeptide or fragment thereof having at least 70% amino acid sequence identity to an amino acid sequence selected from the group consisting of SEQ ID NO:23, SEQ ID NO:28 and SEQ ID NO:64. Also, the present invention includes a purified polypeptide or fragment thereof comprising an amino acid sequence having 1–6 additional amino acids at the C-terminus of SEQ ID NO:28. The invention also includes a purified polypeptide or fragment thereof comprising an amino acid sequence as in SEQ ID NO:23 in which any one or more of the five C-terminal amino acids have been changed from cysteine to alanine. Further, the present invention also includes a polyclonal or monoclonal antibody directed against these purified polypeptides.

The present invention also includes a composition comprising a polypeptide, wherein the polypeptide comprises an amino acid sequence selected from the group consisting of SEQ ID NO:23, SEQ ID NO:28 and SEQ ID NO:64. This composition may be used as a diagnostic reagent, and the polypeptide of the composition may be produced by recombinant or synthetic means.

Additionally, the present invention includes a method for detecting the presence of IgM antibodies to *Toxoplasma gondii* in a test sample comprising the steps of: a) contacting the test sample suspected of containing the IgM antibodies with a composition comprising a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64; and b) detecting the presence of polypeptide/IgM antibody complexes, wherein presence of the complexes indicates presence of the IgM antibodies in the test sample.

Furthermore, the present invention also includes a method for detecting the presence of IgM antibodies to *Toxoplasma gondii* in a test sample comprising the steps of: a) contacting the test sample suspected of containing the IgM antibodies with a composition comprising a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64, for a time and under conditions sufficient for the formation of IgM antibody/antigen complexes; b) adding a conjugate to the resulting IgM antibody/antigen complexes for a time and under conditions sufficient to allow said conjugate to bind to the bound antibody, wherein the conjugate comprises an antibody attached to a signal-generating compound capable of generating a detectable signal; and c) detecting presence of IgM antibodies which may be present in the test sample by detecting presence of a signal generated by the signal-generating compound.

Moreover, the present invention encompasses a method for detecting the presence of IgG antibodies to *Toxoplasma gondii* in a test sample comprising the steps of: a) contacting the test sample suspected of containing the IgG antibodies with a composition comprising: 1) a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64 and 2) P35; and b) detecting presence of antigen/IgG antibody complexes, presence of the complexes indicating presence of said IgG antibodies in the test sample.

The invention also encompasses a method for detecting the presence of IgG antibodies to *Toxoplasma gondii* in a test sample comprising the steps of: a) contacting the test sample suspected of containing the IgG antibodies with a composition comprising: 1) a polypeptide, wherein the polypeptide comprises an amino acid sequence having at least 70% amino acid identity to an amino acid sequence selected from the group consisting of SEQ ID NO:23, SEQ ID NO:28 and SEQ ID NO:64 and 2) P35, for a time and under conditions sufficient for formation of IgG antibody/antigen complexes; b) adding a conjugate to resulting IgG antibody/antigen complexes for a time and under conditions sufficient to allow the conjugate to bind to bound antibody, wherein the conjugate comprises an antibody attached to a signal-generating compound capable of generating a detectable signal; and c) detecting IgG antibodies which may be present in the test sample by detecting presence of a signal generated by said signal-generating compound.

Furthermore, the present invention includes a method for detecting the presence of IgM antibodies to *Toxoplasma gondii* in a test sample comprising the steps of: a) contacting the test sample suspected of containing the IgM antibodies with anti-antibody specific for the IgM antibodies for a time and under conditions sufficient to allow for formation of anti-antibody/IgM antibody complexes; b) adding a conjugate to resulting anti-antibody/IgM antibody complexes for a time and under conditions sufficient to allow the conjugate to bind to bound antibody, wherein the conjugate comprises a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, attached to a signal generating compound capable of generating a detectable signal; and c) detecting IgM antibodies which may be present in the test sample by detecting presence of a signal generated by the signal-generating compound.

Further, the present invention includes a method for detecting the presence of IgG antibodies to *Toxoplasma gondii* in a test sample comprising the steps of: a) contacting the test sample suspected of containing the IgG antibodies with anti-antibody specific for the IgG antibodies for a time and under conditions sufficient to allow for formation of anti-antibody/IgG antibody complexes; b) adding a conjugate to resulting anti-antibody/IgG antibody complexes for a time and under conditions sufficient to allow the conjugate to bind to bound antibody, wherein the conjugate comprises: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal; and c) detecting IgG antibodies which may be present in the test sample by detecting the presence of a signal generated by each of the signal-generating compounds.

The present invention also encompasses a vaccine comprising: a) at least one polypeptide selected from the group consisting of: 1) a polypeptide, wherein the polypeptide comprises amino acid sequence having at least 70% amino acid sequence identity to an amino acid sequence selected from the group consisting of SEQ ID NO:23, SEQ ID NO:28 and SEQ ID NO:64 and 2) P35, and b) a pharmaceutically acceptable adjuvant.

Also, the invention includes a kit for determining the presence of IgM antibodies to *Toxoplasma gondii* in a test sample comprising a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; and a conjugate comprising an antibody attached to a signal-generating compound capable of generating a detectable signal.

Also, the present invention includes a kit for determining the presence of IgG antibodies to *Toxoplasma gondii* in a test sample comprising: a composition comprising 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64 and 2) P35; and a conjugate comprising an antibody attached to a signal-generating compound capable of generating a detectable signal.

Additionally, the present invention encompasses a kit for determining the presence of IgM antibodies to *Toxoplasma gondii* in a test sample comprising:
a) an anti-antibody specific for IgM antibody; and
b) a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64.

Furthermore, the present invention includes a kit for determining the presence of IgM antibodies to *Toxoplasma gondii* in a test sample comprising:
a) an anti-antibody specific for IgM antibody;
b) a conjugate comprising: 1) a composition comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, attached to 2) a signal-generating compound capable of generating a detectable signal.

Also, the invention includes a kit for determining the presence of IgG antibodies to *Toxoplasma gondii* in a test sample comprising:
a) an anti-antibody specific for IgG antibody; and
b) a composition comprising: 1) a polypeptide, wherein said polypeptide comprises an amino acid sequence having at least 70% amino acid sequence identity to an amino acid sequence selected from the group consisting of SEQ ID NO:23, SEQ ID NO:28 and SEQ ID NO:64 and 2) P35.

Another kit of the present invention includes a kit for determining the presence of IgG antibodies to *Toxoplasma gondii* in a test sample comprising:
a) an anti-antibody specific for IgG antibody;
b) a conjugate comprising: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal.

Further, the present invention includes a method for detecting the presence of IgM antibodies to *Toxoplasma gondii* in a test sample comprising the steps of: (a) contacting said test sample suspected of containing IgM antibodies with anti-antibody specific for the IgM antibodies for a time and under conditions sufficient to allow for formation of anti-antibody IgM complexes; (b) adding antigen to resulting anti-antibody/IgM complexes for a time and under conditions sufficient to allow the antigen to bind to bound IgM antibody, the antigen comprising a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; and (c) adding a conjugate to resulting anti-antibody/IgM/antigen complexes, the conjugate comprising a composition comprising monoclonal or polyclonal antibody attached to a signal-generating compound capable of generating a detectable signal; and (d) detecting IgM antibodies which may be present in the test sample by detecting a signal generated by the signal-generating compound.

Additionally, the invention includes a method for detecting the presence of IgG antibodies to *Toxoplasma gondii* in a test sample comprising the steps of: (a) contacting the test sample suspected of containing IgG antibodies with anti-antibody specific for the IgG antibodies for a time and under conditions sufficient to allow for formation of anti-antibody IgG complexes; (b) adding antigen to resulting anti-antibody/IgG complexes for a time and under conditions sufficient to allow the antigen to bind to bound IgG antibody, the antigen comprising a mixture of 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35; (c) adding a conjugate to resulting anti-antibody/IgG/antigen complexes, the conjugate comprising a composition comprising a monoclonal or polyclonal antibody attached to a signal-generating compound capable of generating a detectable signal; and (d) detecting IgG antibodies which may be present in the test sample by detecting a signal generated by the signal-generating compound.

The present invention also includes a method for detecting the presence of IgM and IgG antibodies to *Toxoplasma gondii* in a test sample comprising the steps of: a) contacting the test sample suspected of containing said IgM and IgG antibodies with a composition comprising 1) a polypeptide, wherein said polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, for a time and under conditions sufficient for the formation of IgM and IgG antibody/antigen complexes; b) adding a conjugate to the resulting IgM antibody/antigen complexes and IgG antibody/antigen complexes for a time and under conditions sufficient to allow the conjugate to bind to the bound IgM and IgG antibody, wherein the conjugate comprises an antibody attached to a signal-generating compound capable of generating a detectable signal; and c) detecting the presence of IgM and IgG antibodies which may be present in said test sample by detecting a signal generated by the signal-generating compound.

The invention also encompasses a method for detecting the presence of IgM and IgG antibodies to *Toxoplasma gondii* in a test sample comprising the steps of: a) contacting the test sample suspected of containing the IgM and IgG antibodies with anti-antibody specific for the IgM antibodies and the IgG antibodies for a time and under conditions sufficient to allow for formation of anti-antibody/IgM antibody complexes and anti-antibody/IgG antibody complexes; b) adding a conjugate to resulting anti-antibody/IgM antibody complexes and resulting anti-antibody/IgG antibody complexes for a time and under conditions sufficient to allow the conjugate to bind to bound antibody, wherein the conjugate comprises a composition comprising: 1) a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64, and 2) P35, each attached to a signal-generating compound capable of generating a detectable signal; and c) detecting IgM and IgG antibodies which may be present in the test sample by detecting a signal generated by the signal-generating compound.

Moreover, the present invention also encompasses a method for detecting the presence of IgM and IgG antibodies to *Toxoplasma gondii* in a test sample comprising the steps of: (a) contacting the test sample suspected of containing IgM and IgG antibodies with anti-antibody specific for the IgM antibodies and with anti-antibody specific for the IgG antibodies for a time and under conditions sufficient to allow for formation of anti-antibody/IgM complexes and anti-antibody/IgG complexes; (b) adding antigen to resulting anti-antibody/IgM complexes and resulting anti-antibody/IgG complexes for a time and under conditions sufficient to allow said antigen to bind to bound IgM and IgG antibody, the antigen comprising a mixture of: 1) a polypeptide, wherein said polypeptide comprises an amino acid sequence selected from the group consisting of SEQ ID NO:23, SEQ ID NO:28 and SEQ ID NO:64 and 2) P35; and (c) adding a conjugate to resulting anti-antibody/IgM/antigen complexes and anti-antibody/IgG/antigen complexes, the conjugate comprising a composition comprising monoclonal or polyclonal antibody attached to a signal-generating compound capable of generating a detectable signal; and (d) detecting IgM and IgG antibodies which may be present in the test sample by detecting a signal generated by the signal-generating compound.

The present invention also includes a method of producing monoclonal antibodies comprising the steps of injecting a non-human mammal with a polypeptide, wherein the polypeptide comprises an amino acid sequence having at least 70% amino acid sequence identity to an amino acid sequence selected from the group consisting of SEQ ID NO:23, SEQ ID NO:28 and SEQ ID NO:64; fusing spleen cells of the non-human mammal with myeloma cells in order to generate hybridomas; and culturing the hybridomas for a time and under conditions sufficient for the hybridomas to produce the monoclonal antibodies.

Moreover, the present invention encompasses the plasmid pMBP-c2X-ToxoP30del3C(52-300aa), the plasmid pMBP-c2X-ToxoP30del4C(52-294aa), as well as the plasmid pMBP-c2X-ToxoP30MIX1.

The invention also includes an isolated nucleotide sequence comprising or complementary to the nucleotide sequence of SEQ ID NO:20 as well as a purified polypeptide comprising the amino acid sequence of SEQ ID NO:21.

Furthermore, the present invention includes an isolated nucleotide sequence comprising or complementary to the nucleotide sequence of SEQ ID NO:25 as well as a purified polypeptide comprising the amino acid sequence of SEQ ID NO:26.

Additionally, the invention includes an isolated nucleotide sequence comprising or complementary to the nucleotide sequence of SEQ ID NO:61 as well as a purified polypeptide comprising the amino acid sequence of SEQ ID NO:62.

The present invention also includes portions or fragments of ToxoP30del3C(52-300aa), ToxoP30del4C(52-294aa), or ToxoP30MIX1, which have the same antigenic properties as the region of ToxoP30del3C(52-300aa) which consists of amino acids 1–249, as the region of ToxoP30del4C(52-294aa) which consists of amino acids 1–243, and the region of ToxoP30MIX1 which consists of amino acids 1–249, respectively.

All U.S. patents and publications referred to herein are hereby incorporated in their entirety by reference.

BRIEF DESCRIPTION OF THE DRAWINGS

FIG. 2 represents the DNA sequence [SEQ ID NO:3] of nucleotides 1–7478 encoding the amino acid sequence [SEQ ID NO:4] of the MBP-ToxoP30(52-336aa) fusion protein of plasmid pMBP-c2X-ToxoP30(52-336aa).

FIG. 3 represents the DNA sequence [SEQ ID NO:5] of nucleotides 1–850 of the ToxoP30(52-336aa) gene and the corresponding encoded amino acid sequence [SEQ ID NO:6] of the ToxoP30(52-336aa) protein.

FIG. 5 represents the DNA sequence [SEQ ID NO:7] of nucleotides 1–7553 and the corresponding encoded amino acid sequence [SEQ ID NO:8] of the MBP-ToxoP30(52-336aa) fusion protein of plasmid pMBP-p2X-ToxoP30(52-336aa).

FIG. 8 represents the DNA sequence [SEQ ID NO:10] of nucleotides 1–7442 and the corresponding encoded amino acid sequence [SEQ ID NO:11] of the MBP-ToxoP30del1C(52-324aa) fusion protein of plasmid pMBP-c2X-ToxoP30del1C(52-324aa).

FIG. 9 represents the DNA sequence [SEQ ID NO:12] of nucleotides 1–819 of the ToxoP30del1C(52–324) gene and the corresponding encoded amino acid sequence [SEQ ID NO:13] of the ToxoP30del1C(52-324aa) protein.

FIG. 11 represents the DNA sequence [SEQ ID NO:15] of nucleotides 1–7403 and the corresponding encoded amino acid sequence [SEQ ID NO:16] of the MBP-ToxoP30del2 (52-311aa) fusion protein of plasmid pMBP-c2X-ToxoP30del2(52-311aa).

FIG. 12 represents the DNA sequence [SEQ ID NO:17] of nucleotides 1–780 of the ToxoP30del2(52-311aa) gene and the corresponding encoded amino acid sequence [SEQ ID NO:18] of the ToxoP30del2(52-311aa) protein.

FIG. 15 represents the DNA sequence [SEQ ID NO:20] of nucleotides 1–7370 and the corresponding encoded amino acid sequence [SEQ ID NO:21] of the MBP-ToxoP30del3C (52-300aa) fusion protein of plasmid pMBP-c2X-ToxoP30del3C(52-300aa).

FIG. 16 represents the DNA sequence [SEQ ID NO:22] of nucleotides 1–747 of the ToxoP30del3(52-300aa) and the corresponding encoded amino acid sequence [SEQ ID NO:23] of the ToxoP30del3C(52-300aa) protein.

FIG. 19 represents the DNA sequence [SEQ ID NO:25] of nucleotides 1–7352 and the corresponding encoded amino acid sequence [SEQ ID NO:26] of the MBP-ToxoP30del4C (52-294aa) fusion protein of plasmid pMBP-c2X-ToxoP30del4C(52-294aa).

FIG. 20 represents the DNA sequence [SEQ ID NO:27] of nucleotides 1–729 of the ToxoP30del4C(52-294aa) gene and the corresponding encoded amino acid sequence [SEQ ID NO:28] of the ToxoP30del4C(52-294aa) protein.

FIG. 22 represents the DNA sequence [SEQ ID NO:30] of nucleotides 1–7259 and the corresponding encoded amino acid sequence [SEQ ID NO:31] of the MBP-ToxoP30del4del8(83-294aa) fusion protein of plasmid pMBP-c2X-ToxoP30del4del8(83-294aa).

FIG. 23 represents the DNA sequence [SEQ ID NO:32] of nucleotides 1–636 of the ToxoP30del4del8(83-294aa) gene and the corresponding amino acid sequence [SEQ ID NO:33] of the ToxoP30del4del8(83-294aa) protein.

FIG. 25 represents the DNA sequence [SEQ ID NO:35] of nucleotides 1–7322 and the corresponding encoded amino acid sequence [SEQ ID NO:36] of the MBP-ToxoP30del10 (52-284aa) fusion protein of plasmid pMBP-c2X-ToxoP30del10(52-284aa).

FIG. 26 represents the DNA sequence [SEQ ID NO:37] of nucleotides 1–699 of the ToxoP30del10(52-284aa) gene and the corresponding encoded amino acid sequence [SEQ ID NO:38] of the ToxoP30del10(52-284aa) protein.

FIG. 28 represents the DNA sequence [SEQ ID NO:40] of nucleotides 1–7112 and the corresponding encoded amino acid sequence [SEQ ID NO:41] of the MBP-ToxoP30del11 (52-214aa) fusion protein of plasmid pMBP-c2X-ToxoP30del11(52-214aa).

FIG. 29 represents the DNA sequence [SEQ ID NO:42] of nucleotides 1–489 of the ToxoP30del11(52-214aa) gene and the corresponding encoded amino acid sequence [SEQ ID NO:43] of the ToxoP30del11(52-214aa) protein.

FIG. 31 represents the DNA sequence [SEQ ID NO:61] of nucleotides 1–7370 and the corresponding encoded amino acid sequence [SEQ ID NO:62] of the MBP-ToxoP30MIX1 fusion protein of plasmid pMBP-c2X-ToxoP30MIX1.

FIG. 32 represents the DNA sequence [SEQ ID NO:63] of nucleotides 1–747 of the ToxoP30MIX1 gene and the corresponding encoded amino acid sequence [SEQ ID NO:64] of the ToxoP30MIX1 protein.

FIG. 33 represents the DNA sequence [SEQ ID NO:66] of nucleotides 1–7370 and the corresponding encoded amino acid sequence [SEQ ID NO:67] of the MBP-ToxoP30MIX3 fusion protein of plasmid pMBP-c2X-ToxoP30MIX3.

FIG. 34 represents the DNA sequence [SEQ ID NO:68] of nucleotides 1–747 of the ToxoP30MIX3 gene and the corresponding amino acid sequence [SEQ ID NO:69] of the ToxoP30MIX3 protein.

FIG. 35 represents the DNA sequence [SEQ ID NO:71] of nucleotides 1–7370 and the corresponding encoded amino acid sequence [SEQ ID NO:72] of the MBP-ToxoP30MIX5 fusion protein of plasmid pMBP-c2X-ToxoP30MIX5.

FIG. 36 represents the DNA sequence [SEQ ID NO:73] of nucleotides 1–747 of the ToxoP30MIX5 gene and the corresponding encoded amino acid sequence [SEQ ID NO:74] of the ToxoP30MIX5 protein.

DETAILED DESCRIPTION OF THE INVENTION

Figure 1:
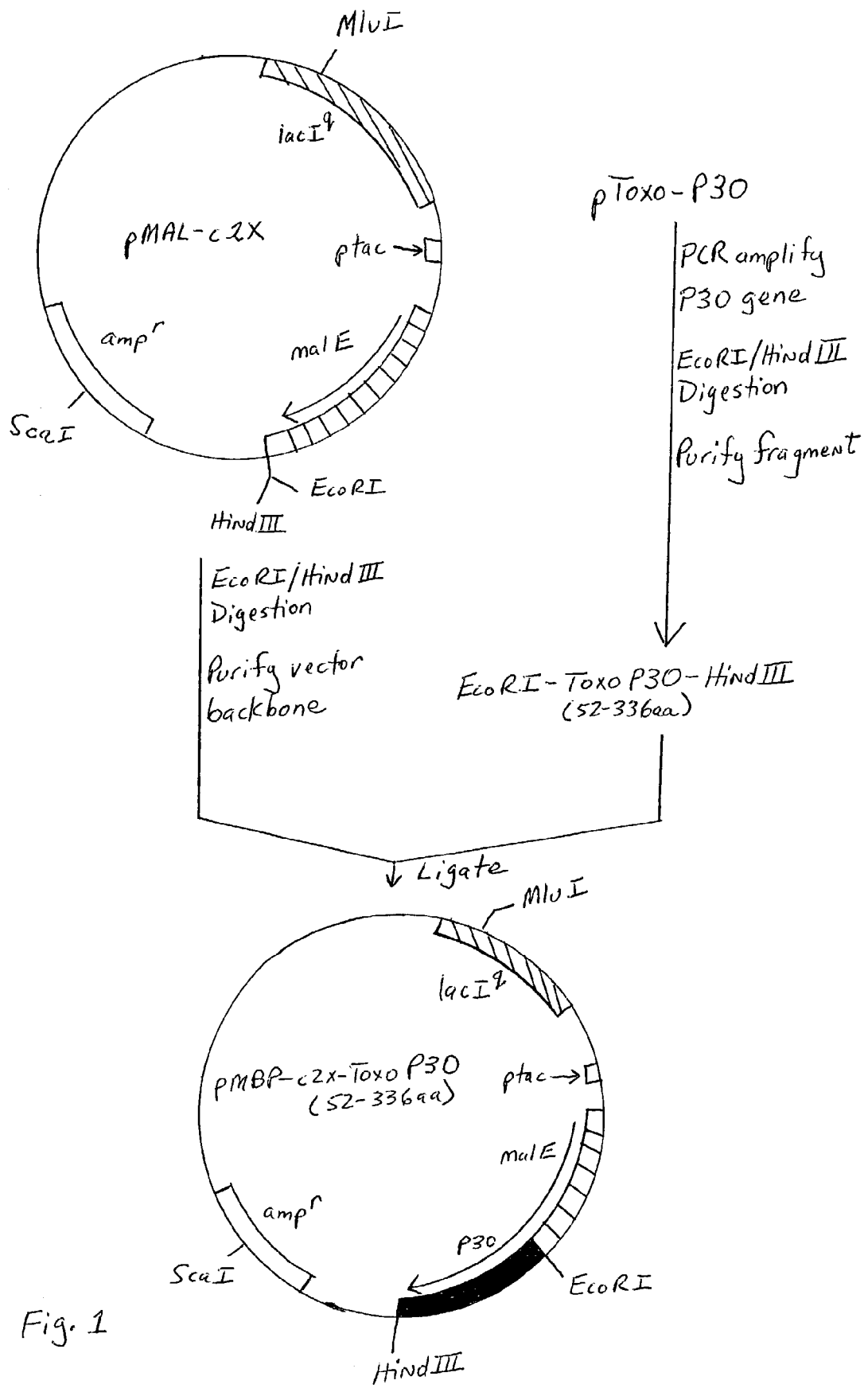
FIG. 1 is a schematic of the construction of plasmid pMBP-c2X-ToxoP30(52-336aa). (The amino acid range in parentheses, noted here and throughout the application, refers to the amino acid sequence (e.g., present in the plasmid, protein, etc.) which has been derived from the native P30 antigen.)
Figure 4:
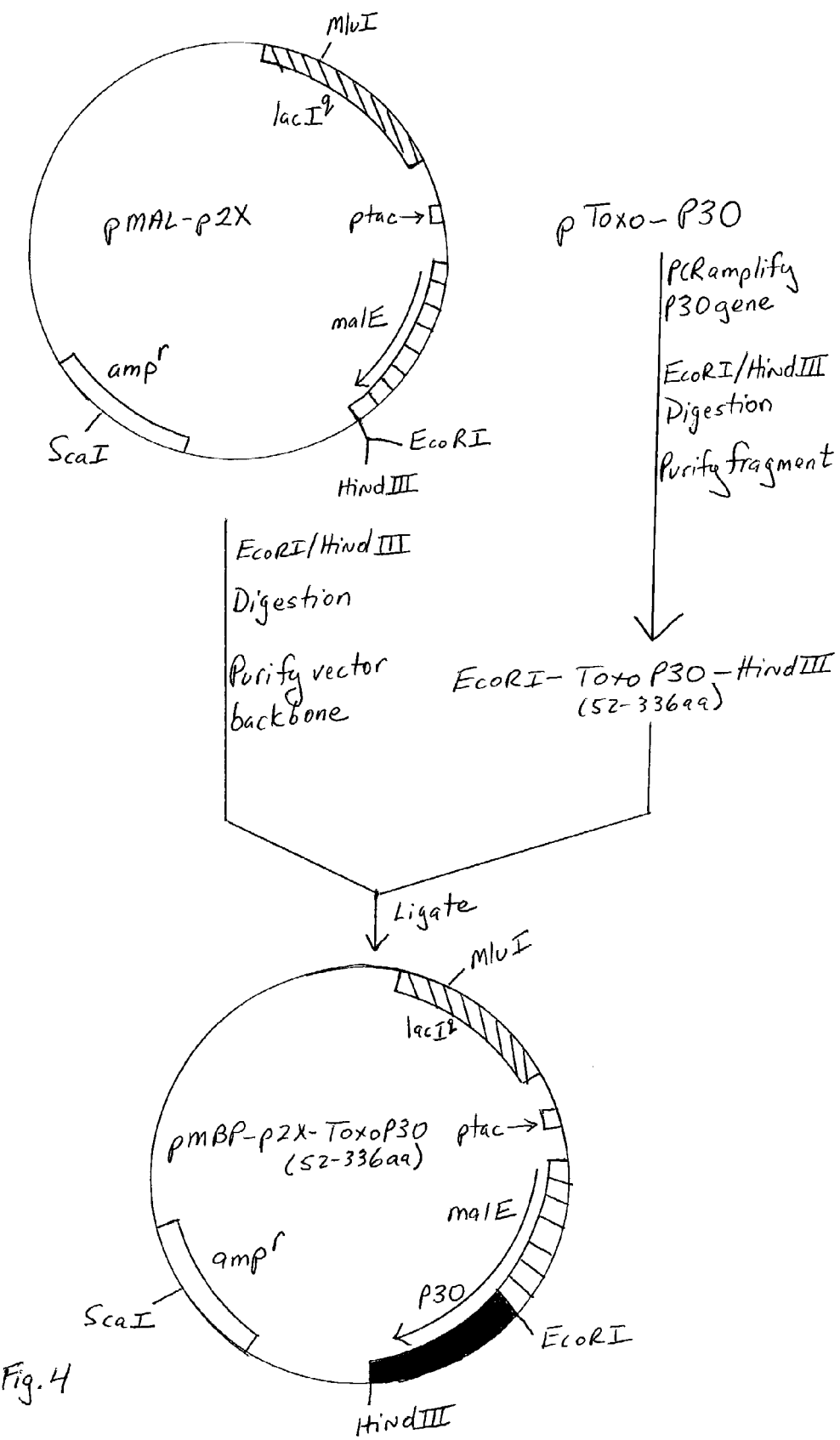
FIG. 4 is a schematic of the construction of plasmid pMBP-p2X-ToxoP30(52-336aa).

The difficulties of known assays for the detection of IgG and IgM antibodies to *T. gondii* have been described, in detail, above. Thus, there was a need to discover immunoassays that could accurately detect the presence of such antibodies in positive serum or plasma, thereby eliminating the problem of false negative or false positive tests. The present invention provides such needed immunoassays and, in particular, an antigen and combinations of antigens which accurately detect the presence of IgG and/or IgM antibodies in human sera.

In particular, the present invention includes genetically engineered versions of the P30 antigen referred to herein as "ToxoP30del3C(52-300aa)" and "ToxoP30del4C(52-294aa)", which contain small and precise deletions at the C-terminus of each protein that maximize the anti-Toxo IgG and IgM immunoreactivity of the P30 antigen in an immunoassay. The present invention also includes a genetically engineered version of the P30 antigen referred to herein as "ToxoP30MIX1", which contains the same deletion at the C-terminus as ToxoP30del3C(52-300aa) as well as five C-terminal cysteine residues changed to alanine. The invention also includes a polypeptide comprising the amino acid sequence of ToxoP30del3C(52-300aa) in which any one or more of the last five cysteines at the C-terminus have been changed to alanine.

The nucleotide sequence of the gene encoding the ToxoP30del3C antigen is shown in FIG. 16 and is represented by SEQ ID NO:22. The amino acid sequence of this antigen is also shown in FIG. 16 and is represented by SEQ ID NO:23. The nucleotide sequence of the gene encoding the ToxoP30del4C antigen is shown in FIG. 20 and is represented by SEQ ID NO:27. The amino acid sequence of this antigen is also shown in FIG. 20 and is represented by SEQ ID NO: 28. The nucleotide sequence of the gene encoding the ToxoP30MIX1 antigen is shown in FIG. 32 and is represented by SEQ ID NO:63. The amino acid sequence of this antigen is also shown in FIG. 32 and is represented by SEQ ID NO:64.

It should be noted that the present invention also encompasses nucleotide sequences comprising or complementary to a nucleotide sequence having at least about 70% nucleotide sequence identity, preferably at least about 80% nucleotide sequence identity, and more preferably at least about 90% nucleotide sequence identity to the nucleotide sequence of SEQ ID NO:22, SEQ ID NO:27 or SEQ ID NO:63. (All integers within the ranges noted above (i.e., between 70 and 100) are also considered to fall within the scope of the present invention.) The sequence having the above-described percent identity or complementary sequences may be derived from species or sources other than from which the isolated, original sequences were derived.

Also, it should be noted that the present invention encompasses a polypeptide sequence comprising an amino acid sequence having at least about 70% amino acid sequence identity, preferably at least about 80% amino acid sequence identity, and more preferably at least about 90% amino acid sequence identity to the amino acid sequence of SEQ ID NO:23, SEQ ID NO:28 or SEQ ID NO:64. (All integers within the ranges noted above (i.e, between 70 and 100) are also considered to fall within the scope of the present invention.)

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Clustal Macaw Pileup (http://cmgm.stanford.edu/biochem218/11Multiple.pdf; Higgins et al., CABIOS. 5L151–153 (1989)), FASTDB (Intelligenetics), BLAST (National Center for Biomedical Information; Altschul et al., Nucleic Acids Research 25:3389–3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

"Similarity" between two amino acid sequences is defined as the presence of a series of identical as well as conserved amino acid residues in both sequences. The higher the degree of similarity between two amino acid sequences, the higher the correspondence, sameness or equivalence of the two sequences. ("Identity between two amino acid sequences is defined as the presence of a series of exactly alike or invariant amino acid residues in both sequences.) The definitions of "complementarity", "identity" and "similarity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which is hybridizable, under moderately stringent conditions, to a nucleic acid having a nucleotide sequence comprising or complementary to the nucleotide sequences described above. A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization. "Hybridization" requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, an "isolated nucleic acid fragment or sequence" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A "fragment" of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferably at least about 25 nucleotides identical or complementary to a region of the specified nucleotide sequence. (See U.S. Pat. No. 6,183,952 B1.) In contrast, a "fragment" of a specified polypeptide refers to an amino acid sequence which comprises at least about 5 amino acids, more preferably at least about 10 amino acids, and even more preferably at least 15 amino acids derived from the specified polypeptide.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "fragment or subfragment that is functionally equivalent" and "functionally equivalent fragment or subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. A fragment or subfragment that is functionally equivalent to the original polypeptide sequence from which it is derived refers to a sequence which has the same properties (e.g., binding, antigenic, etc.) as the original polypeptide.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263–273 (1986); Erlich et al., European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20–50) of melting the template at high temperature, allowing the primers to anneal to complementary sequences within the template and then replicating the template with DNA polymerase.

Furthermore, the present invention also includes a polyclonal or monoclonal antibody raised against ToxoP30del3C, ToxoP30del4C, or ToxoP30MIX1. Such an antibody may be used, for example, in an immunoassay, a vaccine, a kit, or for research purposes.

As noted above, the present invention also encompasses a composition or mixture comprising the following two antigens: genetically engineered P30 and P35. This combination or mixture of antigens may be utilized for the detection of IgG in IgG-positive sera or plasma (i.e., as a diagnostic reagent). Furthermore, the antigens may be produced either recombinantly or synthetically. Additionally, the present invention also includes a composition comprising antibodies raised against these antigens.

Further, as noted above, present invention also includes the genetically engineered P30 antigen. This antigen may be used for the detection of IgM in IgM-positive sera or plasma (i.e., as a diagnostic reagent), and the antigen may be produced either recombinantly or synthetically. Furthermore, the present invention also includes antibodies raised against this antigen.

If, in fact, one wishes to measure both the titer of IgM and IgG in a serum or plasma sample, then a composition or mixture of antigens such as genetically engineered P30 and P35 may be utilized in an immunoassay. Such a combination of antigens is also included within the scope of the present invention.

The present invention also includes methods of detecting IgM and/or IgG using the combinations of antigens described above. More specifically, there are two basic types of assays, competitive and non-competitive (e.g., immunometric and sandwich). In both assays, antibody or antigen reagents are covalently or non-covalently attached to the solid phase. Linking agents for covalent attachment are known and may be part of the solid phase or derivatized to it prior to coating. Examples of solid phases used in immunoassays are porous and non-porous materials, latex particles, magnetic particles, microparticles, beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product (see also U.S. Pat. No. 6,395,472 B1). Examples of such signal generating compounds include chromogens, radioisotopes (e.g., 125I, 131I, 32P, 3H, 35S, and 14C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent may recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

In particular, two illustrative examples of an immunometric antibody-capture based immunoassay are the IMx Toxo IgM and Toxo IgG antibody assays manufactured by Abbott Laboratories (Abbott Park, Ill.). Both assays are automated Microparticle Enzyme Immunoassays (MEIA) which measure antibodies to *Toxoplasma gondii* (*T. gondii*) in human serum or plasma (Safford et al. (1991) J. Clin. Pathol. 44:238–242). One assay qualitatively measures IgM antibodies, indicative of recent exposure or acute infection, and the other assay quantitatively measures IgG, indicative of chronic or past infection. These assays use microparticles coated with *T. gondii* antigens as the solid phase. In particular, specimen is added to the coated microparticles to allow antibodies specific for *T. gondii* to bind. Subsequently, an alkaline phosphatase conjugated anti-human IgM (or anti-human IgG) is added that specifically binds to IgM (or IgG) class antibodies complexed to the *T. gondii* antigens. Following addition of a suitable substrate (e.g., 4-methyumbelliferyl phosphate), the rate of enzyme-catalyzed turnover is monitored based upon fluorescence.

The mixture of genetically engineered P30 and P35 may be used in the IgG Abbott immunoassay, and the genetically engineered P30 antigen alone may be utilized in the IgM Abbott immunoassay. Additionally, a mixture of genetically engineered P30 and P35 may be utilized in either assay, if desired. Furthermore, it must be noted that other non-Abbott assays or platforms may also be utilized, with each antigen or combination of antigens for purposes of the present invention.

Thus, the present invention includes a method of detecting IgM antibodies in a test sample comprising the steps of: (a) contacting the test sample suspected of containing the IgM antibodies with genetically engineered P30; (b) detecting the presence of IgM antibodies present in the test sample. More specifically, the present invention includes a method of detecting IgM antibodies in a test sample comprising the steps of: (a) contacting the test sample suspected of containing the IgM antibodies with genetically engineered P30 for a time and under conditions sufficient to allow the formation of IgM antibody/antigen complexes; (b) adding a conjugate to the resulting IgM antibody/antigen complexes for a time and under conditions sufficient to allow the conjugate to bind to the bound antibody, the conjugate comprising an antibody (directed against the IgM) attached to a signal generating compound capable of generating a detectable signal; (c) detecting the presence of the IgM antibody which may be present in the test sample by detecting the signal generated by the signal generating compound. A control or calibrator may also be used which binds to this antigen. Furthermore, the method may also comprise the use of P35 in addition to genetically engineered P30.

Additionally, the present invention further includes a method for detecting the presence of IgM which may be present in a test sample. This method comprises the steps of: (a) contacting the test sample suspected of containing IgM antibodies with anti-antibody specific for the IgM, for a time and under conditions sufficient to allow for formation of anti-antibody/IgM complexes and (b) detecting the presence of IgM which may be present in the test sample. (Such anti-antibodies are commercially available and may be created, for example, by immunizing a mammal with purified mu-chain of the antibody.)

More specifically, this method may comprise the steps of: (a) contacting the test sample suspected of containing the IgM antibodies with anti-antibody specific for the IgM, under time and conditions sufficient to allow the formation of anti-antibody/IgM complexes; (b) adding a conjugate to the resulting anti-antibody/IgM complexes for a time and under conditions sufficient to allow the conjugate to bind to the bound antibody, the conjugate comprising genetically engineered P30 attached to a signal generating compound capable of generating a detectable signal; and (c) detecting the presence of the IgM antibodies which may be present in the test sample by detecting the signal generated by the signal generating compound. A control or calibrator may be used which comprises antibody to the anti-antibody. Furthermore, the conjugate may also comprise P35, if desired.

In each of the above assays, IgG may be detected by substituting the genetically engineered P30 with a genetically engineered P30 and P35 mixture. Also, anti-antibody specific for IgG will be used. Additionally, if one wishes to detect both IgM and IgG antibodies, genetically engineered P30 and P35 may be utilized in the immunoassay.

The present invention also encompasses a third method for detecting the presence of IgM in a test sample. This method comprises the steps of: (a) contacting the test sample suspected of containing IgM antibodies with anti-antibody specific for the IgM, under time and conditions sufficient to allow the formation of anti-antibody IgM complexes; (b) adding antigen to the resulting anti-antibody/IgM complexes for a time and under conditions sufficient to allow the antigen to bind to the bound IgM antibody, the antigen comprising the genetically engineered P30; and (c) adding a conjugate to the resulting anti-antibody/IgM/antigen complexes, the conjugate comprising a composition comprising monoclonal or polyclonal antibody attached to a signal generating compound capable of detecting a detectable signal, the monoclonal or polyclonal antibody being directed against the antigen; and (d) detecting the presence of the IgM antibodies which may be present in the test sample by detecting the signal generated by the signal generating compound. Again, a control or calibrator may be used which comprises antibody to the anti-antibody. The antigen mixture may further comprise P35, if desired.

In this method, IgG may be detected by substituting the genetically engineered P30 antigen with a genetically engineered P30 and P35 mixture, and utilizing anti-antibody specific for IgG. However, if one wishes to detect both IgM and IgG antibodies, genetically engineered P30 and P35 may be utilized in the immunoassay.

It should also be noted that all of the above methods may be used to detect IgA antibodies (with an alpha-specific conjugate) and/or IgE antibodies (with an epsilon-specific conjugate) should such detection be desired.

Additionally, the present invention also includes a vaccine comprising a mixture of genetically engineered P30 and P35 antigens and a pharmaceutically acceptable adjuvant. Such a vaccine may be administered if one desires to raise IgG antibodies in a mammal. The present invention also includes a vaccine comprising the genetically engineered P30 antigen and a pharmaceutically acceptable adjuvant (e.g., Freund's adjuvant or Phosphate Buffered Saline). Such a vaccine may be administered if one desires to raise IgM antibodies in a mammal. Additionally, the present invention also includes a vaccine comprising a mixture of genetically engineered P30 and P35 antigens as well as a pharmaceutically acceptable adjuvant. This vaccine should be administered if one desires to raise both IgM and IgG antibodies in a mammal.

Kits are also included within the scope of the present invention. More specifically, the present invention includes kits for determining the presence of IgG and/or IgM. In particular, a kit for determining the presence of IgM in a test sample comprises a) genetically engineered P30; and b) a conjugate comprising an antibody (directed against IgM) attached to a signal-generating compound capable of generating a detectable signal. The kit may also contain a control or calibrator which comprises a reagent which binds to genetically engineered P30.

Again, if one desires to detect IgG, rather than IgM, the kit will comprise a mixture of genetically engineered P30 and P35, rather than genetically engineered P30, as well as an antibody directed against IgG. If one wishes to detect both IgM and IgG, the kit will comprise genetically engineered P30 and P35.

The present invention also includes another type of kit for detecting IgM and/or IgG in a test sample. If utilized for detecting the presence of IgM, the kit may comprise a) an anti-antibody specific for IgM, and b) genetically engineered P30. A control or calibrator comprising a reagent which binds to genetically engineered P30 may also be included. More specifically, the kit may comprise a) an anti-antibody specific for IgM, and b) a conjugate comprising genetically engineered P30, the conjugate being attached to a signal-generating compound capable of generating a detectable signal. Again, the kit may also comprise a control or calibrator comprising a reagent which binds to genetically engineered P30.

Additionally, if one desires to detect IgG, rather than IgM, the kit will comprise a mixture of genetically engineered P30 and P35, rather than genetically engineered P30 alone, as well as anti-antibody specific for IgG. If one wishes to detect both IgM and IgG, the kit may comprise genetically engineered P30 and P35.

The present invention may be illustrated by the use of the following non-limiting examples:

EXAMPLE 1

General Methodology

Materials and Sources

Restriction enzymes, T4 DNA ligase, and the pMAL™ Protein Fusion and Purification System were purchased from New England Biolabs, Inc. (Beverly, Mass.).

DNA and protein molecular weight standards, plasmid mini-prep kit, ethidium bromide, and pre-cast polyacrylamide gels, were purchased from BioRad Laboratories (Richmond, Calif.).

Maltose was purchased from Sigma Chemical Co. (St. Louis, Mo.).

QIAquick PCR Purification Kit and QIAquick Gel Extraction Kit were purchased from Qiagen, Inc. (Valencia, Calif.).

Synthetic oligonucleotides were purchased from Sigma Genosys (The Woodlands, Tex.).

EPICURIAN Coli™ XL-1 BLUE (recA1 endA1 gyrA96 thi-1 hsdR17 supE44 relA1 lac [F' proAB lacI$^q$ ZDM15 Tn10 (Tet$^r$)]) supercompetent *E. coli* cells were obtained from Stratagene Cloning Systems, Inc. (La Jolla, Calif.).

A GeneAmp™ reagent kit and AmpliTaq DNA Polymerase were purchased from Perkin-Elmer Cetus (Norwalk, Conn.).

SeaKem GTG agarose was purchased from BioWhittaker Molecular Applications (Rockland, Me.).

Bacto-Tryptone, Bacto-Yeast Extract, Bacto-Agar ampicillin, buffers, isopropyl-β-D-thiogalactoside (IPTG), bovine serum albumin (BSA), Sephacryl S-300, fetal calf serum (Toxo antibody free), sucrose, sodium azide, urea, EDTA, Triton X-100, 1-ethyl-3-(3-dimethylaminopropyl) carbodiimide (EDAC), 2-(N-moropholino)ethanesulfonic acid (MES), inorganic salts, sodium dodecyl sulfate (SDS), Tween 20, glycerol, 4-methylumbelliferyl phosphate (MUP), tris-(hydroxymethyl)aminomethane (Tris), AxSYM Toxo IgG and IgM assay reagents, calibrators, and controls, sulfate-derivatized microparticles, non-fat dry milk, Nipasept, A56620, Brij-35, mouse serum, mannitol, AxSYM instrument, reagents, and commodities were purchased from Abbott Manufacturing, Inc. (Abbott Park, Ill.).

Media, Buffers and General Reagents

"Superbroth II" contained 11.25 g/L tryptone, 22.5 g/L yeast extract, 11.4 g/L potassium phosphate dibasic, 1.7 g/L potassium phosphate monobasic, 10 ml/L glycerol, adjusted pH to 7.2 with sodium hydroxide.

General Methods

All enzyme digestions of DNA were performed according to suppliers' instructions. At least 5 units of enzyme were used per microgram of DNA, and sufficient incubation time was allowed for complete digestion of DNA. Supplier protocols were followed for the various kits used in the manipulation of DNA and transformation of DNA into *E. coli*, for polymerase chain reaction (PCR), and for purification of maltose binding protein (MBP) and MBP fusion proteins. Standard procedures were used for preparation of *E. coli* lysates containing CMP-KDO synthetase (CKS) (U.S. Pat. No. 6,329,157 B1), restriction analysis of DNA on agarose gels, purification of DNA fragments from agarose gels, and ligation of DNA fragments with T4 DNA ligase. (Maniatis et al., *Molecular Cloning: A Laboratory Manual*, 2$^{nd}$ ed. (Cold Spring Harbor Laboratory Press, New York, 1989)). DNA sequence analysis was performed by Lark Technologies, Inc. (Houston, Tex.).

EXAMPLE 2

Construction of pMBP-ToxoP30 Expression Vectors

In order to improve the immunoreactivity of the Toxo antigen cocktails described in U.S. Pat. No. 6,329,157 B1 in an immunoassay, a suitable heterologous protein expression system was pursued that would permit the production of soluble Toxo P30 in *E. coli*. The *E. coli* maltose binding protein (MBP) fusion and purification system described in U.S. Pat. No. 5,643,758 has been found to be useful for the production and purification of soluble fusion proteins in *E. coli*. (In particular, the vectors described therein have sequences coding for the recognition site of a specific protease (e.g., Factor Xa, enterokinase or Genenase™) such that the protein of interest may be cleaved from MBP.) Fusion of proteins to MBP enhances their solubility in *E. coli* (Kapust and Waugh (1999) Protein Science 8, 1668–1674). Several different constructs were made taking into consideration the observation that native Toxo P30 is post-translationally cleaved prior to insertion into the tachyzoite membrane (Burg et al. (1988) J. Immunol. 141: 3584–3591). The exact cleavage sites for Toxo P30 are unknown.

Plasmid pToxo-P30 described in U.S. Pat. No. 6,329,157 B1 was used as template DNA for a series of PCR reactions to generate DNA fragments containing different portions of the Toxo P30 gene. The pToxo-P30 plasmid DNA was prepared using standard methods. The pMAL-c2X (cytoplasmic expression vector) and pMAL-p2X (periplasmic expression vector) plasmids were purchased from New England Biolabs, Beverly Mass. and were digested with the restriction enzymes EcoRI and HindIII in preparation for subcloning the Toxo P30 gene fragments.

Step A: Construction of pMBP-c2X-ToxoP30(52-336aa)

The plasmid pMBP-c2X-ToxoP30(52-336aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 1). Plasmid pMAL-c2X was digested with EcoRI/HindIII and the vector backbone was purified with a Qiaquick PCR purification kit. A sense primer, starting at nucleotide 464 of the P30 gene containing an EcoRI site and an antisense primer containing a HindIII site, starting at nucleotide 1318 of the P30 gene (Burg et al. (1988) J. Immunol. 141:3584–3591) were synthesized as shown below:

Sense Primer [SEQ ID NO:1] 5'-GGC GAATTCCTTGTTGCCAATCAAGTTGTCACC-3' (EcoRI site is underlined)

Antisense Primer [SEQ ID NO:2] 5'-CGCT-GAAGCTTTCACGCGACACAAGCTGCGA-3' (HindIII site is underlined)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 855 base pair DNA fragment containing Toxo P30 was purified with a Qiaquick PCR purification kit. The purified 855 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30(52-336aa) contained the Toxo P30 gene cloned at the EcoRI/HindIII sites of pMAL-c2X. The complete DNA sequence [SEQ ID NO:3] of plasmid pMBP-c2X-ToxoP30(52-336aa) is shown in FIG. 2 and the corresponding amino acid sequence [SEQ ID NO:4] of the MBP-ToxoP30(52-336aa) fusion protein is also shown in FIG. 2, wherein amino acid residues 392–676 of SEQ ID NO:4 correspond to amino acids 52–336 of the P30 antigen of *Toxoplasma gondii*. The DNA sequence [SEQ ID NO:5] of ToxoP30(52-336aa) is shown in FIG. 3, and the corresponding amino acid sequence [SEQ ID NO:6] of the ToxoP30(52-336aa) protein is also shown in FIG. 3, wherein amino acid residues 1–285 of SEQ ID NO:6 correspond to amino acids 52–336 of the P30 antigen of *Toxoplasma gondii.*

Step B: Construction of pMBP-p2X-ToxoP30(52-336aa)

The plasmid pMBP-p2X-ToxoP30(52-336aa) was constructed by cloning a DNA fragment containing Toxo P30, obtained by PCR amplification of Toxo P30 DNA contained in plasmid pToxo-P30, into the EcoRI/HindIII sites of pMAL-p2X (FIG. 4). Plasmid pMAL-p2X was digested with EcoRI/HindIII, and the vector backbone was purified with a Qiaquick PCR purification kit. A sense primer, starting at nucleotide 464 of the P30 gene containing an EcoRI site, and an antisense primer containing a HindIII site, starting at nucleotide 1318 of the P30 gene (Burg et al. (1988) J. Immunol. 141:3584–3591) were synthesized as shown below:

Sense Primer [SEQ ID NO:1] 5'-GGC GAATTCCTTGTTGCCAATCAAGTTGTCACC-3' (EcoRI site is underlined.)

Antisense Primer [SEQ ID NO:2] 5'-CGCT-GAAGCTTTCACGCGACACAAGCTGCGA-3' (HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 855 base pair DNA fragment containing Toxo P30 was purified with a Qiaquick PCR purification kit. The purified 855 base pair fragment was ligated to pMAL-p2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-p2X-ToxoP30(52-336aa) contained the Toxo P30 gene cloned at the EcoRI/HindIII sites of pMAL-p2X. The complete DNA sequence [SEQ ID NO:7] of plasmid pMBP-p2X-ToxoP30(52-336aa) is shown in FIG. 5, and the corresponding amino acid sequence [SEQ ID NO:8] of the MBP-ToxoP30P(52-336aa) fusion protein is shown in FIG. 5, wherein amino acid residues 417–701 of SEQ ID NO:8 correspond to amino acids 52–336 of the P30 antigen of *Toxoplasma gondii*.

Step C: Construction of pMBP-c2X-ToxoP30del1C(52-324aa)

Figure 6:
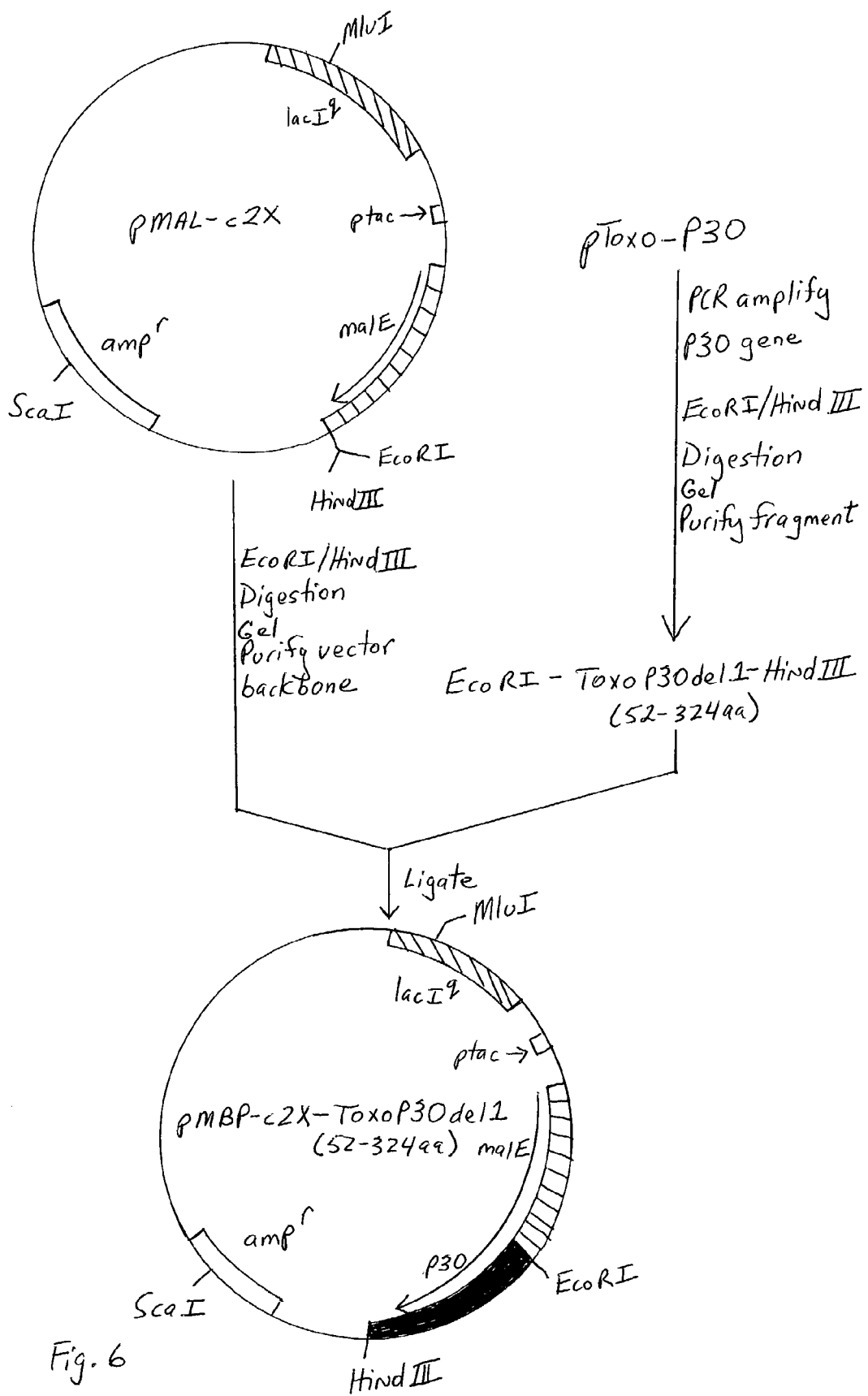
FIG. 6 is a schematic of the construction of plasmid pMBP-c2X-ToxoP30del1(52-324aa).

The plasmid pMBP-c2X-ToxoP30del1(52-324aa), an intermediate in the construction of plasmid pMBP-c2X-ToxoP30del1C, was constructed by cloning a DNA fragment containing Toxo P30, obtained by PCR amplification of Toxo P30 DNA contained in plasmid pToxo-P30, into the EcoRI/HindIII sites of pMAL-c2X (FIG. 6). Plasmid pMAL-c2X was digested with EcoRI/HindIII and the vector backbone was purified on an agarose gel. A sense primer, starting at nucleotide 464 of the P30 gene containing an EcoRI site and an antisense primer containing a HindIII site, starting at nucleotide 1282 of the P30 gene (Burg et al. (1988) J. Immunol. 141:3584-3591) were synthesized as shown below:

Sense Primer [SEQ ID NO:1] 5'-GGC GAATTCCTTGTTGCCAATCAAGTTGTCACC-3' (EcoRI site is underlined.)
Antisense Primer [SEQ ID NO:9] 5'-CAGGT CAAGCTTTCACACCATGGCAAAAATGGAAACGTG-3' (HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 819 base pair DNA fragment containing Toxo P30del1 was purified on an agarose gel. The purified 819 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del1(52-324aa) contained the Toxo P30del1 gene cloned at the EcoRI/HindIII sites of pMAL-c2X.

Figure 7:
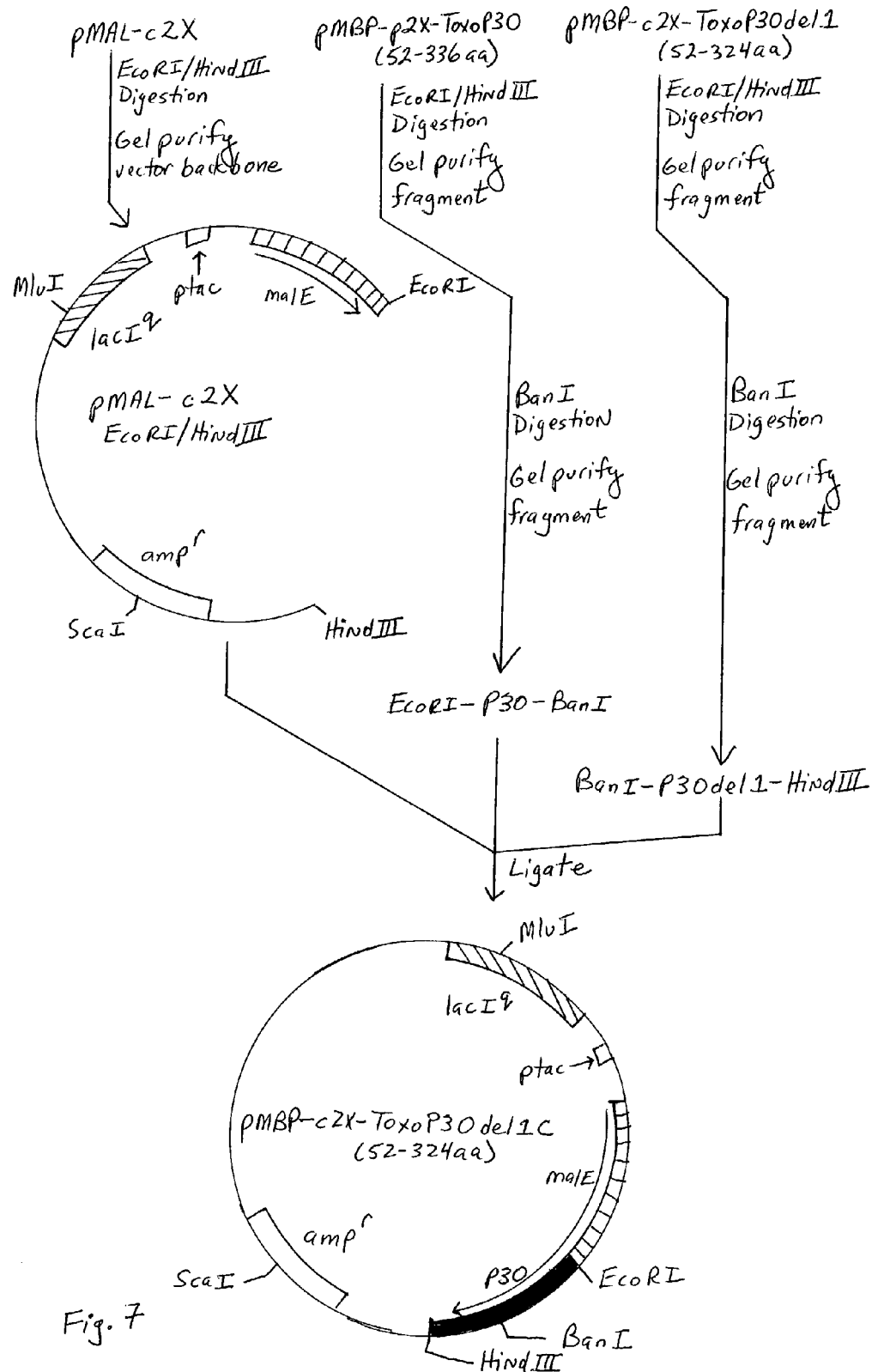
FIG. 7 is a schematic of the construction of plasmid pMBP-c2X-ToxoP30del1C(52-324aa).

Analysis of the DNA sequence of plasmid pMBP-c2X-ToxoP30del1(52-324aa) and analysis of the corresponding amino acid sequence revealed base changes in the P30 gene resulting in two amino acid changes from the published sequence (Burg et al. (1988) J. Immunol. 141:3584–3591). These mutations were located downstream of the synthetic EcoRI site (nucleotide 464) and upstream of a BanI site (nucleotide 1100) following the numbering convention of Burg et al., cited above. The mutations in plasmid pMBP-c2X-ToxoP30del1(52-324aa) were corrected as follows: Plasmid pMBP-c2X-ToxoP30del1C(52-324aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del1(52-324aa), containing the 3' portion of the Toxo P30del1 gene, into the EcoRI/HindIII sites of pMAL-c2X (FIG. 7). Plasmid pMAL-c2X was digested with EcoRI/HindIII, and the vector backbone was purified on an agarose gel. Plasmid DNAs pMBP-p2X-ToxoP30(52-336aa) and pMBP-c2X-ToxoP30del1(52-324aa) were prepared by general methods. Plasmids pMBP-p2X-ToxoP30(52-336aa) and pMBP-c2X-ToxoP30del1(52-324aa) were digested with EcoRI/HindIII and the 855 and 819 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 819 base pair EcoRI/HindIII fragment was digested with BanI and the 182 base pair BanI/HindIII fragment, containing the 3' portion of the Toxo P30del1 gene, was purified on an agarose gel. The purified 637 and 182 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del1C (52-324aa) contained the Toxo P30del1C gene cloned at the EcoRI/HindIII sites of pMAL-c2X. The complete DNA sequence [SEQ ID NO:10] of plasmid pMBP-c2X-ToxoP30del1C(52-324aa) is shown in FIG. 8 and the corresponding amino acid sequence [SEQ ID NO:11] of the MBP-ToxoP30del1C(52-324aa) fusion protein is also shown in FIG. 8, wherein amino acid residues 392–664 of SEQ ID NO:11 correspond to amino acids 52–324 of the P30 antigen of *Toxoplasma gondii*. The DNA sequence [SEQ ID NO:12] of ToxoP30del1C(52-324aa) is shown in FIG. 9 and the corresponding amino acid sequence [SEQ ID NO:13] of the ToxoP30del1C(52-324aa) protein is also shown in FIG. 9, wherein amino acid residues 1–273 of SEQ ID NO:13 correspond to amino acids 52–324 of the P30 antigen of *Toxoplasma gondii*.

Step D: Construction of pMBP-c2X-ToxoP30del2(52-311aa)

Figure 10:
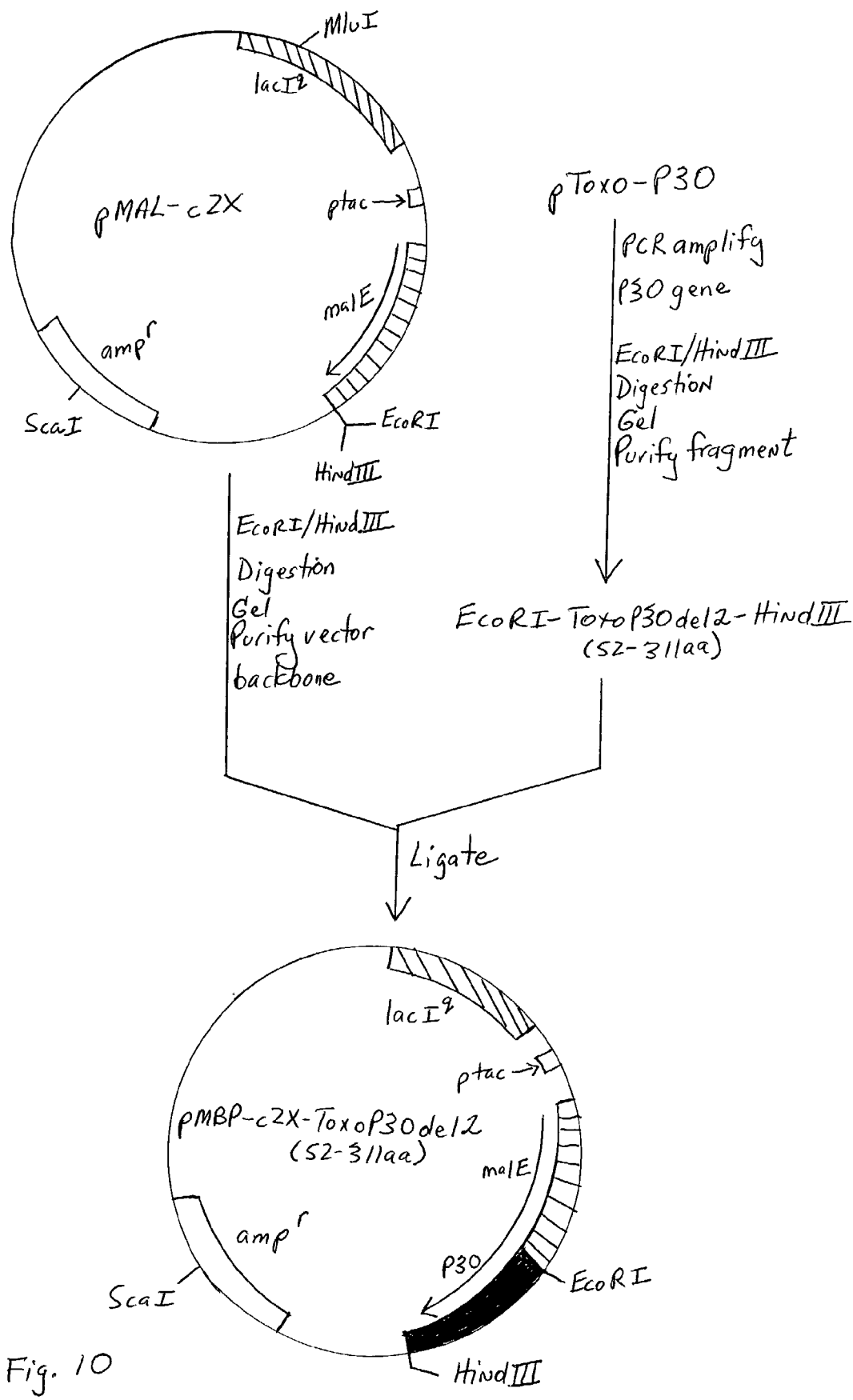
FIG. 10 is a schematic of the construction of plasmid pMBP-c2X-ToxoP30del2(52-311aa).

The plasmid pMBP-c2X-ToxoP30del2(52-311aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 10). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1243 of the P30 gene (Burg et al. (1988) J. Immunol. 141:3584–3591) were synthesized as shown below:

Sense Primer [SEQ ID NO:1] 5'-GGC GAATTCCTTGTTGCCAATCAAGTTGTCACC-3' (EcoRI site is underlined.)
Antisense Primer [SEQ ID NO:14] 5'-CAGGTC AAGCTTTCAAGCCGATTTTGCTGACCCTGCAGCCC-3' (HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 780 base pair DNA fragment containing Toxo P30del2 was purified on an agarose gel. The purified 780 base pair fragment was ligated to pMAL-c2X/EcoRI/HindIII overnight at 16° C. The ligation mixture was transformed into competent XL-1 Blue cells.

Miniprep DNA was prepared from the transformants and screened for the presence of the P30 DNA sequence by restriction enzyme analysis. Plasmid pMBP-c2X-ToxoP30del2(52-311aa) contained the Toxo P30del2 gene cloned at the EcoRI/HindIII sites of PMAL-c2X. The complete DNA sequence [SEQ ID NO:15] of plasmid pMBP-c2X-ToxoP30del2(52-311aa) is shown in FIG. 11, and the corresponding amino acid sequence [SEQ ID NO:16] of the MBP-ToxoP30del2(52-311aa) fusion protein is also shown in FIG. 11, wherein amino acid residues 392–651 of SEQ ID NO:16 correspond to amino acids 52–311 of the P30 antigen of *Toxoplasma gondii*. The DNA sequence [SEQ ID NO:17] of ToxoP30del2(52-311aa) is shown in FIG. 12 and the corresponding amino acid sequence [SEQ ID NO:18] of the ToxoP30del2(52-311aa) protein is also shown in FIG. 12, wherein amino acid residues 1–260 of SEQ ID NO:18 correspond to amino acids 52–311 of the P30 antigen of *Toxoplasma gondii*.

Step E: Construction of pMBP-c2X-ToxoP30del3C(52-300aa)

Figure 13:
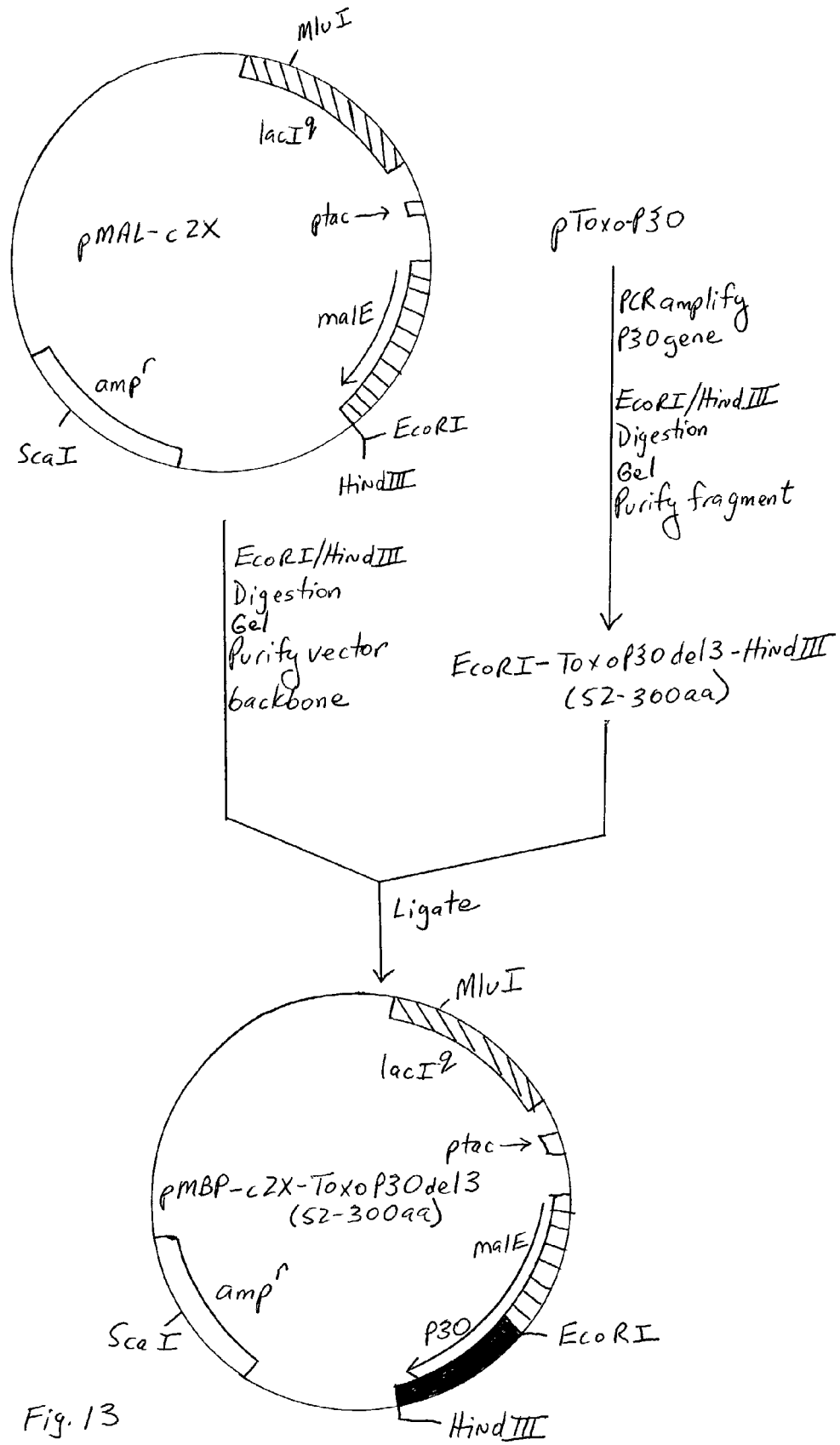
FIG. 13 is a schematic of the construction of plasmid pMBP-c2X-ToxoP30del3(52-300aa).

The plasmid pMBP-c2X-ToxoP30del3(52-300aa), an intermediate in the construction of plasmid pMBP-c2X-ToxoP30del3C(52-300aa), was constructed by cloning a DNA fragment containing Toxo P30, obtained by PCR amplification of Toxo P30 DNA contained in plasmid pToxo-P30, into the EcoRI/HindIII sites of pMAL-c2X (FIG. 13). Plasmid pMAL-c2X was digested with EcoRI/HindIII, and the vector backbone was purified on an agarose gel. A sense primer, starting at nucleotide 464 of the P30 gene containing an EcoRI site, and an antisense primer containing a HindIII site, starting at nucleotide 1210 of the P30 gene (Burg et al. (1988) J. Immunol. 141:3584–3591) were synthesized as shown below:

Sense Primer [SEQ ID NO:1] 5'-GGC GAATTCCTTGTTGCCAATCAAGTTGTCACC-3'
(EcoRI site is underlined.)
Antisense Primer [SEQ ID NO:19] 5'-CAGGTC AAGCTTTCACTCCAGTTTCACGGTACAGTG-3'
(HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 747 base pair DNA fragment containing Toxo P30del3 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del3(52-300aa) contained the Toxo P30del3 gene cloned at the EcoRI/HindIII sites of pMAL-c2X.

Figure 14:
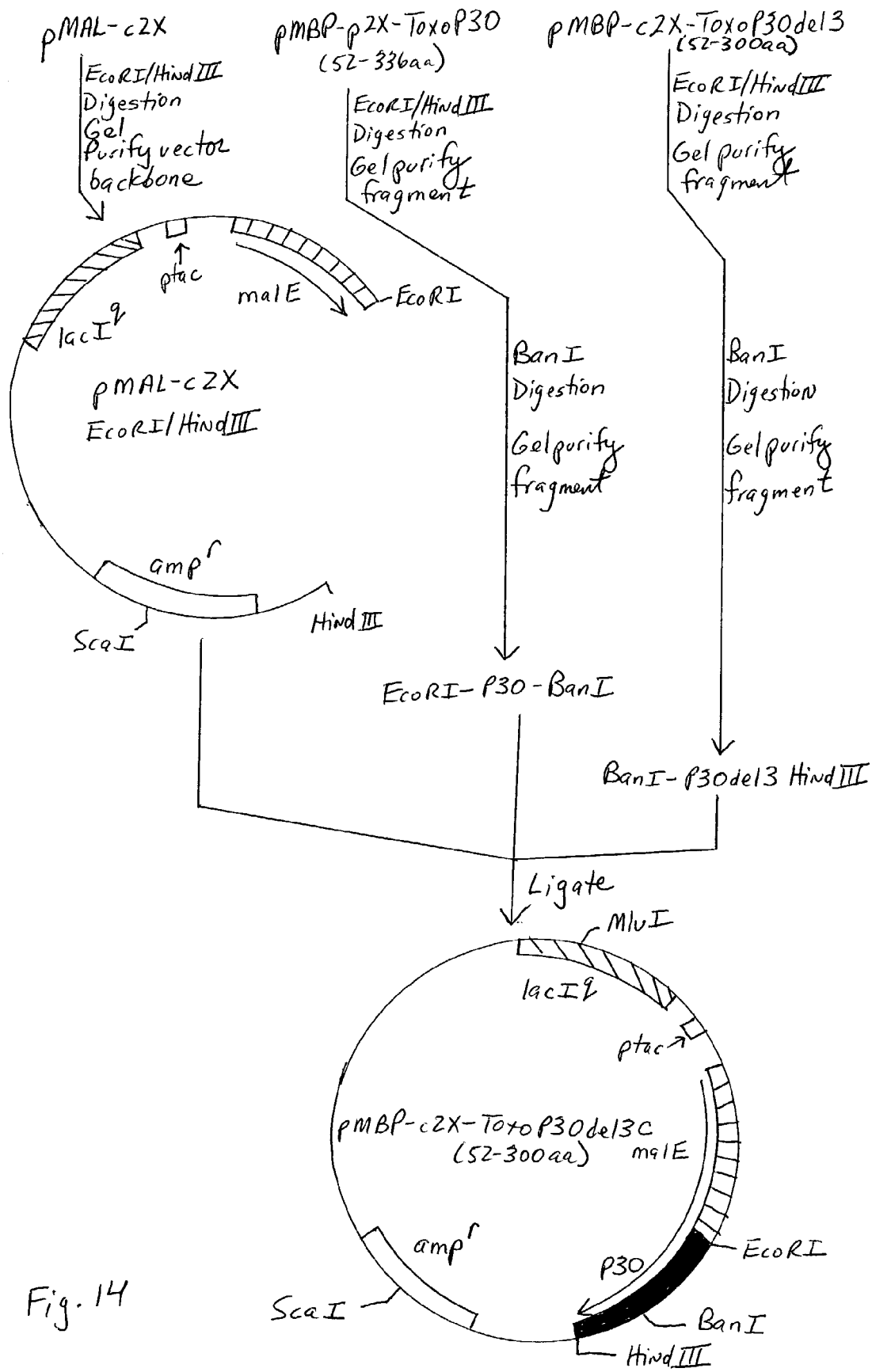
FIG. 14 is a schematic of the construction of plasmid pMBP-c2X-ToxoP30del3C(52-300aa).

Analysis of the DNA sequence of plasmid pMBP-c2X-ToxoP30del3(52-300aa) and analysis of the corresponding amino acid sequence revealed a single base change in the P30 gene that resulted in the substitution of an amino acid for a stop codon, leading to premature chain termination of the P30 protein. This mutation was located downstream of the synthetic EcoRI site (nucleotide 464) and upstream of a BanI site (nucleotide 1100) following the numbering convention of Burg et al. The mutation in plasmid pMBP-c2X-ToxoP30del3(52-300aa) was corrected as follows:

Plasmid pMBP-c2X-ToxoP30del3C(52-300aa) was constructed by cloning an EcoRI/BanI fragment from plasmid pMBP-p2X-ToxoP30(52-336aa), containing the 5' corrected portion of the Toxo P30 gene, and a BanI/HindIII fragment from plasmid pMBP-c2X-ToxoP30del3(52-300aa), containing the 3' portion of the Toxo P30del3 gene, into the EcoRI/HindIII sites of pMAL-c2X (FIG. 14). Plasmid pMBP-c2X-ToxoP30del3C(52-300aa) was deposited with the ATCC 10801 University Boulevard, Manassas, Va. 20110–2209, under terms of the Budapest Treaty on Sep. 26, 2002, and was accorded Accession No. ATCC 4722.

Plasmid pMAL-c2X was digested with EcoRI/HindIII and the vector backbone was purified on an agarose gel. Plasmid DNAs pMBP-p2X-ToxoP30(52–336aa) and pMBP-c2X-ToxoP30del3(52-300aa) were prepared by general methods. Plasmids pMBP-p2X-ToxoP30(52–336aa) and pMBP-c2X-ToxoP30del3(52-300aa) were digested with EcoRI/HindIII and the 855 and 747 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 747 base pair EcoRI/HindIII fragment was digested with BanI and the 110 base pair BanI/HindIII fragment, containing the 3' portion of the Toxo P30del3 gene, was purified on an agarose gel. The purified 637 and 110 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del3C (52-300aa) contained the ToxoP30del3C gene cloned at the EcoRI/HindIII sites of pMAL-c2X. The complete DNA sequence [SEQ ID NO:20] of plasmid pMBP-c2X-ToxoP30del3C(52-300aa) is shown in FIG. 15 and the corresponding amino acid sequence [SEQ ID NO:21] of the MBP-ToxoP30del3C(52-300aa) fusion protein is also shown in FIG. 15, wherein amino acid residues 392–640 of SEQ ID NO:21 correspond to amino acids 52–300 of the P30 antigen of *Toxoplasma gondii*. The DNA sequence [SEQ ID NO:22] of ToxoP30del3C(52-300aa) is shown in FIG. 16 and the corresponding amino acid sequence [SEQ ID NO:23] of the ToxoP30del3C(52-300aa) protein is also shown in FIG. 16, wherein amino acid residues 1–249 of SEQ ID NO:23 correspond to amino acids 52–300 of the P30 antigen of *Toxoplasma gondii*.

Step F: Construction of pMBP-c2X-ToxoP30del4C(52-294aa)

Figure 17:
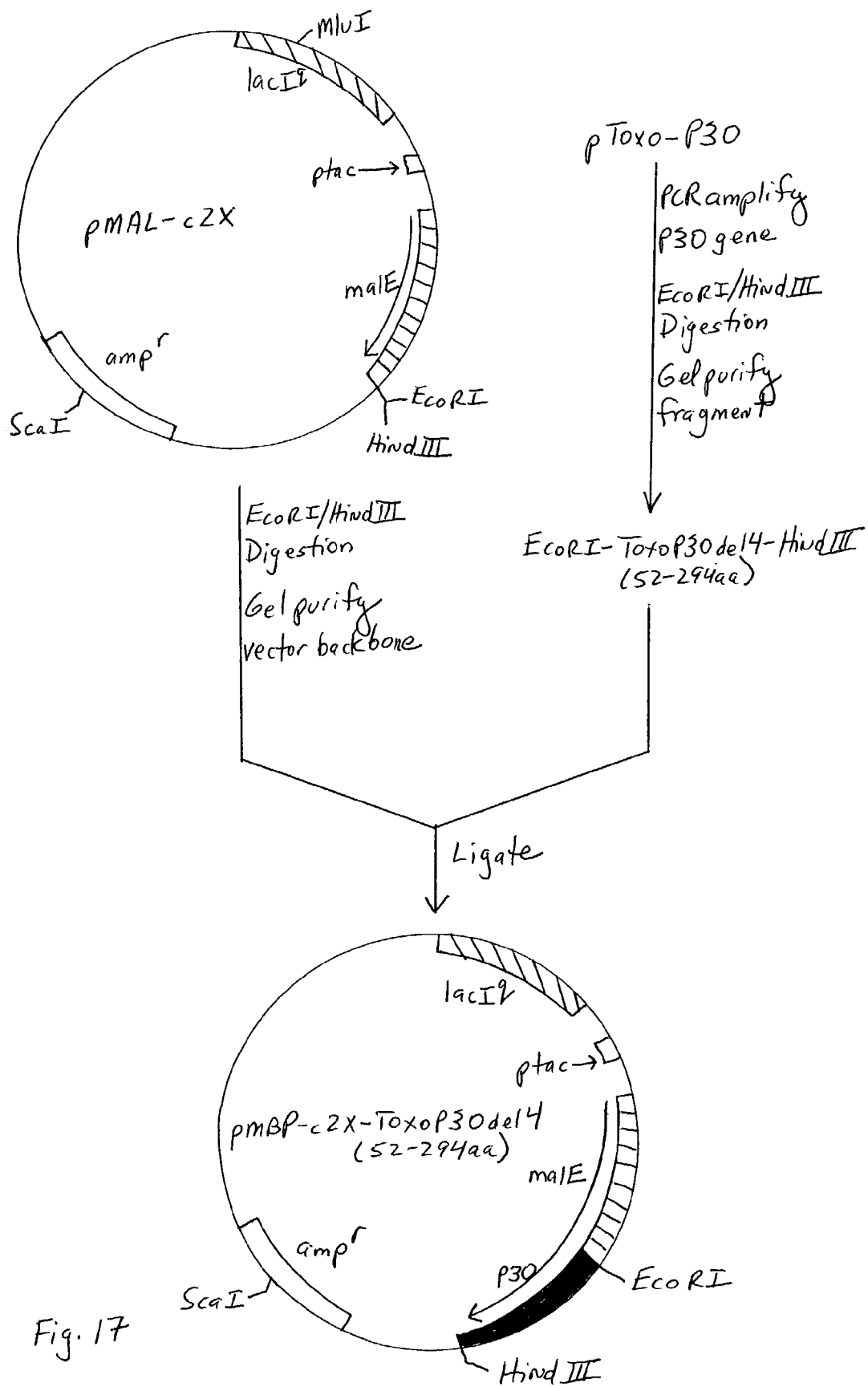
FIG. 17 is a schematic of the construction of plasmid pMBP-c2X-ToxoP30del4(52-294aa).
Figure 18:
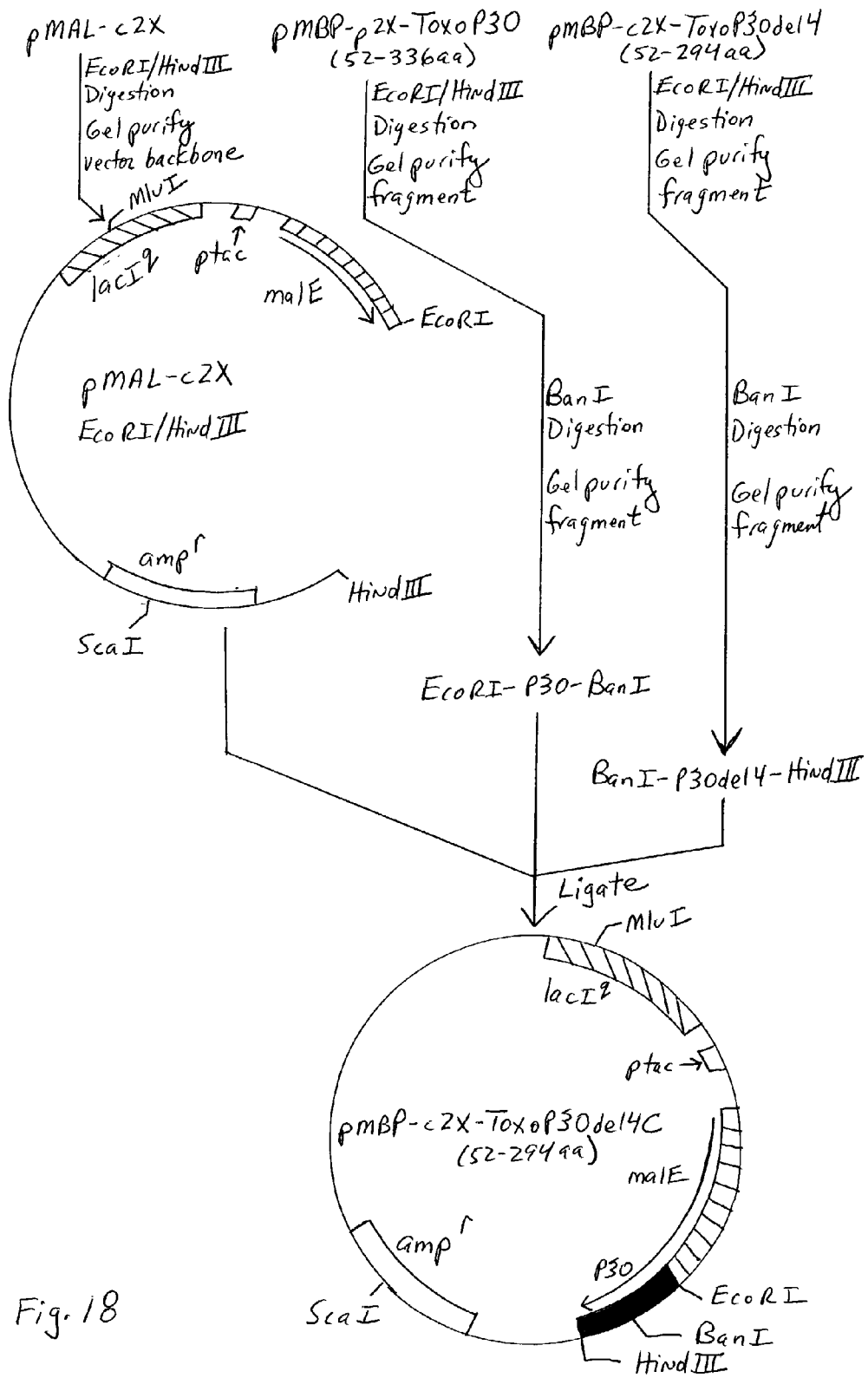
FIG. 18 is a schematic of the construction of plasmid pMBP-c2X-ToxoP30del4C(52-294aa).
Figure 21:
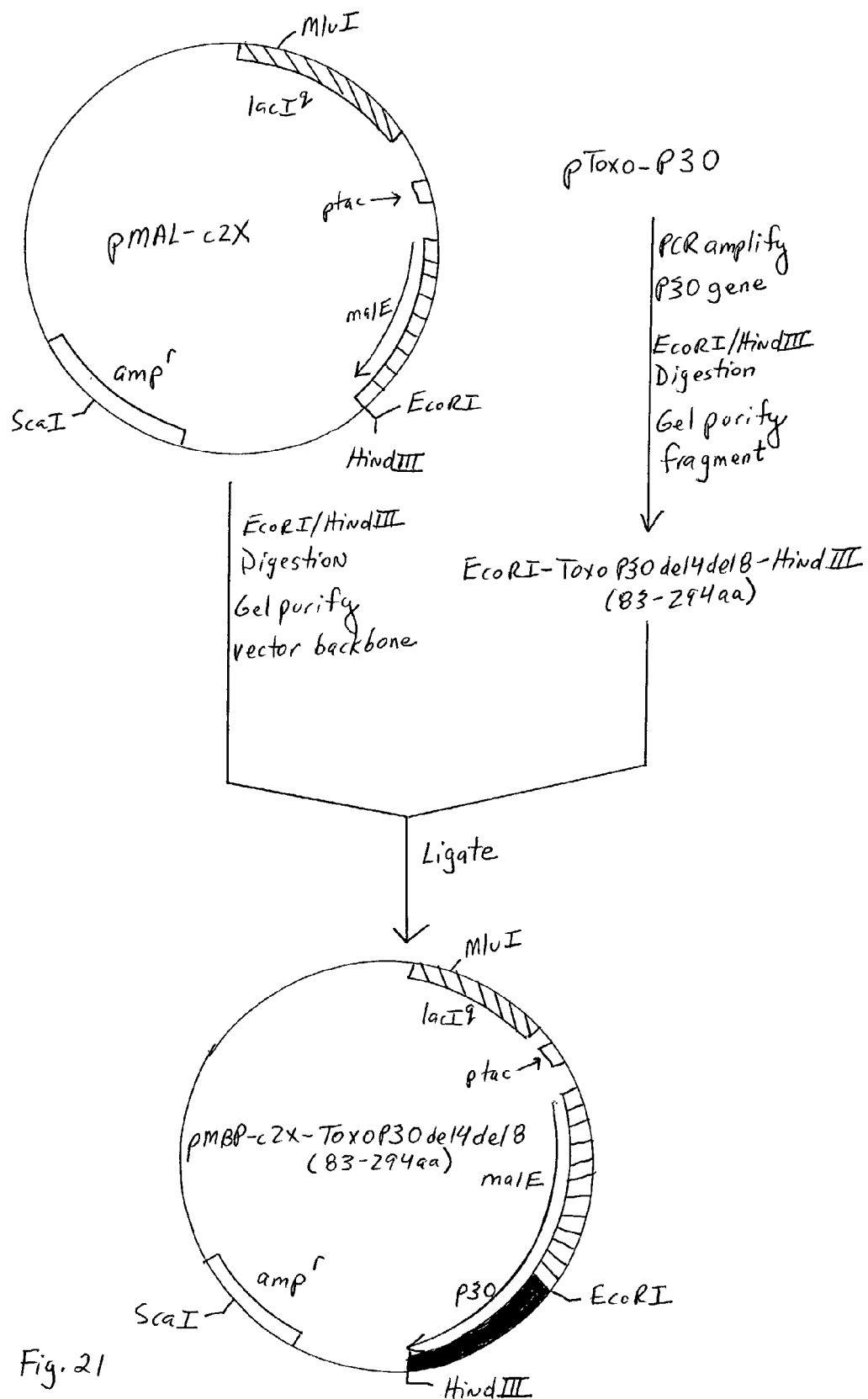
FIG. 21 is a schematic of the construction of plasmid pMBP-c2X-ToxoP30del4del8(83-294aa).
Figure 24:
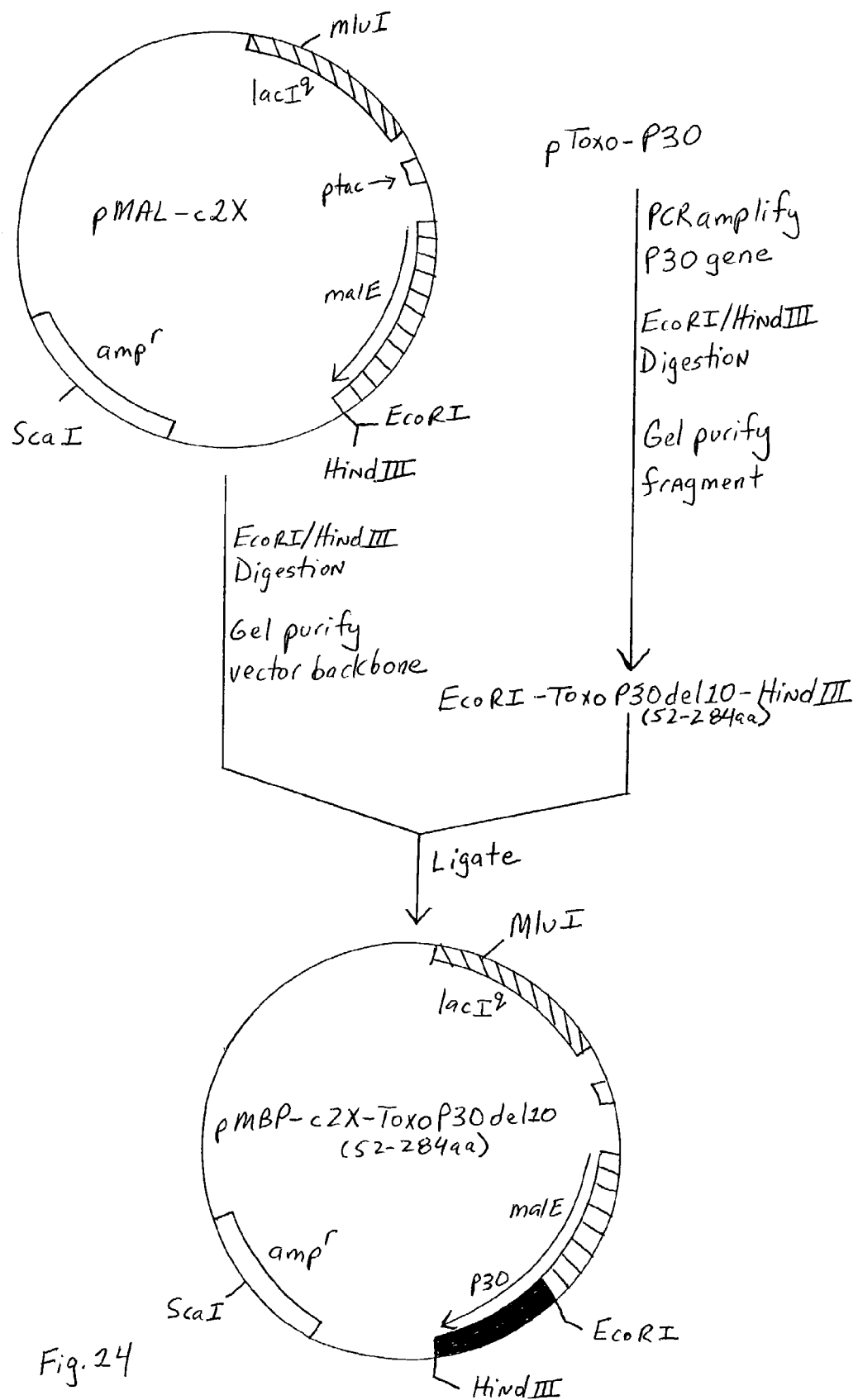
FIG. 24 is a schematic of the construction of plasmid pMBP-c2X-ToxoP30del10(52-284aa).
Figure 27:
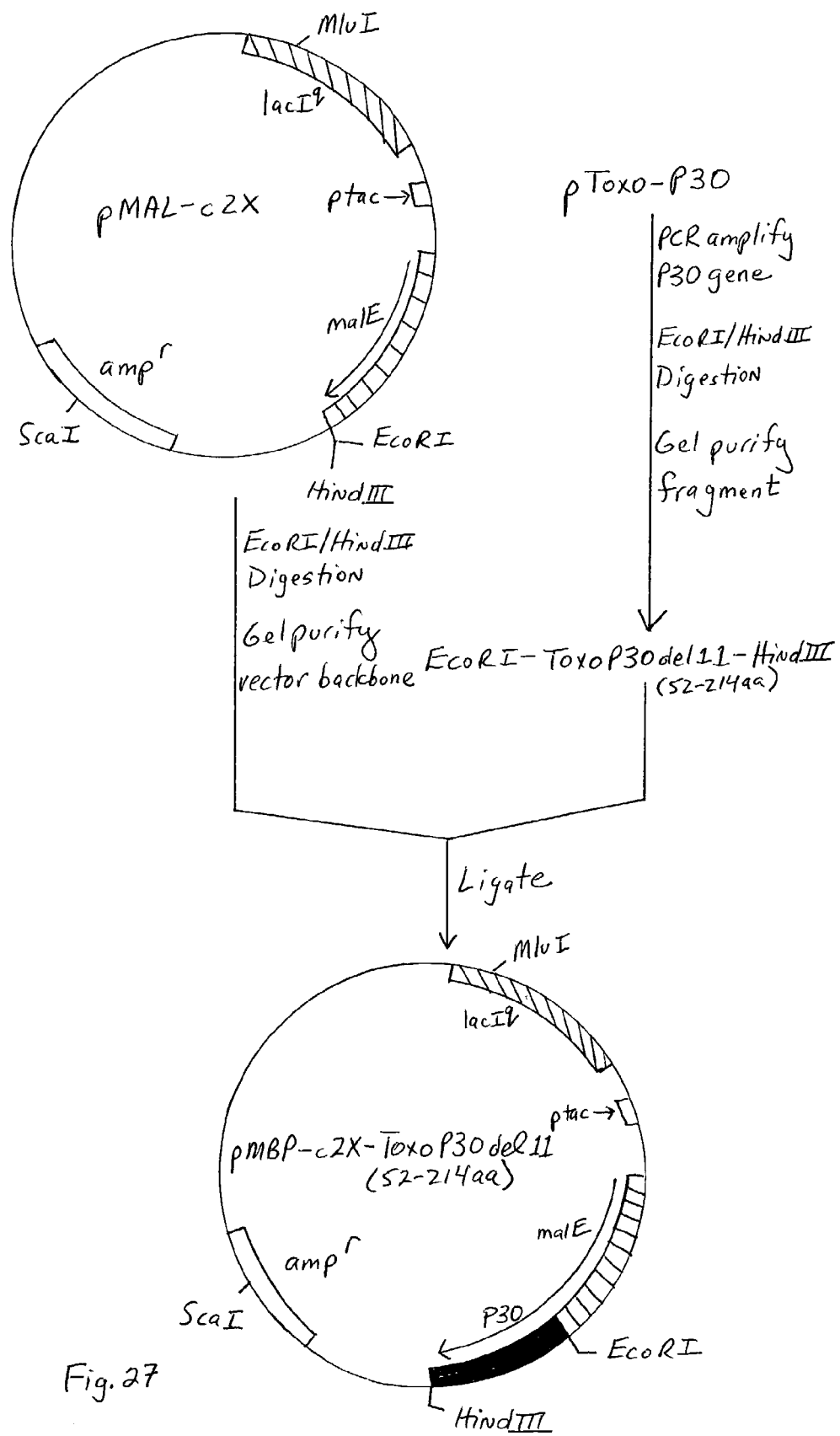
FIG. 27 is a schematic of the construction of plasmid pMBP-c2X-ToxoP30del11(52-214aa).

The plasmid pMBP-c2X-ToxoP30del4(52-294aa), an intermediate in the construction of plasmid pMBP-c2X-ToxoP30del4C(52-294aa), was constructed by cloning a DNA fragment containing Toxo P30, obtained by PCR amplification of Toxo P30 DNA contained in plasmid p-ToxoP30, into the EcoRI/HindIII sites of pMAL-c2X (FIG. 17). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1192 of the P30 gene (Burg et al. (1988) J. Immunol. 141:3584–3591) were synthesized as shown below:

Sense Primer [SEQ ID NO:1] 5'-GGC GAATTCCTTGTTGCCAATCAAGTTGTCACC-3'
(EcoRI site is underlined)
Antisense Primer [SEQ ID NO:24] 5'-CAGGTC AAGCTTTCAGTGATGCTTCTCAGGCGATCCCC-3'
(HindIII site is underlined)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 729 base pair DNA fragment containing Toxo P30del4 was purified on an agarose gel. The purified 729 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4(52-294aa) contained the Toxo P30del4 gene cloned at the EcoRI/HindIII sites of pMAL-c2X.

Analysis of the DNA sequence of plasmid pMBP-c2X-ToxoP30del4(52-294aa) and analysis of the corresponding amino acid sequence revealed base changes in the P30 gene resulting in two amino acid changes from the published sequence (Burg et al. (1988) J. Immunol. 141:3584–3591). These mutations were located downstream of the synthetic EcoRI site (nucleotide 464) and upstream of a BanI site (nucleotide 1100) following the numbering convention of Burg et al. The mutations in plasmid pMBP-c2X-ToxoP30del4(52-294aa) were corrected as follows:

Plasmid pMBP-c2X-ToxoP30del4C(52-294aa) was constructed by cloning an EcoRI/BanI fragment from plasmid pMBP-p2X-ToxoP30(52–336aa), containing the 5' corrected portion of the Toxo P30 gene, and a BanI/HindIII fragment from plasmid pMBP-c2X-ToxoP30del4(52-294aa), containing the 3' portion of the ToxoP30del4 gene, into the EcoRI/HindIII sites of pMAL-c2X (FIG. 18). Plasmid pMBP-c2X-ToxoP30del4C(52-294aa) was deposited with the ATCC 10801 University Boulevard, Manassas, Va. 20110–2209, under terms of the Budapest Treaty on Sep. 26, 2002, and was accorded Accession No. ATCC 4723.

Plasmid pMAL-c2X was digested with EcoRI/HindIII and the vector backbone was purified on an agarose gel. Plasmid DNAs pMBP-p2X-ToxoP30(52–336aa) and pMBP-c2X-ToxoP30del4(52-294aa) were prepared by general methods. Plasmids pMBP-p2X-ToxoP30(52–336aa) and pMBP-c2X-ToxoP30del4(52-294aa) were digested with EcoRI/HindIII and the 855 and 729 base pair fragments, containing the Toxo P30 gene, were purified on an agarose gel. The 855 base pair EcoRI/HindIII fragment was digested with BanI and the 637 base pair EcoRI/BanI fragment, containing the 5' corrected portion of the Toxo P30 gene, was purified on an agarose gel. The 729 base pair EcoRI/HindIII fragment was digested with BanI and the 92 base pair BanI/HindIII fragment, containing the 3' portion of the Toxo P30del4 gene and purified on an agarose gel. The purified 637 and 92 base pair fragments were ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4C (52-294aa) contained the Toxo P30del4C gene cloned at the EcoRI/HindIII sites of pMAL-c2X. The complete DNA sequence [SEQ ID NO:25] of plasmid pMBP-c2X-ToxoP30del4C(52-294aa) is shown in FIG. 19 and the corresponding amino acid sequence [SEQ ID NO:26] of the MBP-ToxoP30del4C(52-294aa) fusion protein is also shown in FIG. 19, wherein amino acid residues 392–634 of SEQ ID NO:26 correspond to amino acids 52–294 of the P30 antigen of *Toxoplasma gondii*. The DNA sequence [SEQ ID NO:27] of ToxoP30del4C(52-294aa) is shown in FIG. 20 and the corresponding amino acid sequence [SEQ ID NO:28] of the ToxoP30del4C(52-294aa) protein is also shown in FIG. 20, wherein amino acid residues 1–243 of SEQ ID NO:28 correspond to amino acids 52–294 of the P30 antigen of *Toxoplasma gondii.*

Step G: Construction of pMBP-c2X-ToxoP30del4del8(83-294aa)

The plasmid pMBP-c2X-ToxoP30del4del8(83-294aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 21). Plasmid pMAL-c2X was digested with EcoRI/HindIII and the vector backbone was purified on an agarose gel. A sense primer, starting at nucleotide 557 of the P30 gene containing an EcoRI site, and an antisense primer containing a HindIII site, starting at nucleotide 1192 of the P30 gene (Burg et al. (1988) J. Immunol. 141:3584–3591) were synthesized as shown below:

Sense Primer [SEQ ID NO:29] 5'-GGC GAATTCCCTAAAACAGCGCTCACAGAG-3' (EcoRI site is underlined.)

Antisense Primer [SEQ ID NO:24] 5'-CAGGTC AAGCTTTCAGTGATGCTTCTCAGGCGATCCCC-3' (HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 636 base pair DNA fragment containing Toxo P30del4del8 was purified on an agarose gel. The purified 636 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del4del8(83-294aa) contained the ToxoP30del4del8 gene cloned at the EcoRI/HindIII sites of pMAL-c2X. The complete DNA sequence [SEQ ID NO:30] of plasmid pMBP-c2X-ToxoP30del4del8(83-294aa) is shown in FIG. 22 and the corresponding amino acid sequence [SEQ ID NO:31] of the MBP-ToxoP30del4del8 (83-294aa) fusion protein is also shown in FIG. 22, wherein amino acid residues 392–603 of SEQ ID NO:31 correspond to amino acids 83–294 of the P30 antigen of *Toxoplasma gondii*. The DNA sequence [SEQ ID NO:32] of ToxoP30del4del8(83-294aa) is shown in FIG. 23 and the corresponding amino acid sequence [SEQ ID NO:33] of the ToxoP30del4del8(83-294aa) protein is also shown in FIG. 23, wherein amino acid residues 1–212 of SEQ ID NO:33 correspond to amino acids 83–294 of the P30 antigen of *Toxoplasma gondii.*

Step H: Construction of pMBP-c2X-ToxoP30del10 (52–284aa)

The plasmid pMBP-c2X-ToxoP30del10(52–284aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 24). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 1162 of the P30 gene (Burg et al. (1988) J. Immunol. 141:3584–3591) were synthesized as shown below:

Sense Primer [SEQ ID NO:1] 5'-GGC GAATTCCTTGTTGCCAATCAAGTTGTCACC-3' (EcoRI site is underlined.)

Antisense Primer [SEQ ID NO:34] 5'-CAGGTC AAGCTTTCATCCAATAATGACGCTTTTTGACTC-3' (HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 699 base pair DNA fragment containing Toxo P30del10 was purified on an agarose gel. The purified 699 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del10(52–284aa) contained the Toxo P30del10 gene cloned at the EcoRI/HindIII sites of pMAL-c2X. The complete DNA sequence [SEQ ID NO:35] of plasmid pMBP-c2X-ToxoP30del10(52–284aa) is shown in FIG. 25 and the corresponding amino acid sequence [SEQ ID NO:36] of the MBP-ToxoP30del10(52–284aa) fusion protein is also shown in FIG. 25, wherein amino acid residues 392–624 of SEQ ID NO:36 correspond to amino acids 52–284 of the P30 antigen of *Toxoplasma gondii*, with the exception that amino acid residue 546 of SEQ ID NO:36 is glycine instead of glutamic acid. The DNA sequence [SEQ ID NO:37] of ToxoP30del10(52–284aa) is shown in FIG. 26 and the corresponding amino acid sequence [SEQ ID NO:38] of the ToxoP30del10(52–284aa) protein is also shown in FIG. 26, wherein amino acid residues 1–233 of SEQ ID NO:38 correspond to amino acids 52–284 of the P30 antigen of *Toxoplasma gondii*, with the exception that amino acid residue 155 of SEQ ID NO:38 is glycine instead of glutamic acid.

Step I: Construction of pMBP-c2X-ToxoP30del11(52-214aa)

The plasmid pMBP-c2X-ToxoP30del11(52-214aa) was constructed by cloning a DNA fragment containing Toxo P30, obtained by PCR amplification of Toxo P30 DNA contained in plasmid pToxo-P30, into the EcoRI/HindIII sites of pMAL-c2X (FIG. 27). Plasmid pMAL-c2X was digested with EcoRI/HindIII and the vector backbone was purified on an agarose gel. A sense primer, starting at nucleotide 464 of the P30 gene containing an EcoRI site, and an antisense primer containing a HindIII site, starting at nucleotide 952 of the P30 gene (Burg et al. (1988) J. Immunol. 141:3584–3591) were synthesized as shown below:

Sense Primer [SEQ ID NO:1] 5'-GGC GAATTCCTTGTTGCCAATCAAGTTGTCACC-3'
(EcoRI site is underlined.)

Antisense Primer [SEQ ID NO:39] 5'-CAGGTC AAGCTTTCACACGAGGGTCATTGTAGTGGG-3'
(HindIII site is underlined.)

The sense and antisense primers were added to a PCR reaction mixture containing plasmid pToxo-P30. After PCR amplification and purification of the reaction mixture with a Qiaquick PCR purification kit, the reaction mixture was digested with EcoRI and HindIII, and the 489 base pair DNA fragment containing Toxo P30del11 was purified on an agarose gel. The purified 489 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 DNA sequence by restriction enzyme analysis. Plasmid pMBP-c2X-ToxoP30del11(52-214aa) contained the Toxo P30del11 gene cloned at the EcoRI/HindIII sites of pMAL-c2X. The complete DNA sequence [SEQ ID NO:40] of plasmid pMBP-c2X-ToxoP30del11(52-214aa) is shown in FIG. 28 and the corresponding amino acid sequence [SEQ ID NO:41] of the MBP-ToxoP30del11(52-214aa) fusion protein is also shown in FIG. 28, wherein amino acid residues 392–554 of SEQ ID NO:41 correspond to amino acids 52–214 of the P30 antigen of *Toxoplasma gondii*. The DNA sequence [SEQ ID NO:42] of ToxoP30del11(52-214aa) is shown in FIG. 29 and the corresponding amino acid sequence [SEQ ID NO:43] of the ToxoP30del11(52-214aa) protein is also shown in FIG. 29, wherein amino acid residues 1–163 of SEQ ID NO:43 correspond to amino acids 52–214 of the P30 antigen of *Toxoplasma gondii*.

EXAMPLE 3

Expression of rpMBP-c2X-ToxoP30 Antigens in *E. coli*

Step A: Expression of Cloned Genes in *E. coli*

Bacterial clones pMBP-c2X-ToxoP30(52–336aa), pMBP-c2X-ToxoP30del1C(52–324aa), pMBP-c2X-ToxoP30del2(52–311aa), pMBP-c2X-ToxoP30del3C(52-300aa), pMBP-c2X-ToxoP30del4C(52-294aa), pMBP-c2X-ToxoP30del4del8(83-294aa), pMBP-c2X-ToxoP30del10 (52–284aa) and pMBP-c2X-ToxoP30del11(52-214aa) expressing the MBP fusion proteins rpMBP-c2X-ToxoP30 (52–336aa), rpMBP-c2X-ToxoP30del1C(52–324aa), rpMBP-c2X-ToxoP30del2(52–311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52–284aa) and rpMBP-c2X-ToxoP30del11(52-214aa) of Example 2 were grown in "SUPERBROTH II" media containing 100 μg/ml ampicillin to log phase, and the synthesis of the MBP-ToxoP30 fusion proteins was induced by the addition of IPTG as previously described (Robinson et al. (1993) J. Clin. Microbiol. 31:629–635). After 4 hours post-induction, the cells were harvested, and the cell pellets were stored at −80° C. until protein purification occurred.

Step B: Purification of MBP-ToxoP30 Fusion Proteins

Soluble fusion proteins rpMBP-c2X-ToxoP30 (52–336aa), rpMBP-c2X-ToxoP30del1C(52–324aa), rpMBP-c2X-ToxoP30del2(52–311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11(52-214aa) were purified after lysis from cell paste following the New England Biolabs pMAL Protein Fusion and Purification instruction manual. Following lysis and centrifugation, the crude supernatants containing the fusion proteins were loaded onto an amylose affinity column. Following washing of the column, the fusion proteins were eluted from the column with maltose, appropriate column fractions were pooled and filtered through a 0.2μ filter, and then stored at 2–8° C. until coating onto microparticles.

EXAMPLE 4

Evaluation of rpMBP-c2X-ToxoP30 Antigens in an Automated Toxo IgG and IgM Immunoassay Step A: Coating of rpMBP-c2X-ToxoP30 Antigens onto Microparticles Prior to coating microparticles, the rpMBP-c2X-ToxoP30 (52–336aa), rpMBP-c2X-ToxoP30del1C(52–324aa), rpMBP-c2X-ToxoP30del2(52–311aa), rpMBP-c2X-ToxoP30del3C(52-300aa), rpMBP-c2X-ToxoP30del4C(52-294aa), rpMBP-c2X-ToxoP30del4del8(83-294aa), rpMBP-c2X-ToxoP30del10(52-284aa) and rpMBP-c2X-ToxoP30del11(52-214aa) antigens were diluted to a concentration of 1 mg/ml and incubated at 37° C. for 24 hours. Following the heat treatment step, the rpMBP-c2X-ToxoP30 antigens were coated separately onto sulfate-derivatized polystyrene microparticles (1–5% solids) in a vessel containing MES pH 6.2 buffer with EDAC for 30 minutes at room temperature, on an end over end rotator. The coated microparticles were then collected by centrifugation at 14,000×g for 10 minutes, and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1–0.3% solids and filled into plastic bottles.

Step B: Description of the AxSYM® Toxo IgG v2 Reagent Pack, Calibrators, Controls, Panel 6, and Assay Diskette The reagent pack for the automated AxSYM Toxo IgG v2 assay is designed for the detection of human anti-Toxo IgG and consists of the following components. Bottle number one contains microparticles coated with purified recombinant Toxo antigens (Example 4A) in a microparticle storage buffer. In order to prevent human anti-MBP or anti-CKS antibodies causing a false positive reaction in the assay, purified MBP or CKS can be added to the microparticle storage buffer. Bottle number two contains the preferred conjugate, a goat anti-human IgG alkaline phosphatase conjugate. This conjugate is titered to determine a working concentration of 0.1–5 µg/ml. The conjugate is diluted into a conjugate diluent containing Tris buffer, pH 7.4, sodium, calcium, magnesium, and zinc chloride, Nipasept, A56620, non-fat dry milk, Brij-35, mouse serum, and mannitol. Bottle number three contains the preferred assay diluent to minimize non-specific binding to the microparticles and assay matrix. This assay diluent consists of a Tris buffer, pH 7.5 containing sodium chloride, sodium EDTA, non-fat dry milk, Nipasept, A56620, and Tween 20. Bottle number four contains a phosphate buffer line diluent.

Six Assay Calibrators labeled A–F are derived from Toxo IgG positive plasma pools or human anti-Toxo IgG monoclonal antibodies and are required to calibrate the AxSYM® Toxo IgG v2 assay. These calibrators are matched to calibrators previously matched to the TOX-S WHO International Standard. The concentration range of these calibrators is 0–300 IU/ml. Positive and Negative controls are required to evaluate the assay calibration and establish assay validity. The Positive Control is prepared from Toxo IgG positive plasma pools or human anti-Toxo IgG monoclonal antibodies. The Negative Control is prepared from Toxo IgG negative plasma pools. Panel 6 is a pool of Toxo IgG and IgM positive plasma units derived from blood donors with an acute toxoplasmosis.

The assay diskette for the AxSYM® Toxo IgG v2 assay contains the assay protocol software necessary to run the automated immunoassay on the Abbott "AxSYM®" instrument (Abbott Laboratories, Abbott Park, Ill.). In addition to the AxSYM® Toxo IgG v2 Reagent Pack, assay Calibrators, and Controls described above, the following assay components located on the instrument are required to run the assay: Sample Cups, AxSYM® Line Diluent, MEIA buffer, Reaction Vessels, MUP, and Matrix Cells. The sequence of events for the automated assay are as follows: The pipetting probe in the kitting center delivers the patient sample and line diluent to the reaction vessel sample well; the pipetting probe then kits the appropriate volumes of assay diluent, line diluent, and conjugate required for the assay from the reagent pack into the designated reaction vessel wells; this probe then delivers the recombinant Toxo antigen coated microparticles from the reagent pack and an aliquot of the diluted sample to the designated reaction vessel well; the reaction vessel is then transferred to the process carousel; Toxo-specific antibodies bind to the Toxo recombinant antigen coated microparticles forming an antigen-antibody complex; assay diluent is added to the reaction mixture and matrix cell and then an aliquot of the reaction mixture is transferred to the glass fiber matrix in the auxiliary carousel; the microparticles bind irreversibly to the matrix; the matrix is washed with MEIA buffer and line diluent to remove unbound antibodies; goat anti-human IgG alkaline phosphate conjugate is added to the matrix and binds to the Toxo-specific IgG captured by the Toxo recombinant antigens; the matrix is then washed with MEIA buffer to remove any unbound enzyme-antibody conjugate; the enzyme substrate MUP is added to the matrix; the alkaline phosphatase enzyme present on the matrix attached to the goat anti-human IgG catalyzes the hydrolysis of the phosphoryl moiety from MUP, producing a highly fluorescent product which is measured by the AxSYM MEIA optical system; the signal intensity (rate counts) is proportional to the amount of Toxo-specific IgG antibodies present in the sample.

Step C: Description of the AxSYM Toxo® IgM v2 Reagent Pack, Index Calibrator, Controls, and Assay Diskette The reagent pack for the automated AxSYM Toxo IgM v2 assay is designed for the detection of human anti-Toxo IgM and consists of the following components. Bottle number one contains microparticles coated with purified recombinant Toxo antigens (Example 4A) in a microparticle storage buffer. In order to prevent human anti-MBP or anti-CKS antibodies causing a false positive reaction in the assay, purified MBP or CKS can be added to the microparticle storage buffer. Bottle number two contains the preferred conjugate, a goat anti-human IgM alkaline phosphatase conjugate. This conjugate is titered to determine a working concentration of 0.1–5 µg/ml. The conjugate is diluted into a conjugate diluent containing Tris buffer, pH 7.4, sodium, calcium, magnesium, and zinc chloride, Nipasept, A56620, non-fat dry milk, Brij-35, mouse serum, and mannitol. Bottle number three contains the preferred assay diluent to minimize non-specific binding to the microparticles and assay matrix. This assay diluent consists of a Tris buffer, pH 7.5 containing sodium chloride, sodium EDTA, non-fat dry milk, Nipasept, A56620, and Tween 20. Bottle number four contains either phosphate buffer line diluent or RF Neutralization Buffer.

The Index Calibrator is derived from Toxo IgM positive plasma pools or human anti-Toxo IgM monoclonal antibodies and is required to calibrate the AxSYM® Toxo IgM v2 assay. Positive and Negative controls are required to evaluate the assay calibration and establish assay validity. The Positive Control is prepared from Toxo IgM positive plasma pools or human anti-Toxo IgM monoclonal antibodies. The Negative Control is prepared from Toxo IgM negative plasma pools.

The assay diskette for the AxSYM® Toxo IgM v2 assay contains the assay protocol software necessary to run the automated immunoassay on the Abbott "AxSYM" instrument (Abbott Laboratories, Abbott Park, Ill.). In addition to the AxSYM® Toxo IgM v2 Reagent Pack, Index Calibrator, and Controls described above, the following assay components located on the instrument are required to run the assay: Sample Cups, AxSYM® Line Diluent, MEIA buffer, Reaction Vessels, MUP, and Matrix Cells. The sequence of events for the automated assay are as follows: The pipetting probe in the kitting center delivers the patient sample and line diluent to the reaction vessel sample well; the pipetting probe then kits the appropriate volumes of assay diluent, line diluent or RF Neutralization Buffer, and conjugate required for the assay from the reagent pack into the designated reaction vessel wells; this probe then delivers the recombinant Toxo antigen coated microparticles from the reagent pack and an aliquot of the diluted sample to the designated reaction vessel well; the reaction vessel is then transferred to the process carousel; Toxo-specific antibodies bind to the Toxo recombinant antigen coated microparticles forming an antigen-antibody complex; assay diluent is added to the reaction mixture and matrix cell and then an aliquot of the reaction mixture is transferred to the glass fiber matrix in the auxiliary carousel; the microparticles bind irreversibly to the matrix; the matrix is washed with MEIA buffer and line diluent or RF Neutralization Buffer to remove unbound antibodies; goat anti-human IgM alkaline phosphate conjugate is added to the matrix and binds to the Toxo-specific IgM captured by the Toxo recombinant antigens; the matrix is then washed with MEIA buffer to remove any unbound enzyme-antibody conjugate; the enzyme substrate MUP is added to the matrix; the alkaline phosphatase enzyme present on the matrix attached to the goat anti-human IgM catalyzes the hydrolysis of the phosphoryl moiety from MUP, producing a highly fluorescent product which is measured by the AxSYM® MEIA optical system; the signal intensity (rate counts) is proportional to the amount of Toxo-specific IgM antibodies present in the sample.

Step D: Evaluation of MBP fusion proteins rpMBP-c2X-ToxoP30(52-336aa), rpMBP-c2X-ToxoP30del1C(52-324aa), rpMBP-c2X-ToxoP30del2(52–311aa), rpMBP-c2X-ToxoP30del3C(52-300aa), rpMBP-c2X-ToxoP30del4C(52-294aa), rpMBP-c2X-ToxoP30del4del8 (83-294aa), rpMBP-c2X-ToxoP30del10(52-284aa) and rpMBP-c2X-ToxoP30del11(52-214aa) in the AxSYM® Toxo TgG v2 and Toxo IgM v2 Immunoassays The AxSYM® Toxo IgG and IgM reagent packs were assembled as described in Examples 4B and 4C using the microparticles coated with the Toxo antigens described in Example 4A. The Toxo IgG A and F calibrators (Acal and Fcal) and Panel 6 (PNL6) were tested with the AxSYM Toxo IgG v2 reagent packs and the Toxo IgM Negative Control (NC), Index Calibrator (IC), and Panel 6 (PNL6) were tested with the AxSYM® Toxo IgM v2 reagent packs. The results are shown below in Tables 1 and 2.

TABLE 1

Evaluation of the rpMBP-c2X-ToxoP30 Antigens in the AxSYM ® Toxo IgG v2 Assay

| | Rate Counts | | | | |
|---|---|---|---|---|---|
| Antigen Coated | Acal | Fcal | Fcal/ Acal | PNL6 | PNL6 / Acal |
| rpMBP-c2X-ToxoP30 (52-336aa) | 40 | 3495 | 87 | 643 | 16 |
| rpMBP-c2X-ToxoP30 del1C(52-324aa) | 29 | 2599 | 90 | 544 | 19 |
| rpMBP-c2X-ToxoP30 del2(52-311aa) | 28 | 3191 | 114 | 1129 | 40 |
| rpMBP-c2X-ToxoP30 del3C(52-300aa) | 29 | 3199 | 110 | 1112 | 38 |
| rpMBP-c2X-ToxoP30 del4C(52-294aa) | 29 | 3352 | 116 | 1302 | 45 |
| rpMBP-c2X-ToxoP30 del10(52-284aa) | 40 | 4277 | 107 | 1285 | 32 |
| rpMBP-c2X-ToxoP30 del11(52-214aa) | 48 | 4076 | 85 | 1118 | 23 |
| rpMBP-c2X-ToxoP30 del4del8(83-294aa) | 34 | 59 | 1.7 | 37 | 1.1 |

TABLE 2

Evaluation of the rpMBP-c2X-ToxoP30 Antigens in the AxSYM® Toxo IgM v2 Assay

| | Rate Counts | | | |
|---|---|---|---|---|
| Antigen Coated | NC | IC | PNL6 | PNL6/ NC |
| rpMBP-c2X-ToxoP30 (52-336aa) | 33 | 175 | 210 | 6.4 |
| rpMBP-c2X-ToxoP30del1C (52-324aa) | 48 | 189 | 250 | 5.2 |
| rpMBP-c2X-ToxoP30del2 (52-311aa) | 43 | 315 | 440 | 10.2 |
| rpMBP-c2X-ToxoP30del3C (52-300aa) | 49 | 187 | 459 | 9.4 |
| rpMBP-c2X-ToxoP30del4C (52-294aa) | 51 | 203 | 527 | 10.3 |
| rpMBP-c2X-ToxoP30del10 (52-284aa) | 39 | 158 | 370 | 9.5 |
| rpMBP-c2X-ToxoP30del11 (52-214aa) | 36 | 130 | 312 | 8.7 |
| rpMBP-c2X-ToxoP30del4 del8 (83-294aa) | 38 | 75 | 38 | 1.0 |

As can be seen in both Tables 1 and 2, a surprising result was obtained. In particular, deletion of amino acids from the C-terminus of the ToxoP30 antigen resulted in improved Toxo-specific IgG and IgM immunoreactivity, as measured by increased rate counts for Panel 6 and improved rate count ratios for Fcal/Acal, Panel 6/Acal, and Panel 6/NC, up to a deletion of 42 amino acids (compare protein rpMBP-c2X-ToxoP30del4C(52-294aa) with protein rpMBP-c2X-ToxoP30(52-336aa) in Tables 1 and 2). The genetically engineered rpMBP-c2X-ToxoP30del4C(52-294aa) protein yielded maximal rate counts for Panel 6 and maximal rate count ratios in both assays. These results suggest that small deletions of the C-terminus of ToxoP30 reveal or make available new epitopes for binding of Toxo-specific IgG and IgM that are occluded in the full-length protein. Deletion of additional C-terminal amino acids (compare protein rpMBP-c2X-ToxoP30del10(52-284aa) and rpMBP-c2X-

ToxoP30del11(52-214aa) with protein rpMBP-c2X-ToxoP30del4C(52-294aa) in Tables 1 and 2) resulted in reduced immunoreactivity, suggesting the loss of IgG and IgM epitopes with larger C-terminal deletions. In contrast, the introduction of a small 30 amino acid deletion in the N-terminus of the optimal protein rpMBP-c2X-ToxoP30del4C, which generated the protein rpMBP-c2X-ToxoP30del4del8(83-294aa), completely abolished Toxo-specific IgG and IgM immunoreactivity. These results also suggest that some of the cysteine residues present in the C-terminal portion of the ToxoP30 protein are dispensable for optimal Toxo IgG and IgM immunoreactivity. For example, the optimal protein rpMBP-c2X-ToxoP30del4C (52-294aa) contains 11 cysteine residues and the protein rpMBP-c2X-ToxoP30del11(52-214aa), which demonstrated good but not optimal immunoreactivity, contains 7 cysteine residues.

EXAMPLE 5

Construction of Toxo P30 Synthetic Genes Containing Mutations Which Change Cysteine Residues to Alanine Based on the results obtained from deletion analysis of the Toxo P30 gene in Example 4D, a new series of MBP-ToxoP30 fusion proteins was constructed. Since there are 12 cysteine residues present in the mature Toxo P30 protein (Burg et al. (1988) J. Immunol. 141:3584–3591; Velge-Roussel et al. (1994) Molec. Biochem. Parasitol. 66:31–38), there are mathematically $2^{12}$ or 4,096 different Toxo P30 proteins that can be constructed which contain various combinations of changing one or more of the twelve cysteine residues to alanine. It would certainly be impossible to try all 4,096 different cysteine to alanine combinations to further optimize the immunoreactivity of the Toxo P30 antigen. Hence, the results in Example 4D were used to narrow the number of different mutant Toxo P30 genes to build that have the potential for improved Toxo IgG and IgM immunoreactivity in an automated immunoassay. Mutant oligonucleotides were designed for the in vitro synthesis of three Toxo P30 genes that contain mutations which change various cysteine residues to alanine, and also introduce the same 3' deletion in the Toxo P30 gene present in ToxoP30del3C(52-300aa) (SEQ ID NO:22 and FIG. 16).

The synthesis of each Toxo P30 gene required the synthesis and assembly of 16 overlapping oligonucleotides. These oligonucleotides ranged from 67–72 bases in length with neighboring oligonucleotides overlapping by 20–23 residues. The P30 genes were assembled by recursive PCR followed by PCR amplification of the assembled genes (Withers-Martinez et al. (1999) Protein Engr. 12:1113–1120; Prytulla et al. (1996) FEBS Lett. 399:283–289; Kataoka et al. (1998) Biochem. Biophys. Res. Comm. 250:409–413) using a P30 sense primer containing an EcoRI site and an antisense primer containing a HindIII site. After PCR amplification, the P30 gene was digested with EcoRI and HindIII, purified on an agarose gel, and ligated to the pMAL-c2X vector backbone which had been digested by EcoRI and HindIII as shown schematically in FIG. 30.

Step A: Construction of pMBP-c2X-ToxoP30MIX1

Figure 30:
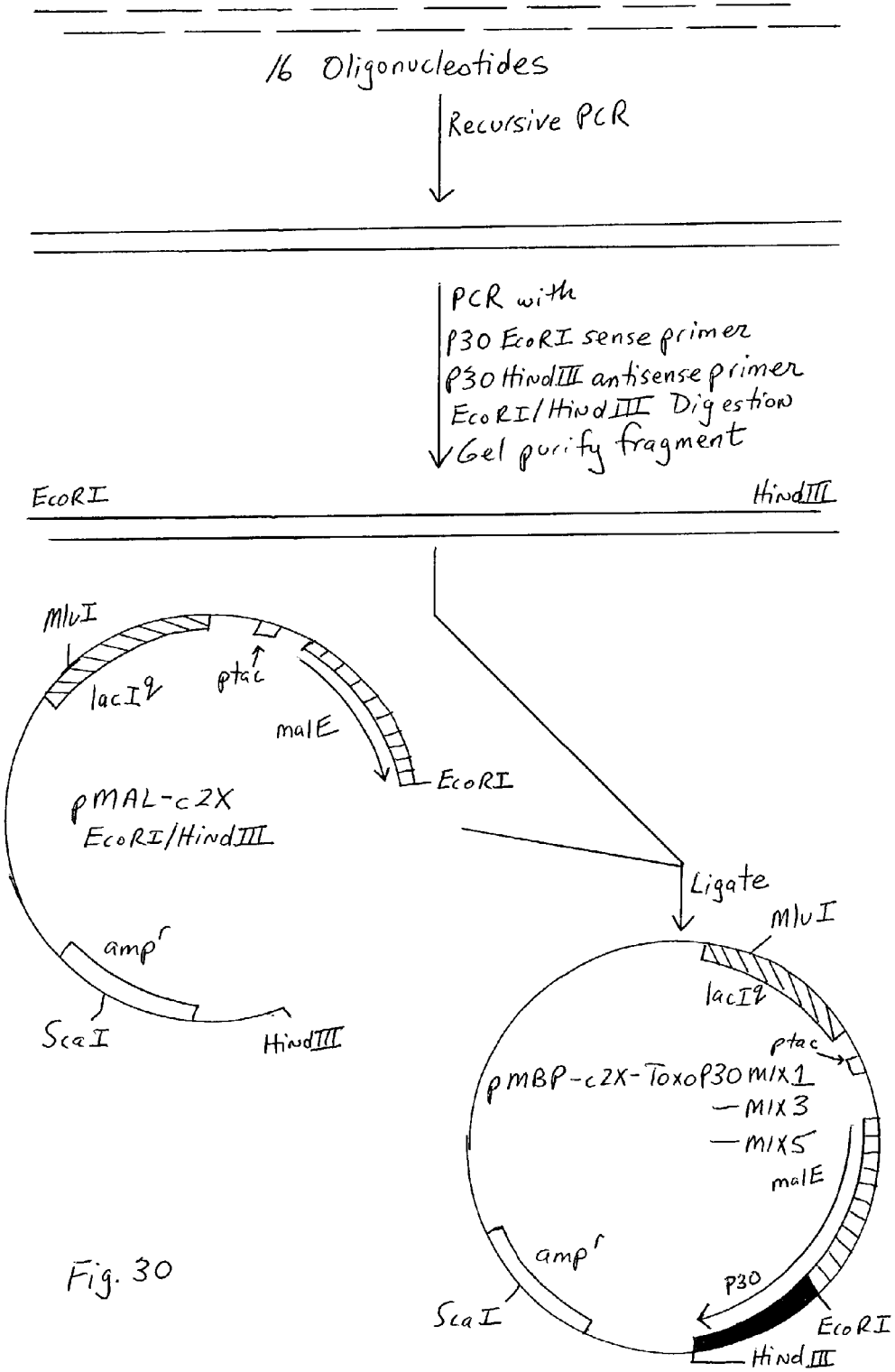
FIG. 30 is a schematic of the construction of plasmids pMBP-c2X-ToxoP30MIX1, pMBP-c2X-ToxoP30MIX3, and pMBP-c2X-ToxoP30MIX5.

The plasmid pMBP-c2X-ToxoP30MIX1 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX1 has been changed so that five of the twelve cysteine residues of Toxo P30 (cysteine nos. 8–12) have been changed to alanine. Plasmid pMAL-c2X was digested with EcoRI/HindIII and the vector backbone was purified on an agarose gel. The following oligonucleotides were synthesized for construction of the ToxoP30MIX1 gene:

P30.001
5'-CTTGTTGCCAATCAAGTTGTCACCTGCCCAGAT [SEQ ID NO:44]
AAAAAATCGACAGCCGCGGTCATTCTCACACCGACG
G-3'

P30.002
5'-GAGGCTCTGTGAGCGCTGTTTTAGGGCACTTGA [SEQ ID NO:45]
GAGTGAAGTGGTTCTCCGTCGGTGTGAGAATGACCG
-3'

P30.003
5'-CCTAAAACAGCGCTCACAGAGCCTCCCACTCTT [SEQ ID NO:46]
GCGTACTCACCCAACAGGCAAATCTGCCCAGCGG
-3'

P30.004
5'-GGAATCAAGGAGCTCAATGTTACAGCCTTTGAT [SEQ ID NO:47]
GTACAGCTACTTGTAGTACCCGCTGGGCAGATTTGC
CTC-3'

P30.005
5'-GTAACATTGAGCTCCTTGATTCCTGAAGCAGAA [SEQ ID NO:48]
GATAGCTGGTGGACGGGGGATTCTGCTAGTCTCGAC
ACGG-3'

P30.006
5'-CTGCGTTGTCACGGGGAACTTCTCGATTGGAAC [SEQ ID NO:49]
TGTGAGTTTGATGCCTGCCGTGTCGAGACTAGCAGA
ATC-3'

P30.007
5'-GAAGTTCCCCGTGACAACGCAGACGTTTGTGGT [SEQ ID NO:50]
CGGTTGCATCAAGGGAGACGACGCACAGAGTTGTAT
G-3'

P30.008
5'-GCGACATTATTGACGACCGATGAGGCTCTGGCT [SEQ ID NO:51]
TGTACTGTCACCGTGACCATACAACTCTGTGCGTCG
TC-3'

P30.009
5'-CATCGGTCGTCAATAATGTCGCAAGGTGCTCCT [SEQ ID NO:52]
ACGGTGCAGACAGCACTCTTGGTCCTGTCAAGTTGT
C-3'

P30.010Ala8
5'-GACTCCATCTTTCCCAGCCACGAGGGTCATTGT [SEQ ID NO:53]
AGTGGGTCCTTCCGCAGACAACTTGACAGGACCAAG

-continued

AG-3'

P30.011Ala8Ala9
5'-GTGGCTGGGAAAGATGGAGTCAAAGTTCCTCAA [SEQ ID NO:54]

GACAACAATCAGTACGCTTCCGGGACGACGCTGACT

GG-3'

P30.012Ala9Ala10
5'-GTTCTCAGTTAATTTTGGCAAAATATCTTTGAA [SEQ ID NO:55]

CGATTTCTCGTTAGCACCAGTCAGCGTCGTCCCGGA

AG-3'

P30.013
5'-GATATTTTGCCAAAATTAACTGAGAACCCGTGG [SEQ ID NO:56]

CAGGGTAACGCTTCGAGTGATAAGGGTGCCACGCTA

AC-3'

P30.014
5'-CCAATAATGACGCTTTTTGACTCGGCTGGAAAT [SEQ ID NO:57]

GCTTCCTTCTTGATCGTTAGCGTGGCACCCTTATCA

C-3'

P30.015Ala11Ala12
5'-GTCAAAAAGCGTCATTATTGGAGCTACAGGGGG [SEQ ID NO:58]

ATCGCCTGAGAAGCATCACGCTACCGTGAAACTGGA

C-3'

P30.01GAla12
5'-GACTGGCTGTTCCCGCAGCCGATTTTGCTGACC [SEQ ID NO:59]

CTGCAGCCCCGGCAAACTCCAGTTTCACGGTAGCGT

G-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141: 3584–3591) were synthesized as shown below:
Sense Primer [SEQ ID NO:1] 5'-GGC GAATTCCTTGTTGCCAATCAAGTTGTCACC-3'
(EcoRI site is underlined.)
Antisense Primer [SEQ ID NO:60] 5'-CAGGTC AAGCTTTCACTCCAGTTTCACGGTAGCGTG-3'
(HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX1 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX1 contained the Toxo P30MIX1 gene cloned at the EcoRI/HindIII sites of pMAL-c2X. The complete DNA sequence [SEQ ID NO:61] of plasmid pMBP-c2X-ToxoP30MIX1 is shown in FIG. 31, and the corresponding amino acid sequence [SEQ ID NO:62] of the MBP-ToxoP30MIX1 fusion protein is also shown in FIG. 31, wherein cysteine amino acid residues located at 555, 570, 578, 625, 635 of SEQ ID NO:21 are now alanine amino acids located at 555, 570, 578, 625, 635 of SEQ ID NO:62. Plasmid pMBP-c2X-ToxoP30MIX1 was deposited with the ATCC 10801 University Boulevard, Manassas, Va. 20110–2209, under terms of the Budapest Treaty on Sep. _____, 2002, and was accorded Accession No. ATCC _____. The DNA sequence [SEQ ID NO:63] of ToxoP30MIX1 is shown in FIG. 32, and the corresponding amino acid sequence [SEQ ID NO:64] of the ToxoP30MIX1 protein is also shown in FIG. 32, wherein cysteine amino acid residues located at 164, 179, 187, 234, 244 of SEQ ID NO:23 are now alanine amino acids located at 164, 179, 187, 234, 244 of SEQ ID NO:64.

Step B: Construction of pMBP-c2X-ToxoP30MIX3

The plasmid pMBP-c2X-ToxoP30MIX3 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX3 has been changed so that six of the twelve cysteine residues of Toxo P30 (cysteine nos. 7–12) have been changed to alanine. Plasmid pMAL-c2X was digested with EcoRI/HindIII, and the vector backbone was purified on an agarose gel. The following oligonucleotides were synthesized for construction of the ToxoP30MIX3 gene:

P30.001
5'-CTTGTTGCCAATCAAGTTGTCACCTGCCCAGAT [SEQ ID NO:44]

AAAAAATCGACAGCCGCGGTCATTCTCACACCGACG

G-3'

P30.002
5'-GAGGCTCTGTGAGCGCTGTTTTAGGGCACTTGA [SEQ ID NO:45]

GAGTGAAGTGGTTCTCCGTCGGTGTGAGAATGACCG

-3'

P30.003
5'-CCTAAAACAGCGCTCACAGAGCCTCCCACTCTT [SEQ ID NO:46]

GCGTACTCACCCAACAGGCAAATCTGCCCAGCGG

-3'

P30.004
5'-GGAATCAAGGAGCTCAATGTTACAGCCTTTGAT [SEQ ID NO:47]

GTACAGCTACTTGTAGTACCCGCTGGGCAGATTTGC

CTC-3'

P30.005
5'-GTAACATTGAGCTCCTTGATTCCTGAAGCAGAA [SEQ ID NO:48]

GATAGCTGGTGGACGGGGGATTCTGCTAGTCTCGAC

ACGG-3'

P30.006
5'-CTGCGTTGTCACGGGGAACTTCTCGATTGGAAC [SEQ ID NO:49]

TGTGAGTTTGATGCCTGCCGTGTCGAGACTAGCAGA

-continued

ATC-3'

P30.007
5'-GAAGTTCCCCGTGACAACGCAGACGTTTGTGGT [SEQ ID NO:50]
CGGTTGCATCAAGGGAGACGACGCACAGAGTTGTAT
G-3'

P30.008
5'-GCGACATTATTGACGACCGATGAGGCTCTGGCT [SEQ ID NO:51]
TGTACTGTCACCGTGACCATACAACTCTGTGCGTCG
TC-3'

P30.009Ala7
5'-CATCGGTCGTCAATAATGTCGCAAGGGCTTCCT [SEQ ID NO:65]
ACGGTGCAGACAGCACTCTTGGTCCTGTCAAGTTGT
C-3'

P30.010Ala8
5'-GACTCCATCTTTCCCAGCCACGAGGGTCATTGT [SEQ ID NO:53]
AGTGGGTCCTTCCGCAGACAACTTGACAGGACCAAG
AG-3'

P30.011Ala8Ala9
5'-GTGGCTGGGAAAGATGGAGTCAAAGTTCCTCAA [SEQ ID NO:54]
GACAACAATCAGTACGCTTCCGGGACGACGCTGACT
GG-3'

P30.012Ala9Ala10
5'-GTTCTCAGTTAATTTTGGCAAAATATCTTTGAA [SEQ ID NO:55]
CGATTTCTCGTTAGCACCAGTCAGCGTCGTCCCGGA
AG-3'

P30.013
5'-GATATTTTGCCAAAATTAACTGAGAACCCGTGG [SEQ ID NO:56]
CAGGGTAACGCTTCGAGTGATAAGGGTGCCACGCTA
AC-3'

P30.014
5'-CCAATAATGACGCTTTTTGACTCGGCTGGAAAT [SEQ ID NO:57]
GCTTCCTTCTTGATCGTTAGCGTGGCACCCTTATCA
C-3'

P30.015Ala11Ala12
5'-GTCAAAAAGCGTCATTATTGGAGCTACAGGGGG [SEQ ID NO:58]
ATCGCCTGAGAAGCATCACGCTACCGTGAAACTGGA
G-3'

P30.016Ala12
5'-GACTGGCTGTTCCCGCAGC- [SEQ ID NO:59]
CGATTTTGCTGACCC
TGCAGCCCCGGCAAACTCCAGTTTCACGGTAGCGTG
-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141: 3584–3591) were synthesized as shown below:

Sense Primer [SEQ ID NO:1] 5'-GGC GAATTCCTTGTTGCCAATCAAGTTGTCACC-3' (EcoRI site is underlined.)

Antisense Primer [SEQ ID NO:60] 5'-CAGGTC AAGCTTTCACTCCAGTTTCACGGTAGCGTG-3' (HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX3 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX3 contained the Toxo P30MIX3 gene cloned at the EcoRI/HindIII sites of pMAL-c2X. The complete DNA sequence [SEQ ID NO:66] of plasmid pMBP-c2X-ToxoP30MIX3 is shown in FIG. 33, and the corresponding amino acid sequence [SEQ ID NO:67] of the MBP-ToxoP30MIX3 fusion protein is also shown in FIG. 33, wherein cysteine amino acid residues located at 530, 555, 570, 578, 625, 635 of SEQ ID NO:21 are now alanine amino acids located at 530, 555, 570, 578, 625, 635 of SEQ ID NO:67. The DNA sequence [SEQ ID NO:68] of ToxoP30MIX3 is shown in FIG. 34, and the corresponding amino acid sequence [SEQ ID NO:69] of the ToxoP30MIX3 protein is also shown in FIG. 34, wherein cysteine amino acid residues located at 139, 164, 179, 187, 234, 244 of SEQ ID NO:23 are now alanine amino acids located at 139, 164, 179, 187, 234, 244 of SEQ ID NO:69.

Step C: Construction of pMBP-c2X-ToxoP30MIX5

The plasmid pMBP-c2X-ToxoP30MIX5 was constructed by cloning a synthetic DNA fragment containing Toxo P30, obtained by the synthesis and assembly of 16 oligonucleotides, into the EcoRI/HindIII sites of pMAL-c2X (FIG. 30). This plasmid differs from plasmid pMBP-c2X-ToxoP30del3C(52-300aa) of EXAMPLE 2E in that the Toxo P30 DNA sequence in plasmid pMBP-c2X-ToxoP30MIX5 has been changed so that six of the twelve cysteine residues of Toxo P30 (cysteine nos. 2 and 8–12) have been changed to alanine. Plasmid pMAL-c2X was digested with EcoRI/HindIII and the vector backbone was purified on an agarose gel. The following oligonucleotides were synthesized for construction of the ToxoP30MIX5 gene:

P30.001
5'-CTTGTTGCCAATCAAGTTGTCACCTGCCCACAT [SEQ ID NO:44]
AAAAAATCGACAGCCGCGGTCATTCTCACACCGACG
G-3'

P30.002Ala2
5'-GAGGCTCTGTGAGCGCTGTTTTAGGAGCCTTGA [SEQ ID NO:70]
GAGTGAAGTGGTTCTCCGTCGGTGTGAGAATGACCG

-continued

P30.003
5'-CCTAAAACAGCGCTCACAGAGCCTCCCACTCTT [SEQ ID NO:46]
GCGTACTCACCCAACAGGCAAATCTGCCCAGCGG
-3'

P30.004
5'-GGAATCAAGGAGCTCAATGTTACAGCCTTTGAT [SEQ ID NO:47]
GTACAGCTACTTGTAGTACCCGCTGGGCAGATTTGC
CTG-3'

P30.005
5'-GTAACATTGAGCTCCTTGATTCCTGAAGCAGAA [SEQ ID NO:48]
GATAGCTGGTGGACGGGGGATTCTGCTAGTCTCGAC
ACGG-3'

P30.006
5'-CTGCGTTGTCACGGGGAACTTCTCGATTGGAAC [SEQ ID NO:49]
TGTGAGTTTGATGCCTGCCGTGTCGAGACTAGCAGA
ATC-3'

P30.007
5'-GAAGTTCCCCGTGACAACGCAGACGTTTGTGGT [SEQ ID NO:50]
CGGTTGCATCAAGGGAGACGACGCACAGAGTTGTAT
G-3'

P30.008
5'-GCGACATTATTGACGACCGATGAGGCTCTGGCT [SEQ ID NO:51]
TGTACTGTCACCGTGACCATACAACTCTGTGCGTCG
TC-3'

P30.009
5'-CATCGGTCGTCAATAATGTCGCAAGGTGCTCCT [SEQ ID NO:52]
ACGGTGCAGACAGCACTCTTGGTCCTGTCAAGTTGT
C-3'

P30.010Ala8
5'-GACTCCATCTTTCCCAGCCACGAGGGTCATTGT [SEQ ID NO:53]
AGTGGGTCCTTCCGCAGACAACTTGACAGGACCAAG
AG-3'

P30.011Ala8Ala9
5'-GTGGCTGGGAAAGATGGAGTCAAAGTTCCTCAA [SEQ ID NO:54]
GACAACAATCAGTACGCTTCCGGGACGACGCTGACT
GG-3'

P30.012Ala9Ala10
5'-GTTCTCAGTTAATTTTGGCAAAATATCTTTGAA [SEQ ID NO:55]
CGATTTCTCGTTAGCACCAGTCAGCGTCGTCCCGGA
AG-3'

P30.013
5'-GATATTTTGCCAAAATTAACTGAGAACCCGTGG [SEQ ID NO:56]
CAGGGTAACGCTTCGAGTGATAAGGGTGCCACGCTA
AC-3'

P30.014
5'-CCAATAATGACGCTTTTTGACTCGGCTGGAAAT [SEQ ID NO:57]
GCTTCCTTCTTGATCGTTAGCGTGGCACCCTTATCA
C-3'

P30.015Ala11Ala12
5'-GTCAAAAAGCGTCATTATTGGAGCTACAGGGGG [SEQ ID NO:58]
ATCGCCTGAGAAGCATCACGCTACCGTGAAACTGGA
G-3'

P30.016Ala12
5'-GACTGGCTGTTCCCGCAGCCGATTTTGCTGACC [SEQ ID NO:59]
CTGCAGCCCCGGCAAACTCCAGTTTCACGGTAGCGT
G-3'

In the first step of gene synthesis, 4 picomoles of each oligonucleotide were mixed together and assembled using recursive PCR as follows: 1 cycle at 95° C. for 5 minutes followed by 35 cycles at 95° C. for 1 minute, 55° C. for 2 minutes, 72° C. for 2 minutes; 1 cycle at 72° C. for 10 minutes followed by a soak cycle at 4° C. In the second step of gene synthesis, a sense primer, starting at nucleotide 464 of the P30 gene containing an EcoRI site, and an antisense primer containing a HindIII site, starting at nucleotide 1210 of the P30 gene (Burg et al. (1988) J. Immunol. 141: 3584–3591) were synthesized as shown below:

Sense Primer [SEQ ID NO:1] 5'-GGC GAATTCCTTGTTGCCAATCAAGTTGTCACC-3' (EcoRI site is underlined.)

Antisense Primer [SEQ ID NO:60] 5'-CAGGTC AAGCTTTCACTCCAGTTTCACGGTAGCGTG-3' (HindIII site is underlined.)

The sense and antisense primers were added to a PCR reaction mixture containing the assembled oligonucleotides from the first step of gene synthesis. After PCR amplification and purification of the reaction mixture with a Qiaquick PCR purification kit, the reaction mixture was digested with EcoRI and HindIII, and the 747 base pair DNA fragment containing Toxo P30MIX5 was purified on an agarose gel. The purified 747 base pair fragment was ligated to pMAL-c2X/EcoRI/HindIII overnight at 16° C. The ligation mixture was transformed into competent XL-1 Blue cells. Miniprep DNA was prepared from the transformants and screened for the presence of the P30 synthetic DNA sequence by restriction enzyme analysis. Plasmid pMBP-c2X-ToxoP30MIX5 contained the Toxo P30MIX5 gene cloned at the EcoRI/HindIII sites of pMAL-c2X. The complete DNA sequence [SEQ ID NO:71] of plasmid pMBP-c2X-ToxoP30MIX5 is shown in FIG. 35, and the corresponding amino acid sequence [SEQ ID NO:72] of the MBP-ToxoP30MIX5 fusion protein is also shown in FIG. 35, wherein cysteine amino acid residues located at 422, 555, 570, 578, 625, 635 of SEQ ID NO:21 are now alanine amino acids located at 422, 555, 570, 578, 625, 635 of SEQ ID NO:72. The DNA sequence [SEQ ID NO:73] of ToxoP30MIX5 is shown in FIG. 36, and the corresponding amino acid sequence [SEQ ID NO:74] of the ToxoP30MIX5 protein is also shown in FIG. 36, wherein cysteine amino acid residues located at 31, 164, 179, 187, 234, 244 of SEQ ID NO:23 are now alanine amino acids located at 31, 164, 179, 187, 234, 244 of SEQ ID NO:74.

EXAMPLE 6

Expression of rpMBP-c2X-ToxoP30MIX Antigens in *E. coli*

Step A: Expression of Cloned Genes in *E. coli*

Bacterial clones pMBP-c2X-ToxoP30MTX1, pMBP-c2X-ToxoP30MIX3, and pMBP-c2X-ToxoP30MIX5 expressing the MBP fusion proteins rpMBP-c2X-ToxoP30MIX1, rpMBP-c2X-ToxoP30MIX3, and rpMBP-c2X-ToxoP30MIX5 of Example 5 were grown in "SUPER-BROTH II" media containing 100 µg/ml ampicillin to log phase, and the synthesis of the MBP-ToxoP30MIX fusion proteins was induced by the addition of IPTG as previously described (Robinson et al. (1993) J. Clin. Microbiol. 31:629–635). After 4 hours post-induction, the cells were harvested, and the cell pellets were stored at −80° C. until protein purification occurred.

Step B: Purification of MBP-ToxoP30MIX Fusion Proteins

Soluble fusion proteins rpMBP-c2X-ToxoP30MIX1, rpMBP-c2X-ToxoP30MIX3, and rpMBP-c2X-ToxoP30MIX5 were purified after lysis from cell paste following the New England Biolabs pMAL Protein Fusion and Purification instruction manual. Following lysis and centrifugation, the crude supernatants containing the fusion proteins were loaded onto an amylose affinity column. Following washing of the column, the fusion proteins were eluted from the column with maltose, appropriate column fractions were pooled and filtered through a 0.2µ filter, and then stored at 2–8° C. until coating onto microparticles.

EXAMPLE 7

Evaluation of rpMBP-c2X-ToxoP30MIX Antigens in an Automated Toxo IgG and IgM Immunoassay Step A: Coating of rpMBP-c2X-ToxoP30MIX Antigens onto Microparticles Prior to coating microparticles, the rpMBP-c2X-ToxoP30MIX1, rpMBP-c2X-ToxoP30MIX3 and rpMBP-c2X-ToxoP30MIX5 antigens were diluted to a concentration of 1 mg/ml and incubated at 37° C. for 24 hours. Following the heat treatment step, the rpMBP-c2X-ToxoP30MIX antigens were coated separately onto sulfate-derivatized polystyrene microparticles (1–5% solids) in a vessel containing MES pH 6.2 buffer with EDAC for 30 minutes at room temperature, on an end over end rotator. The coated microparticles were then collected by centrifugation at 14,000×g for 10 minutes and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1–0.3% solids and filled into plastic bottles.

Step B: Evaluation of MBP fusion proteins rpMBP-c2X-ToxoP30MIX1, rpMBP-c2X-ToxoP30MIX3 and rpMBP-c2X-ToxoP30MIX5 in the AxSYM Toxo IgG v2 and Toxo IgM v2 Immunoassays The AXSYM® Toxo IgG and IgM reagent packs were assembled as described in Examples 4B and 4C using the microparticles coated with the Toxo antigens described in Example 7A. The Toxo IgG A and F calibrators (Acal and Fcal) and Panel 6 (PNL6) were tested with the AxSYM Toxo IgG v2 reagent packs and the Toxo IgM Negative Control (NC), Index Calibrator (IC), and Panel 6 (PNL6) were tested with the AxSYM Toxo IgM v2 reagent packs. The results are shown below in Tables 3 and 4.

TABLE 3

Evaluation of the rpMBP-c2X-ToxoP30MIX Antigens in the AxSYM Toxo IgG v2 Assay

| | Rate Counts | | | | |
|---|---|---|---|---|---|
| Antigen Coated | Acal | Fcal | Fcal/Acal | PNL6 | PNL6/Acal |
| rpMBP-c2X-ToxoP30 MIX1 (Ala8-12) | 34 | 3847 | 113 | 1445 | 43 |
| rpMBP-c2X-ToxoP30 MIX3 (Ala7-12) | 35 | 3704 | 106 | 1043 | 30 |
| rpMBP-c2X-Toxop30 MIX5 (Ala2, Ala8-12) | 35 | 57 | 1.6 | 23 | 0.7 |

TABLE 4

Evaluation of the rpMBP-c2X-ToxoP30MIX Antigens in the AxSYM Toxo IgM v2 Assay

| | Rate Counts | | | |
|---|---|---|---|---|
| Antigen Coated | NC | IC | PNL6 | PNL6/NC |
| rpMBP-c2X-ToxoP30 MIX1 (Ala8-12) | 37 | 149 | 459 | 12.4 |
| rpMBP-c2X-ToxoP30 MIX3 (Ala7-12) | 44 | 111 | 368 | 8.4 |
| rpMBP-c2X-ToxoP30 MIX5 (Ala2, Ala8-12) | 31 | 49 | 27 | 0.9 |

As can be seen in Tables 3 and 4, the genetically engineered rpMBP-c2X-ToxoP30MIX1 antigen, which contained five C-terminal cysteine residues substituted with alanine, yielded the best Toxo IgG and IgM immunoreactivity as measured by the highest rate counts for Panel 6 and highest rate count ratios for Fcal/Acal, Panel 6/Acal, and Panel 6/NC. In addition, the rpMBP-c2X-ToxoP30MIX1 antigen yielded the highest rate counts for Panel6 and the highest Panel6/NC rate count ratio in the Toxo IgM v2 assay for any rpMBP-c2X-ToxoP30 antigen tested (see Tables 1 and 2). The rpMBP-c2X-ToxoP30MIX5 antigen, which contained five C-terminal cysteine residues substituted with alanine residues plus the substitution of cysteine no. 2 with alanine, was not immunoreactive in either assay. This result was consistent with the results obtained with the rpMBP-c2X-ToxoP30del4del8(83-294aa) antigen (see Tables 1 and 2), in which deletion of the first two cysteine residues of Toxo P30 resulted in complete loss of immunoreactivity. Thus, the surprising result was obtained that substitution of several cysteine residues in the C-terminal half of Toxo P30 with alanine results in superior Toxo IgG and IgM immunoreactivity of the antigen whereas substitution of a single cysteine with alanine in the N-terminal half of Toxo P30 completely abolishes immunoreactivity.

EXAMPLE 8

Purification and Coating of the rpToxoP35S Antigen

The rpToxoP35S antigen described in U.S. Pat. No. 6,329,157 B1 was expressed in *E. coli*, and cell paste was harvested as described in Example 6A. This antigen was then purified from cell paste and coated onto microparticles as described below.

Step A: Purification of the rpToxoP35S Antigen

The rpToxoP35S antigen was expressed in E. coli as an insoluble fusion protein. Following lysis of the cell paste, the inclusion bodies containing the rpToxoP35S antigen were washed with water, phosphate buffer, Triton X-100, and urea. The rpToxoP35S antigen was then solubilized in a SDS/DTT buffer and applied to a Sephacryl S-300 column. The appropriate column fractions were pooled, diluted to a concentration of 1 mg/ml and filtered through a 0.2µ filter, and then stored at −80° C. until coating.

Step B: Coating of the rpToxoP35S Antigen onto Microparticles

The rpToxoP35S antigen was thawed and brought into solution by mild warming followed by centrifugation to remove particulate matter. This antigen was then dialyzed against three changes of MES buffer, pH 6.2 at room temperature overnight and then coated onto sulfate-derivatized polystyrene microparticles (1–5% solids) in a vessel containing MES pH 6.2 buffer with EDAC for 30 minutes at room temperature, on an end over end rotator. The coated microparticles were then collected by centrifugation at 14,000×g for 10 minutes and the supernatant was discarded. The microparticles were resuspended in a microparticle storage buffer containing Tris buffer, pH 7.5, EDTA, sodium chloride, Tween 20, fetal calf serum (Toxo antibody free), sodium azide, and sucrose using a syringe and needle. The microparticles were then diluted with microparticle storage buffer to a final concentration of 0.1–0.3% solids and filled into plastic bottles.

EXAMPLE 9

Development of Antigen Cocktails Employing the Genetically Engineered P30 Antigens After achieving a significant improvement in the Toxo IgG and IgM immunoreactivity of the P30 antigen through genetic engineering (Examples 4 and 7), a preliminary re-evaluation of microparticles coated with the Toxo antigens described in U.S. Pat. No. 6,329,157 B1 in the AxSYM® Toxo IgG v2 and IgM v2 assays was performed. Evaluation of these antigen coated microparticles in conjunction with microparticles coated with the P30 antigens rpMBP-c2X-ToxoP30del3C(52-300aa), rpMBP-c2X-ToxoP30del4C(52-294aa), and rpMBP-c2X-ToxoP30MIX1 suggested that a new combination of either the rpMBP-c2X-ToxoP30del3C(52-300aa), rpMBP-c2X-ToxoP30del4C(52-294aa), or rpMBP-c2X-ToxoP30MIX1 antigen with the rpToxoP35S antigen could improve the performance of the AXSYM® Toxo IgG v2 assay. In addition, the rpMBP-c2X-ToxoP30del3C(52-300aa), rpMBP-c2X-ToxoP30del4C(52-294aa), or rpMBP-c2X-ToxoP30MIX1 antigens alone could improve the performance of the AxSYM® Toxo IgM v2 assay. In order to demonstrate the diagnostic utility of the genetically engineered P30 antigens and the new genetically engineered P30/P35 antigen cocktail, human sera negative for Toxo antibodies and sera sourced from patients with an acute or chronic toxoplasmosis were tested in the AxSYM® Toxo IgG v2 and IgM v2 assays as described below.

Step A: Assembly of AxSYM® Toxo IgG v2 Reagent Packs

Purified Toxo antigens rpMBP-c2X-ToxoP30del3C(52-300aa), rpMBP-c2X-ToxoP30del4C(52-294aa), rpMBP-c2X-ToxoP30MIX1, and rpToxoP35S were coated unto microparticles as previously described in Examples 4A and 7A. The microparticles were then diluted to a final concentration 0.2% solids and the following three microparticle blends were made: 2:1 v/v blend of rpMBP-c2X-ToxoP30del3C(52-300aa):rpToxoP35S coated microparticles (labeled as P30del3/P35); 2:1 v/v blend of rpMBP-c2X-ToxoP30del4C(52-294aa):rpToxoP35S coated microparticles (labeled as P30del4/P35); and a 2:1 v/v blend of rpMBP-c2X-ToxoP30MIX1:rpToxoP35S coated microparticles (labeled as P30MIX1/P35). These three microparticle blends were filled into plastic bottles, assembled into individual AxSYM® Toxo IgG v2 reagent kits as described in Example 4B, and labeled as P30del3C/35, P30del4C/P35, and P30MIX1/P35.

Step B: Assembly of AxSYM® Toxo IgM v2 Reagent Packs

Purified Toxo antigens rpMBP-c2X-ToxoP30del3C(52-300aa), rpMBP-c2X-ToxoP30del4C(52-294aa), rpMBP-c2X-ToxoP30MIX1, and rpToxoP35S were coated onto microparticles as previously described in Examples 4A and 7A. The microparticles were then diluted to a final concentration of 0.2% solids and filled into plastic bottles. AxSYM® Toxo IgM v2 kits were assembled with each coated microparticle as described in Example 4C and labeled as P30del3C, P30del4C, and P30MIX1.

Step C: Human sera for Testing

Three groups of human sera from a French population were tested in this evaluation: Group 1 (n=100) human sera negative for Toxo IgG and IgM antibodies by the Abbott IMx® Toxo IgG and IgM assays, respectively (Abbott Laboratories, Abbott Park, Ill.); Group 2 (n=56) human sera positive for Toxo IgG and negative for Toxo IgM antibodies by the Abbott IMx® Toxo IgG and IgM assays, respectively; Group 3 (n=52) human sera positive for Toxo IgG antibodies by a high sensitivity direct agglutination assay (HSDA) (Desmonts, G. and Remington, J. S. (1980) J. Clin. Microbiol. 11:562–568) and positive for Toxo IgM antibodies by an IgM immunocapture assay (IC-M) (Pouletty et al. (1985) J. Immunol. Methods 76:289–298). The assay calibrators and controls for the AxSYM® Toxo IgG v2 and Toxo IgM v2 assays were run as previously described in Examples 4B–D. The Abbott AxSYM® Toxo IgG and IgM assays (Abbott Laboratories Abbott Park, Ill.), which use the tachyzoite antigen for detection of Toxo-specific IgG and IgM, were included as reference assays during specimen testing.

Step D: Evaluation of the AxSYM® Toxo IgG v2 Assays

All specimens in Groups 1–3 were tested by the AxSYM® Toxo IgG v2 assays (P30del3C/35, P30del4C/P35, and P30MIX1/P35) and by the AxSYM® Toxo IgG assay. The same assay cutoff of 3 IU/ml for the AxSYM Toxo IgG assay was employed for AxSYM® Toxo IgG v2 assays, with an equivocal zone from 2–3 IU/ml. The performance of the recombinant antigen based AxSYM® Toxo IgG v2 assays was compared to the tachyzoite antigen based AxSYM® Toxo IgG assay and is shown in Tables 5–7.

TABLE 5

Evaluation of the AxSYM ® Toxo IgG v2 P30del3C/P35 assay

| | | AxSYM® Toxo IgG | | | |
|---|---|---|---|---|---|
| | | POS | EQV | NEG | TOTAL |
| AxSYM® Toxo IgG v2 P30del3C/P35 | POS | 108 | 0 | 0 | 108 |
| | EQV | 0 | 0 | 1 | 1 |
| | NEG | 0 | 0 | 99 | 99 |
| | TOTAL | 108 | 0 | 100 | 208 |

Sensitivity: 108/108 = 100%
Specificity: 99/99 = 100%
Agreement: 207/207 = 100%
Correlation Coefficient: r = 0.9751

TABLE 6

Evaluation of the AxSYM ® Toxo IgG v2 P30del14C/P35 assay

| | | AxSYM® Toxo IgG | | | |
|---|---|---|---|---|---|
| | | POS | EQV | NEG | TOTAL |
| AxSYM® Toxo IgG v2 P30del4C/P35 | POS | 108 | 0 | 0 | 108 |
| | EQV | 0 | 0 | 1 | 1 |
| | NEG | 0 | 0 | 99 | 99 |
| | TOTAL | 108 | 0 | 100 | 208 |

Sensitivity: 108/108 = 100%
Specificity: 99/99 = 100%
Agreement: 207/207 = 100%
Correlation Coefficient: r = 0.9778

TABLE 7

Evaluation of the AxSYM ® Toxo IgG v2 P30MIX1/P35 assay

| | | AxSYM® Toxo IgG | | | |
|---|---|---|---|---|---|
| | | POS | EQV | NEG | TOTAL |
| AxSYM® Toxo IgG v2 P30MIX1/P35 | POS | 108 | 0 | 0 | 108 |
| | EQV | 0 | 0 | 1 | 1 |
| | NEG | 0 | 0 | 99 | 99 |
| | TOTAL | 108 | 0 | 100 | 208 |

Sensitivity: 108/108 = 100%
Specificity: 99/99 = 100%
Agreement: 207/207 = 100%
Correlation Coefficient: r = 0.9563

As can be seen from Tables 5–7, the AxSYM® Toxo IgG v2 assay using the combination of a genetically engineered antigen P30 antigen (P30del3C, P30del4C, or P30MIX1) with the P35 antigen is both a sensitive and specific assay for the detection of Toxoplasma-specific IgG as demonstrated by the overall high relative diagnostic sensitivity (100%), specificity (100%), and agreement (100%). All three AxSYM® Toxo IgG v2 assays were in excellent agreement quantitatively with the AxSYM® Toxo IgG assay, as measured by the correlation coefficients, all of which were 0.95 or greater. The Toxo recombinant antigen cocktail comprised of the genetically engineered Toxo P30 antigen (P30del3C, P30del4C, or P30MIX1) and the P35 antigen, in combination with the AxSYM® Toxo IgG v2 assay, is both necessary and sufficient to replace the tachyzoite for the detection of Toxoplasma-specific IgG antibody.

Furthermore, there are several advantages of the recombinant antigen cocktail over the tachyzoite antigen for use in detection of IgG antibodies. First, the antigens are purified, and the amount of each antigen loaded into the immunoassay can be accurately determined and standardized, e.g., protein concentration. This minimizes between lot differences commonly observed in kits manufactured with different tachyzoite antigen lots. Hence, different lots of kits manufactured with different antigen cocktail lots will be very consistent from lot to lot. Secondly, mouse or human monoclonal antibodies to the individual recombinant Toxo antigens are used to monitor coating of the proteins to the solid phase. This further ensures that each lot produced is consistent. Third, the true clinical sensitivity of the assay using the purified antigens will be higher by virtue of the fact of the higher specific activity of the purified antigens. Finally, kits manufactured with the antigen cocktail are more stable during storage over time, and the performance of the assay using these antigens remains consistent over the shelf life of the assay. Kits manufactured with the tachyzoite antigen are not as stable and their performance may vary over time.

Additionally, there are many advantages of using a cocktail over using a single antigen alone. For example, an immune response to infection varies by individual. Some individuals produce antibodies to P35 and not to P30 early in infection (acute toxoplasmosis), whereas some individuals produce antibodies to P30 and not to P35 later in infection (chronic toxoplasmosis). Thus, the antigen cocktail of the present invention will detect both groups of individuals.

Moreover, immune responses vary with time. For example, one individual may produce antibodies against P35 first and then later produce antibodies to only P30. Thus, the present cocktail will detect both types of "positive" individuals.

Furthermore, individuals may be infected with different Toxo serotypes, strains or isolates. Thus, the immune response may be such that multiple antigens are needed to detect the presence of all antibodies being produced. Again, the present cocktail allows for such detection.

Also, it is known from previous Western Blot experiments with tachyzoite proteins that the immune response to Toxoplasma is directed against several antigens. Once again, the present antigen cocktail will allow for the detection of all antibodies produced in response to these antigens.

Step E: Evaluation of the AxSYM® Toxo IgM v2 Assays

All specimens in Groups 1–3 were tested by the AxSYM® Toxo IgM v2 assays (P30del3C, P30del4C, and P30MIX1) and by the AxSYM® Toxo IgM assay. A receiver operator characteristic (ROC) was used to assist the determination of the preliminary cutoff for the AxSYM® Toxo IgM v2 assays (Index value ≧0.6) (Zweig, H M (1993) Clin. Chem. 39:561–577). In addition, an equivocal zone of Index value 0.500–0.599 was introduced to account for assay imprecision. The performance of the recombinant antigen based AxSYM® Toxo IgM v2 assays was compared to the tachyzoite antigen based AxSYM® Toxo IgM assay and is shown in Tables 8–10.

TABLE 8

Evaluation of the AxSYM ® Toxo IgM v2 P30del13X assay

| | | AxSYM® Toxo IgM | | | |
|---|---|---|---|---|---|
| | | POS | EQV | NEG | TOTAL |
| AxSYM® Toxo IgM v2 P30del3C | POS | 33 | 2 | 7 | 42 |
| | EQV | 5 | 1 | 3 | 9 |
| | NEG | 0 | 2 | 155 | 157 |
| | TOTAL | 38 | 5 | 165 | 208 |

Sensitivity: 33/33 = 100%
Specificity: 155/162 = 95.7%
Agreement: 188/195 = 96.4%

TABLE 9

Evaluation of the AxSYM ® Toxo IgM v2 P30del14C assay

| | | AxSYM® Toxo IgM | | | |
|---|---|---|---|---|---|
| | | POS | EQV | NEG | TOTAL |
| AxSYM® Toxo IgM v2 P30del4C | POS | 34 | 2 | 9 | 45 |
| | EQV | 4 | 2 | 2 | 8 |
| | NEG | 0 | 1 | 154 | 155 |
| | TOTAL | 38 | 5 | 165 | 208 |

Sensitivity: 34/34 = 100%
Specificity: 154/163 = 94.5%
Agreement: 188/197 = 95.4%

TABLE 10

Evaluation of the AxSYM ® Toxo IgM v2 P30MIX1 assay

| | | AxSYM® Toxo IgM | | | |
|---|---|---|---|---|---|
| | | POS | EQV | NEG | TOTAL |
| AxSYM® Toxo IgM v2 P30MIX1 | POS | 35 | 2 | 8 | 45 |
| | EQV | 2 | 0 | 3 | 5 |
| | NEG | 1 | 3 | 154 | 158 |
| | TOTAL | 38 | 5 | 165 | 208 |

Sensitivity: 35/36 = 97.2%
Specificity: 154/162 = 95.1%
Agreement: 189/198 = 95.5%

As can be seen from Tables 8–10, the AxSYM® Toxo IgM v2 assay using the genetically engineered antigen P30 antigen (P30del3C, P30del4C, or P30MIX1) is both a sensitive and specific assay for the detection of Toxoplasma-specific IgG as demonstrated by the overall high relative diagnostic sensitivity (range=97.2%–100%), specificity (range 94.5%–95.7%), and agreement (range=95.4%–96.4%). The genetically engineered Toxo recombinant P30 antigen (P30del3C, P30del4C, or P30MIX1), in combination with the AxSYM® Toxo IgM v2 assay, is both necessary and sufficient to replace the tachyzoite for the detection of Toxoplasma-specific IgM antibody.

Furthermore, there are several advantages of the genetically engineered recombinant Toxo P30 antigen over the tachyzoite antigen for use in detection of IgM antibodies. First, the antigen is purified, and the amount of antigen loaded into the immunoassay can be accurately determined and standardized, e.g., protein concentration. This minimizes lot-to-to differences commonly observed in kits manufactured with different tachyzoite antigen lots. Hence, different lots of kits manufactured with different recombinant antigen lots will be very consistent from lot to lot. Secondly, mouse or human monoclonal antibodies to the recombinant Toxo antigen are used to monitor coating of the proteins to the solid phase. This further ensures that each lot produced is consistent. Third, the true clinical sensitivity of the assay using the purified antigens will be higher by virtue of the fact of the higher specific activity of the purified antigen. Finally, kits manufactured with the recombinant antigen are more stable during storage over time, and the performance of the assay using this antigen remains consistent over the shelf life of the assay. Kits manufactured with the tachyzoite antigen are not as stable and their performance may vary over time.

The invention claimed is:

1. A purified polypeptide comprising the amino acid sequence of SEQ ID NO:64.

2. A purified polypeptide encoded by the nucleotide sequence of SEQ ID NO:63.

3. A composition comprising a purified polypeptide, wherein said polypeptide comprises the amino acid sequence of SEQ ID NO:64.

4. The composition of claim 3 further comprising P35 of *Toxoplasma gondii*.

5. A vaccine comprising: a) a composition comprising: 1) purified a polypeptide, wherein said polypeptide comprises the amino acid sequence of SEQ ID NO:64 and 2) P35, and b) a pharmaceutically acceptable adjuvant.

6. A kit for determining the presence of IgM antibodies to *Toxoplasma gondii* in a test sample comprising:
   a) a composition comprising a purified polypeptide, wherein said polypeptide comprises the amino acid sequence of SEQ ID NO:64; and b) a conjugate comprising an antibody attached to a signal-generating compound capable of generating a detectable signal.

7. A kit for determining the presence of IgG antibodies to *Toxoplasma gondii* in a test sample comprising:
   a) a composition comprising: 1) a purified polypeptide, wherein said polypeptide comprises the amino acid sequence of SEQ ID NO:64 and 2) P35; and
   b) a conjugate comprising an antibody attached to a signal-generating compound capable of generating a detectable signal.

8. A kit for determining the presence of IgM antibodies to *Toxoplasma gondii* in a test sample comprising:
   a) an anti-antibody specific for IgM antibody; and
   b) a composition comprising a purified polypeptide, wherein said polypeptide comprises the amino acid sequence of SEQ ID NO:64.

9. A kit for determining the presence of IgM antibodies to *Toxoplasma gondii* in a test sample comprising:
   a) an anti-antibody specific for IgM antibody;
   b) a conjugate comprising: 1) a composition comprising a purified polypeptide, wherein said polypeptide comprises the amino acid sequence of SEQ ID NO:64, attached to 2) a signal-generating compound capable of generating a detectable signal.

10. A kit for determining the presence of IgG antibodies to *Toxoplasma gondii* in a test sample comprising:
    a) an anti-antibody specific for IgG antibody; and
    b) a composition comprising: 1) a purified polypeptide, wherein said polypeptide comprises the amino acid sequence of SEQ ID NO:64 and 2) P35.

11. A kit for determining the presence of IgG antibodies to *Toxoplasma gondii* in a test sample comprising:
    a) an anti-antibody specific for IgG antibody;
    b) a conjugate comprising: 1) a purified polypeptide, wherein said polypeptide comprises the amino acid sequence of SEQ ID NO:64 and 2) P35, each attached to a signal generating compound capable of generating a detectable signal.

* * * * *

UNITED STATES PATENT AND TRADEMARK OFFICE
CERTIFICATE OF CORRECTION

PATENT NO.         : 7,094,879 B2
APPLICATION NO. : 10/263153
DATED               : August 22, 2006
INVENTOR(S)      : Gregory T. Maine et al.

It is certified that error appears in the above-identified patent and that said Letters Patent is hereby corrected as shown below:

Col. 36, line 12
 replace "Budapest Treaty on September__, 2002,"
 with --Budapest Treaty on September 26, 2002--.

Col. 36, line 13
 replace "Accession No. ATCC__."
 with --Accession No. ATCC 4721.--.

Signed and Sealed this

Fifth Day of December, 2006

JON W. DUDAS
*Director of the United States Patent and Trademark Office*

SEQUENCE LISTING

<160> NUMBER OF SEQ ID NOS: 74

<210> SEQ ID NO 1
<211> LENGTH: 33
<212> TYPE: DNA
<213> ORGANISM: Artificial Sequence
<220> FEATURE:
<223> OTHER INFORMATION: Sense Primer

<400> SEQUENCE: 1

-continued ggcgaattcc ttgttgccaa tcaagttgtc acc                              33

<210> SEQ ID NO 2
<211> LENGTH: 31
<212> TYPE: DNA
<213> ORGANISM: Artificial Sequence
<220> FEATURE:
<223> OTHER INFORMATION: Antisense Primer

<400> SEQUENCE: 2
cgctgaagct tcacgcgac acaagctgcg a                                 31

<210> SEQ ID NO 3
<211> LENGTH: 7478
<212> TYPE: DNA
<213> ORGANISM: Toxoplasma gondii
<220> FEATURE:
<221> NAME/KEY: CDS
<222> LOCATION: (1528)...(3555)
<223> OTHER INFORMATION: pMBP-c2X-ToxoP30 (52-336aa)

<400> SEQUENCE: 3

```
ccgacaccat cgaatggtgc aaacctttc gcggtatggc atgatagcgc ccggaagaga      60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc gccgttaac caccatcaaa caggattttc    960
gcctgctggg gcaaaccagc gtggaccgct tgctgcaact ctctcagggc caggcggtga   1020
agggcaatca gctgttgccc gtctcactgg tgaaaagaaa aaccaccctg gcgcccaata   1080
cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgtttttt gcgccgacat cataacggtt   1380
ctggcaaata ttctgaaatg agctgttgac aattaatcat cggctcgtat aatgtgtgga   1440
attgtgagcg gataacaatt tcacacagga acagccagt ccgtttaggt gttttcacga   1500
gcacttcacc aacaaggacc atagcat atg aaa atc gaa gaa ggt aaa ctg gta   1554
                              Met Lys Ile Glu Glu Gly Lys Leu Val
```

```
                    1                   5
atc tgg att aac ggc gat aaa ggc tat aac ggt ctc gct gaa gtc ggt        1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg        1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc        1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa        1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag        1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att        1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat        1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat        1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa        1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg        2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat        2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa        2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc        2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg        2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg        2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca        2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc        2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac        2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg        2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa        2514
```

```
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345 act gcg gtc atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405 att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470 gct agt ctc gac acg gca ggc atc aaa ctc acg gtt cca atc gag aag      2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca      3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535 ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550 gtg tgc ggg aaa gat gga gtc aaa gtt cct caa gac aac aat cag tac      3234
Val Cys Gly Lys Asp Gly Val Lys Val Pro Gln Asp Asn Asn Gln Tyr
    555                 560                 565 tgt tcc ggg acg acg ctg act ggt tgc aac gag aaa tcg ttc aaa gat      3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615 tca aaa agc gtc att att gga tgc aca ggg gga tcg cct gag aag cat      3426
Ser Lys Ser Val Ile Ile Gly Cys Thr Gly Gly Ser Pro Glu Lys His
        620                 625                 630
```

```
cac tgt acc gtg aaa ctg gag ttt gcc ggg gct gca ggg tca gca aaa      3474
His Cys Thr Val Lys Leu Glu Phe Ala Gly Ala Ala Gly Ser Ala Lys
        635                 640                 645 tcg gct gcg gga aca gcc agt cac gtt tcc att ttt gcc atg gtg atc      3522
Ser Ala Ala Gly Thr Ala Ser His Val Ser Ile Phe Ala Met Val Ile
650                 655                 660                 665 gga ctt att ggc tct atc gca gct tgt gtc gcg tgaaagcttg gcactggccg    3575
Gly Leu Ile Gly Ser Ile Ala Ala Cys Val Ala
                670                 675 tcgttttaca acgtcgtgac tgggaaaacc ctggcgttac ccaacttaat cgccttgcag    3635
cacatccccc tttcgccagc tggcgtaata gcgaagaggc ccgcaccgat cgcccttccc    3695
aacagttgcg cagcctgaat ggcgaatggc agcttggctg ttttggcgga tgagataaga    3755
ttttcagcct gatacagatt aaatcagaac gcagaagcgg tctgataaaa cagaatttgc    3815
ctggcggcag tagcgcggtg gtcccacctg accccatgcc gaactcagaa gtgaaacgcc    3875
gtagcgccga tggtagtgtg gggtctcccc atgcgagagt agggaactgc caggcatcaa    3935
ataaaacgaa aggctcagtc gaaagactgg gcctttcgtt ttatctgttg tttgtcggtg    3995
aacgctctcc tgagtaggac aaatccgccg ggagcggatt tgaacgttgc gaagcaacgg    4055
cccggagggt ggcgggcagg acgcccgcca taaactgcca ggcatcaaat taagcagaag    4115
gccatcctga cggatggcct ttttgcgttt ctacaaactc ttttttgttta tttttctaaa    4175 tacattcaaa tatgtatccg ctcatgagac aataaccctg ataaatgctt caataatatt    4235 gaaaaggaa gagtatgagt attcaacatt tccgtgtcgc ccttattccc ttttttgcgg     4295
cattttgcct tcctgttttt gctcacccag aaacgctggt gaaagtaaaa gatgctgaag    4355
atcagttggg tgcacgagtg ggttacatcg aactggatct caacagcggt aagatccttg    4415
agagttttcg ccccgaagaa cgttctccaa tgatgagcac ttttaaagtt ctgctatgtg    4475
gcgcggtatt atcccgtgtt gacgccgggc aagagcaact cggtcgccgc atacactatt    4535
ctcagaatga cttggttgag tactcaccag tcacagaaaa gcatcttacg gatggcatga    4595
cagtaagaga attatgcagt gctgccataa ccatgagtga taacactgcg gccaacttac    4655
ttctgacaac gatcggagga ccgaaggagc taaccgcttt tttgcacaac atgggggatc    4715
atgtaactcg ccttgatcgt tgggaaccgg agctgaatga agccatacca aacgacgagc    4775
gtgacaccac gatgcctgta gcaatggcaa caacgttgcg caaactatta actggcgaac    4835
tacttactct agcttcccgg caacaattaa tagactggat ggaggcggat aaagttgcag    4895
gaccacttct gcgctcggcc cttccggctg gctggtttat tgctgataaa tctggagccg    4955
gtgagcgtgg gtctcgcggt atcattgcag cactggggcc agatggtaag ccctcccgta    5015
tcgtagttat ctacacgacg gggagtcagg caactatgga tgaacgaaat agacagatcg    5075
ctgagatagg tgcctcactg attaagcatt ggtaactgtc agaccaagtt tactcatata    5135
tactttagat tgatttaccc cggttgataa tcagaaaagc cccaaaaaca ggaagattgt    5195
ataagcaaat atttaaattg taaacgttaa tattttgtta aaattcgcgt taaattttg     5255 ttaaatcagc tcattttta accaataggc cgaaatcggc aaaatccctt ataaatcaaa     5315
agaatagacc gagatagggt tgagtgttgt tccagtttgg aacaagagtc cactattaaa    5375
gaacgtggac tccaacgtca aagggcgaaa accgtctat cagggcgatg cccactacg      5435 tgaaccatca cccaaatcaa gttttttggg gtcgaggtgc cgtaaagcac taaatcggaa    5495
ccctaaaggg agcccccgat ttagagcttg acggggaaag ccggcgaacg tggcgagaaa    5555
ggaagggaag aaagcgaaag gagcgggcgc tagggcgctg gcaagtgtag cggtcacgct    5615
```

-continued

| | |
|---|---|
| gcgcgtaacc accacacccg ccgcgcttaa tgcgccgcta cagggcgcgt aaaaggatct | 5675 |
| aggtgaagat ccttttttgat aatctcatga ccaaaatccc ttaacgtgag ttttcgttcc | 5735 |
| actgagcgtc agaccccgta gaaaagatca aggatcttc ttgagatcct ttttttctgc | 5795 |
| gcgtaatctg ctgcttgcaa acaaaaaaac caccgctacc agcggtggtt tgtttgccgg | 5855 |
| atcaagagct accaactctt tttccgaagg taactggctt cagcagagcg cagataccaa | 5915 |
| atactgtcct tctagtgtag ccgtagttag gccaccactt caagaactct gtagcaccgc | 5975 |
| ctacatacct cgctctgcta atcctgttac cagtggctgc tgccagtggc gataagtcgt | 6035 |
| gtcttaccgg gttggactca agacgatagt taccggataa ggcgcagcgg tcgggctgaa | 6095 |
| cggggggttc gtgcacacag cccagcttgg agcgaacgac ctacaccgaa ctgagatacc | 6155 |
| tacagcgtga gctatgagaa agcgccacgc ttcccgaagg gagaaaggcg gacaggtatc | 6215 |
| cggtaagcgg cagggtcgga acaggagagc gcacgaggga gcttccaggg ggaaacgcct | 6275 |
| ggtatcttta tagtcctgtc gggtttcgcc acctctgact tgagcgtcga ttttttgtgat | 6335 |
| gctcgtcagg gggcggagc ctatggaaaa acgccagcaa cgcggccttt ttacggttcc | 6395 |
| tggccttttg ctggcctttt gctcacatgt tctttcctgc gttatcccct gattctgtgg | 6455 |
| ataaccgtat taccgccttt gagtgagctg ataccgctcg ccgcagccga acgaccgagc | 6515 |
| gcagcgagtc agtgagcgag gaagcggaag agcgcctgat gcggtatttt ctccttacgc | 6575 |
| atctgtgcgg tatttcacac cgcatatatg gtgcactctc agtacaatct gctctgatgc | 6635 |
| cgcatagtta agccagtata cactccgcta tcgctacgtg actgggtcat ggctgcgccc | 6695 |
| cgacacccgc caacacccgc tgacgcgccc tgacgggctt gtctgctccc ggcatccgct | 6755 |
| tacagacaag ctgtgaccgt ctccgggagc tgcatgtgtc agaggttttc accgtcatca | 6815 |
| ccgaaacgcg cgaggcagct gcggtaaagc tcatcagcgt ggtcgtgcag cgattcacag | 6875 |
| atgtctgcct gttcatccgc gtccagctcg ttgagtttct ccagaagcgt taatgtctgg | 6935 |
| cttctgataa agcgggccat gttaagggcg gttttttcct gtttggtcac tgatgcctcc | 6995 |
| gtgtaagggg gatttctgtt catgggggta atgataccga tgaaacgaga gaggatgctc | 7055 |
| acgatacggg ttactgatga tgaacatgcc cggttactgg aacgttgtga gggtaaacaa | 7115 |
| ctggcggtat ggatgcggcg ggaccagaga aaaatcactc agggtcaatg ccagcgcttc | 7175 |
| gttaatacag atgtaggtgt tccacagggt agccagcagc atcctgcgat gcagatccgg | 7235 |
| aacataatgg tgcagggcgc tgacttccgc gtttccagac tttacgaaac acggaaaccg | 7295 |
| aagaccattc atgttgttgc tcaggtcgca gacgttttgc agcagcagtc gcttcacgtt | 7355 |
| cgctcgcgta tcggtgattc attctgctaa ccagtaaggc aaccccgcca gcctagccgg | 7415 |
| gtcctcaacg acaggagcac gatcatgcgc acccgtggcc aggacccaac gctgcccgaa | 7475 |
| att | 7478 |

<210> SEQ ID NO 4
<211> LENGTH: 676
<212> TYPE: PRT
<213> ORGANISM: Toxoplasma gondii
<220> FEATURE:
<223> OTHER INFORMATION: pMBP-c2X-ToxoP30 (52-336aa)

<400> SEQUENCE: 4

Met Lys Ile Glu Glu Gly Lys Leu Val Ile Trp Ile Asn Gly Asp Lys
 1               5                   10                  15

Gly Tyr Asn Gly Leu Ala Glu Val Gly Lys Lys Phe Glu Lys Asp Thr

```
                20                  25                  30
Gly Ile Lys Val Thr Val Glu His Pro Asp Lys Leu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
             85                  90                  95

Ala Val Arg Tyr Asn Gly Lys Leu Ile Ala Tyr Pro Ile Ala Val Glu
             100                 105                 110

Ala Leu Ser Leu Ile Tyr Asn Lys Asp Leu Leu Pro Asn Pro Pro Lys
             115                 120                 125

Thr Trp Glu Glu Ile Pro Ala Leu Asp Lys Glu Leu Lys Ala Lys Gly
 130                 135                 140

Lys Ser Ala Leu Met Phe Asn Leu Gln Glu Pro Tyr Phe Thr Trp Pro
 145                 150                 155                 160

Leu Ile Ala Ala Asp Gly Gly Tyr Ala Phe Lys Tyr Glu Asn Gly Lys
             165                 170                 175

Tyr Asp Ile Lys Asp Val Gly Val Asp Asn Ala Gly Ala Lys Ala Gly
             180                 185                 190

Leu Thr Phe Leu Val Asp Leu Ile Lys Asn Lys His Met Asn Ala Asp
             195                 200                 205

Thr Asp Tyr Ser Ile Ala Glu Ala Ala Phe Asn Lys Gly Glu Thr Ala
 210                 215                 220

Met Thr Ile Asn Gly Pro Trp Ala Trp Ser Asn Ile Asp Thr Ser Lys
 225                 230                 235                 240

Val Asn Tyr Gly Val Thr Val Leu Pro Thr Phe Lys Gly Gln Pro Ser
             245                 250                 255

Lys Pro Phe Val Gly Val Leu Ser Ala Gly Ile Asn Ala Ala Ser Pro
             260                 265                 270

Asn Lys Glu Leu Ala Lys Glu Phe Leu Glu Asn Tyr Leu Leu Thr Asp
 275                 280                 285

Glu Gly Leu Glu Ala Val Asn Lys Asp Lys Pro Leu Gly Ala Val Ala
 290                 295                 300

Leu Lys Ser Tyr Glu Glu Glu Leu Ala Lys Asp Pro Arg Ile Ala Ala
 305                 310                 315                 320

Thr Met Glu Asn Ala Gln Lys Gly Glu Ile Met Pro Asn Ile Pro Gln
             325                 330                 335

Met Ser Ala Phe Trp Tyr Ala Val Arg Thr Ala Val Ile Asn Ala Ala
             340                 345                 350

Ser Gly Arg Gln Thr Val Asp Glu Ala Leu Lys Asp Ala Gln Thr Asn
             355                 360                 365

Ser Ser Ser Asn Asn Asn Asn Asn Asn Asn Asn Asn Asn Leu Gly Ile
             370                 375                 380

Glu Gly Arg Ile Ser Glu Phe Leu Val Ala Asn Gln Val Val Thr Cys
 385                 390                 395                 400

Pro Asp Lys Lys Ser Thr Ala Ala Val Ile Leu Thr Pro Thr Glu Asn
             405                 410                 415

His Phe Thr Leu Lys Cys Pro Lys Thr Ala Leu Thr Glu Pro Pro Thr
             420                 425                 430

Leu Ala Tyr Ser Pro Asn Arg Gln Ile Cys Pro Ala Gly Thr Thr Ser
             435                 440                 445
```

```
Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640

Phe Ala Gly Ala Ala Gly Ser Ala Lys Ser Ala Ala Gly Thr Ala Ser
                645                 650                 655

His Val Ser Ile Phe Ala Met Val Ile Gly Leu Ile Gly Ser Ile Ala
            660                 665                 670

Ala Cys Val Ala
        675

<210> SEQ ID NO 5
<211> LENGTH: 855
<212> TYPE: DNA
<213> ORGANISM: Toxoplasma gondii
<220> FEATURE:
<221> NAME/KEY: CDS
<222> LOCATION: (1)...(855)
<223> OTHER INFORMATION: ToxoP30 (52-336aa)

<400> SEQUENCE: 5 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
1               5                   10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
            20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
        35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
    50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
65              70                  75                  80 gat tct gct agt ctc gac acg gca ggc atc aaa ctc acg gtt cca atc     288
Asp Ser Ala Ser Leu Asp Thr Ala Gly Ile Lys Leu Thr Val Pro Ile
```

-continued

| | | | | | | | | | | | | | | | |
|---|---|---|---|---|---|---|---|---|---|---|---|---|---|---|---|
| Asp | Ser | Ala | Ser | Leu | Asp | Thr | Ala | Gly | Ile | Lys | Leu | Thr | Val | Pro | Ile |
| | | | 85 | | | | | 90 | | | | | 95 | | |

```
gag aag ttc ccc gtg aca acg cag acg ttt gtg gtc ggt tgc atc aag      336
Glu Lys Phe Pro Val Thr Thr Gln Thr Phe Val Val Gly Cys Ile Lys
                100                 105                 110 gga gac gac gca cag agt tgt atg gtc aca gtg aca gta caa gcc aga      384
Gly Asp Asp Ala Gln Ser Cys Met Val Thr Val Thr Val Gln Ala Arg
            115                 120                 125 gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
        130                 135                 140 agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat      528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc      576
Gln Tyr Cys Ser Gly Thr Thr Leu Thr Gly Cys Asn Glu Lys Ser Phe
            180                 185                 190 aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca      672
Ser Ser Asp Lys Gly Ala Thr Leu Thr Ile Lys Lys Glu Ala Phe Pro
210                 215                 220 gcc gag tca aaa agc gtc att att gga tgc aca ggg gga tcg cct gag      720
Ala Glu Ser Lys Ser Val Ile Ile Gly Cys Thr Gly Gly Ser Pro Glu
                225                 230                 235                 240 aag cat cac tgt acc gtg aaa ctg gag ttt gcc ggg gct gca ggg tca      768
Lys His His Cys Thr Val Lys Leu Glu Phe Ala Gly Ala Ala Gly Ser
            245                 250                 255 gca aaa tcg gct gcg gga aca gcc agt cac gtt tcc att ttt gcc atg      816
Ala Lys Ser Ala Ala Gly Thr Ala Ser His Val Ser Ile Phe Ala Met
        260                 265                 270 gtg atc gga ctt att ggc tct atc gca gct tgt gtc gcg                  855
Val Ile Gly Leu Ile Gly Ser Ile Ala Ala Cys Val Ala
275                 280                 285

<210> SEQ ID NO 6
<211> LENGTH: 285
<212> TYPE: PRT
<213> ORGANISM: Toxoplasma gondii
<220> FEATURE:
<223> OTHER INFORMATION: ToxoP30 (52-336aa)

<400> SEQUENCE: 6
```

| | | | | | | | | | | | | | | | |
|---|---|---|---|---|---|---|---|---|---|---|---|---|---|---|---|
| Leu | Val | Ala | Asn | Gln | Val | Val | Thr | Cys | Pro | Asp | Lys | Lys | Ser | Thr | Ala |
| 1 | | | | 5 | | | | | 10 | | | | | 15 | |
| Ala | Val | Ile | Leu | Thr | Pro | Thr | Glu | Asn | His | Phe | Thr | Leu | Lys | Cys | Pro |
| | | | 20 | | | | | 25 | | | | | 30 | | |
| Lys | Thr | Ala | Leu | Thr | Glu | Pro | Pro | Thr | Leu | Ala | Tyr | Ser | Pro | Asn | Arg |
| | | | | 35 | | | | | 40 | | | | | 45 | |
| Gln | Ile | Cys | Pro | Ala | Gly | Thr | Thr | Ser | Ser | Cys | Thr | Ser | Lys | Ala | Val |
| | | 50 | | | | | 55 | | | | | 60 | | | |
| Thr | Leu | Ser | Ser | Leu | Ile | Pro | Glu | Ala | Glu | Asp | Ser | Trp | Trp | Thr | Gly |
| 65 | | | | | 70 | | | | | 75 | | | | | 80 |
| Asp | Ser | Ala | Ser | Leu | Asp | Thr | Ala | Gly | Ile | Lys | Leu | Thr | Val | Pro | Ile |
| | | | 85 | | | | | 90 | | | | | 95 | | |

```
Glu Lys Phe Pro Val Thr Thr Gln Thr Phe Val Val Gly Cys Ile Lys
                100                 105                 110

Gly Asp Asp Ala Gln Ser Cys Met Val Thr Val Thr Val Gln Ala Arg
            115                 120                 125

Ala Ser Ser Val Val Asn Asn Val Ala Arg Cys Ser Tyr Gly Ala Asp
        130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
210                 215                 220

Ala Glu Ser Lys Ser Val Ile Ile Gly Cys Thr Gly Gly Ser Pro Glu
225                 230                 235                 240

Lys His His Cys Thr Val Lys Leu Glu Phe Ala Gly Ala Gly Ser
                245                 250                 255

Ala Lys Ser Ala Ala Gly Thr Ala Ser His Val Ser Ile Phe Ala Met
            260                 265                 270

Val Ile Gly Leu Ile Gly Ser Ile Ala Ala Cys Val Ala
        275                 280                 285

<210> SEQ ID NO 7
<211> LENGTH: 7553
<212> TYPE: DNA
<213> ORGANISM: Toxoplasma gondii
<220> FEATURE:
<221> NAME/KEY: CDS
<222> LOCATION: (1528)...(3630)
<223> OTHER INFORMATION: pMBP-p2X-ToxoP30 (52-336aa)

<400> SEQUENCE: 7
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc ggcgttatt cttgatgtc ctgaccaga     540 cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgcg tatctcggta gtgggatacg     900
acgataccga agacagctca tgttatatcc gccgttaac caccatcaaa caggattttc     960
```

-continued

```
gcctgctggg gcaaaccagc gtggaccgct tgctgcaact ctctcagggc caggcggtga      1020
agggcaatca gctgttgccc gtctcactgg tgaaaagaaa aaccaccctg gcgcccaata      1080
cgcaaaccgc ctctccccgc gcgttggccg attcattaat gcagctggca cgacaggttt      1140
cccgactgga aagcgggcag tgagcgcaac gcaattaatg taagttagct cactcattag      1200
gcacaattct catgtttgac agcttatcat cgactgcacg gtgcaccaat gcttctggcg      1260
tcaggcagcc atcggaagct gtggtatggc tgtgcaggtc gtaaatcact gcataattcg      1320
tgtcgctcaa ggcgcactcc cgttctggat aatgttttt gcgccgacat cataacggtt      1380
ctggcaaata ttctgaaatg agctgttgac aattaatcat cggctcgtat aatgtgtgga      1440
attgtgagcg gataacaatt tcacacagga acagccagt ccgtttaggt gttttcacga      1500
gcacttcacc aacaaggacc atagcat atg aaa ata aaa aca ggt gca cgc atc      1554
                               Met Lys Ile Lys Thr Gly Ala Arg Ile
                                 1                5 ctc gca tta tcc gca tta acg acg atg atg ttt tcc gcc tcg gct ctc       1602
Leu Ala Leu Ser Ala Leu Thr Thr Met Met Phe Ser Ala Ser Ala Leu
 10              15                  20                  25 gcc aaa atc gaa gaa ggt aaa ctg gta atc tgg att aac ggc gat aaa       1650
Ala Lys Ile Glu Glu Gly Lys Leu Val Ile Trp Ile Asn Gly Asp Lys
             30                  35                  40 ggc tat aac ggt ctc gct gaa gtc ggt aag aaa ttc gag aaa gat acc       1698
Gly Tyr Asn Gly Leu Ala Glu Val Gly Lys Lys Phe Glu Lys Asp Thr
         45                  50                  55 gga att aaa gtc acc gtt gag cat ccg gat aaa ctg gaa gag aaa ttc       1746
Gly Ile Lys Val Thr Val Glu His Pro Asp Lys Leu Glu Glu Lys Phe
     60                  65                  70 cca cag gtt gcg gca act ggc gat ggc cct gac att atc ttc tgg gca       1794
Pro Gln Val Ala Ala Thr Gly Asp Gly Pro Asp Ile Ile Phe Trp Ala
 75                  80                  85 cac gac cgc ttt ggt ggc tac gct caa tct ggc ctg ttg gct gaa atc       1842
His Asp Arg Phe Gly Gly Tyr Ala Gln Ser Gly Leu Leu Ala Glu Ile
             90                  95                 100             105 acc ccg gac aaa gcg ttc cag gac aag ctg tat ccg ttt acc tgg gat       1890
Thr Pro Asp Lys Ala Phe Gln Asp Lys Leu Tyr Pro Phe Thr Trp Asp
                    110                 115                 120 gcc gta cgt tac aac ggc aag ctg att gct tac ccg atc gct gtt gaa       1938
Ala Val Arg Tyr Asn Gly Lys Leu Ile Ala Tyr Pro Ile Ala Val Glu
            125                 130                 135 gcg tta tcg ctg att tat aac aaa gat ctg ctg ccg aac ccg cca aaa       1986
Ala Leu Ser Leu Ile Tyr Asn Lys Asp Leu Leu Pro Asn Pro Pro Lys
        140                 145                 150 acc tgg gaa gag atc ccg gcg ctg gat aaa gaa ctg aaa gcg aaa ggt       2034
Thr Trp Glu Glu Ile Pro Ala Leu Asp Lys Glu Leu Lys Ala Lys Gly
    155                 160                 165 aag agc gcg ctg atg ttc aac ctg caa gaa ccg tac ttc acc tgg ccg       2082
Lys Ser Ala Leu Met Phe Asn Leu Gln Glu Pro Tyr Phe Thr Trp Pro
170                 175                 180                 185 ctg att gct gct gac ggg ggt tat gcg ttc aag tat gaa aac ggc aag       2130
Leu Ile Ala Ala Asp Gly Gly Tyr Ala Phe Lys Tyr Glu Asn Gly Lys
                190                 195                 200 tac gac att aaa gac gtg ggc gtg gat aac gct ggc gcg aaa gcg ggt       2178
Tyr Asp Ile Lys Asp Val Gly Val Asp Asn Ala Gly Ala Lys Ala Gly
            205                 210                 215 ctg acc ttc ctg gtt gac ctg att aaa aac aaa cac atg aat gca gac       2226
Leu Thr Phe Leu Val Asp Leu Ile Lys Asn Lys His Met Asn Ala Asp
        220                 225                 230
```

```
acc gat tac tcc atc gca gaa gct gcc ttt aat aaa ggc gaa aca gcg    2274
Thr Asp Tyr Ser Ile Ala Glu Ala Ala Phe Asn Lys Gly Glu Thr Ala
235                 240                 245 atg acc atc aac ggc ccg tgg gca tgg tcc aac atc gac acc agc aaa    2322
Met Thr Ile Asn Gly Pro Trp Ala Trp Ser Asn Ile Asp Thr Ser Lys
250                 255                 260                 265 gtg aat tat ggt gta acg gta ctg ccg acc ttc aag ggt caa cca tcc    2370
Val Asn Tyr Gly Val Thr Val Leu Pro Thr Phe Lys Gly Gln Pro Ser
            270                 275                 280 aaa ccg ttc gtt ggc gtg ctg agc gca ggt att aac gcc gcc agt ccg    2418
Lys Pro Phe Val Gly Val Leu Ser Ala Gly Ile Asn Ala Ala Ser Pro
        285                 290                 295 aac aaa gag ctg gca aaa gag ttc ctc gaa aac tat ctg ctg act gat    2466
Asn Lys Glu Leu Ala Lys Glu Phe Leu Glu Asn Tyr Leu Leu Thr Asp
    300                 305                 310 gaa ggt ctg gaa gcg gtt aat aaa gac aaa ccg ctg ggt gcc gta gcg    2514
Glu Gly Leu Glu Ala Val Asn Lys Asp Lys Pro Leu Gly Ala Val Ala
315                 320                 325 ctg aag tct tac gag gaa gag ttg gcg aaa gat cca cgt att gcc gcc    2562
Leu Lys Ser Tyr Glu Glu Glu Leu Ala Lys Asp Pro Arg Ile Ala Ala
330                 335                 340                 345 act atg gaa aac gcc cag aaa ggt gaa atc atg ccg aac atc ccg cag    2610
Thr Met Glu Asn Ala Gln Lys Gly Glu Ile Met Pro Asn Ile Pro Gln
                350                 355                 360 atg tcc gct ttc tgg tat gcc gtg cgt act gcg gtg atc aac gcc gcc    2658
Met Ser Ala Phe Trp Tyr Ala Val Arg Thr Ala Val Ile Asn Ala Ala
            365                 370                 375 agc ggt cgt cag act gtc gat gaa gcc ctg aaa gac gcg cag act aat    2706
Ser Gly Arg Gln Thr Val Asp Glu Ala Leu Lys Asp Ala Gln Thr Asn
        380                 385                 390 tcg agc tcg aac aac aac aac aat aac aat aac aac aac ctc ggg atc    2754
Ser Ser Ser Asn Asn Asn Asn Asn Asn Asn Asn Asn Asn Leu Gly Ile
    395                 400                 405 gag gga agg att tca gaa ttc ctt gtt gcc aat caa gtt gtc acc tgc    2802
Glu Gly Arg Ile Ser Glu Phe Leu Val Ala Asn Gln Val Val Thr Cys
410                 415                 420                 425 cca gat aaa aaa tcg aca gcc gcg gtc att ctc aca ccg acg gag aac    2850
Pro Asp Lys Lys Ser Thr Ala Ala Val Ile Leu Thr Pro Thr Glu Asn
                430                 435                 440 cac ttc act ctc aag tgc cct aaa aca gcg ctc aca gag cct ccc act    2898
His Phe Thr Leu Lys Cys Pro Lys Thr Ala Leu Thr Glu Pro Pro Thr
            445                 450                 455 ctt gcg tac tca ccc aac agg caa atc tgc cca gcg ggt act aca agt    2946
Leu Ala Tyr Ser Pro Asn Arg Gln Ile Cys Pro Ala Gly Thr Thr Ser
        460                 465                 470 agc tgt aca tca aag gct gta aca ttg agc tcc ttg att cct gaa gca    2994
Ser Cys Thr Ser Lys Ala Val Thr Leu Ser Ser Leu Ile Pro Glu Ala
    475                 480                 485 gaa gat agc tgg tgg acg ggg gat tct gct agt ctc gac acg gca ggc    3042
Glu Asp Ser Trp Trp Thr Gly Asp Ser Ala Ser Leu Asp Thr Ala Gly
490                 495                 500                 505 atc aaa ctc aca gtt cca atc gag aag ttc ccc gtg aca acg cag acg    3090
Ile Lys Leu Thr Val Pro Ile Glu Lys Phe Pro Val Thr Thr Gln Thr
                510                 515                 520 ttt gtg gtc ggt tgc atc aag gga gac gac gca cag agt tgt atg gtc    3138
Phe Val Val Gly Cys Ile Lys Gly Asp Asp Ala Gln Ser Cys Met Val
            525                 530                 535 aca gtg aca gta caa gcc aga gcc tca tcg gtc gtc aat aat gtc gca    3186
Thr Val Thr Val Gln Ala Arg Ala Ser Ser Val Val Asn Asn Val Ala
        540                 545                 550
```

-continued

| | | |
|---|---|---|
| agg tgc tcc tac ggt gca gac agc act ctt ggt cct gtc aag ttg tct<br>Arg Cys Ser Tyr Gly Ala Asp Ser Thr Leu Gly Pro Val Lys Leu Ser<br>555                            560                       565 | | 3234 |
| gcg gaa gga ccc act aca atg acc ctc gtg tgc ggg aaa gat gga gtc<br>Ala Glu Gly Pro Thr Thr Met Thr Leu Val Cys Gly Lys Asp Gly Val<br>570                            575                       580                       585 | | 3282 |
| aaa gtt cct caa gac aac aat cag tac tgt tcc ggg acg acg ctg act<br>Lys Val Pro Gln Asp Asn Asn Gln Tyr Cys Ser Gly Thr Thr Leu Thr<br>                      590                       595                       600 | | 3330 |
| ggt tgc aac gag aaa tcg ttc aaa gat att ttg cca aaa tta act gag<br>Gly Cys Asn Glu Lys Ser Phe Lys Asp Ile Leu Pro Lys Leu Thr Glu<br>605                            610                       615 | | 3378 |
| aac ccg tgg cag ggt aac gct tcg agt gat aag ggt gcc acg cta acg<br>Asn Pro Trp Gln Gly Asn Ala Ser Ser Asp Lys Gly Ala Thr Leu Thr<br>                      620                       625                       630 | | 3426 |
| atc aag aag gaa gca ttt cca gcc gag tca aaa agc gtc att att gga<br>Ile Lys Lys Glu Ala Phe Pro Ala Glu Ser Lys Ser Val Ile Ile Gly<br>635                            640                       645 | | 3474 |
| tgc aca ggg gga tcg cct gag aag cat cac tgt acc gtg aaa ctg gag<br>Cys Thr Gly Gly Ser Pro Glu Lys His His Cys Thr Val Lys Leu Glu<br>650                            655                       660                       665 | | 3522 |
| ttt gcc ggg gct gca ggg tca gca aaa tcg gct gcg gga aca gcc agt<br>Phe Ala Gly Ala Ala Gly Ser Ala Lys Ser Ala Ala Gly Thr Ala Ser<br>                      670                       675                       680 | | 3570 |
| cac gtt tcc att ttt gcc atg gtg atc gga ctt att ggc tct atc gca<br>His Val Ser Ile Phe Ala Met Val Ile Gly Leu Ile Gly Ser Ile Ala<br>685                            690                       695 | | 3618 |
| gct tgt gtc gcg tgaaagcttg gcactggccg tcgttttaca acgtcgtgac<br>Ala Cys Val Ala<br>         700 | | 3670 |
| tgggaaaacc ctggcgttac ccaacttaat cgccttgcag cacatccccc tttcgccagc | | 3730 |
| tggcgtaata gcgaagaggc ccgcaccgat cgcccttccc aacagttgcg cagcctgaat | | 3790 |
| ggcgaatggc agcttggctg ttttggcgga tgagataaga ttttcagcct gatacagatt | | 3850 |
| aaatcagaac gcagaagcgg tctgataaaa cagaatttgc ctggcggcag tagcgcggtg | | 3910 |
| gtcccacctg accccatgcc gaactcagaa gtgaaacgcc gtagcgccga tggtagtgtg | | 3970 |
| gggtctcccc atgcgagagt agggaactgc caggcatcaa ataaaacgaa aggctcagtc | | 4030 |
| gaaagactgg gcctttcgtt ttatctgttg tttgtcggtg aacgctctcc tgagtaggac | | 4090 |
| aaatccgccg ggagcggatt tgaacgttgc gaagcaacgg cccggagggt ggcgggcagg | | 4150 |
| acgcccgcca taaactgcca ggcatcaaat taagcagaag gccatcctga cggatggcct | | 4210 |
| ttttgcgttt ctacaaactc tttttgttta tttttctaaa tacattcaaa tatgtatccg | | 4270 |
| ctcatgagac aataaccctg ataaatgctt caataatatt gaaaaggaa gagtatgagt | | 4330 |
| attcaacatt tccgtgtcgc ccttattccc ttttttgcgg cattttgcct tcctgttttt | | 4390 |
| gctcacccag aaacgctggt gaaagtaaaa gatgctgaag atcagttggg tgcacgagtg | | 4450 |
| ggttacatcg aactggatct caacagcggt aagatccttg agagttttcg ccccgaagaa | | 4510 |
| cgttctccaa tgatgagcac ttttaaagtt ctgctatgtg gcgcggtatt atcccgtgtt | | 4570 |
| gacgccgggc aagagcaact cggtcgccgc atacactatt ctcagaatga cttggttgag | | 4630 |
| tactcaccag tcacagaaaa gcatcttacg gatggcatga cagtaagaga attatgcagt | | 4690 |
| gctgccataa ccatgagtga taacactgcg gccaacttac ttctgacaac gatcggagga | | 4750 |
| ccgaaggagc taaccgcttt tttgcacaac atggggatc atgtaactcg ccttgatcgt | | 4810 |

```
tgggaaccgg agctgaatga agccatacca aacgacgagc gtgacaccac gatgcctgta    4870
gcaatggcaa caacgttgcg caaactatta actggcgaac tacttactct agcttcccgg    4930
caacaattaa tagactggat ggaggcggat aaagttgcag gaccacttct gcgctcggcc    4990
cttccggctg gctggtttat tgctgataaa tctggagccg gtgagcgtgg gtctcgcggt    5050
atcattgcag cactgggccc agatggtaag ccctcccgta tcgtagttat ctacacgacg    5110
gggagtcagg caactatgga tgaacgaaat agacagatcg ctgagatagg tgcctcactg    5170
attaagcatt ggtaactgtc agaccaagtt tactcatata ctttagat tgatttaccc      5230 cggttgataa tcagaaaagc cccaaaaaca ggaagattgt ataagcaaat atttaaattg    5290
taaacgttaa tattttgtta aaattcgcgt taaattttg ttaaatcagc tcattttta      5350 accataggc cgaaatcggc aaaatcccctt ataaatcaaa agaatagacc gagataggggt   5410 tgagtgttgt tccagtttgg aacaagagtc cactattaaa gaacgtggac tccaacgtca    5470
aagggcgaaa aaccgtctat cagggcgatg gcccactacg tgaaccatca cccaaatcaa    5530
gttttttggg gtcgaggtgc cgtaaagcac taaatcggaa ccctaaaggg agccccgat     5590 ttagagcttg acggggaaag ccggcgaacg tggcgagaaa ggaagggaag aaagcgaaag    5650
gagcgggcgc tagggcgctg gcaagtgtag cggtcacgct gcgcgtaacc accacaccccg   5710 ccgcgcttaa tgcgccgcta cagggcgcgt aaaaggatct aggtgaagat ccttttttgat   5770 aatctcatga ccaaaatccc ttaacgtgag ttttcgttcc actgagcgtc agaccccgta    5830
gaaaagatca aaggatcttc ttgagatcct ttttttctgc gcgtaatctg ctgcttgcaa    5890
acaaaaaaac caccgctacc agcggtggtt tgtttgccgg atcaagagct accaactctt    5950
tttccgaagg taactggctt cagcagagcg cagataccaa atactgtcct tctagtgtag    6010
ccgtagttag gccaccactt caagaactct gtagcaccgc ctacatacct cgctctgcta    6070
atcctgttac cagtggctgc tgccagtggc gataagtcgt gtcttaccgg gttggactca    6130
agacgatagt taccggataa ggcgcagcgg tcgggctgaa cggggggttc gtgcacacag    6190
cccagcttgg agcgaacgac ctacaccgaa ctgagatacc tacagcgtga gctatgagaa    6250
agcgccacgc ttcccgaagg gagaaaggcg gacaggtatc cggtaagcgg cagggtcgga    6310
acaggagagc gcacgaggga gcttccaggg ggaaacgcct ggtatcttta tagtcctgtc    6370
gggtttcgcc acctctgact tgagcgtcga ttttttgtgat gctcgtcagg ggggcggagc    6430
ctatggaaaa acgccagcaa cgcggccttt ttacggttcc tggccttttg ctggccttt     6490 gctcacatgt tctttcctgc gttatcccct gattctgtgg ataaccgtat taccgccttt    6550
gagtgagctg ataccgctcg ccgcagccga acgaccgagc gcagcgagtc agtgagcgag    6610
gaagcggaag agcgcctgat gcggtatttt ctccttacgc atctgtgcgg tatttcacac    6670
cgcatatatg gtgcactctc agtacaatct gctctgatgc cgcatagtta agccagtata    6730
cactccgcta tcgctacgtg actgggtcat ggctgcgccc cgacacccgc caacacccgc    6790
tgacgcgccc tgacgggctt gtctgctccc ggcatccgct tacagacaag ctgtgaccgt    6850
ctccgggagc tgcatgtgtc agaggttttc accgtcatca ccgaaacgcg cgaggcagct    6910
gcggtaaagc tcatcagcgt ggtcgtgcag cgattcacag atgtctgcct gttcatccgc    6970
gtccagctcg ttgagtttct ccagaagcgt taatgtctgg cttctgataa agcgggccat    7030
gttaagggcg gttttttcct gtttggtcac tgatgcctcc gtgtaagggg gatttctgtt    7090
catgggggta atgataccga tgaaacgaga aggatgctc acgatacggg ttactgatga    7150
tgaacatgcc cggttactgg aacgttgtga gggtaaacaa ctggcggtat ggatgcggcg    7210
```

```
ggaccagaga aaaatcactc agggtcaatg ccagcgcttc gttaatacag atgtaggtgt    7270
tccacagggt agccagcagc atcctgcgat gcagatccgg aacataatgg tgcagggcgc    7330
tgacttccgc gtttccagac tttacgaaac acggaaaccg aagaccattc atgttgttgc    7390
tcaggtcgca gacgttttgc agcagcagtc gcttcacgtt cgctcgcgta tcggtgattc    7450
attctgctaa ccagtaaggc aaccccgcca gcctagccgg gtcctcaacg acaggagcac    7510
gatcatgcgc acccgtggcc aggacccaac gctgcccgaa att    7553
```

<210> SEQ ID NO 8
<211> LENGTH: 701
<212> TYPE: PRT
<213> ORGANISM: Toxoplasma gondii
<220> FEATURE:
<223> OTHER INFORMATION: pMBP-p2X-ToxoP30 (52-336aa)

<400> SEQUENCE: 8

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
                 20                  25                  30

Leu Val Ile Trp Ile Asn Gly Asp Lys Gly Tyr Asn Gly Leu Ala Glu
             35                  40                  45

Val Gly Lys Lys Phe Glu Lys Asp Thr Gly Ile Lys Val Thr Val Glu
         50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300
```

```
Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
                340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
370                 375                 380

Glu Ala Leu Lys Asp Ala Gln Thr Asn Ser Ser Ser Asn Asn Asn Asn
385                 390                 395                 400

Asn Asn Asn Asn Asn Leu Gly Ile Glu Gly Arg Ile Ser Glu Phe
                405                 410                 415

Leu Val Ala Asn Gln Val Val Thr Cys Pro Asp Lys Lys Ser Thr Ala
            420                 425                 430

Ala Val Ile Leu Thr Pro Thr Glu Asn His Phe Thr Leu Lys Cys Pro
            435                 440                 445

Lys Thr Ala Leu Thr Glu Pro Pro Thr Leu Ala Tyr Ser Pro Asn Arg
450                 455                 460

Gln Ile Cys Pro Ala Gly Thr Thr Ser Ser Cys Thr Ser Lys Ala Val
465                 470                 475                 480

Thr Leu Ser Ser Leu Ile Pro Glu Ala Glu Asp Ser Trp Trp Thr Gly
                485                 490                 495

Asp Ser Ala Ser Leu Asp Thr Ala Gly Ile Lys Leu Thr Val Pro Ile
            500                 505                 510

Glu Lys Phe Pro Val Thr Thr Gln Thr Phe Val Val Gly Cys Ile Lys
            515                 520                 525

Gly Asp Asp Ala Gln Ser Cys Met Val Thr Val Thr Val Gln Ala Arg
            530                 535                 540

Ala Ser Ser Val Val Asn Asn Val Ala Arg Cys Ser Tyr Gly Ala Asp
545                 550                 555                 560

Ser Thr Leu Gly Pro Val Lys Leu Ser Ala Glu Gly Pro Thr Thr Met
                565                 570                 575

Thr Leu Val Cys Gly Lys Asp Gly Val Lys Val Pro Gln Asp Asn Asn
                580                 585                 590

Gln Tyr Cys Ser Gly Thr Thr Leu Thr Gly Cys Asn Glu Lys Ser Phe
            595                 600                 605

Lys Asp Ile Leu Pro Lys Leu Thr Glu Asn Pro Trp Gln Gly Asn Ala
            610                 615                 620

Ser Ser Asp Lys Gly Ala Thr Leu Thr Ile Lys Lys Glu Ala Phe Pro
625                 630                 635                 640

Ala Glu Ser Lys Ser Val Ile Ile Gly Cys Thr Gly Gly Ser Pro Glu
                645                 650                 655

Lys His His Cys Thr Val Lys Leu Glu Phe Ala Gly Ala Gly Ser
            660                 665                 670

Ala Lys Ser Ala Ala Gly Thr Ala Ser His Val Ser Ile Phe Ala Met
            675                 680                 685

Val Ile Gly Leu Ile Gly Ser Ile Ala Ala Cys Val Ala
            690                 695                 700

<210> SEQ ID NO 9
<211> LENGTH: 39
```

-continued

```
<212> TYPE: DNA
<213> ORGANISM: Artificial Sequence
<220> FEATURE:
<223> OTHER INFORMATION: Antisense Primer

<400> SEQUENCE: 9
caggtcaagc tttcacacca tggcaaaaat ggaaacgtg                               39

<210> SEQ ID NO 10
<211> LENGTH: 7442
<212> TYPE: DNA
<213> ORGANISM: Toxoplasma gondii
<220> FEATURE:
<221> NAME/KEY: CDS
<222> LOCATION: (1528)...(3519)
<223> OTHER INFORMATION: pMBP-c2X-ToxoP30dellC (52-324aa)

<400> SEQUENCE: 10
ccgacaccat cgaatggtgc aaaacctttc gcggtatggc atgatagcgc ccggaagaga         60
gtcaattcag ggtggtgaat gtgaaaccag taacgttata cgatgtcgca gagtatgccg        120
gtgtctctta tcagaccgtt tcccgcgtgg tgaaccaggc cagccacgtt tctgcgaaaa        180
cgcgggaaaa agtggaagcg gcgatggcgg agctgaatta cattcccaac cgcgtggcac        240
aacaactggc gggcaaacag tcgttgctga ttggcgttgc cacctccagt ctggccctgc        300
acgcgccgtc gcaaattgtc gcggcgatta atctcgcgc cgatcaactg ggtgccagcg        360
tggtggtgtc gatggtagaa cgaagcggcg tcgaagcctg taaagcggcg gtgcacaatc        420
ttctcgcgca acgcgtcagt gggctgatca ttaactatcc gctggatgac caggatgcca        480
ttgctgtgga agctgcctgc actaatgttc cggcgttatt tcttgatgtc tctgaccaga        540
cacccatcaa cagtattatt ttctcccatg aagacggtac gcgactgggc gtggagcatc        600
tggtcgcatt gggtcaccag caaatcgcgc tgttagcggg cccattaagt tctgtctcgg        660
cgcgtctgcg tctggctggc tggcataaat atctcactcg caatcaaatt cagccgatag        720
cggaacggga aggcgactgg agtgccatgt ccggttttca acaaaccatg caaatgctga        780
atgagggcat cgttcccact gcgatgctgg ttgccaacga tcagatgcgc ctgggcgcaa        840
tgcgcgccat taccgagtcc gggctgcgcg ttggtgcgga tatctcggta gtgggatacg        900
acgataccga agacagctca tgttatatcc gccgttaac caccatcaaa caggattttc        960
gcctgctggg gcaaaccagc gtggaccgct tgctgcaact ctctcagggc caggcggtga       1020
agggcaatca gctgttgccc gtctcactgg tgaaaagaaa aaccaccctg gcgcccaata       1080
cgcaaaccgc ctctccccgc gcgttggccg attcattaat gcagctggca cgacaggttt       1140
cccgactgga aagcgggcag tgagcgcaac gcaattaatg taagttagct cactcattag       1200
gcacaattct catgtttgac agcttatcat cgactgcacg gtgcaccaat gcttctggcg       1260
tcaggcagcc atcggaagct gtggtatggc tgtgcaggtc gtaaatcact gcataattcg       1320
tgtcgctcaa ggcgcactcc cgttctggat aatgttttt gcgccgacat cataacggtt       1380
ctggcaaata ttctgaaatg agctgttgac aattaatcat cggctcgtat aatgtgtgga       1440
attgtgagcg gataacaatt tcacacagga acagccagt ccgtttaggt gttttcacga       1500
gcacttcacc aacaaggacc atagcat atg aaa atc gaa gaa ggt aaa ctg gta      1554
                                Met Lys Ile Glu Glu Gly Lys Leu Val
                                  1               5 atc tgg att aac ggc gat aaa ggc tat aac ggt ctc gct gaa gtc ggt          1602
Ile Trp Ile Asn Gly Asp Lys Gly Tyr Asn Gly Leu Ala Glu Val Gly
 10              15                  20                  25
```

```
aag aaa ttc gag aaa gat acc gga att aaa gtc acc gtt gag cat ccg      1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345
```

```
act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
            350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
        365                 370                 375 aat aac aac aac ctc ggg atc gag gga agg att tca gaa ttc ctt gtt    2706
Asn Asn Asn Asn Leu Gly Ile Glu Gly Arg Ile Ser Glu Phe Leu Val
    380                 385                 390 gcc aat caa gtt gtc acc tgc cca gat aaa aaa tcg aca gcc gcg gtc    2754
Ala Asn Gln Val Val Thr Cys Pro Asp Lys Lys Ser Thr Ala Ala Val
395                 400                 405 att ctc aca ccg acg gag aac cac ttc act ctc aag tgc cct aaa aca    2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc    2850
Ala Leu Thr Glu Pro Pro Thr Leu Ala Tyr Ser Pro Asn Arg Gln Ile
            430                 435                 440 tgc cca gcg ggt act aca agt agc tgt aca tca aag gct gta aca ttg    2898
Cys Pro Ala Gly Thr Thr Ser Ser Cys Thr Ser Lys Ala Val Thr Leu
        445                 450                 455 agc tcc ttg att cct gaa gca gaa gat agc tgg tgg acg ggg gat tct    2946
Ser Ser Leu Ile Pro Glu Ala Glu Asp Ser Trp Trp Thr Gly Asp Ser
    460                 465                 470 gct agt ctc gac acg gca ggc atc aaa ctc aca gtt cca atc gag aag    2994
Ala Ser Leu Asp Thr Ala Gly Ile Lys Leu Thr Val Pro Ile Glu Lys
475                 480                 485 ttc ccc gtg aca acg cag acg ttt gtg gtc ggt tgc atc aag gga gac    3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca    3090
Asp Ala Gln Ser Cys Met Val Thr Val Thr Val Gln Ala Arg Ala Ser
            510                 515                 520 tcg gtc gtc aat aat gtc gca agg tgc tcc tac ggt gca gac agc act    3138
Ser Val Val Asn Asn Val Ala Arg Cys Ser Tyr Gly Ala Asp Ser Thr
        525                 530                 535 ctt ggt cct gtc aag ttg tct gcg gaa gga ccc act aca atg acc ctc    3186
Leu Gly Pro Val Lys Leu Ser Ala Glu Gly Pro Thr Thr Met Thr Leu
    540                 545                 550 gtg tgc ggg aaa gat gga gtc aaa gtt cct caa gac aac aat cag tac    3234
Val Cys Gly Lys Asp Gly Val Lys Val Pro Gln Asp Asn Asn Gln Tyr
555                 560                 565 tgt tcc ggg acg acg ctg act ggt tgc aac gag aaa tcg ttc aaa gat    3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt    3330
Ile Leu Pro Lys Leu Thr Glu Asn Pro Trp Gln Gly Asn Ala Ser Ser
            590                 595                 600 gat aag ggt gcc acg cta acg atc aag aag gaa gca ttt cca gcc gag    3378
Asp Lys Gly Ala Thr Leu Thr Ile Lys Lys Glu Ala Phe Pro Ala Glu
        605                 610                 615 tca aaa agc gtc att att gga tgc aca ggg gga tcg cct gag aag cat    3426
Ser Lys Ser Val Ile Ile Gly Cys Thr Gly Gly Ser Pro Glu Lys His
    620                 625                 630 cac tgt acc gtg aaa ctg gag ttt gcc ggg gct gca ggg tca gca aaa    3474
His Cys Thr Val Lys Leu Glu Phe Ala Gly Ala Ala Gly Ser Ala Lys
635                 640                 645 tcg gct gcg gga aca gcc agt cac gtt tcc att ttt gcc atg gtg        3519
Ser Ala Ala Gly Thr Ala Ser His Val Ser Ile Phe Ala Met Val
```

-continued

```
                 650                 655                 660
tgaaagcttg gcactggccg tcgttttaca acgtcgtgac tgggaaaacc ctggcgttac     3579
ccaacttaat cgccttgcag cacatccccc tttcgccagc tggcgtaata gcgaagaggc     3639
ccgcaccgat cgcccttccc aacagttgcg cagcctgaat ggcgaatggc agcttggctg     3699
ttttggcgga tgagataaga ttttcagcct gatacagatt aaatcagaac gcagaagcgg     3759
tctgataaaa cagaatttgc ctggcggcag tagcgcggtg gtcccacctg accccatgcc     3819
gaactcagaa gtgaaacgcc gtagcgccga tggtagtgtg gggtctcccc atgcgagagt     3879
agggaactgc caggcatcaa ataaaacgaa aggctcagtc gaaagactgg cctttcgtt     3939 ttatctgttg tttgtcggtg aacgctctcc tgagtaggac aaatccgccg ggagcggatt     3999
tgaacgttgc gaagcaacgg cccggagggt ggcgggcagg acgcccgcca taaactgcca     4059
ggcatcaaat taagcagaag gccatcctga cggatggcct ttttgcgttt ctacaaactc     4119
tttttgttta tttttctaaa tacattcaaa tatgtatccg ctcatgagac aataaccctg     4179
ataaatgctt caataatatt gaaaaaggaa gagtatgagt attcaacatt tccgtgtcgc     4239
ccttattccc ttttttgcgg cattttgcct tcctgttttt gctcacccag aaacgctggt     4299
gaaagtaaaa gatgctgaag atcagttggg tgcacgagtg ggttacatcg aactggatct     4359
caacagcggt aagatccttg agagttttcg ccccgaagaa cgttctccaa tgatgagcac     4419
ttttaaagtt ctgctatgtg gcgcggtatt atcccgtgtt gacgccgggc aagagcaact     4479
cggtcgccgc atacactatt ctcagaatga cttggttgag tactcaccag tcacagaaaa     4539
gcatcttacg gatggcatga cagtaagaga attatgcagt gctgccataa ccatgagtga     4599
taacactgcg gccaacttac ttctgacaac gatcggagga ccgaaggagc taaccgcttt     4659
tttgcacaac atgggggatc atgtaactcg ccttgatcgt tgggaaccgg agctgaatga     4719
agccatacca aacgacgagc gtgacaccac gatgcctgta gcaatggcaa caacgttgcg     4779
caaactatta actggcgaac tacttactct agcttcccgg caacaattaa tagactggat     4839
ggaggcggat aaagttgcag gaccacttct gcgctcggcc cttccggctg gctggtttat     4899
tgctgataaa tctggagccg gtgagcgtgg gtctcgcggt atcattgcag cactgggcc      4959 agatggtaag ccctcccgta tcgtagttat ctacacgacg gggagtcagg caactatgga     5019
tgaacgaaat agacagatcg ctgagatagg tgcctcactg attaagcatt ggtaactgtc     5079
agaccaagtt tactcatata ctttagat tgatttaccc cggttgataa tcagaaaagc     5139
cccaaaaaca ggaagattgt ataagcaaat atttaaattg taaacgttaa tattttgtta     5199
aaattcgcgt taaattttg ttaaatcagc tcattttta accataggc cgaaatcggc      5259 aaaatccctt ataatcaaa agaatagacc gagatagggt tgagtgttgt tccagtttgg     5319
aacaagagtc cactattaaa gaacgtggac tccaacgtca agggcgaaa aaccgtctat      5379 cagggcgatg gcccactacg tgaaccatca cccaaatcaa gttttttggg gtcgaggtgc     5439
cgtaaagcac taaatcggaa ccctaaaggg agccccgat ttagagcttg acggggaaag     5499
ccggcgaacg tggcgagaaa ggaagggaag aaagcgaaag gagcgggcgc tagggcgctg     5559
gcaagtgtag cggtcacgct gcgcgtaacc accacccg ccgcgcttaa tgcgccgcta      5619
cagggcgcgt aaaaggatct aggtgaagat cctttttgat aatctcatga ccaaaatccc     5679
ttaacgtgag ttttcgttcc actgagcgtc agaccccgta gaaagatca aaggatcttc      5739 ttgagatcct ttttttctgc gcgtaatctg ctgcttgcaa acaaaaaaac caccgctacc     5799
agcggtggtt tgtttgccgg atcaagagct accaactctt tttccgaagg taactggctt     5859
```

-continued

```
cagcagagcg cagataccaa atactgtcct tctagtgtag ccgtagttag gccaccactt   5919
caagaactct gtagcaccgc ctacatacct cgctctgcta atcctgttac cagtggctgc   5979
tgccagtggc gataagtcgt gtcttaccgg gttggactca agacgatagt taccggataa   6039
ggcgcagcgg tcgggctgaa cggggggttc gtgcacacag cccagcttgg agcgaacgac   6099
ctacaccgaa ctgagatacc tacagcgtga gctatgagaa agcgccacgc ttcccgaagg   6159
gagaaaggcg gacaggtatc cggtaagcgg cagggtcgga acaggagagc gcacgaggga   6219
gcttccaggg ggaaacgcct ggtatcttta tagtcctgtc gggtttcgcc acctctgact   6279
tgagcgtcga tttttgtgat gctcgtcagg ggggcggagc ctatggaaaa acgccagcaa   6339
cgcggccttt ttacggttcc tggccttttg ctggcctttt gctcacatgt tctttcctgc   6399
gttatcccct gattctgtgg ataaccgtat taccgccttt gagtgagctg ataccgctcg   6459
ccgcagccga acgaccgagc gcagcgagtc agtgagcgag gaagcggaag agcgcctgat   6519
gcggtatttt ctccttacgc atctgtgcgg tatttcacac cgcatatatg gtgcactctc   6579
agtacaatct gctctgatgc cgcatagtta agccagtata cactccgcta tcgctacgtg   6639
actgggtcat ggctgcgccc cgacacccgc caacacccgc tgacgcgccc tgacgggctt   6699
gtctgctccc ggcatccgct tacagacaag ctgtgaccgt ctccgggagc tgcatgtgtc   6759
agaggttttc accgtcatca ccgaaacgcg cgaggcagct gcggtaaagc tcatcagcgt   6819
ggtcgtgcag cgattcacag atgtctgcct gttcatccgc gtccagctcg ttgagtttct   6879
ccagaagcgt taatgtctgg cttctgataa agcgggccat gttaagggcg gttttttcct   6939
gtttggtcac tgatgcctcc gtgtaagggg gatttctgtt catgggggta atgataccga   6999
tgaaacgaga gaggatgctc acgatacggg ttactgatga tgaacatgcc cggttactgg   7059
aacgttgtga gggtaaacaa ctggcggtat ggatgcggcg ggaccagaga aaaatcactc   7119
agggtcaatg ccagcgcttc gttaatacag atgtaggtgt tccacagggt agccagcagc   7179
atcctgcgat gcagatccgg aacataatgg tgcagggcgc tgacttccgc gtttccagac   7239
tttacgaaac acggaaaccg aagaccattc atgttgttgc tcaggtcgca gacgttttgc   7299
agcagcagtc gcttcacgtt cgctcgcgta tcggtgattc attctgctaa ccagtaaggc   7359
aaccccgcca gcctagccgg gtcctcaacg acaggagcac gatcatgcgc acccgtggcc   7419
aggacccaac gctgcccgaa att                                           7442
```

```

<210> SEQ ID NO 11
<211> LENGTH: 664
<212> TYPE: PRT
<213> ORGANISM: Toxoplasma gondii
<220> FEATURE:
<223> OTHER INFORMATION: pMBP-c2X-ToxoP30del1C (52-324aa)

<400> SEQUENCE: 11

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80
```

```
Thr Pro Asp Lys Ala Phe Gln Asp Lys Leu Tyr Pro Phe Thr Trp Asp
                 85                  90                  95
Ala Val Arg Tyr Asn Gly Lys Leu Ile Ala Tyr Pro Ile Ala Val Glu
            100                 105                 110
Ala Leu Ser Leu Ile Tyr Asn Lys Asp Leu Leu Pro Asn Pro Pro Lys
        115                 120                 125
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
    290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
        355                 360                 365
Ser Ser Ser Asn Asn Asn Asn Asn Asn Asn Asn Asn Leu Gly Ile
    370                 375                 380
Glu Gly Arg Ile Ser Glu Phe Leu Val Ala Asn Gln Val Val Thr Cys
385                 390                 395                 400
Pro Asp Lys Lys Ser Thr Ala Ala Val Ile Leu Thr Pro Thr Glu Asn
                405                 410                 415
His Phe Thr Leu Lys Cys Pro Lys Thr Ala Leu Thr Glu Pro Pro Thr
            420                 425                 430
Leu Ala Tyr Ser Pro Asn Arg Gln Ile Cys Pro Ala Gly Thr Thr Ser
        435                 440                 445
Ser Cys Thr Ser Lys Ala Val Thr Leu Ser Ser Leu Ile Pro Glu Ala
    450                 455                 460
Glu Asp Ser Trp Trp Thr Gly Asp Ser Ala Ser Leu Asp Thr Ala Gly
465                 470                 475                 480
Ile Lys Leu Thr Val Pro Ile Glu Lys Phe Pro Val Thr Thr Gln Thr
                485                 490                 495
```

```
Phe Val Val Gly Cys Ile Lys Gly Asp Asp Ala Gln Ser Cys Met Val
                500             505             510
Thr Val Thr Val Gln Ala Arg Ala Ser Ser Val Val Asn Asn Val Ala
            515             520             525
Arg Cys Ser Tyr Gly Ala Asp Ser Thr Leu Gly Pro Val Lys Leu Ser
        530             535             540
Ala Glu Gly Pro Thr Thr Met Thr Leu Val Cys Gly Lys Asp Gly Val
545             550             555             560
Lys Val Pro Gln Asp Asn Asn Gln Tyr Cys Ser Gly Thr Thr Leu Thr
                565             570             575
Gly Cys Asn Glu Lys Ser Phe Lys Asp Ile Leu Pro Lys Leu Thr Glu
            580             585             590
Asn Pro Trp Gln Gly Asn Ala Ser Ser Asp Lys Gly Ala Thr Leu Thr
        595             600             605
Ile Lys Lys Glu Ala Phe Pro Ala Glu Ser Lys Ser Val Ile Ile Gly
    610             615             620
Cys Thr Gly Gly Ser Pro Glu Lys His His Cys Thr Val Lys Leu Glu
625             630             635             640
Phe Ala Gly Ala Ala Gly Ser Ala Lys Ser Ala Ala Gly Thr Ala Ser
                645             650             655
His Val Ser Ile Phe Ala Met Val
            660

<210> SEQ ID NO 12
<211> LENGTH: 819
<212> TYPE: DNA
<213> ORGANISM: Toxoplasma gondii
<220> FEATURE:
<221> NAME/KEY: CDS
<222> LOCATION: (1)...(819)
<223> OTHER INFORMATION: ToxoP30del1C (52-324aa)

<400> SEQUENCE: 12
```

| | | | | | | | | | | | | | | | | |
|---|---|---|---|---|---|---|---|---|---|---|---|---|---|---|---|---|
| ctt | gtt | gcc | aat | caa | gtt | gtc | acc | tgc | cca | gat | aaa | aaa | tcg | aca | gcc | 48 |
| Leu | Val | Ala | Asn | Gln | Val | Val | Thr | Cys | Pro | Asp | Lys | Lys | Ser | Thr | Ala | |
| 1 | | | | 5 | | | | | 10 | | | | | 15 | | |
| gcg | gtc | att | ctc | aca | ccg | acg | gag | aac | cac | ttc | act | ctc | aag | tgc | cct | 96 |
| Ala | Val | Ile | Leu | Thr | Pro | Thr | Glu | Asn | His | Phe | Thr | Leu | Lys | Cys | Pro | |
| | | | 20 | | | | | 25 | | | | | 30 | | | |
| aaa | aca | gcg | ctc | aca | gag | cct | ccc | act | ctt | gcg | tac | tca | ccc | aac | agg | 144 |
| Lys | Thr | Ala | Leu | Thr | Glu | Pro | Pro | Thr | Leu | Ala | Tyr | Ser | Pro | Asn | Arg | |
| | | 35 | | | | | 40 | | | | | 45 | | | | |
| caa | atc | tgc | cca | gcg | ggt | act | aca | agt | agc | tgt | aca | tca | aag | gct | gta | 192 |
| Gln | Ile | Cys | Pro | Ala | Gly | Thr | Thr | Ser | Ser | Cys | Thr | Ser | Lys | Ala | Val | |
| | 50 | | | | | 55 | | | | | 60 | | | | | |
| aca | ttg | agc | tcc | ttg | att | cct | gaa | gca | gaa | gat | agc | tgg | tgg | acg | ggg | 240 |
| Thr | Leu | Ser | Ser | Leu | Ile | Pro | Glu | Ala | Glu | Asp | Ser | Trp | Trp | Thr | Gly | |
| 65 | | | | | 70 | | | | | 75 | | | | | 80 | |
| gat | tct | gct | agt | ctc | gac | acg | gca | ggc | atc | aaa | ctc | aca | gtt | cca | atc | 288 |
| Asp | Ser | Ala | Ser | Leu | Asp | Thr | Ala | Gly | Ile | Lys | Leu | Thr | Val | Pro | Ile | |
| | | | | 85 | | | | | 90 | | | | | 95 | | |
| gag | aag | ttc | ccc | gtg | aca | acg | cag | acg | ttt | gtg | gtc | ggt | tgc | atc | aag | 336 |
| Glu | Lys | Phe | Pro | Val | Thr | Thr | Gln | Thr | Phe | Val | Val | Gly | Cys | Ile | Lys | |
| | | | 100 | | | | | 105 | | | | | 110 | | | |
| gga | gac | gac | gca | cag | agt | tgt | atg | gtc | aca | gtg | aca | gta | caa | gcc | aga | 384 |
| Gly | Asp | Asp | Ala | Gln | Ser | Cys | Met | Val | Thr | Val | Thr | Val | Gln | Ala | Arg | |
| | | 115 | | | | | 120 | | | | | 125 | | | | |
| gcc | tca | tcg | gtc | gtc | aat | aat | gtc | gca | agg | tgc | tcc | tac | ggt | gca | gac | 432 |
| Ala | Ser | Ser | Val | Val | Asn | Asn | Val | Ala | Arg | Cys | Ser | Tyr | Gly | Ala | Asp | |

-continued

```
                130                 135                 140
agc act ctt ggt cct gtc aag ttg tct gcg gaa gga ccc act aca atg    480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat    528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc    576
Gln Tyr Cys Ser Gly Thr Thr Leu Thr Gly Cys Asn Glu Lys Ser Phe
            180                 185                 190 aaa gat att ttg cca aaa tta act gag aac ccg tgg cag ggt aac gct    624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca    672
Ser Ser Asp Lys Gly Ala Thr Leu Thr Ile Lys Lys Glu Ala Phe Pro
    210                 215                 220 gcc gag tca aaa agc gtc att att gga tgc aca ggg gga tcg cct gag    720
Ala Glu Ser Lys Ser Val Ile Ile Gly Cys Thr Gly Gly Ser Pro Glu
225                 230                 235                 240 aag cat cac tgt acc gtg aaa ctg gag ttt gcc ggg gct gca ggg tca    768
Lys His His Cys Thr Val Lys Leu Glu Phe Ala Gly Ala Ala Gly Ser
                245                 250                 255 gca aaa tcg gct gcg gga aca gcc agt cac gtt tcc att ttt gcc atg    816
Ala Lys Ser Ala Ala Gly Thr Ala Ser His Val Ser Ile Phe Ala Met
            260                 265                 270 gtg                                                                819
Val
```

<210> SEQ ID NO 13
<211> LENGTH: 273
<212> TYPE: PRT
<213> ORGANISM: Toxoplasma gondii
<220> FEATURE:
<223> OTHER INFORMATION: ToxoP30del1C (52-324aa)

<400> SEQUENCE: 13

```
Leu Val Ala Asn Gln Val Val Thr Cys Pro Asp Lys Lys Ser Thr Ala
1               5                   10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175
```

```
Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Cys Thr Gly Ser Pro Glu
225                 230                 235                 240

Lys His His Cys Thr Val Lys Leu Glu Phe Ala Gly Ala Gly Ser
            245                 250                 255

Ala Lys Ser Ala Ala Gly Thr Ala Ser His Val Ser Ile Phe Ala Met
        260                 265                 270

Val
```

<210> SEQ ID NO 14
<211> LENGTH: 41
<212> TYPE: DNA
<213> ORGANISM: Artificial Sequence
<220> FEATURE:
<223> OTHER INFORMATION: Antisense Primer

<400> SEQUENCE: 14

```
caggtcaagc tttcaagccg attttgctga ccctgcagcc c                    41
```

<210> SEQ ID NO 15
<211> LENGTH: 7403
<212> TYPE: DNA
<213> ORGANISM: Toxoplasma gondii
<220> FEATURE:
<221> NAME/KEY: CDS
<222> LOCATION: (1528)...(3480)
<223> OTHER INFORMATION: pMBP-c2X-ToxoP30del2 (52-311aa)

<400> SEQUENCE: 15

```
ccgacaccat cgaatggtgc aaaacctttc gcggtatggc atgatagcgc ccggaagaga     60
gtcaattcag gtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta aatctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatgcgc ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct tgctgcaact ctctcagggc caggcggtga   1020
```

```
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga    1440
attgtgagcg gataacaatt tcacacagga aacagccagt ccgtttaggt gttttcacga    1500
gcacttcacc aacaaggacc atagcat atg aaa atc gaa gaa ggt aaa ctg gta    1554
                             Met Lys Ile Glu Glu Gly Lys Leu Val
                              1               5 atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg      1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
     60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90                  95                  100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
             110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
         125                 130                 135 aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
     140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
 155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
             190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
         205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
     220                 225                 230 tcc aac atc gac acc agc aaa gtg aat tat ggt gta acg gta ctg ccg      2274
Ser Asn Ile Asp Thr Ser Lys Val Asn Tyr Gly Val Thr Val Leu Pro
 235                 240                 245
```

```
acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt    2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt    2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc    2754
Ala Asn Gln Val Val Thr Cys Pro Asp Lys Lys Ser Thr Ala Ala Val
    395                 400                 405 att ctc aca ccg acg gag aac cac ttc act ctc aag tgc cct aaa aca    2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc    2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg    2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct    2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag    2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac    3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca    3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act    3138
Ser Val Val Asn Asn Val Ala Arg Cys Ser Tyr Gly Ala Asp Ser Thr
            525                 530                 535 ctt ggt cct gtc aag ttg tct gcg gaa gga ccc act aca atg acc ctc    3186
Leu Gly Pro Val Lys Leu Ser Ala Glu Gly Pro Thr Thr Met Thr Leu
        540                 545                 550 gtg tgc ggg aaa gat gga gtc aaa gtt cct caa gac aac aat cag tac    3234
Val Cys Gly Lys Asp Gly Val Lys Val Pro Gln Asp Asn Asn Gln Tyr
```

|  |  |
|---|---|
| tgt tcc ggg acg acg ctg act ggt tgc aac gag aaa tcg ttc aaa gat<br>Cys Ser Gly Thr Thr Leu Thr Gly Cys Asn Glu Lys Ser Phe Lys Asp<br>570                 575                 580                 585 | 3282 |
| att ttg cca aaa tta act gag aac ccg tgg cag ggt aac gct tcg agt<br>Ile Leu Pro Lys Leu Thr Glu Asn Pro Trp Gln Gly Asn Ala Ser Ser<br>               590                 595                 600 | 3330 |
| gat aag ggt gcc acg cta acg atc aag aag gaa gca ttt cca gcc gag<br>Asp Lys Gly Ala Thr Leu Thr Ile Lys Lys Glu Ala Phe Pro Ala Glu<br>               605                 610                 615 | 3378 |
| tca aaa agc gtc att att gga tgc aca ggg gga tcg cct gag aag cat<br>Ser Lys Ser Val Ile Ile Gly Cys Thr Gly Gly Ser Pro Glu Lys His<br>     620                 625                 630 | 3426 |
| cac tgt acc gtg aaa ctg gag ttt gcc ggg gct gca ggg tca gca aaa<br>His Cys Thr Val Lys Leu Glu Phe Ala Gly Ala Ala Gly Ser Ala Lys<br>     635                 640                 645 | 3474 |
| tcg gct tgaaagcttg gcactggccg tcgttttaca acgtcgtgac tgggaaaacc<br>Ser Ala<br>650 | 3530 |
| ctggcgttac ccaacttaat cgccttgcag cacatccccc tttcgccagc tggcgtaata | 3590 |
| gcgaagaggc ccgcaccgat cgcccttccc aacagttgcg cagcctgaat ggcgaatggc | 3650 |
| agcttggctg ttttggcgga tgagataaga ttttcagcct gatacagatt aaatcagaac | 3710 |
| gcagaagcgg tctgataaaa cagaatttgc ctggcggcag tagcgcggtg gtcccacctg | 3770 |
| accccatgcc gaactcagaa gtgaaacgcc gtagcgccga tggtagtgtg ggtctcccc | 3830 |
| atgcgagagt agggaactgc caggcatcaa ataaaacgaa aggctcagtc gaaagactgg | 3890 |
| gcctttcgtt ttatctgttg tttgtcggtg aacgctctcc tgagtaggac aaatccgccg | 3950 |
| ggagcggatt tgaacgttgc gaagcaacgg cccggagggt ggcgggcagg acgcccgcca | 4010 |
| taaactgcca ggcatcaaat taagcagaag gccatcctga cggatggcct ttttgcgttt | 4070 |
| ctacaaactc ttttttgttta tttttctaaa tacattcaaa tatgtatccg ctcatgagac | 4130 |
| aataaccctg ataaatgctt caataatatt gaaaaggaa gagtatgagt attcaacatt | 4190 |
| tccgtgtcgc ccttattccc ttttttgcgg cattttgcct tcctgttttt gctcacccag | 4250 |
| aaacgctggt gaaagtaaaa gatgctgaag atcagttggg tgcacgagtg ggttacatcg | 4310 |
| aactggatct caacagcggt aagatccttg agttttcg ccccgaagaa cgttctccaa | 4370 |
| tgatgagcac ttttaaagtt ctgctatgtg gcgcggtatt atcccgtgtt gacgccgggc | 4430 |
| aagagcaact cggtcgccgc atacactatt ctcagaatga cttggttgag tactcaccag | 4490 |
| tcacagaaaa gcatcttacg gatggcatga cagtaagaga attatgcagt gctgccataa | 4550 |
| ccatgagtga taacactgcg gccaacttac ttctgacaac gatcggagga ccgaaggagc | 4610 |
| taaccgcttt tttgcacaac atgggggatc atgtaactcg ccttgatcgt tgggaaccgg | 4670 |
| agctgaatga agccatacca aacgacgagc gtgacaccac gatgcctgta gcaatggcaa | 4730 |
| caacgttgcg caaactatta actggcgaac tacttactct agcttcccgg caacaattaa | 4790 |
| tagactggat ggaggcggat aaagttgcag gaccacttct gcgctcggcc cttccggctg | 4850 |
| gctggtttat tgctgataaa tctggagccg gtgagcgtgg gtctcgcggt atcattgcag | 4910 |
| cactggggcc agatggtaag ccctcccgta tcgtagttat ctacacgacg gggagtcagg | 4970 |
| caactatgga tgaacgaaat agacagatcg ctgagatagg tgcctcactg attaagcatt | 5030 |
| ggtaactgtc agaccaagtt tactcatata ctttagat tgatttaccc cggttgataa | 5090 |
| tcagaaaagc cccaaaaaca ggaagattgt ataagcaaat atttaaattg taaacgttaa | 5150 |

-continued

```
tattttgtta aaattcgcgt taaattttg ttaaatcagc tcatttttta accaataggc    5210
cgaaatcggc aaaatcccttt ataaatcaaa agaatagacc gagatagggt tgagtgttgt   5270
tccagtttgg aacaagagtc cactattaaa gaacgtggac tccaacgtca aagggcgaaa   5330
aaccgtctat cagggcgatg gcccactacg tgaaccatca cccaaatcaa gttttttggg   5390
gtcgaggtgc cgtaaagcac taaatcggaa ccctaaaggg agcccccgat ttagagcttg   5450
acggggaaag ccggcgaacg tggcgagaaa ggaagggaag aaagcgaaag gagcgggcgc   5510
tagggcgctg gcaagtgtag cggtcacgct gcgcgtaacc accacacccg ccgcgcttaa   5570
tgcgccgcta cagggcgcgt aaaggatct aggtgaagat cctttttgat aatctcatga   5630
ccaaaatccc ttaacgtgag ttttcgttcc actgagcgtc agaccccgta gaaaagatca   5690
aaggatcttc ttgagatcct ttttttctgc gcgtaatctg ctgcttgcaa acaaaaaaac   5750
caccgctacc agcggtggtt tgtttgccgg atcaagagct accaactctt tttccgaagg   5810
taactggctt cagcagagcg cagataccaa atactgtcct tctagtgtag ccgtagttag   5870
gccaccactt caagaactct gtagcaccgc ctacatacct cgctctgcta atcctgttac   5930
cagtggctgc tgccagtggc gataagtcgt gtcttaccgg gttggactca agacgatagt   5990
taccggataa ggcgcagcgg tcgggctgaa cggggggttc gtgcacacag cccagcttgg   6050
agcgaacgac ctacaccgaa ctgagatacc tacagcgtga gctatgagaa agcgccacgc   6110
ttcccgaagg gagaaaggcg gacaggtatc cggtaagcgg cagggtcgga acaggagagc   6170
gcacgaggga gcttccaggg ggaaacgcct ggtatcttta tagtcctgtc gggtttcgcc   6230
acctctgact tgagcgtcga tttttgtgat gctcgtcagg gggcggagc ctatggaaaa    6290 acgccagcaa cgcggccttt ttacggttcc tggccttttg ctggcctttt gctcacatgt   6350
tctttcctgc gttatcccct gattctgtgg ataaccgtat taccgccttt gagtgagctg   6410
ataccgctcg ccgcagccga acgaccgagc gcagcgagtc agtgagcgag gaagcggaag   6470
agcgcctgat gcggtatttt ctccttacgc atctgtgcgg tatttcacac cgcatatatg   6530
gtgcactctc agtacaatct gctctgatgc cgcatagtta agccagtata cactccgcta   6590
tcgctacgtg actgggtcat ggctgcgccc cgacacccgc caacacccgc tgacgcgccc   6650
tgacgggctt gtctgctccc ggcatccgct tacagacaag ctgtgaccgt ctccgggagc   6710
tgcatgtgtc agaggttttc accgtcatca ccgaaacgcg cgaggcagct gcggtaaagc   6770
tcatcagcgt ggtcgtgcag cgattcacag atgtctgcct gttcatccgc gtccagctcg   6830
ttgagtttct ccagaagcgt taatgtctgg cttctgataa agcgggccat gttaagggcg   6890
gttttttcct gtttggtcac tgatgcctcc gtgtaagggg gatttctgtt catgggggta   6950
atgataccga tgaaacgaga gaggatgctc acgatacggg ttactgatga tgaacatgcc   7010
cggttactgg aacgttgtga gggtaaacaa ctggcggtat ggatgcggcg ggaccagaga   7070
aaaatcactc agggtcaatg ccagcgcttc gttaatacag atgtaggtgt tccacagggt   7130
agccagcagc atcctgcgat gcagatccgg aacataatgg tgcagggcgc tgacttccgc   7190
gtttccagac tttacgaaac acggaaaccg aagaccattc atgttgttgc tcaggtcgca   7250
gacgttttgc agcagcagtc gcttcacgtt cgctcgcgta tcggtgattc attctgctaa   7310
ccagtaaggc aaccccgcca gcctagcggg gtcctcaacg acaggagcac gatcatgcgc   7370
acccgtggcc aggacccaac gctgcccgaa att                                 7403
```

<210> SEQ ID NO 16

<211> LENGTH: 651
<212> TYPE: PRT
<213> ORGANISM: Toxoplasma gondii
<220> FEATURE:
<223> OTHER INFORMATION: pMBP-c2X-ToxoP30del2 (52-311aa)

<400> SEQUENCE: 16

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380
```

```
Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640

Phe Ala Gly Ala Ala Gly Ser Ala Lys Ser Ala
                645                 650

<210> SEQ ID NO 17
<211> LENGTH: 780
<212> TYPE: DNA
<213> ORGANISM: Toxoplasma gondii
<220> FEATURE:
<221> NAME/KEY: CDS
<222> LOCATION: (1)...(780)
<223> OTHER INFORMATION: ToxoP30del2 (52-311aa)

<400> SEQUENCE: 17 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
             20                  25                  30 aaa aca gcg ctc aca gag cct ccc act ctt gcg tac tca ccc aac agg    144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta    192
Gln Ile Cys Pro Ala Gly Thr Thr Ser Ser Cys Thr Ser Lys Ala Val
     50                  55                  60
```

-continued

```
aca ttg agc tcc ttg att cct gaa gca gaa gat agc tgg tgg acg ggg    240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc    288
Asp Ser Ala Ser Leu Asp Thr Ala Gly Ile Lys Leu Thr Val Pro Ile
             85                  90                  95 gag aag ttc ccc gtg aca acg cag acg ttt gtg gtc ggt tgc atc aag    336
Glu Lys Phe Pro Val Thr Thr Gln Thr Phe Val Val Gly Cys Ile Lys
        100                 105                 110 gga gac gac gca cag agt tgt atg gtc aca gtg aca gta caa gcc aga    384
Gly Asp Asp Ala Gln Ser Cys Met Val Thr Val Thr Val Gln Ala Arg
    115                 120                 125 gcc tca tcg gtc gtc aat aat gtc gca agg tgc tcc tac ggt gca gac    432
Ala Ser Ser Val Val Asn Asn Val Ala Arg Cys Ser Tyr Gly Ala Asp
130                 135                 140 agc act ctt ggt cct gtc aag ttg tct gcg gaa gga ccc act aca atg    480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat    528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc    576
Gln Tyr Cys Ser Gly Thr Thr Leu Thr Gly Cys Asn Glu Lys Ser Phe
            180                 185                 190 aaa gat att ttg cca aaa tta act gag aac ccg tgg cag ggt aac gct    624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca    672
Ser Ser Asp Lys Gly Ala Thr Leu Thr Ile Lys Lys Glu Ala Phe Pro
    210                 215                 220 gcc gag tca aaa agc gtc att att gga tgc aca ggg gga tcg cct gag    720
Ala Glu Ser Lys Ser Val Ile Ile Gly Cys Thr Gly Gly Ser Pro Glu
225                 230                 235                 240 aag cat cac tgt acc gtg aaa ctg gag ttt gcc ggg gct gca ggg tca    768
Lys His His Cys Thr Val Lys Leu Glu Phe Ala Gly Ala Ala Gly Ser
                245                 250                 255 gca aaa tcg gct                                                    780
Ala Lys Ser Ala
            260
```

<210> SEQ ID NO 18
<211> LENGTH: 260
<212> TYPE: PRT
<213> ORGANISM: Toxoplasma gondii
<220> FEATURE:
<223> OTHER INFORMATION: ToxoP30del2 (52-311aa)

<400> SEQUENCE: 18

```
Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
             20                  25                  30

Lys Thr Ala Leu Thr Glu Pro Pro Thr Leu Ala Tyr Ser Pro Asn Arg
         35                  40                  45

Gln Ile Cys Pro Ala Gly Thr Thr Ser Ser Cys Thr Ser Lys Ala Val
     50                  55                  60

Thr Leu Ser Ser Leu Ile Pro Glu Ala Glu Asp Ser Trp Trp Thr Gly
 65                  70                  75                  80

Asp Ser Ala Ser Leu Asp Thr Ala Gly Ile Lys Leu Thr Val Pro Ile
```

```
                    85                  90                  95
Glu Lys Phe Pro Val Thr Thr Gln Thr Phe Val Gly Cys Ile Lys
            100                 105                 110
Gly Asp Asp Ala Gln Ser Cys Met Val Thr Val Thr Val Gln Ala Arg
        115                 120                 125
Ala Ser Ser Val Val Asn Asn Val Ala Arg Cys Ser Tyr Gly Ala Asp
    130                 135                 140
Ser Thr Leu Gly Pro Val Lys Leu Ser Ala Glu Gly Pro Thr Thr Met
145                 150                 155                 160
Thr Leu Val Cys Gly Lys Asp Gly Val Lys Val Pro Gln Asp Asn Asn
                165                 170                 175
Gln Tyr Cys Ser Gly Thr Thr Leu Thr Gly Cys Asn Glu Lys Ser Phe
            180                 185                 190
Lys Asp Ile Leu Pro Lys Leu Thr Glu Asn Pro Trp Gln Gly Asn Ala
        195                 200                 205
Ser Ser Asp Lys Gly Ala Thr Leu Thr Ile Lys Lys Glu Ala Phe Pro
    210                 215                 220
Ala Glu Ser Lys Ser Val Ile Ile Gly Cys Thr Gly Ser Pro Glu
225                 230                 235                 240
Lys His His Cys Thr Val Lys Leu Glu Phe Ala Gly Ala Ala Gly Ser
                245                 250                 255
Ala Lys Ser Ala
            260

<210> SEQ ID NO 19
<211> LENGTH: 36
<212> TYPE: DNA
<213> ORGANISM: Artificial Sequence
<220> FEATURE:
<223> OTHER INFORMATION: Antisense Primer

<400> SEQUENCE: 19
caggtcaagc tttcactcca gtttcacggt acagtg                                36

<210> SEQ ID NO 20
<211> LENGTH: 7370
<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-Toxo30del3C (52-300aa)

<400> SEQUENCE: 20
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt ccccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
```

```
tggtcgcatt gggtcaccag caaatcgcgc tgttagcggg cccattaagt tctgtctcgg      660
cgcgtctgcg tctggctggc tggcataaat atctcactcg caatcaaatt cagccgatag      720
cggaacggga aggcgactgg agtgccatgt ccggttttca acaaaccatg caaatgctga      780
atgagggcat cgttcccact gcgatgctgg ttgccaacga tcagatggcg ctgggcgcaa      840
tgcgcgccat taccgagtcc gggctgcgcg ttggtgcgga tatctcggta gtgggatacg      900
acgataccga agacagctca tgttatatcc cgccgttaac caccatcaaa caggattttc      960
gcctgctggg gcaaaccagc gtggaccgct tgctgcaact ctctcagggc caggcggtga     1020
agggcaatca gctgttgccc gtctcactgg tgaaaagaaa aaccaccctg cgcccaata      1080 cgcaaaccgc ctctccccgc gcgttggccg attcattaat gcagctggca cgacaggttt     1140
cccgactgga aagcgggcag tgagcgcaac gcaattaatg taagttagct cactcattag     1200
gcacaattct catgtttgac agcttatcat cgactgcacg gtgcaccaat gcttctggcg     1260
tcaggcagcc atcggaagct gtggtatggc tgtgcaggtc gtaaatcact gcataattcg     1320
tgtcgctcaa ggcgcactcc cgttctggat aatgtttttt gcgccgacat cataacggtt     1380
ctggcaaata ttctgaaatg agctgttgac aattaatcat cggctcgtat aatgtgtgga     1440
attgtgagcg gataacaatt tcacacagga acagccagt ccgtttaggt gttttcacga      1500
gcacttcacc aacaaggacc atagcat atg aaa atc gaa gaa ggt aaa ctg gta     1554
                              Met Lys Ile Glu Glu Gly Lys Leu Val
                                1               5 atc tgg att aac ggc gat aaa ggc tat aac ggt ctc gct gaa gtc ggt       1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg       1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc       1698
Asp Lys Leu Glu Glu Lys Phe Pro Gln Val Ala Ala Thr Gly Asp Gly
                 45                  50                  55 cct gac att atc ttc tgg gca cac gac cgc ttt ggt ggc tac gct caa       1746
Pro Asp Ile Ile Phe Trp Ala His Asp Arg Phe Gly Gly Tyr Ala Gln
             60                  65                  70 tct ggc ctg ttg gct gaa atc acc ccg gac aaa gcg ttc cag gac aag       1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att       1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat       1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat       1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa       1986
Lys Glu Leu Lys Ala Lys Gly Lys Ser Ala Leu Met Phe Asn Leu Gln
            140                 145                 150 gaa ccg tac ttc acc tgg ccg ctg att gct gct gac ggg ggt tat gcg       2034
Glu Pro Tyr Phe Thr Trp Pro Leu Ile Ala Ala Asp Gly Gly Tyr Ala
155                 160                 165 ttc aag tat gaa aac ggc aag tac gac att aaa gac gtg ggc gtg gat       2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa       2130
```

-continued

```
                Asn Ala Gly Ala Lys Ala Gly Leu Thr Phe Leu Val Asp Leu Ile Lys
                                190                 195                 200 aac aaa cac atg aat gca gac acc gat tac tcc atc gca gaa gct gcc         2178
Asn Lys His Met Asn Ala Asp Thr Asp Tyr Ser Ile Ala Glu Ala Ala
                205                 210                 215 ttt aat aaa ggc gaa aca gcg atg acc atc aac ggc ccg tgg gca tgg         2226
Phe Asn Lys Gly Glu Thr Ala Met Thr Ile Asn Gly Pro Trp Ala Trp
            220                 225                 230 tcc aac atc gac acc agc aaa gtg aat tat ggt gta acg gta ctg ccg         2274
Ser Asn Ile Asp Thr Ser Lys Val Asn Tyr Gly Val Thr Val Leu Pro
        235                 240                 245 acc ttc aag ggt caa cca tcc aaa ccg ttc gtt ggc gtg ctg agc gca         2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc         2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac         2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg         2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa         2514
Lys Asp Pro Arg Ile Ala Ala Thr Met Glu Asn Ala Gln Lys Gly Glu
315                 320                 325 atc atg ccg aac atc ccg cag atg tcc gct ttc tgg tat gcc gtg cgt         2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc         2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac         2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt         2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc         2754
Ala Asn Gln Val Val Thr Cys Pro Asp Lys Lys Ser Thr Ala Ala Val
395                 400                 405 att ctc aca ccg acg gag aac cac ttc act ctc aag tgc cct aaa aca         2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc         2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg         2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct         2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag         2994
Ala Ser Leu Asp Thr Ala Gly Ile Lys Leu Thr Val Pro Ile Glu Lys
475                 480                 485 ttc ccc gtg aca acg cag acg ttt gtg gtc ggt tgc atc aag gga gac         3042
Phe Pro Val Thr Thr Gln Thr Phe Val Val Gly Cys Ile Lys Gly Asp
490                 495                 500                 505
```

-continued

| | | |
|---|---|---|
| gac gca cag agt tgt atg gtc aca gtg aca gta caa gcc aga gcc tca<br>Asp Ala Gln Ser Cys Met Val Thr Val Thr Val Gln Ala Arg Ala Ser<br>510 515 520 | | 3090 |
| tcg gtc gtc aat aat gtc gca agg tgc tcc tac ggt gca gac agc act<br>Ser Val Val Asn Asn Val Ala Arg Cys Ser Tyr Gly Ala Asp Ser Thr<br>525 530 535 | | 3138 |
| ctt ggt cct gtc aag ttg tct gcg gaa gga ccc act aca atg acc ctc<br>Leu Gly Pro Val Lys Leu Ser Ala Glu Gly Pro Thr Thr Met Thr Leu<br>540 545 550 | | 3186 |
| gtg tgc ggg aaa gat gga gtc aaa gtt cct caa gac aac aat cag tac<br>Val Cys Gly Lys Asp Gly Val Lys Val Pro Gln Asp Asn Asn Gln Tyr<br>555 560 565 | | 3234 |
| tgt tcc ggg acg acg ctg act ggt tgc aac gag aaa tcg ttc aaa gat<br>Cys Ser Gly Thr Thr Leu Thr Gly Cys Asn Glu Lys Ser Phe Lys Asp<br>570 575 580 585 | | 3282 |
| att ttg cca aaa tta act gag aac ccg tgg cag ggt aac gct tcg agt<br>Ile Leu Pro Lys Leu Thr Glu Asn Pro Trp Gln Gly Asn Ala Ser Ser<br>590 595 600 | | 3330 |
| gat aag ggt gcc acg cta acg atc aag aag gaa gca ttt cca gcc gag<br>Asp Lys Gly Ala Thr Leu Thr Ile Lys Lys Glu Ala Phe Pro Ala Glu<br>605 610 615 | | 3378 |
| tca aaa agc gtc att att gga tgc aca ggg gga tcg cct gag aag cat<br>Ser Lys Ser Val Ile Ile Gly Cys Thr Gly Gly Ser Pro Glu Lys His<br>620 625 630 | | 3426 |
| cac tgt acc gtg aaa ctg gag tgaaagcttg gcactggccg tcgttttaca<br>His Cys Thr Val Lys Leu Glu<br>635 640 | | 3477 |
| acgtcgtgac tgggaaaacc ctggcgttac ccaacttaat cgccttgcag cacatccccc | | 3537 |
| tttcgccagc tggcgtaata gcgaagaggc ccgcaccgat cgcccttccc aacagttgcg | | 3597 |
| cagcctgaat ggcgaatggc agcttggctg ttttggcgga tgagataaga ttttcagcct | | 3657 |
| gatacagatt aaatcagaac gcagaagcgg tctgataaaa cagaatttgc ctggcggcag | | 3717 |
| tagcgcggtg gtcccacctg accccatgcc gaactcagaa gtgaaacgcc gtagcgccga | | 3777 |
| tggtagtgtg gggtctcccc atgcgagagt agggaactgc caggcatcaa ataaaacgaa | | 3837 |
| aggctcagtc gaaagactgg gcctttcgtt ttatctgttg tttgtcggtg aacgctctcc | | 3897 |
| tgagtaggac aaatccgccg ggagcggatt tgaacgttgc gaagcaacgg cccggagggt | | 3957 |
| ggcgggcagg acgcccgcca taaactgcca ggcatcaaat taagcagaag gccatcctga | | 4017 |
| cggatggcct ttttgcgttt ctacaaactc ttttttgttta ttttttctaaa tacattcaaa | | 4077 |
| tatgtatccg ctcatgagac aataaccctg ataaatgctt caataatatt gaaaaaggaa | | 4137 |
| gagtatgagt attcaacatt tccgtgtcgc ccttattccc ttttttgcgg cattttgcct | | 4197 |
| tcctgttttt gctcacccag aaacgctggt gaaagtaaaa gatgctgaag atcagttggg | | 4257 |
| tgcacgagtg ggttacatcg aactggatct caacagcggt aagatccttg agagttttcg | | 4317 |
| ccccgaagaa cgttctccaa tgatgagcac ttttaaagtt ctgctatgtg gcgcggtatt | | 4377 |
| atcccgtgtt gacgccgggc aagagcaact cggtcgccgc atacactatt ctcagaatga | | 4437 |
| cttggttgag tactcaccag tcacagaaaa gcatcttacg gatggcatga cagtaagaga | | 4497 |
| attatgcagt gctgccataa ccatgagtga taacactgcg gccaacttac ttctgacaac | | 4557 |
| gatcggagga ccgaaggagc taaccgcttt tttgcacaac atgggggatc atgtaactcg | | 4617 |
| ccttgatcgt tgggaaccgg agctgaatga agccatacca aacgacgagc gtgacaccac | | 4677 |
| gatgcctgta gcaatggcaa caacgttgcg caaactatta actggcgaac tacttactct | | 4737 |
| agcttcccgg caacaattaa tagactggat ggaggcggat aaagttgcag gaccacttct | | 4797 |

-continued

```
gcgctcggcc cttccggctg gctggtttat tgctgataaa tctggagccg gtgagcgtgg    4857
gtctcgcggt atcattgcag cactggggcc agatggtaag ccctcccgta tcgtagttat    4917
ctacacgacg gggagtcagg caactatgga tgaacgaaat agacagatcg ctgagatagg    4977
tgcctcactg attaagcatt ggtaactgtc agaccaagtt tactcatata tactttagat    5037
tgatttaccc cggttgataa tcagaaaagc cccaaaaaca ggaagattgt ataagcaaat    5097
atttaaattg taaacgttaa tattttgtta aaattcgcgt taaattttg ttaaatcagc    5157 tcatttttta accataggc cgaaatcggc aaaatccctt ataaatcaaa gaatagacc    5217 gagatagggt tgagtgttgt tccagtttgg aacaagagtc cactattaaa gaacgtggac    5277
tccaacgtca aagggcgaaa aaccgtctat cagggcgatg gcccactacg tgaaccatca    5337
cccaaatcaa gttttttggg gtcgaggtgc cgtaaagcac taaatcggaa ccctaaaggg    5397
agcccccgat ttagagcttg acggggaaag ccggcgaacg tggcgagaaa ggaagggaag    5457
aaagcgaaag gagcgggcgc tagggcgctg gcaagtgtag cggtcacgct gcgcgtaacc    5517
accacacccg ccgcgcttaa tgcgccgcta cagggcgcgt aaaaggatct aggtgaagat    5577 ccttttttgat aatctcatga ccaaaatccc ttaacgtgag ttttcgttcc actgagcgtc    5637 agacccgta gaaagatca aaggatcttc ttgagatcct ttttttctgc gcgtaatctg    5697
ctgcttgcaa acaaaaaaac caccgctacc agcggtggtt tgtttgccgg atcaagagct    5757
accaactctt tttccgaagg taactggctt cagcagagcg cagataccaa atactgtcct    5817
tctagtgtag ccgtagttag gccaccactt caagaactct gtagcaccgc ctacatacct    5877
cgctctgcta atcctgttac cagtggctgc tgccagtggc gataagtcgt gtcttaccgg    5937
gttggactca agacgatagt taccggataa ggcgcagcgg tcgggctgaa cggggggttc    5997
gtgcacacag cccagcttgg agcgaacgac ctacaccgaa ctgagatacc tacagcgtga    6057
gctatgagaa agcgccacgc ttcccgaagg gagaaaggcg acaggtatc cggtaagcgg    6117 cagggtcgga acaggagagc gcacgaggga gcttccaggg ggaaacgcct ggtatcttta    6177
tagtcctgtc gggtttcgcc acctctgact tgagcgtcga ttttttgtgat gctcgtcagg    6237 ggggcggagc ctatggaaaa acgccagcaa cgcggccttt ttacggttcc tggccttttg    6297
ctggcctttt gctcacatgt tctttcctgc gttatcccct gattctgtgg ataaccgtat    6357
taccgccttt gagtgagctg ataccgctcg ccgcagccga acgaccgagc gcagcgagtc    6417
agtgagcgag gaagcggaag agcgcctgat gcggtatttt ctccttacgc atctgtgcgg    6477
tatttcacac cgcatatatg gtgcactctc agtacaatct gctctgatgc cgcatagtta    6537
agccagtata cactccgcta tcgctacgtg actgggtcat ggctgcgccc cgacacccgc    6597
caacacccgc tgacgcgccc tgacgggctt gtctgctccc ggcatccgct tacagacaag    6657
ctgtgaccgt ctccgggagc tgcatgtgtc agaggttttc accgtcatca ccgaaacgcg    6717
cgaggcagct gcggtaaagc tcatcagcgt ggtcgtgcag cgattcacag atgtctgcct    6777
gttcatccgc gtccagctcg ttgagttttct ccagaagcgt taatgtctgg cttctgataa    6837
agcgggccat gttaagggcg gttttttcct gtttggtcac tgatgcctcc gtgtaagggg    6897
gatttctgtt catggggta atgataccga tgaaacgaga gaggatgctc acgatacggg    6957
ttactgatga tgaacatgcc cggttactgg aacgttgtga gggtaaacaa ctggcggtat    7017
ggatgcggcg gaccagaga aaaatcactc agggtcaatg ccagcgcttc gttaatacag    7077
atgtaggtgt tccacagggt agccagcagc atcctgcgat gcagatccgg aacataatgg    7137
```

```
tgcagggcgc tgacttccgc gtttccagac tttacgaaac acggaaaccg aagaccattc    7197
atgttgttgc tcaggtcgca gacgttttgc agcagcagtc gcttcacgtt cgctcgcgta    7257
tcggtgattc attctgctaa ccagtaaggc aacccccgcca gcctagccgg gtcctcaacg    7317
acaggagcac gatcatgcgc accgtggcc aggacccaac gctgcccgaa att            7370
```

<210> SEQ ID NO 21
<211> LENGTH: 640
<212> TYPE: PRT
<213> ORGANISM: Toxoplasma gondii
<220> FEATURE:
<223> OTHER INFORMATION: pMBP-c2X-Toxo30del3C (52-300aa)

<400> SEQUENCE: 21

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
```

```
                        325                 330                 335
Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
        370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
                420                 425                 430

Leu Ala Tyr Ser Pro Asn Arg Gln Ile Cys Pro Ala Gly Thr Thr Ser
            435                 440                 445

Ser Cys Thr Ser Lys Ala Val Thr Leu Ser Ser Leu Ile Pro Glu Ala
450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His Cys Thr Val Lys Leu Glu
625                 630                 635                 640

<210> SEQ ID NO 22
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: Toxo30del3C (52-300aa)

<400> SEQUENCE: 22 ctt gtt gcc aat caa gtt gtc acc tgc cca gat aaa aaa tcg aca gcc     48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct     96
Ala Val Ile Leu Thr Pro Thr Glu Asn His Phe Thr Leu Lys Cys Pro
            20                  25                  30
```

```
aaa aca gcg ctc aca gag cct ccc act ctt gcg tac tca ccc aac agg      144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta      192
Gln Ile Cys Pro Ala Gly Thr Thr Ser Ser Cys Thr Ser Lys Ala Val
 50                  55                  60 aca ttg agc tcc ttg att cct gaa gca gaa gat agc tgg tgg acg ggg      240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc      288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag      336
Glu Lys Phe Pro Val Thr Thr Gln Thr Phe Val Val Gly Cys Ile Lys
             100                 105                 110 gga gac gac gca cag agt tgt atg gtc aca gtg aca gta caa gcc aga      384
Gly Asp Asp Ala Gln Ser Cys Met Val Thr Val Thr Val Gln Ala Arg
         115                 120                 125 gcc tca tcg gtc gtc aat aat gtc gca agg tgc tcc tac ggt gca gac      432
Ala Ser Ser Val Val Asn Asn Val Ala Arg Cys Ser Tyr Gly Ala Asp
130                 135                 140 agc act ctt ggt cct gtc aag ttg tct gcg gaa gga ccc act aca atg      480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat      528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc      576
Gln Tyr Cys Ser Gly Thr Thr Leu Thr Gly Cys Asn Glu Lys Ser Phe
            180                 185                 190 aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca      672
Ser Ser Asp Lys Gly Ala Thr Leu Thr Ile Lys Lys Glu Ala Phe Pro
210                 215                 220 gcc gag tca aaa agc gtc att att gga tgc aca ggg gga tcg cct gag      720
Ala Glu Ser Lys Ser Val Ile Ile Gly Cys Thr Gly Gly Ser Pro Glu
225                 230                 235                 240 aag cat cac tgt acc gtg aaa ctg gag                                  747
Lys His His Cys Thr Val Lys Leu Glu
                245
```

<210> SEQ ID NO 23
<211> LENGTH: 249
<212> TYPE: PRT
<213> ORGANISM: Toxoplasma gondii
<220> FEATURE:
<223> OTHER INFORMATION: Toxo30del3C (52-300aa)

<400> SEQUENCE: 23

```
Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
                 20                  25                  30

Lys Thr Ala Leu Thr Glu Pro Pro Thr Leu Ala Tyr Ser Pro Asn Arg
             35                  40                  45

Gln Ile Cys Pro Ala Gly Thr Thr Ser Ser Cys Thr Ser Lys Ala Val
         50                  55                  60

Thr Leu Ser Ser Leu Ile Pro Glu Ala Glu Asp Ser Trp Trp Thr Gly
```

```
                65                  70                  75                  80
Asp Ser Ala Ser Leu Asp Thr Ala Gly Ile Lys Leu Thr Val Pro Ile
                    85                  90                  95

Glu Lys Phe Pro Val Thr Thr Gln Thr Phe Val Val Gly Cys Ile Lys
                100                 105                 110

Gly Asp Asp Ala Gln Ser Cys Met Val Thr Val Thr Val Gln Ala Arg
                115                 120                 125

Ala Ser Ser Val Val Asn Asn Val Ala Arg Cys Ser Tyr Gly Ala Asp
            130                 135                 140

Ser Thr Leu Gly Pro Val Lys Leu Ser Ala Glu Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
                180                 185                 190

Lys Asp Ile Leu Pro Lys Leu Thr Glu Asn Pro Trp Gln Gly Asn Ala
                195                 200                 205

Ser Ser Asp Lys Gly Ala Thr Leu Thr Ile Lys Lys Glu Ala Phe Pro
        210                 215                 220

Ala Glu Ser Lys Ser Val Ile Ile Gly Cys Thr Gly Gly Ser Pro Glu
225                 230                 235                 240

Lys His His Cys Thr Val Lys Leu Glu
                245

<210> SEQ ID NO 24
<211> LENGTH: 38
<212> TYPE: DNA
<213> ORGANISM: Artificial Sequence
<220> FEATURE:
<223> OTHER INFORMATION: Antisense Primer

<400> SEQUENCE: 24
caggtcaagc tttcagtgat gcttctcagg cgatcccc                               38

<210> SEQ ID NO 25
<211> LENGTH: 7352
<212> TYPE: DNA
<213> ORGANISM: Toxoplasma gondii
<220> FEATURE:
<221> NAME/KEY: CDS
<222> LOCATION: (1528)...(3429)
<223> OTHER INFORMATION: pMBP-c2X-ToxoP30del4C (52-294aa)

<400> SEQUENCE: 25
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg    120
gtgtctctta tcagaccgtt tcccgcgtgg tgaaccaggc cagccacgtt tctgcgaaaa    180
cgcgggaaaa agtggaagcg gcgatggcgg agctgaatta cattcccaac cgcgtggcac    240
aacaactggc gggcaaacag tcgttgctga ttggcgttgc cacctccagt ctggccctgc    300
acgcgccgtc gcaaattgtc gcggcgatta atctcgcgc cgatcaactg ggtgccagcg    360
tggtggtgtc gatggtagaa cgaagcggcg tcgaagcctg taaagcggcg gtgcacaatc    420
ttctcgcgca acgcgtcagt gggctgatca ttaactatcc gctggatgac caggatgcca    480
ttgctgtgga agctgcctgc actaatgttc cggcgttatt tcttgatgtc tctgaccaga    540
cacccatcaa cagtattatt ttctcccatg aagacggtac gcgactgggc gtggagcatc    600
```

-continued

```
tggtcgcatt gggtcaccag caaatcgcgc tgttagcggg cccattaagt tctgtctcgg    660
cgcgtctgcg tctggctggc tggcataaat atctcactcg caatcaaatt cagccgatag    720
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggatttc    960
gcctgctggg gcaaaccagc gtggaccgct tgctgcaact ctctcagggc caggcggtga   1020
agggcaatca gctgttgccc gtctcactgg tgaaaagaaa accaccctg gcgcccaata   1080
cgcaaaccgc ctctccccgc gcgttggccg attcattaat gcagctggca cgacaggttt   1140
cccgactgga aagcgggcag tgagcgcaac gcaattaatg taagttagct cactcattag   1200
gcacaattct catgtttgac agcttatcat cgactgcacg gtgcaccaat gcttctggcg   1260
tcaggcagcc atcggaagct gtggtatggc tgtgcaggtc gtaaatcact gcataattcg   1320
tgtcgctcaa ggcgcactcc cgttctggat aatgttttt gcgccgacat cataacggtt   1380
ctggcaaata ttctgaaatg agctgttgac aattaatcat cggctcgtat aatgtgtgga   1440
attgtgagcg gataacaatt tcacacagga acagccagt ccgtttaggt gttttcacga   1500
gcacttcacc aacaaggacc atagcat atg aaa atc gaa gaa ggt aaa ctg gta   1554
                               Met Lys Ile Glu Glu Gly Lys Leu Val
                                 1               5 atc tgg att aac ggc gat aaa ggc tat aac ggt ctc gct gaa gtc ggt     1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg     1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc     1698
Asp Lys Leu Glu Glu Lys Phe Pro Gln Val Ala Ala Thr Gly Asp Gly
 45                  50                  55 cct gac att atc ttc tgg gca cac gac cgc ttt ggt ggc tac gct caa     1746
Pro Asp Ile Ile Phe Trp Ala His Asp Arg Phe Gly Gly Tyr Ala Gln
         60                  65                  70 tct ggc ctg ttg gct gaa atc acc ccg gac aaa gcg ttc cag gac aag     1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att     1842
Leu Tyr Pro Phe Thr Trp Asp Ala Val Arg Tyr Asn Gly Lys Leu Ile
 90                  95                  100                 105 gct tac ccg atc gct gtt gaa gcg tta tcg ctg att tat aac aaa gat     1890
Ala Tyr Pro Ile Ala Val Glu Ala Leu Ser Leu Ile Tyr Asn Lys Asp
            110                 115                 120 ctg ctg ccg aac ccg cca aaa acc tgg gaa gag atc ccg gcg ctg gat     1938
Leu Leu Pro Asn Pro Pro Lys Thr Trp Glu Glu Ile Pro Ala Leu Asp
        125                 130                 135 aaa gaa ctg aaa gcg aaa ggt aag agc gcg ctg atg ttc aac ctg caa     1986
Lys Glu Leu Lys Ala Lys Gly Lys Ser Ala Leu Met Phe Asn Leu Gln
            140                 145                 150 gaa ccg tac ttc acc tgg ccg ctg att gct gct gac ggg ggt tat gcg     2034
Glu Pro Tyr Phe Thr Trp Pro Leu Ile Ala Ala Asp Gly Gly Tyr Ala
        155                 160                 165 ttc aag tat gaa aac ggc aag tac gac att aaa gac gtg ggc gtg gat     2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa     2130
```

-continued

```
                    Asn Ala Gly Ala Lys Ala Gly Leu Thr Phe Leu Val Asp Leu Ile Lys
                                    190                 195                 200 aac aaa cac atg aat gca gac acc gat tac tcc atc gca gaa gct gcc              2178
Asn Lys His Met Asn Ala Asp Thr Asp Tyr Ser Ile Ala Glu Ala Ala
                205                 210                 215 ttt aat aaa ggc gaa aca gcg atg acc atc aac ggc ccg tgg gca tgg              2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg              2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca              2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc              2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac              2418
Glu Asn Tyr Leu Leu Thr Asp Glu Gly Leu Glu Ala Val Asn Lys Asp
        285                 290                 295 aaa ccg ctg ggt gcc gta gcg ctg aag tct tac gag gaa gag ttg gcg              2466
Lys Pro Leu Gly Ala Val Ala Leu Lys Ser Tyr Glu Glu Glu Leu Ala
    300                 305                 310 aaa gat cca cgt att gcc gcc act atg gaa aac gcc cag aaa ggt gaa              2514
Lys Asp Pro Arg Ile Ala Ala Thr Met Glu Asn Ala Gln Lys Gly Glu
315                 320                 325 atc atg ccg aac atc ccg cag atg tcc gct ttc tgg tat gcc gtg cgt              2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc              2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac              2658
Leu Lys Asp Ala Gln Thr Asn Ser Ser Ser Asn Asn Asn Asn Asn Asn
        365                 370                 375 aat aac aac aac ctc ggg atc gag gga agg att tca gaa ttc ctt gtt              2706
Asn Asn Asn Asn Leu Gly Ile Glu Gly Arg Ile Ser Glu Phe Leu Val
    380                 385                 390 gcc aat caa gtt gtc acc tgc cca gat aaa aaa tcg aca gcc gcg gtc              2754
Ala Asn Gln Val Val Thr Cys Pro Asp Lys Lys Ser Thr Ala Ala Val
395                 400                 405 att ctc aca ccg acg gag aac cac ttc act ctc aag tgc cct aaa aca              2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc              2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg              2898
Cys Pro Ala Gly Thr Thr Ser Ser Cys Thr Ser Lys Ala Val Thr Leu
        445                 450                 455 agc tcc ttg att cct gaa gca gaa gat agc tgg tgg acg ggg gat tct              2946
Ser Ser Leu Ile Pro Glu Ala Glu Asp Ser Trp Trp Thr Gly Asp Ser
    460                 465                 470 gct agt ctc gac acg gca ggc atc aaa ctc aca gtt cca atc gag aag              2994
Ala Ser Leu Asp Thr Ala Gly Ile Lys Leu Thr Val Pro Ile Glu Lys
475                 480                 485 ttc ccc gtg aca acg cag acg ttt gtg gtc ggt tgc atc aag gga gac              3042
Phe Pro Val Thr Thr Gln Thr Phe Val Val Gly Cys Ile Lys Gly Asp
490                 495                 500                 505
```

```
gac gca cag agt tgt atg gtc aca gtg aca gta caa gcc aga gcc tca    3090
Asp Ala Gln Ser Cys Met Val Thr Val Thr Val Gln Ala Arg Ala Ser
            510                 515                 520 tcg gtc gtc aat aat gtc gca agg tgc tcc tac ggt gca gac agc act    3138
Ser Val Val Asn Asn Val Ala Arg Cys Ser Tyr Gly Ala Asp Ser Thr
        525                 530                 535 ctt ggt cct gtc aag ttg tct gcg gaa gga ccc act aca atg acc ctc    3186
Leu Gly Pro Val Lys Leu Ser Ala Glu Gly Pro Thr Thr Met Thr Leu
    540                 545                 550 gtg tgc ggg aaa gat gga gtc aaa gtt cct caa gac aac aat cag tac    3234
Val Cys Gly Lys Asp Gly Val Lys Val Pro Gln Asp Asn Asn Gln Tyr
555                 560                 565 tgt tcc ggg acg acg ctg act ggt tgc aac gag aaa tcg ttc aaa gat    3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt    3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag    3378
Asp Lys Gly Ala Thr Leu Thr Ile Lys Lys Glu Ala Phe Pro Ala Glu
            605                 610                 615 tca aaa agc gtc att att gga tgc aca ggg gga tcg cct gag aag cat    3426
Ser Lys Ser Val Ile Ile Gly Cys Thr Gly Gly Ser Pro Glu Lys His
        620                 625                 630 cac tgaaagcttg gcactggccg tcgttttaca acgtcgtgac tgggaaaacc         3479
His ctggcgttac ccaacttaat cgccttgcag cacatccccc tttcgccagc tggcgtaata  3539
gcgaagaggc ccgcaccgat cgcccttccc aacagttgcg cagcctgaat ggcgaatggc  3599
agcttggctg ttttggcgga tgagataaga ttttcagcct gatacagatt aaatcagaac  3659
gcagaagcgg tctgataaaa cagaatttgc ctggcggcag tagcgcggtg gtcccacctg  3719
accccatgcc gaactcagaa gtgaaacgcc gtagcgccga tggtagtgtg gggtctcccc  3779
atgcgagagt agggaactgc caggcatcaa ataaaacgaa aggctcagtc gaaagactgg  3839
gcctttcgtt ttatctgttg tttgtcggtg aacgctctcc tgagtaggac aaatccgccg  3899
ggagcggatt tgaacgttgc gaagcaacgg cccggagggt ggcgggcagg acgcccgcca  3959
taaactgcca ggcatcaaat taagcagaag gccatcctga cggatggcct ttttgcgttt  4019
ctacaaactc ttttttgttta ttttttctaaa tacattcaaa tatgtatccg ctcatgagac  4079
aataaccctg ataaatgctt caataatatt gaaaaaggaa gagtatgagt attcaacatt  4139
tccgtgtcgc ccttattccc ttttttgcgg cattttgcct tcctgttttt gctcacccag  4199
aaacgctggt gaaagtaaaa gatgctgaag atcagttggg tgcacgagtg ggttacatcg  4259
aactggatct caacagcggt aagatccttg agagttttcg ccccgaagaa cgttctccaa  4319
tgatgagcac ttttaaagtt ctgctatgtg gcgcggtatt atcccgtgtt gacgccgggc  4379
aagagcaact cggtcgccgc atacactatt ctcagaatga cttggttgag tactcaccag  4439
tcacagaaaa gcatcttacg gatggcatga cagtaagaga attatgcagt gctgccataa  4499
ccatgagtga taacactgcg gccaacttac ttctgacaac gatcggagga ccgaaggagc  4559
taaccgcttt tttgcacaac atgggggatc atgtaactcg ccttgatcgt tgggaaccgg  4619
agctgaatga agccatacca aacgacgagc gtgacaccac gatgcctgta gcaatggcaa  4679
caacgttgcg caaactatta actggcgaac tacttactct agcttcccgg caacaattaa  4739
tagactggat ggaggcggat aaagttgcag gaccacttct gcgctcggcc cttccggctg  4799
```

```
gctggtttat tgctgataaa tctggagccg gtgagcgtgg gtctcgcggt atcattgcag    4859
cactggggcc agatggtaag ccctcccgta tcgtagttat ctacacgacg gggagtcagg    4919
caactatgga tgaacgaaat agacagatcg ctgagatagg tgcctcactg attaagcatt    4979
ggtaactgtc agaccaagtt tactcatata tactttagat tgatttaccc cggttgataa    5039
tcagaaaagc cccaaaaaca ggaagattgt ataagcaaat atttaaattg taaacgttaa    5099
tattttgtta aaattcgcgt taaatttttg ttaaatcagc tcatttttta accaataggc    5159
cgaaatcggc aaaatccctt ataaatcaaa agaatagacc gagatagggt tgagtgttgt    5219
tccagtttgg aacaagagtc cactattaaa gaacgtggac tccaacgtca aagggcgaaa    5279
aaccgtctat cagggcgatg gcccactacg tgaaccatca cccaaatcaa gttttttggg    5339
gtcgaggtgc cgtaaagcac taaatcggaa ccctaagggg agcccccgat ttagagcttg    5399
acggggaaag ccggcgaacg tggcgagaaa ggaagggaag aaagcgaaag gagcgggcgc    5459
tagggcgctg gcaagtgtag cggtcacgct gcgcgtaacc accacacccg ccgcgcttaa    5519
tgcgccgcta cagggcgcgt aaaaggatct aggtgaagat cctttttgat aatctcatga    5579
ccaaaatccc ttaacgtgag ttttcgttcc actgagcgtc agaccccgta gaaaagatca    5639
aaggatcttc ttgagatcct ttttttctgc gcgtaatctg ctgcttgcaa acaaaaaaac    5699
caccgctacc agcggtggtt tgtttgccgg atcaagagct accaactctt tttccgaagg    5759
taactggctt cagcagagcg cagataccaa atactgtcct tctagtgtag ccgtagttag    5819
gccaccactt caagaactct gtagcaccgc ctacatacct cgctctgcta atcctgttac    5879
cagtggctgc tgccagtggc gataagtcgt gtcttaccgg gttggactca agacgatagt    5939
taccggataa ggcgcagcgg tcgggctgaa cggggggttc gtgcacacag cccagcttgg    5999
agcgaacgac ctacaccgaa ctgagatacc tacagcgtga gctatgagaa agcgccacgc    6059
ttcccgaagg gagaaaggcg gacaggtatc cggtaagcgg cagggtcgga acaggagagc    6119
gcacgaggga gcttccaggg ggaaacgcct ggtatcttta tagtcctgtc gggtttcgcc    6179
acctctgact tgagcgtcga ttttgtgat gctcgtcagg ggggcggagc ctatggaaaa    6239
acgccagcaa cgcggccttt ttacggttcc tggccttttg ctggcctttt gctcacatgt    6299
tctttcctgc gttatcccct gattctgtgg ataaccgtat taccgccttt gagtgagctg    6359
ataccgctcg ccgcagccga acgaccgagc gcagcgagtc agtgagcgag gaagcggaag    6419
agcgcctgat gcggtatttt ctccttacgc atctgtgcgg tatttcacac cgcatatatg    6479
gtgcactctc agtacaatct gctctgatgc cgcatagtta agccagtata cactccgcta    6539
tcgctacgtg actgggtcat ggctgcgccc cgacacccgc caacacccgc tgacgcgccc    6599
tgacgggctt gtctgctccc ggcatccgct tacagacaag ctgtgaccgt ctccgggagc    6659
tgcatgtgtc agaggttttc accgtcatca ccgaaacgcg cgaggcagct gcggtaaagc    6719
tcatcagcgt ggtcgtgcag cgattcacag atgtctgcct gttcatccgc gtccagctcg    6779
ttgagtttct ccagaagcgt taatgtctgg cttctgataa agcgggccat gttaagggcg    6839
gttttttcct gtttggtcac tgatgcctcc gtgtaagggg gatttctgtt catgggggta    6899
atgataccga tgaaacgaga gaggatgctc acgatacggg ttactgatga tgaacatgcc    6959
cggttactgg aacgttgtga gggtaaacaa ctggcggtat ggatgcggcg gaccagaga    7019 aaaatcactc agggtcaatg ccagcgcttc gttaatacag atgtaggtgt tccacagggt    7079
agccagcagc atcctgcgat gcagatccgg aacataatgg tgcagggcgc tgacttccgc    7139
gtttccagac tttacgaaac acggaaaccg aagaccattc atgttgttgc tcaggtcgca    7199
```

```
gacgttttgc agcagcagtc gcttcacgtt cgctcgcgta tcggtgattc attctgctaa    7259
ccagtaaggc aaccccgcca gcctagccgg gtcctcaacg acaggagcac gatcatgcgc    7319
acccgtggcc aggacccaac gctgcccgaa att                                 7352
```

<210> SEQ ID NO 26
<211> LENGTH: 634
<212> TYPE: PRT
<213> ORGANISM: Toxoplasma gondii
<220> FEATURE:
<223> OTHER INFORMATION: pMBP-c2X-ToxoP30del4C (52-294aa)

<400> SEQUENCE: 26

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

-continued

```
Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
                420                 425                 430

Leu Ala Tyr Ser Pro Asn Arg Gln Ile Cys Pro Ala Gly Thr Thr Ser
            435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
    515                 520                 525

Arg Cys Ser Tyr Gly Ala Asp Ser Thr Leu Gly Pro Val Lys Leu Ser
530                 535                 540

Ala Glu Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

Cys Thr Gly Gly Ser Pro Glu Lys His His
625                 630
```

<210> SEQ ID NO 27
<211> LENGTH: 729
<212> TYPE: DNA
<213> ORGANISM: Toxoplasma gondii
<220> FEATURE:
<221> NAME/KEY: CDS
<222> LOCATION: (1)...(729)
<223> OTHER INFORMATION: ToxoP30del4C (52-294aa)

<400> SEQUENCE: 27

```
ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
                20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
```

```
Lys Thr Ala Leu Thr Glu Pro Pro Thr Leu Ala Tyr Ser Pro Asn Arg
            35                  40                  45 caa atc tgc cca gcg ggt act aca agt agc tgt aca tca aag gct gta        192
Gln Ile Cys Pro Ala Gly Thr Thr Ser Ser Cys Thr Ser Lys Ala Val
        50                  55                  60 aca ttg agc tcc ttg att cct gaa gca gaa gat agc tgg tgg acg ggg        240
Thr Leu Ser Ser Leu Ile Pro Glu Ala Glu Asp Ser Trp Trp Thr Gly
65                  70                  75                  80 gat tct gct agt ctc gac acg gca ggc atc aaa ctc aca gtt cca atc        288
Asp Ser Ala Ser Leu Asp Thr Ala Gly Ile Lys Leu Thr Val Pro Ile
                85                  90                  95 gag aag ttc ccc gtg aca acg cag acg ttt gtg gtc ggt tgc atc aag        336
Glu Lys Phe Pro Val Thr Thr Gln Thr Phe Val Val Gly Cys Ile Lys
            100                 105                 110 gga gac gac gca cag agt tgt atg gtc aca gtg aca gta caa gcc aga        384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac        432
Ala Ser Ser Val Val Asn Asn Val Ala Arg Cys Ser Tyr Gly Ala Asp
    130                 135                 140 agc act ctt ggt cct gtc aag ttg tct gcg gaa gga ccc act aca atg        480
Ser Thr Leu Gly Pro Val Lys Leu Ser Ala Glu Gly Pro Thr Thr Met
145                 150                 155                 160 acc ctc gtg tgc ggg aaa gat gga gtc aaa gtt cct caa gac aac aat        528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc        576
Gln Tyr Cys Ser Gly Thr Thr Leu Thr Gly Cys Asn Glu Lys Ser Phe
            180                 185                 190 aaa gat att ttg cca aaa tta act gag aac ccg tgg cag ggt aac gct        624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca        672
Ser Ser Asp Lys Gly Ala Thr Leu Thr Ile Lys Lys Glu Ala Phe Pro
    210                 215                 220 gcc gag tca aaa agc gtc att att gga tgc aca ggg gga tcg cct gag        720
Ala Glu Ser Lys Ser Val Ile Ile Gly Cys Thr Gly Gly Ser Pro Glu
225                 230                 235                 240 aag cat cac                                                            729
Lys His His <210> SEQ ID NO 28
<211> LENGTH: 243
<212> TYPE: PRT
<213> ORGANISM: Toxoplasma gondii
<220> FEATURE:
<223> OTHER INFORMATION: ToxoP30del4C (52-294aa)

<400> SEQUENCE: 28

Leu Val Ala Asn Gln Val Thr Cys Pro Asp Lys Lys Ser Thr Ala
1               5                   10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80
```

```
Asp Ser Ala Ser Leu Asp Thr Ala Gly Ile Lys Leu Thr Val Pro Ile
                85                  90                  95
Glu Lys Phe Pro Val Thr Thr Gln Thr Phe Val Val Gly Cys Ile Lys
            100                 105                 110
Gly Asp Asp Ala Gln Ser Cys Met Val Thr Val Thr Val Gln Ala Arg
        115                 120                 125
Ala Ser Ser Val Val Asn Asn Val Ala Arg Cys Ser Tyr Gly Ala Asp
    130                 135                 140
Ser Thr Leu Gly Pro Val Lys Leu Ser Ala Glu Gly Pro Thr Thr Met
145                 150                 155                 160
Thr Leu Val Cys Gly Lys Asp Gly Val Lys Val Pro Gln Asp Asn Asn
                165                 170                 175
Gln Tyr Cys Ser Gly Thr Thr Leu Thr Gly Cys Asn Glu Lys Ser Phe
            180                 185                 190
Lys Asp Ile Leu Pro Lys Leu Thr Glu Asn Pro Trp Gln Gly Asn Ala
        195                 200                 205
Ser Ser Asp Lys Gly Ala Thr Leu Thr Ile Lys Lys Glu Ala Phe Pro
    210                 215                 220
Ala Glu Ser Lys Ser Val Ile Ile Gly Cys Thr Gly Gly Ser Pro Glu
225                 230                 235                 240
Lys His His

<210> SEQ ID NO 29
<211> LENGTH: 30
<212> TYPE: DNA
<213> ORGANISM: Artificial Sequence
<220> FEATURE:
<223> OTHER INFORMATION: Sense Primer

<400> SEQUENCE: 29
ggcgaattcc ctaaaacagc gctcacagag                                      30

<210> SEQ ID NO 30
<211> LENGTH: 7259
<212> TYPE: DNA
<213> ORGANISM: Toxoplasma gondii
<220> FEATURE:
<221> NAME/KEY: CDS
<222> LOCATION: (1528)...(3336)
<223> OTHER INFORMATION: pMBP-c2X-ToxoP30del4del8 (83-294aa)

<400> SEQUENCE: 30
ccgacaccat cgaatggtgc aaaacctttc gcggtatggc atgatagcgc ccggaagaga     60
gtcaattcag gtggtgaat gtgaaaccag taacgttata cgatgtcgca gagtatgccg    120
gtgtctctta tcagaccgtt tcccgcgtgg tgaaccaggc cagccacgtt tctgcgaaaa   180
cgcgggaaaa agtggaagcg gcgatggcgg agctgaatta cattcccaac cgcgtggcac   240
aacaactggc gggcaaacag tcgttgctga ttggcgttgc cacctccagt ctggccctgc   300
acgcgccgtc gcaaattgtc gcggcgatta aatctcgcgc cgatcaactg ggtgccagcg   360
tggtggtgtc gatggtagaa cgaagcggcg tcgaagcctg taaagcggcg gtgcacaatc   420
ttctcgcgca acgcgtcagt gggctgatca ttaactatcc gctggatgac caggatgcca   480
ttgctgtgga agctgcctgc actaatgttc cggcgttatt tcttgatgtc tctgaccaga   540
cacccatcaa cagtattatt ttctcccatg aagacggtac gcgactgggc gtggagcatc   600
tggtcgcatt gggtcaccag caaatcgcgc tgttagcggg cccattaagt tctgtctcgg   660
cgcgtctgcg tctggctggc tggcataaat atctcactcg caatcaaatt cagccgatag   720
```

-continued

```
cggaacggga aggcgactgg agtgccatgt ccggttttca acaaaccatg caaatgctga    780
atgagggcat cgttcccact gcgatgctgg ttgccaacga tcagatggcg ctgggcgcaa    840
tgcgcgccat taccgagtcc gggctgcgcg ttggtgcgga tatctcggta gtgggatacg    900
acgataccga agacagctca tgttatatcc cgccgttaac caccatcaaa caggattttc    960
gcctgctggg gcaaaccagc gtggaccgct gctgcaact ctctcagggc caggcggtga    1020
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcacttcacc aacaaggacc atagcat atg aaa atc gaa gaa ggt aaa ctg gta    1554
                                Met Lys Ile Glu Glu Gly Lys Leu Val
                                 1               5 atc tgg att aac ggc gat aaa ggc tat aac ggt ctc gct gaa gtc ggt    1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg    1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc    1698
Asp Lys Leu Glu Glu Lys Phe Pro Gln Val Ala Ala Thr Gly Asp Gly
             45                  50                  55 cct gac att atc ttc tgg gca cac gac cgc ttt ggt ggc tac gct caa    1746
Pro Asp Ile Ile Phe Trp Ala His Asp Arg Phe Gly Gly Tyr Ala Gln
         60                  65                  70 tct ggc ctg ttg gct gaa atc acc ccg gac aaa gcg ttc cag gac aag    1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
                 110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
                 125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
         140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
 155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
                 190                 195                 200
```

```
aac aaa cac atg aat gca gac acc gat tac tcc atc gca gaa gct gcc    2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg    2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg    2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt    2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc cct aaa    2706
Asn Asn Asn Asn Leu Gly Ile Glu Gly Arg Ile Ser Glu Phe Pro Lys
        380                 385                 390 aca gcg ctc aca gag cct ccc act ctt gcg tac tca ccc aac agg caa    2754
Thr Ala Leu Thr Glu Pro Pro Thr Leu Ala Tyr Ser Pro Asn Arg Gln
    395                 400                 405 atc tgc cca gcg ggt act aca agt agc tgt aca tca aag gct gta aca    2802
Ile Cys Pro Ala Gly Thr Thr Ser Ser Cys Thr Ser Lys Ala Val Thr
410                 415                 420                 425 ttg agc tcc ttg att cct gaa gca gaa gat agc tgg tgg acg ggg gat    2850
Leu Ser Ser Leu Ile Pro Glu Ala Glu Asp Ser Trp Trp Thr Gly Asp
                430                 435                 440 tct gct agt ctc gac acg gca ggc atc aaa ctc aca gtt cca atc gag    2898
Ser Ala Ser Leu Asp Thr Ala Gly Ile Lys Leu Thr Val Pro Ile Glu
            445                 450                 455 aag ttc ccc gtg aca acg cag acg ttt gtg gtc ggt tgc atc aag gga    2946
Lys Phe Pro Val Thr Thr Gln Thr Phe Val Val Gly Cys Ile Lys Gly
        460                 465                 470 gac gac gca cag agt tgt atg gtc aca gtg aca gta caa gcc aga gcc    2994
Asp Asp Ala Gln Ser Cys Met Val Thr Val Thr Val Gln Ala Arg Ala
    475                 480                 485 tca tcg gtc gtc aat aat gtc gca agg tgc tcc tac ggt gca gac agc    3042
Ser Ser Val Val Asn Asn Val Ala Arg Cys Ser Tyr Gly Ala Asp Ser
490                 495                 500                 505 act ctt ggt cct gtc aag ttg tct gcg gaa gga ccc act aca atg acc    3090
Thr Leu Gly Pro Val Lys Leu Ser Ala Glu Gly Pro Thr Thr Met Thr
                510                 515                 520
```

-continued

```
ctc gtg tgc ggg aaa gat gga gtc aaa gtt cct caa gac aac aat cag    3138
Leu Val Cys Gly Lys Asp Gly Val Lys Val Pro Gln Asp Asn Asn Gln
        525                 530                 535 tac tgt tcc ggg acg acg ctg act ggt tgc aac gag aaa tcg ttc aaa    3186
Tyr Cys Ser Gly Thr Thr Leu Thr Gly Cys Asn Glu Lys Ser Phe Lys
    540                 545                 550 gat att ttg cca aaa tta act gag aac ccg tgg cag ggt aac gct tcg    3234
Asp Ile Leu Pro Lys Leu Thr Glu Asn Pro Trp Gln Gly Asn Ala Ser
555                 560                 565 agt gat aag ggt gcc acg cta acg atc aag aag gaa gca ttt cca gcc    3282
Ser Asp Lys Gly Ala Thr Leu Thr Ile Lys Lys Glu Ala Phe Pro Ala
570                 575                 580                 585 gag tca aaa agc gtc att att gga tgc aca ggg gga tcg cct gag aag    3330
Glu Ser Lys Ser Val Ile Ile Gly Cys Thr Gly Gly Ser Pro Glu Lys
            590                 595                 600 cat cac tgaaagcttg gcactggccg tcgttttaca acgtcgtgac tgggaaaacc     3386
His His ctggcgttac ccaacttaat cgccttgcag cacatccccc tttcgccagc tggcgtaata    3446
gcgaagaggc ccgcaccgat cgcccttccc aacagttgcg cagcctgaat ggcgaatggc    3506
agcttggctg ttttggcgga tgagataaga ttttcagcct gatacagatt aaatcagaac    3566
gcagaagcgt ctgataaaaa cagaatttgc ctggcggcag tagcgcggtg gtcccacctg    3626
accccatgcc gaactcagaa gtgaaacgcc gtagcgccga tggtagtgtg ggtctcccc     3686
atgcgagagt agggaactgc caggcatcaa ataaaacgaa aggctcagtc gaaagactgg    3746
gcctttcgtt ttatctgttg tttgtcggtg aacgctctcc tgagtaggac aaatccgccg    3806
ggagcggatt tgaacgttgc gaagcaacgg cccggagggt ggcgggcagg acgcccgcca    3866
taaactgcca ggcatcaaat taagcagaag gccatcctga cggatggcct ttttgcgttt    3926
ctacaaactc tttttgttta tttttctaaa tacattcaaa tatgtatccg ctcatgagac    3986
ataaccctg ataaatgctt caataatatt gaaaaggaa gagtatgagt attcaacatt      4046
tccgtgtcgc ccttattccc ttttttgcgg cattttgcct tcctgttttt gctcacccag    4106
aaacgctggt gaaagtaaaa gatgctgaag atcagttggg tgcacgagtg ggttacatcg    4166
aactggatct caacagcggt aagatccttg agttttcg ccccgaagaa cgttctccaa      4226
tgatgagcac ttttaaagtt ctgctatgtg gcgcggtatt atcccgtgtt gacgccgggc    4286
aagagcaact cggtcgccgc atacactatt ctcagaatga cttggttgag tactcaccag    4346
tcacagaaaa gcatcttacg gatggcatga cagtaagaga attatgcagt gctgccataa    4406
ccatgagtga taacactgcg gccaacttac ttctgacaac gatcggagga ccgaaggagc    4466
taaccgcttt tttgcacaac atgggggatc atgtaactcg ccttgatcgt tgggaaccgg    4526
agctgaatga agccatacca acgacgagc gtgacaccac gatgcctgta gcaatggcaa     4586
caacgttgcg caaactatta actggcgaac tacttactct agcttcccgg caacaattaa    4646
tagactggat ggaggcggat aaagttgcag gaccacttct gcgctcggcc cttccggctg    4706
gctggtttat tgctgataaa tctggagccg gtgagcgtgg gtctcgcggt atcattgcag    4766
cactggggcc agatggtaag ccctcccgta tcgtagttat ctacacgacg gggagtcagg    4826
caactatgga tgaacgaaat agacagatcg ctgagatagg tgcctcactg attaagcatt    4886
ggtaactgtc agaccaagtt tactcatata tactttagat tgatttaccc cggttgataa    4946
tcagaaaagc cccaaaaaca ggaagattgt ataagcaaat atttaaattg taaacgttaa    5006
tattttgtta aaattcgcgt taaattttg ttaaatcagc tcatttttta accaataggc     5066
```

-continued

```
cgaaatcggc aaaatccctt ataaatcaaa agaatagacc gagatagggt tgagtgttgt    5126
tccagtttgg aacaagagtc cactattaaa gaacgtggac tccaacgtca aagggcgaaa    5186
aaccgtctat cagggcgatg gcccactacg tgaaccatca cccaaatcaa gttttttggg    5246
gtcgaggtgc cgtaaagcac taaatcggaa ccctaaaggg agcccccgat ttagagcttg    5306
acggggaaag ccggcgaacg tggcgagaaa ggaagggaag aaagcgaaag gagcgggcgc    5366
tagggcgctg gcaagtgtag cggtcacgct gcgcgtaacc accacacccg ccgcgcttaa    5426
tgcgccgcta cagggcgcgt aaaggatctc aggtgaagat cctttttgat aatctcatga    5486
ccaaaatccc ttaacgtgag ttttcgttcc actgagcgtc agacccgta gaaaagatca    5546 aaggatcttc ttgagatcct ttttttctgc gcgtaatctg ctgcttgcaa acaaaaaaac    5606
caccgctacc agcggtggtt tgtttgccgg atcaagagct accaactctt tttccgaagg    5666
taactggctt cagcagagcg cagataccaa atactgtcct tctagtgtag ccgtagttag    5726
gccaccactt caagaactct gtagcaccgc ctacatacct cgctctgcta atcctgttac    5786
cagtggctgc tgccagtggc gataagtcgt gtcttaccgg gttggactca agacgatagt    5846
taccggataa ggcgcagcgg tcgggctgaa cggggggttc gtgcacacag cccagcttgg    5906
agcgaacgac ctacaccgaa ctgagatacc tacagcgtga gctatgagaa agcgccacgc    5966
ttcccgaagg gagaaaggcg gacaggtatc cggtaagcgg cagggtcgga acaggagagc    6026
gcacgaggga gcttccaggg ggaaacgcct ggtatcttta tagtcctgtc gggtttcgcc    6086
acctctgact tgagcgtcga ttttttgtgat gctcgtcagg ggggcggagc ctatggaaaa    6146
acgccagcaa cgcggccttt ttacggttcc tggccttttg ctggccttttt gctcacatgt    6206 tctttcctgc gttatcccct gattctgtgg ataaccgtat taccgccttt gagtgagctg    6266
ataccgctcg ccgcagccga acgaccgagc gcagcgagtc agtgagcgag gaagcggaag    6326
agcgcctgat gcggtatttt ctccttacgc atctgtgcgg tatttcacac cgcatatatg    6386
gtgcactctc agtacaatct gctctgatgc cgcatagtta agccagtata cactccgcta    6446
tcgctacgtg actgggtcat ggctgcgccc cgacacccgc caacacccgc tgacgcgccc    6506
tgacgggctt gtctgctccc ggcatccgct tacagacaag ctgtgaccgt ctccgggagc    6566
tgcatgtgtc agaggttttc accgtcatca ccgaaacgcg cgaggcagct gcggtaaagc    6626
tcatcagcgt ggtcgtgcag cgattcacag atgtctgcct gttcatccgc gtccagctcg    6686
ttgagtttct ccagaagcgt taatgtctgg cttctgataa agcgggccat gttaagggcg    6746
gttttttcct gtttggtcac tgatgcctcc gtgtaagggg gatttctgtt catggggta    6806 atgataccga tgaaacgaga gaggatgctc acgatacggg ttactgatga tgaacatgcc    6866
cggttactgg aacgttgtga gggtaaacaa ctggcggtat ggatgcggcg ggaccagaga    6926
aaaatcactc agggtcaatg ccagcgcttc gttaatacag atgtaggtgt tccacagggt    6986
agccagcagc atcctgcgat gcagatccgg aacataatgg tgcagggcgc tgacttccgc    7046
gtttccagac tttacgaaac acggaaaccg aagaccattc atgttgttgc tcaggtcgca    7106
gacgttttgc agcagcagtc gcttcacgtt cgctcgcgta tcggtgattc attctgctaa    7166
ccagtaaggc aaccccgcca gcctagccgg gtcctcaacg acaggagcac gatcatgcgc    7226
acccgtggcc aggacccaac gctgcccgaa att                                  7259
```

<210> SEQ ID NO 31
<211> LENGTH: 603
<212> TYPE: PRT

-continued

<213> ORGANISM: Toxoplasma gondii
<220> FEATURE:
<223> OTHER INFORMATION: pMBP-c2X-ToxoP30del4del8 (83-294aa)

<400> SEQUENCE: 31

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Pro Lys Thr Ala Leu Thr Glu Pro Pro
```

-continued

```
            385                 390                 395                 400
Thr Leu Ala Tyr Ser Pro Asn Arg Gln Ile Cys Pro Ala Gly Thr Thr
                    405                 410                 415

Ser Ser Cys Thr Ser Lys Ala Val Thr Leu Ser Ser Leu Ile Pro Glu
            420                 425                 430

Ala Glu Asp Ser Trp Trp Thr Gly Asp Ser Ala Ser Leu Asp Thr Ala
            435                 440                 445

Gly Ile Lys Leu Thr Val Pro Ile Glu Lys Phe Pro Val Thr Thr Gln
        450                 455                 460

Thr Phe Val Val Gly Cys Ile Lys Gly Asp Asp Ala Gln Ser Cys Met
465                 470                 475                 480

Val Thr Val Thr Val Gln Ala Arg Ala Ser Ser Val Val Asn Asn Val
                485                 490                 495

Ala Arg Cys Ser Tyr Gly Ala Asp Ser Thr Leu Gly Pro Val Lys Leu
            500                 505                 510

Ser Ala Glu Gly Pro Thr Thr Met Thr Leu Val Cys Gly Lys Asp Gly
            515                 520                 525

Val Lys Val Pro Gln Asp Asn Asn Gln Tyr Cys Ser Gly Thr Thr Leu
        530                 535                 540

Thr Gly Cys Asn Glu Lys Ser Phe Lys Asp Ile Leu Pro Lys Leu Thr
545                 550                 555                 560

Glu Asn Pro Trp Gln Gly Asn Ala Ser Ser Asp Lys Gly Ala Thr Leu
                565                 570                 575

Thr Ile Lys Lys Glu Ala Phe Pro Ala Glu Ser Lys Ser Val Ile Ile
            580                 585                 590

Gly Cys Thr Gly Gly Ser Pro Glu Lys His His
            595                 600

<210> SEQ ID NO 32
<211> LENGTH: 636
<212> TYPE: DNA
<213> ORGANISM: Toxoplasma gondii
<220> FEATURE:
<221> NAME/KEY: CDS
<222> LOCATION: (1)...(636)
<223> OTHER INFORMATION: ToxoP30del4del8 (83-294aa)

<400> SEQUENCE: 32 cct aaa aca gcg ctc aca gag cct ccc act ctt gcg tac tca ccc aac      48
Pro Lys Thr Ala Leu Thr Glu Pro Pro Thr Leu Ala Tyr Ser Pro Asn
1               5                   10                  15 agg caa atc tgc cca gcg ggt act aca agt agc tgt aca tca aag gct      96
Arg Gln Ile Cys Pro Ala Gly Thr Thr Ser Ser Cys Thr Ser Lys Ala
            20                  25                  30 gta aca ttg agc tcc ttg att cct gaa gca gaa gat agc tgg tgg acg     144
Val Thr Leu Ser Ser Leu Ile Pro Glu Ala Glu Asp Ser Trp Trp Thr
        35                  40                  45 ggg gat tct gct agt ctc gac acg gca ggc atc aaa ctc aca gtt cca     192
Gly Asp Ser Ala Ser Leu Asp Thr Ala Gly Ile Lys Leu Thr Val Pro
    50                  55                  60 atc gag aag ttc ccc gtg aca acg cag acg ttt gtg gtc ggt tgc atc     240
Ile Glu Lys Phe Pro Val Thr Thr Gln Thr Phe Val Val Gly Cys Ile
65                  70                  75                  80 aag gga gac gac gca cag agt tgt atg gtc aca gtg aca gta caa gcc     288
Lys Gly Asp Asp Ala Gln Ser Cys Met Val Thr Val Thr Val Gln Ala
                85                  90                  95 aga gcc tca tcg gtc gtc aat aat gtc gca agg tgc tcc tac ggt gca     336
Arg Ala Ser Ser Val Val Asn Asn Val Ala Arg Cys Ser Tyr Gly Ala
```

-continued

```
                    100                 105                 110
gac agc act ctt ggt cct gtc aag ttg tct gcg aa gga ccc act aca      384
Asp Ser Thr Leu Gly Pro Val Lys Leu Ser Ala Glu Gly Pro Thr Thr
            115                 120                 125 atg acc ctc gtg tgc ggg aaa gat gga gtc aaa gtt cct caa gac aac      432
Met Thr Leu Val Cys Gly Lys Asp Gly Val Lys Val Pro Gln Asp Asn
        130                 135                 140 aat cag tac tgt tcc ggg acg acg ctg act ggt tgc aac gag aaa tcg      480
Asn Gln Tyr Cys Ser Gly Thr Thr Leu Thr Gly Cys Asn Glu Lys Ser
145                 150                 155                 160 ttc aaa gat att ttg cca aaa tta act gag aac ccg tgg cag ggt aac      528
Phe Lys Asp Ile Leu Pro Lys Leu Thr Glu Asn Pro Trp Gln Gly Asn
                165                 170                 175 gct tcg agt gat aag ggt gcc acg cta acg atc aag aag gaa gca ttt      576
Ala Ser Ser Asp Lys Gly Ala Thr Leu Thr Ile Lys Lys Glu Ala Phe
            180                 185                 190 cca gcc gag tca aaa agc gtc att att gga tgc aca ggg gga tcg cct      624
Pro Ala Glu Ser Lys Ser Val Ile Ile Gly Cys Thr Gly Gly Ser Pro
        195                 200                 205 gag aag cat cac                                                       636
Glu Lys His His
    210
```

<210> SEQ ID NO 33
<211> LENGTH: 212
<212> TYPE: PRT
<213> ORGANISM: Toxoplasma gondii
<220> FEATURE:
<223> OTHER INFORMATION: ToxoP30del4del8 (83-294aa)

<400> SEQUENCE: 33

```
Pro Lys Thr Ala Leu Thr Glu Pro Pro Thr Leu Ala Tyr Ser Pro Asn
1               5                   10                  15

Arg Gln Ile Cys Pro Ala Gly Thr Thr Ser Ser Cys Thr Ser Lys Ala
            20                  25                  30

Val Thr Leu Ser Ser Leu Ile Pro Glu Ala Glu Asp Ser Trp Trp Thr
        35                  40                  45

Gly Asp Ser Ala Ser Leu Asp Thr Ala Gly Ile Lys Leu Thr Val Pro
    50                  55                  60

Ile Glu Lys Phe Pro Val Thr Thr Gln Thr Phe Val Val Gly Cys Ile
65                  70                  75                  80

Lys Gly Asp Asp Ala Gln Ser Cys Met Val Thr Val Thr Val Gln Ala
                85                  90                  95

Arg Ala Ser Ser Val Val Asn Asn Val Ala Arg Cys Ser Tyr Gly Ala
            100                 105                 110

Asp Ser Thr Leu Gly Pro Val Lys Leu Ser Ala Glu Gly Pro Thr Thr
        115                 120                 125

Met Thr Leu Val Cys Gly Lys Asp Gly Val Lys Val Pro Gln Asp Asn
    130                 135                 140

Asn Gln Tyr Cys Ser Gly Thr Thr Leu Thr Gly Cys Asn Glu Lys Ser
145                 150                 155                 160

Phe Lys Asp Ile Leu Pro Lys Leu Thr Glu Asn Pro Trp Gln Gly Asn
                165                 170                 175

Ala Ser Ser Asp Lys Gly Ala Thr Leu Thr Ile Lys Lys Glu Ala Phe
            180                 185                 190

Pro Ala Glu Ser Lys Ser Val Ile Ile Gly Cys Thr Gly Gly Ser Pro
        195                 200                 205
```

-continued

Glu Lys His His
    210

<210> SEQ ID NO 34
<211> LENGTH: 39
<212> TYPE: DNA
<213> ORGANISM: Artificial Sequence
<220> FEATURE:
<223> OTHER INFORMATION: Antisense Primer

<400> SEQUENCE: 34
caggtcaagc tttcatccaa taatgacgct ttttgactc                    39

<210> SEQ ID NO 35
<211> LENGTH: 7322
<212> TYPE: DNA
<213> ORGANISM: Toxoplasma gondii
<220> FEATURE:
<221> NAME/KEY: CDS
<222> LOCATION: (1528)...(3399)
<223> OTHER INFORMATION: pMBP-c2X-ToxoP30del10 (52-284aa)

<400> SEQUENCE: 35
ccgacaccat cgaatggtgc aaaacctttc gcggtatggc atgatagcgc ccggaagaga    60
gtcaattcag ggtggtgaat gtgaaaccag taacgttata cgatgtcgca gagtatgccg   120
gtgtctctta tcagaccgtt tcccgcgtgg tgaaccaggc cagccacgtt tctgcgaaaa   180
cgcgggaaaa agtggaagcg gcgatggcgg agctgaatta cattcccaac cgcgtggcac   240
aacaactggc gggcaaacag tcgttgctga ttggcgttgc cacctccagt ctggccctgc   300
acgcgccgtc gcaaattgtc gcggcgatta atctcgcgc cgatcaactg ggtgccagcg   360
tggtggtgtc gatggtagaa cgaagcggcg tcgaagcctg taaagcggcg gtgcacaatc   420
ttctcgcgca acgcgtcagt gggctgatca ttaactatcc gctggatgac caggatgcca   480
ttgctgtgga agctgcctgc actaatgttc cggcgttatt tcttgatgtc tctgaccaga   540
cacccatcaa cagtattatt ttctcccatg aagacggtac gcgactgggc gtggagcatc   600
tggtcgcatt gggtcaccag caaatcgcgc tgttagcggg cccattaagt tctgtctcgg   660
cgcgtctgcg tctggctggc tggcataaat atctcactcg caatcaaatt cagccgatag   720
cggaacggga aggcgactgg agtgccatgt ccggttttca acaaaccatg caaatgctga   780
atgagggcat cgttcccact gcgatgctgg ttgccaacga tcagatggcg ctgggcgcaa   840
tgcgcgccat taccgagtcc gggctgcgcg ttggtgcgga tatctcggta gtgggatacg   900
acgataccga agacagctca tgttatatcc gccgttaac caccatcaaa caggattttc   960
gcctgctggg gcaaaccagc gtggaccgct tgctgcaact ctctcagggc caggcggtga  1020
agggcaatca gctgttgccc gtctcactgg tgaaaagaaa aaccaccctg gcgcccaata  1080
cgcaaaccgc ctctccccgc gcgttggccg attcattaat gcagctggca cgacaggttt  1140
cccgactgga aagcgggcag tgagcgcaac gcaattaatg taagttagct cactcattag  1200
gcacaattct catgtttgac agcttatcat cgactcacg gtgcaccaat gcttctggcg  1260
tcaggcagcc atcggaagct gtggtatggc tgtgcaggtc gtaaatcact gcataattcg  1320
tgtcgctcaa ggcgcactcc cgttctggat aatgttttt gcgccgacat cataacggtt  1380
ctggcaaata ttctgaaatg agctgttgac aattaatcat cggctcgtat aatgtgtgga  1440
attgtgagcg gataacaatt tcacacagga acagccagt ccgtttaggt gttttcacga  1500
gcacttcacc aacaaggacc atagcat atg aaa atc gaa gaa ggt aaa ctg gta   1554
                              Met Lys Ile Glu Glu Gly Lys Leu Val

```
                            1               5
atc tgg att aac ggc gat aaa ggc tat aac ggt ctc gct gaa gtc ggt    1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg    1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc    1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa    1746
Pro Asp Ile Ile Phe Trp Ala His Asp Arg Phe Gly Gly Tyr Ala Gln
                 60                  65                  70 tct ggc ctg ttg gct gaa atc acc ccg gac aaa gcg ttc cag gac aag    1794
Ser Gly Leu Leu Ala Glu Ile Thr Pro Asp Lys Ala Phe Gln Asp Lys
     75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc    2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg    2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg    2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa    2514
```

```
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395                 400                 405 att ctc aca ccg acg gag aac cac ttc act ctc aag tgc cct aaa aca      2802
Ile Leu Thr Pro Thr Glu Asn His Phe Thr Leu Lys Cys Pro Lys Thr
410                 415                 420                 425 gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505 gac gca cag agt tgt atg gtc aca gtg aca gta caa gcc aga gcc tca      3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535 ctt ggt cct gtc aag ttg tct gcg gga gga ccc act aca atg acc ctc      3186
Leu Gly Pro Val Lys Leu Ser Ala Gly Gly Pro Thr Thr Met Thr Leu
        540                 545                 550 gtg tgc ggg aaa gat gga gtc aaa gtt cct caa gac aac aat cag tac      3234
Val Cys Gly Lys Asp Gly Val Lys Val Pro Gln Asp Asn Asn Gln Tyr
    555                 560                 565 tgt tcc ggg acg acg ctg act ggt tgc aac gag aaa tcg ttc aaa gat      3282
Cys Ser Gly Thr Thr Leu Thr Gly Cys Asn Glu Lys Ser Phe Lys Asp
570                 575                 580                 585 att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615 tca aaa agc gtc att att gga tgaaagcttg gcactggccg tcgttttaca        3429
Ser Lys Ser Val Ile Ile Gly
        620
```

```
acgtcgtgac tgggaaaacc ctggcgttac ccaacttaat cgccttgcag cacatccccc    3489
tttcgccagc tggcgtaata gcgaagaggc ccgcaccgat cgcccttccc aacagttgcg    3549
cagcctgaat ggcgaatggc agcttggctg ttttggcgga tgagataaga ttttcagcct    3609
gatacagatt aaatcagaac gcagaagcgg tctgataaaa cagaatttgc ctggcggcag    3669
tagcgcggtg gtcccacctg acccatgcc gaactcagaa gtgaaacgcc gtagcgccga    3729
tggtagtgtg gggtctcccc atgcgagagt agggaactgc caggcatcaa ataaaacgaa    3789
aggctcagtc gaaagactgg gcctttcgtt ttatctgttg tttgtcggtg aacgctctcc    3849
tgagtaggac aaatccgccg ggagcggatt tgaacgttgc gaagcaacgg cccggagggt    3909
ggcgggcagg acgcccgcca taaactgcca ggcatcaaat taagcagaag gccatcctga    3969
cggatggcct ttttgcgttt ctacaaactc tttttgttta tttttctaaa tacattcaaa    4029
tatgtatccg ctcatgagac aataaccctg ataaatgctt caataatatt gaaaaggaa    4089 gagtatgagt attcaacatt tccgtgtcgc ccttattccc ttttttgcgg cattttgcct    4149
tcctgttttt gctcacccag aaacgctggt gaaagtaaaa gatgctgaag atcagttggg    4209
tgcacgagtg ggttacatcg aactggatct caacagcggt aagatccttg agagttttcg    4269
ccccgaagaa cgttctccaa tgatgagcac ttttaaagtt ctgctatgtg gcgcggtatt    4329
atcccgtgtt gacgccgggc aagagcaact cggtcgccgc atacactatt ctcagaatga    4389
cttggttgag tactcaccag tcacagaaaa gcatcttacg gatggcatga cagtaagaga    4449
attatgcagt gctgccataa ccatgagtga taacactgcg ccaacttac ttctgacaac    4509 gatcggagga ccgaaggagc taaccgcttt tttgcacaac atgggggatc atgtaactcg    4569
ccttgatcgt tgggaaccgg agctgaatga agccatacca aacgacgagc gtgacaccac    4629
gatgcctgta gcaatggcaa caacgttgcg caaactatta actggcgaac tacttactct    4689
agcttcccgg caacaattaa tagactggat ggaggcggat aaagttgcag gaccacttct    4749
gcgctcggcc cttccggctg gctggtttat tgctgataaa tctggagccg gtgagcgtgg    4809
gtctcgcggt atcattgcag cactgggggcc agatggtaag ccctcccgta tcgtagttat    4869
ctacacgacg gggagtcagg caactatgga tgaacgaaat agacagatcg ctgagatagg    4929
tgcctcactg attaagcatt ggtaactgtc agaccaagtt tactcatata ctttagat     4989 tgatttaccc cggttgataa tcagaaaagc cccaaaaaca ggaagattgt ataagcaaat    5049
atttaaattg taaacgttaa tattttgtta aaattcgcgt taaatttttg ttaaatcagc    5109 tcattttttta accataggc cgaaatcggc aaaatccctt ataaatcaaa agaatagacc    5169
gagatagggt tgagtgttgt tccagtttgg aacaagagtc cactattaaa gaacgtggac    5229
tccaacgtca aagggcgaaa aaccgtctat cagggcgatg gcccactacg tgaaccatca    5289
cccaaatcaa gttttttggg gtcgaggtgc cgtaaagcac taaatcggaa ccctaaaggg    5349
agcccccgat ttagagcttg acggggaaag ccggcgaacg tggcgagaaa ggaagggaag    5409
aaagcgaaag gagcgggcgc tagggcgctg gcaagtgtag cggtcacgct gcgcgtaacc    5469
accacacccg ccgcgcttaa tgcgccgcta cagggcgcgt aaaaggatct aggtgaagat    5529 ccttttttgat aatctcatga ccaaaatccc ttaacgtgag ttttcgttcc actgagcgtc    5589 agacccgta gaaagatca aggatcttc ttgagatcct tttttctgc gcgtaatctg    5649 ctgcttgcaa acaaaaaaac caccgctacc agcggtggtt tgtttgccgg atcaagagct    5709
accaactctc tttccgaagg taactggctt cagcagagcg cagataccaa atactgtcct    5769
tctagtgtag ccgtagttag gccaccactt caagaactct gtagcaccgc ctacatacct    5829
```

-continued

```
cgctctgcta atcctgttac cagtggctgc tgccagtggc gataagtcgt gtcttaccgg   5889
gttggactca agacgatagt taccggataa ggcgcagcgg tcgggctgaa cggggggttc   5949
gtgcacacag cccagcttgg agcgaacgac ctacaccgaa ctgagatacc tacagcgtga   6009
gctatgagaa agcgccacgc ttcccgaagg gagaaaggcg gacaggtatc cggtaagcgg   6069
cagggtcgga acaggagagc gcacgaggga gcttccaggg ggaaacgcct ggtatcttta   6129
tagtcctgtc gggtttcgcc acctctgact tgagcgtcga tttttgtgat gctcgtcagg   6189
ggggcggagc ctatggaaaa acgccagcaa cgcggccttt ttacggttcc tggccttttg   6249
ctggcctttt gctcacatgt tctttcctgc gttatcccct gattctgtgg ataaccgtat   6309
taccgccttt gagtgagctg ataccgctcg ccgcagccga acgaccgagc gcagcgagtc   6369
agtgagcgag gaagcggaag agcgcctgat gcggtatttt ctccttacgc atctgtgcgg   6429
tatttcacac cgcatatatg gtgcactctc agtacaatct gctctgatgc cgcatagtta   6489
agccagtata cactccgcta tcgctacgtg actgggtcat ggctgcgccc cgacacccgc   6549
caacacccgc tgacgcgccc tgacgggctt gtctgctccc ggcatccgct tacagacaag   6609
ctgtgaccgt ctccgggagc tgcatgtgtc agaggttttc accgtcatca ccgaaacgcg   6669
cgaggcagct gcggtaaagc tcatcagcgt ggtcgtgcag cgattcacag atgtctgcct   6729
gttcatccgc gtccagctcg ttgagtttct ccagaagcgt taatgtctgg cttctgataa   6789
agcgggccat gttaagggcg gttttttcct gtttggtcac tgatgcctcc gtgtaagggg   6849
gatttctgtt catgggggta atgataccga tgaaacgaga gaggatgctc acgatacggg   6909
ttactgatga tgaacatgcc cggttactgg aacgttgtga gggtaaacaa ctggcggtat   6969
ggatgcggcg ggaccagaga aaaatcactc agggtcaatg ccagcgcttc gttaatacag   7029
atgtaggtgt tccacagggt agccagcagc atcctgcgat gcagatccgg aacataatgg   7089
tgcagggcgc tgacttccgc gtttccagac tttacgaaac acggaaaccg aagaccattc   7149
atgttgttgc tcaggtcgca gacgttttgc agcagcagtc gcttcacgtt cgctcgcgta   7209
tcggtgattc attctgctaa ccagtaaggc aaccccgcca gcctagccgg gtcctcaacg   7269
acaggagcac gatcatgcgc acccgtggcc aggacccaac gctgcccgaa att          7322
```

```

<210> SEQ ID NO 36
<211> LENGTH: 624
<212> TYPE: PRT
<213> ORGANISM: Toxoplasma gondii
<220> FEATURE:
<223> OTHER INFORMATION: pMBP-c2X-ToxoP30del10 (52-284aa)

<400> SEQUENCE: 36

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95
```

-continued

```
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
```

```
                    515                 520                 525
Arg Cys Ser Tyr Gly Ala Asp Ser Thr Leu Gly Pro Val Lys Leu Ser
        530                 535                 540

Ala Gly Gly Pro Thr Thr Met Thr Leu Val Cys Gly Lys Asp Gly Val
545                 550                 555                 560

Lys Val Pro Gln Asp Asn Asn Gln Tyr Cys Ser Gly Thr Thr Leu Thr
                565                 570                 575

Gly Cys Asn Glu Lys Ser Phe Lys Asp Ile Leu Pro Lys Leu Thr Glu
                580                 585                 590

Asn Pro Trp Gln Gly Asn Ala Ser Ser Asp Lys Gly Ala Thr Leu Thr
        595                 600                 605

Ile Lys Lys Glu Ala Phe Pro Ala Glu Ser Lys Ser Val Ile Ile Gly
    610                 615                 620

<210> SEQ ID NO 37
<211> LENGTH: 699
<212> TYPE: DNA
<213> ORGANISM: Toxoplasma gondii
<220> FEATURE:
<221> NAME/KEY: CDS
<222> LOCATION: (1)...(699)
<223> OTHER INFORMATION: ToxoP30del10 (52-284aa)

<400> SEQUENCE: 37 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
1               5                   10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
            20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
        35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
    50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
65                  70                  75                  80 gat tct gct agt ctc gac acg gca ggc atc aaa ctc aca gtt cca atc     288
Asp Ser Ala Ser Leu Asp Thr Ala Gly Ile Lys Leu Thr Val Pro Ile
                85                  90                  95 gag aag ttc ccc gtg aca acg cag acg ttt gtg gtc ggt tgc atc aag     336
Glu Lys Phe Pro Val Thr Thr Gln Thr Phe Val Val Gly Cys Ile Lys
            100                 105                 110 gga gac gac gca cag agt tgt atg gtc aca gtg aca gta caa gcc aga     384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac     432
Ala Ser Ser Val Val Asn Asn Val Ala Arg Cys Ser Tyr Gly Ala Asp
    130                 135                 140 agc act ctt ggt cct gtc aag ttg tct gcg gga gga ccc act aca atg     480
Ser Thr Leu Gly Pro Val Lys Leu Ser Ala Gly Gly Pro Thr Thr Met
145                 150                 155                 160 acc ctc gtg tgc ggg aaa gat gga gtc aaa gtt cct caa gac aac aat     528
Thr Leu Val Cys Gly Lys Asp Gly Val Lys Val Pro Gln Asp Asn Asn
                165                 170                 175 cag tac tgt tcc ggg acg acg ctg act ggt tgc aac gag aaa tcg ttc     576
Gln Tyr Cys Ser Gly Thr Thr Leu Thr Gly Cys Asn Glu Lys Ser Phe
            180                 185                 190
```

```
aaa gat att ttg cca aaa tta act gag aac ccg tgg cag ggt aac gct      624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca      672
Ser Ser Asp Lys Gly Ala Thr Leu Thr Ile Lys Lys Glu Ala Phe Pro
    210                 215                 220 gcc gag tca aaa agc gtc att att gga                                  699
Ala Glu Ser Lys Ser Val Ile Ile Gly
225                 230

<210> SEQ ID NO 38
<211> LENGTH: 233
<212> TYPE: PRT
<213> ORGANISM: Toxoplasma gondii
<220> FEATURE:
<223> OTHER INFORMATION: ToxoP30del10 (52-284aa)

<400> SEQUENCE: 38

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Gly Gly Pro Thr Thr Met
145                 150                 155                 160

Thr Leu Val Cys Gly Lys Asp Gly Val Lys Val Pro Gln Asp Asn Asn
                165                 170                 175

Gln Tyr Cys Ser Gly Thr Thr Leu Thr Gly Cys Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly
225                 230

<210> SEQ ID NO 39
<211> LENGTH: 36
<212> TYPE: DNA
<213> ORGANISM: Artificial Sequence
<220> FEATURE:
<223> OTHER INFORMATION: Antisense Primer

<400> SEQUENCE: 39
caggtcaagc tttcacacga gggtcattgt agtggg                               36
```

-continued

<210> SEQ ID NO 40
<211> LENGTH: 7112
<212> TYPE: DNA
<213> ORGANISM: Toxoplasma gondii
<220> FEATURE:
<221> NAME/KEY: CDS
<222> LOCATION: (1528)...(3189)
<223> OTHER INFORMATION: pMBP-c2X-ToxoP30del11 (52-214aa)

<400> SEQUENCE: 40

```
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc cgatcaactg ggtgccagcg      360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc gccgttaac caccatcaaa caggattttc      960
gcctgctggg gcaaaccagc gtggaccgct tgctgcaact ctctcagggc caggcggtga    1020
agggcaatca gctgttgccc gtctcactgg tgaaaagaaa accacccctg cgcccaata     1080 cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga     1500
gcacttcacc aacaaggacc atagcat atg aaa atc gaa gaa ggt aaa ctg gta    1554
                               Met Lys Ile Glu Glu Gly Lys Leu Val
                                 1               5 atc tgg att aac ggc gat aaa ggc tat aac ggt ctc gct gaa gtc ggt       1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg       1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc       1698
Asp Lys Leu Glu Glu Lys Phe Pro Gln Val Ala Ala Thr Gly Asp Gly
         45                  50                  55
```

-continued

```
cct gac att atc ttc tgg gca cac gac cgc ttt ggt ggc tac gct caa    1746
Pro Asp Ile Ile Phe Trp Ala His Asp Arg Phe Gly Gly Tyr Ala Gln
        60                  65                  70 tct ggc ctg ttg gct gaa atc acc ccg gac aaa gcg ttc cag gac aag    1794
Ser Gly Leu Leu Ala Glu Ile Thr Pro Asp Lys Ala Phe Gln Asp Lys
75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
90                  95                  100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc    2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg    2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg    2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt    2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
            365                 370                 375
```

-continued

| | | |
|---|---|---|
| aat aac aac aac ctc ggg atc gag gga agg att tca gaa ttc ctt gtt<br>Asn Asn Asn Asn Leu Gly Ile Glu Gly Arg Ile Ser Glu Phe Leu Val<br>380               385                    390 | | 2706 |
| gcc aat caa gtt gtc acc tgc cca gat aaa aaa tcg aca gcc gcg gtc<br>Ala Asn Gln Val Val Thr Cys Pro Asp Lys Lys Ser Thr Ala Ala Val<br>395                  400                  405 | | 2754 |
| att ctc aca ccg acg gag aac cac ttc act ctc aag tgc cct aaa aca<br>Ile Leu Thr Pro Thr Glu Asn His Phe Thr Leu Lys Cys Pro Lys Thr<br>410                  415                420              425 | | 2802 |
| gcg ctc aca gag cct ccc act ctt gcg tac tca ccc aac agg caa atc<br>Ala Leu Thr Glu Pro Pro Thr Leu Ala Tyr Ser Pro Asn Arg Gln Ile<br>430                435                   440 | | 2850 |
| tgc cca gcg ggt act aca agt agc tgt aca tca aag gct gta aca ttg<br>Cys Pro Ala Gly Thr Thr Ser Ser Cys Thr Ser Lys Ala Val Thr Leu<br>445                  450                455 | | 2898 |
| agc tcc ttg att cct gaa gca gaa gat agc tgg tgg acg ggg gat tct<br>Ser Ser Leu Ile Pro Glu Ala Glu Asp Ser Trp Trp Thr Gly Asp Ser<br>460                465                470 | | 2946 |
| gct agt ctc gac acg gca ggc atc aaa ctc aca gtt cca atc gag aag<br>Ala Ser Leu Asp Thr Ala Gly Ile Lys Leu Thr Val Pro Ile Glu Lys<br>475                  480                485 | | 2994 |
| ttc ccc gtg aca acg cag acg ttt gtg gtc ggt tgc atc aag gga gac<br>Phe Pro Val Thr Thr Gln Thr Phe Val Val Gly Cys Ile Lys Gly Asp<br>490                  495                500              505 | | 3042 |
| gac gca cag agt tgt atg gtc aca gtg aca gta caa gcc aga gcc tca<br>Asp Ala Gln Ser Cys Met Val Thr Val Thr Val Gln Ala Arg Ala Ser<br>510                  515                520 | | 3090 |
| tcg gtc gtc aat aat gtc gca agg tgc tcc tac ggt gca gac agc act<br>Ser Val Val Asn Asn Val Ala Arg Cys Ser Tyr Gly Ala Asp Ser Thr<br>525                530                535 | | 3138 |
| ctt ggt cct gtc aag ttg tct gcg gaa gga ccc act aca atg acc ctc<br>Leu Gly Pro Val Lys Leu Ser Ala Glu Gly Pro Thr Thr Met Thr Leu<br>540                  545                550 | | 3186 |
| gtg tgaaagcttg gcactggccg tcgttttaca acgtcgtgac tgggaaaacc<br>Val | | 3239 |
| ctggcgttac ccaacttaat cgccttgcag cacatccccc tttcgccagc tggcgtaata | | 3299 |
| gcgaagaggc ccgcaccgat cgcccttccc aacagttgcg cagcctgaat ggcgaatggc | | 3359 |
| agcttggctg ttttggcgga tgagataaga ttttcagcct gatacagatt aaatcagaac | | 3419 |
| gcagaagcgg tctgataaaa cagaatttgc ctggcggcag tagcgcggtg gtcccacctg | | 3479 |
| accccatgcc gaactcagaa gtgaaacgcc gtagcgccga tggtagtgtg gggtctcccc | | 3539 |
| atgcgagagt agggaactgc caggcatcaa ataaaacgaa aggctcagtc gaaagactgg | | 3599 |
| gcctttcgtt ttatctgttg tttgtcggtg aacgctctcc tgagtaggac aaatccgccg | | 3659 |
| ggagcggatt tgaacgttgc gaagcaacgg cccggagggt ggcgggcagg acgcccgcca | | 3719 |
| taaactgcca ggcatcaaat taagcagaag gccatcctga cggatggcct ttttgcgttt | | 3779 |
| ctacaaactc ttttttgttta ttttctaaa tacattcaaa tatgtatccg ctcatgagac | | 3839 |
| aataaccctg ataaatgctt caataatatt gaaaaggaa gagtatgagt attcaacatt | | 3899 |
| tccgtgtcgc ccttattccc ttttttgcgg cattttgcct tcctgttttt gctcacccag | | 3959 |
| aaacgctggt gaaagtaaaa gatgctgaag atcagttggg tgcacgagtg ggttacatcg | | 4019 |
| aactggatct caacagcggt aagatccttg agagttttcg ccccgaagaa cgttctccaa | | 4079 |
| tgatgagcac ttttaaagtt ctgctatgtg gcgcggtatt atcccgtgtt gacgccgggc | | 4139 |
| aagagcaact cggtcgccgc atacactatt ctcagaatga cttggttgag tactcaccag | | 4199 |

-continued

```
tcacagaaaa gcatcttacg gatggcatga cagtaagaga attatgcagt gctgccataa    4259
ccatgagtga taacactgcg gccaacttac ttctgacaac gatcggagga ccgaaggagc    4319
taaccgcttt tttgcacaac atggggatc atgtaactcg ccttgatcgt tgggaaccgg     4379
agctgaatga agccatacca acgacgagc gtgacaccac gatgcctgta gcaatggcaa     4439
caacgttgcg caaactatta actggcgaac tacttactct agcttcccgg caacaattaa    4499
tagactggat ggaggcggat aaagttgcag gaccacttct gcgctcggcc cttccggctg    4559
gctggtttat tgctgataaa tctggagccg gtgagcgtgg gtctcgcggt atcattgcag    4619
cactggggcc agatggtaag ccctcccgta tcgtagttat ctacacgacg gggagtcagg    4679
caactatgga tgaacgaaat agacagatcg ctgagatagg tgcctcactg attaagcatt    4739
ggtaactgtc agaccaagtt tactcatata tactttagat tgatttaccc cggttgataa    4799
tcagaaaagc cccaaaaaca ggaagattgt ataagcaaat atttaaattg taaacgttaa    4859
tattttgtta aaattcgcgt taaattttg ttaaatcagc tcatttttta accaataggc     4919
cgaaatcggc aaaatccctt ataaatcaaa agaatagacc gagataggt tgagtgttgt     4979
tccagtttgg aacaagagtc cactattaaa gaacgtggac tccaacgtca aagggcgaaa    5039
aaccgtctat cagggcgatg gcccactacg tgaaccatca cccaaatcaa gttttttggg    5099
gtcgaggtgc cgtaaagcac taaatcggaa ccctaaaggg agcccccgat ttagagcttg    5159
acggggaaag ccggcgaacg tggcgagaaa ggaagggaag aaagcgaaag gagcgggcgc    5219
tagggcgctg gcaagtgtag cggtcacgct gcgcgtaacc accacccccg ccgcgcttaa    5279
tgcgccgcta cagggcgcgt aaaaggatct aggtgaagat ccttttttgat aatctcatga   5339
ccaaaatccc ttaacgtgag ttttcgttcc actgagcgtc agacccgta gaaaagatca     5399
aaggatcttc ttgagatcct ttttttctgc gcgtaatctg ctgcttgcaa acaaaaaaac    5459
caccgctacc agcggtggtt tgtttgccgg atcaagagct accaactctt tttccgaagg    5519
taactggctt cagcagagcg cagataccaa atactgtcct tctagtgtag ccgtagttag    5579
gccaccactt caagaactct gtagcaccgc ctacatacct cgctctgcta atcctgttac    5639
cagtggctgc tgccagtggc gataagtcgt gtcttaccgg gttggactca agacgatagt    5699
taccggataa ggcgcagcgg tcgggctgaa cggggggttc gtgcacacag cccagcttgg    5759
agcgaacgac ctacaccgaa ctgagatacc tacagcgtga gctatgagaa agcgccacgc    5819
ttcccgaagg gagaaaggcg gacaggtatc cggtaagcgg cagggtcgga acaggagagc    5879
gcacgaggga gcttccaggg ggaaacgcct ggtatcttta tagtcctgtc gggtttcgcc    5939
acctctgact tgagcgtcga ttttgtgat gctcgtcagg ggggcggagc ctatggaaaa     5999
acgccagcaa cgcggccttt ttacggttcc tggccttttg ctggcctttt gctcacatgt    6059
tctttcctgc gttatcccct gattctgtgg ataaccgtat taccgccttt gagtgagctg    6119
ataccgctcg ccgcagccga acgaccgagc gcagcgagtc agtgagcgag gaagcggaag    6179
agcgcctgat gcggtatttt ctccttacgc atctgtgcgg tatttcacac cgcatatatg    6239
gtgcactctc agtacaatct gctctgatgc cgcatagtta agccagtata cactccgcta    6299
tcgctacgtg actgggtcat ggctgcgccc cgacacccgc caacacccgc tgacgcgccc    6359
tgacgggctt gtctgctccc ggcatccgct tacagacaag ctgtgaccgt ctccgggagc    6419
tgcatgtgtc agaggttttc accgtcatca ccgaaacgcg cgaggcagct gcggtaaagc    6479
tcatcagcgt ggtcgtgcag cgattcacag atgtctgcct gttcatccgc gtccagctcg    6539
```

-continued

```
ttgagtttct ccagaagcgt taatgtctgg cttctgataa agcgggccat gttaagggcg       6599
gttttttcct gtttggtcac tgatgcctcc gtgtaagggg gatttctgtt catgggggta       6659
atgataccga tgaaacgaga gaggatgctc acgatacggg ttactgatga tgaacatgcc       6719
cggttactgg aacgttgtga gggtaaacaa ctggcggtat ggatgcggcg ggaccagaga       6779
aaaatcactc aggtcaatg ccagcgcttc gttaatacag atgtaggtgt tccacagggt        6839
agccagcagc atcctgcgat gcagatccgg aacataatgg tgcagggcgc tgacttccgc       6899
gtttccagac tttacgaaac acggaaaccg aagaccattc atgttgttgc tcaggtcgca       6959
gacgttttgc agcagcagtc gcttcacgtt cgctcgcgta tcggtgattc attctgctaa       7019
ccagtaaggc aaccccgcca gcctagccgg gtcctcaacg acaggagcac gatcatgcgc       7079
acccgtggcc aggacccaac gctgcccgaa att                                    7112
```

<210> SEQ ID NO 41
<211> LENGTH: 554
<212> TYPE: PRT
<213> ORGANISM: Toxoplasma gondii
<220> FEATURE:
<223> OTHER INFORMATION: pMBP-c2X-ToxoP30del11 (52-214aa)

<400> SEQUENCE: 41

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
    65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
```

```
                260                 265                 270
Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Leu Val Ala Asn Gln Val Thr Cys
385                 390                 395                 400

Pro Asp Lys Lys Ser Thr Ala Ala Val Ile Leu Thr Pro Thr Glu Asn
                405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
                485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
    530                 535                 540

Ala Glu Gly Pro Thr Thr Met Thr Leu Val
545                 550

<210> SEQ ID NO 42
<211> LENGTH: 489
<212> TYPE: DNA
<213> ORGANISM: Toxoplasma gondii
<220> FEATURE:
<221> NAME/KEY: CDS
<222> LOCATION: (1)...(489)
<223> OTHER INFORMATION: ToxoP30del11 (52-214aa)

<400> SEQUENCE: 42 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct     96
Ala Val Ile Leu Thr Pro Thr Glu Asn His Phe Thr Leu Lys Cys Pro
                20                  25                  30 aaa aca gcg ctc aca gag cct ccc act ctt gcg tac tca ccc aac agg    144
Lys Thr Ala Leu Thr Glu Pro Pro Thr Leu Ala Tyr Ser Pro Asn Arg
            35                  40                  45
```

```
caa atc tgc cca gcg ggt act aca agt agc tgt aca tca aag gct gta    192
Gln Ile Cys Pro Ala Gly Thr Thr Ser Ser Cys Thr Ser Lys Ala Val
    50                  55                  60 aca ttg agc tcc ttg att cct gaa gca gaa gat agc tgg tgg acg ggg    240
Thr Leu Ser Ser Leu Ile Pro Glu Ala Glu Asp Ser Trp Trp Thr Gly
65                  70                  75                  80 gat tct gct agt ctc gac acg gca ggc atc aaa ctc aca gtt cca atc    288
Asp Ser Ala Ser Leu Asp Thr Ala Gly Ile Lys Leu Thr Val Pro Ile
                85                  90                  95 gag aag ttc ccc gtg aca acg cag acg ttt gtg gtc ggt tgc atc aag    336
Glu Lys Phe Pro Val Thr Thr Gln Thr Phe Val Val Gly Cys Ile Lys
            100                 105                 110 gga gac gac gca cag agt tgt atg gtc aca gtg aca gta caa gcc aga    384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac    432
Ala Ser Ser Val Val Asn Asn Val Ala Arg Cys Ser Tyr Gly Ala Asp
    130                 135                 140 agc act ctt ggt cct gtc aag ttg tct gcg gaa gga ccc act aca atg    480
Ser Thr Leu Gly Pro Val Lys Leu Ser Ala Glu Gly Pro Thr Thr Met
145                 150                 155                 160 acc ctc gtg                                                        489
Thr Leu Val <210> SEQ ID NO 43
<211> LENGTH: 163
<212> TYPE: PRT
<213> ORGANISM: Toxoplasma gondii
<220> FEATURE:
<223> OTHER INFORMATION: ToxoP30del11 (52-214aa)

<400> SEQUENCE: 43

Leu Val Ala Asn Gln Val Val Thr Cys Pro Asp Lys Ser Thr Ala
  1               5                  10                  15

Ala Val Ile Leu Thr Pro Thr Glu Asn His Phe Thr Leu Lys Cys Pro
                20                  25                  30

Lys Thr Ala Leu Thr Glu Pro Pro Thr Leu Ala Tyr Ser Pro Asn Arg
            35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val

<210> SEQ ID NO 44
<211> LENGTH: 70
<212> TYPE: DNA
<213> ORGANISM: Artificial Sequence
```

```
<220> FEATURE:
<223> OTHER INFORMATION: P30.001 Primer

<400> SEQUENCE: 44
cttgttgcca atcaagttgt cacctgccca gataaaaaat cgacagccgc ggtcattctc    60
acaccgacgg                                                           70

<210> SEQ ID NO 45
<211> LENGTH: 69
<212> TYPE: DNA
<213> ORGANISM: Artificial Sequence
<220> FEATURE:
<223> OTHER INFORMATION: P30.002 Primer

<400> SEQUENCE: 45
gaggctctgt gagcgctgtt ttagggcact tgagagtgaa gtggttctcc gtcggtgtga    60
gaatgaccg                                                            69

<210> SEQ ID NO 46
<211> LENGTH: 67
<212> TYPE: DNA
<213> ORGANISM: Artificial Sequence
<220> FEATURE:
<223> OTHER INFORMATION: P30.003 Primer

<400> SEQUENCE: 46
cctaaaacag cgctcacaga gcctcccact cttgcgtact cacccaacag gcaaatctgc    60
ccagcgg                                                              67

<210> SEQ ID NO 47
<211> LENGTH: 72
<212> TYPE: DNA
<213> ORGANISM: Artificial Sequence
<220> FEATURE:
<223> OTHER INFORMATION: P30.004 Primer

<400> SEQUENCE: 47
ggaatcaagg agctcaatgt tacagccttt gatgtacagc tacttgtagt acccgctggg    60
cagatttgcc tg                                                        72

<210> SEQ ID NO 48
<211> LENGTH: 73
<212> TYPE: DNA
<213> ORGANISM: Artificial Sequence
<220> FEATURE:
<223> OTHER INFORMATION: P30.005 Primer

<400> SEQUENCE: 48
gtaacattga gctccttgat tcctgaagca gaagatagct ggtggacggg ggattctgct    60
agtctcgaca cgg                                                       73

<210> SEQ ID NO 49
<211> LENGTH: 72
<212> TYPE: DNA
<213> ORGANISM: Artificial Sequence
<220> FEATURE:
<223> OTHER INFORMATION: P30.006 Primer

<400> SEQUENCE: 49
ctgcgttgtc acgggaact tctcgattgg aactgtgagt ttgatgcctg ccgtgtcgag     60
actagcagaa tc                                                        72
```

<210> SEQ ID NO 50
<211> LENGTH: 70
<212> TYPE: DNA
<213> ORGANISM: Artificial Sequence
<220> FEATURE:
<223> OTHER INFORMATION: P30.007 Primer

<400> SEQUENCE: 50
gaagttcccc gtgacaacgc agacgtttgt ggtcggttgc atcaagggag acgacgcaca    60
gagttgtatg    70

<210> SEQ ID NO 51
<211> LENGTH: 71
<212> TYPE: DNA
<213> ORGANISM: Artificial Sequence
<220> FEATURE:
<223> OTHER INFORMATION: P30.008 Primer

<400> SEQUENCE: 51
gcgacattat tgacgaccga tgaggctctg gcttgtactg tcaccgtgac catacaactc    60
tgtgcgtcgt c    71

<210> SEQ ID NO 52
<211> LENGTH: 70
<212> TYPE: DNA
<213> ORGANISM: Artificial Sequence
<220> FEATURE:
<223> OTHER INFORMATION: P30.009 Primer

<400> SEQUENCE: 52
catcggtcgt caataatgtc gcaaggtgct cctacggtgc agacagcact cttggtcctg    60
tcaagttgtc    70

<210> SEQ ID NO 53
<211> LENGTH: 71
<212> TYPE: DNA
<213> ORGANISM: Artificial Sequence
<220> FEATURE:
<223> OTHER INFORMATION: P30.010Ala8 Primer

<400> SEQUENCE: 53
gactccatct ttcccagcca cgagggtcat tgtagtgggt ccttccgcag acaacttgac    60
aggaccaaga g    71

<210> SEQ ID NO 54
<211> LENGTH: 71
<212> TYPE: DNA
<213> ORGANISM: Artificial Sequence
<220> FEATURE:
<223> OTHER INFORMATION: P30.011Ala8Ala9 Primer

<400> SEQUENCE: 54
gtggctggga agatggagt caaagttcct caagacaaca atcagtacgc ttccgggacg    60
acgctgactg g    71

<210> SEQ ID NO 55
<211> LENGTH: 71
<212> TYPE: DNA
<213> ORGANISM: Artificial Sequence
<220> FEATURE:
<223> OTHER INFORMATION: P30.012Ala9Ala10 Primer

<400> SEQUENCE: 55

```
gttctcagtt aattttggca aaatatcttt gaacgatttc tcgttagcac cagtcagcgt    60
cgtcccggaa g                                                         71

<210> SEQ ID NO 56
<211> LENGTH: 71
<212> TYPE: DNA
<213> ORGANISM: Artificial Sequence
<220> FEATURE:
<223> OTHER INFORMATION: P30.013 Primer

<400> SEQUENCE: 56
gatattttgc caaaattaac tgagaacccg tggcagggta acgcttcgag tgataagggt    60
gccacgctaa c                                                         71

<210> SEQ ID NO 57
<211> LENGTH: 70
<212> TYPE: DNA
<213> ORGANISM: Artificial Sequence
<220> FEATURE:
<223> OTHER INFORMATION: P30.014 Primer

<400> SEQUENCE: 57
ccaataatga cgcttttga ctcggctgga aatgcttcct tcttgatcgt tagcgtggca    60
cccttatcac                                                           70

<210> SEQ ID NO 58
<211> LENGTH: 70
<212> TYPE: DNA
<213> ORGANISM: Artificial Sequence
<220> FEATURE:
<223> OTHER INFORMATION: P30.015Ala11Ala12 Primer

<400> SEQUENCE: 58 gtcaaaagc gtcattattg gagctacagg gggatcgcct gagaagcatc acgctaccgt     60
gaaactggag                                                           70

<210> SEQ ID NO 59
<211> LENGTH: 70
<212> TYPE: DNA
<213> ORGANISM: Artificial Sequence
<220> FEATURE:
<223> OTHER INFORMATION: P30.016Ala12 Primer

<400> SEQUENCE: 59
gactggctgt tcccgcagcc gattttgctg accctgcagc cccggcaaac tccagtttca    60
cggtagcgtg                                                           70

<210> SEQ ID NO 60
<211> LENGTH: 36
<212> TYPE: DNA
<213> ORGANISM: Artificial Sequence
<220> FEATURE:
<223> OTHER INFORMATION: Antisense Primer

<400> SEQUENCE: 60
caggtcaagc tttcactcca gtttcacggt agcgtg                              36

<210> SEQ ID NO 61
<211> LENGTH: 7370
<212> TYPE: DNA
<213> ORGANISM: Toxoplasma gondii
<220> FEATURE:
```

-continued

```
<221> NAME/KEY: CDS
<222> LOCATION: (1528)...(3447)
<223> OTHER INFORMATION: pMBP-c2X-ToxoP30MIX1

<400> SEQUENCE: 61
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc cgccgttaac caccatcaaa caggattttc     960
gcctgctggg gcaaaccagc gtggaccgct tgctgcaact ctctcagggc caggcggtga    1020
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga aacagccagt ccgtttaggt gttttcacga    1500
gcacttcacc aacaaggacc atagcat atg aaa atc gaa gaa ggt aaa ctg gta    1554
                              Met Lys Ile Glu Glu Gly Lys Leu Val
                               1               5 atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10                  15                  20                  25 aag aaa ttc gag aaa gat acc gga att aaa gtc acc gtt gag cat ccg      1650
Lys Lys Phe Glu Lys Asp Thr Gly Ile Lys Val Thr Val Glu His Pro
                 30                  35                  40 gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
             45                  50                  55 cct gac att atc ttc tgg gca cac gac cgc ttt ggt ggc tac gct caa      1746
Pro Asp Ile Ile Phe Trp Ala His Asp Arg Phe Gly Gly Tyr Ala Gln
         60                  65                  70 tct ggc ctg ttg gct gaa atc acc ccg gac aaa gcg ttc cag gac aag      1794
Ser Gly Leu Leu Ala Glu Ile Thr Pro Asp Lys Ala Phe Gln Asp Lys
     75                  80                  85
```

```
ctg tat ccg ttt acc tgg gat gcc gta cgt tac aac ggc aag ctg att      1842
Leu Tyr Pro Phe Thr Trp Asp Ala Val Arg Tyr Asn Gly Lys Leu Ile
 90              95                 100                 105 gct tac ccg atc gct gtt gaa gcg tta tcg ctg att tat aac aaa gat      1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat      1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa      1986
Lys Glu Leu Lys Ala Lys Gly Lys Ser Ala Leu Met Phe Asn Leu Gln
        140                 145                 150 gaa ccg tac ttc acc tgg ccg ctg att gct gct gac ggg ggt tat gcg      2034
Glu Pro Tyr Phe Thr Trp Pro Leu Ile Ala Ala Asp Gly Gly Tyr Ala
    155                 160                 165 ttc aag tat gaa aac ggc aag tac gac att aaa gac gtg ggc gtg gat      2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa      2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc      2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg      2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg      2274
Ser Asn Ile Asp Thr Ser Lys Val Asn Tyr Gly Val Thr Val Leu Pro
    235                 240                 245 acc ttc aag ggt caa cca tcc aaa ccg ttc gtt ggc gtg ctg agc gca      2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc      2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac      2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg      2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa      2514
Lys Asp Pro Arg Ile Ala Ala Thr Met Glu Asn Ala Gln Lys Gly Glu
    315                 320                 325 atc atg ccg aac atc ccg cag atg tcc gct ttc tgg tat gcc gtg cgt      2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc      2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac      2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt      2706
Asn Asn Asn Asn Leu Gly Ile Glu Gly Arg Ile Ser Glu Phe Leu Val
        380                 385                 390 gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
```

|                                                                                                                     |      |
|---------------------------------------------------------------------------------------------------------------------|------|
|          395                      400                        405                                                    |      |
| att ctc aca ccg acg gag aac cac ttc act ctc aag tgc cct aaa aca                                                     | 2802 |
| Ile Leu Thr Pro Thr Glu Asn His Phe Thr Leu Lys Cys Pro Lys Thr                                                     |      |
| 410                       415                        420                        425                                 |      |
| gcg ctc aca gag cct ccc act ctt gcg tac tca ccc aac agg caa atc                                                     | 2850 |
| Ala Leu Thr Glu Pro Pro Thr Leu Ala Tyr Ser Pro Asn Arg Gln Ile                                                     |      |
|                           430                        435                        440                                 |      |
| tgc cca gcg ggt act aca agt agc tgt aca tca aag gct gta aca ttg                                                     | 2898 |
| Cys Pro Ala Gly Thr Thr Ser Ser Cys Thr Ser Lys Ala Val Thr Leu                                                     |      |
|                 445                        450                        455                                           |      |
| agc tcc ttg att cct gaa gca gaa gat agc tgg tgg acg ggg gat tct                                                     | 2946 |
| Ser Ser Leu Ile Pro Glu Ala Glu Asp Ser Trp Trp Thr Gly Asp Ser                                                     |      |
|                 460                        465                        470                                           |      |
| gct agt ctc gac acg gca ggc atc aaa ctc aca gtt cca atc gag aag                                                     | 2994 |
| Ala Ser Leu Asp Thr Ala Gly Ile Lys Leu Thr Val Pro Ile Glu Lys                                                     |      |
|         475                        480                        485                                                   |      |
| ttc ccc gtg aca acg cag acg ttt gtg gtc ggt tgc atc aag gga gac                                                     | 3042 |
| Phe Pro Val Thr Thr Gln Thr Phe Val Val Gly Cys Ile Lys Gly Asp                                                     |      |
| 490                       495                        500                        505                                 |      |
| gac gca cag agt tgt atg gtc acg gtg aca gta caa gcc aga gcc tca                                                     | 3090 |
| Asp Ala Gln Ser Cys Met Val Thr Val Thr Val Gln Ala Arg Ala Ser                                                     |      |
|                           510                        515                        520                                 |      |
| tcg gtc gtc aat aat gtc gca agg tgc tcc tac ggt gca gac agc act                                                     | 3138 |
| Ser Val Val Asn Asn Val Ala Arg Cys Ser Tyr Gly Ala Asp Ser Thr                                                     |      |
|                 525                        530                        535                                           |      |
| ctt ggt cct gtc aag ttg tct gcg gaa gga ccc act aca atg acc ctc                                                     | 3186 |
| Leu Gly Pro Val Lys Leu Ser Ala Glu Gly Pro Thr Thr Met Thr Leu                                                     |      |
|                 540                        545                        550                                           |      |
| gtg gct ggg aaa gat gga gtc aaa gtt cct caa gac aat aat cag tac                                                     | 3234 |
| Val Ala Gly Lys Asp Gly Val Lys Val Pro Gln Asp Asn Asn Gln Tyr                                                     |      |
|         555                        560                        565                                                   |      |
| gct tcc ggg acg acg ctg act ggt gct aac gag aaa tcg ttc aaa gat                                                     | 3282 |
| Ala Ser Gly Thr Thr Leu Thr Gly Ala Asn Glu Lys Ser Phe Lys Asp                                                     |      |
| 570                       575                        580                        585                                 |      |
| att ttg cca aaa tta act gag aac ccg tgg cag ggt aac gct tcg agt                                                     | 3330 |
| Ile Leu Pro Lys Leu Thr Glu Asn Pro Trp Gln Gly Asn Ala Ser Ser                                                     |      |
|                           590                        595                        600                                 |      |
| gat aag ggt gcc acg cta acg atc aag aag gaa gca ttt cca gcc gag                                                     | 3378 |
| Asp Lys Gly Ala Thr Leu Thr Ile Lys Lys Glu Ala Phe Pro Ala Glu                                                     |      |
|                 605                        610                        615                                           |      |
| tca aaa agc gtc att att gga gct aca ggg gga tcg cct gag aag cat                                                     | 3426 |
| Ser Lys Ser Val Ile Ile Gly Ala Thr Gly Gly Ser Pro Glu Lys His                                                     |      |
|                 620                        625                        630                                           |      |
| cac gct acc gtg aaa ctg gag tgaaagcttg gcactggccg tcgttttaca                                                        | 3477 |
| His Ala Thr Val Lys Leu Glu                                                                                         |      |
|                 635                        640                                                                      |      |
| acgtcgtgac tgggaaaacc ctggcgttac ccaacttaat cgccttgcag cacatccccc                                                   | 3537 |
| tttcgccagc tggcgtaata gcgaagaggc ccgcaccgat cgcccttccc aacagttgcg                                                   | 3597 |
| cagcctgaat ggcgaatggc agcttggctg ttttggcgga tgagataaga ttttcagcct                                                   | 3657 |
| gatacagatt aaatcagaac gcagaagcgg tctgataaaa cagaatttgc ctggcggcag                                                   | 3717 |
| tagcgcggtg gtcccacctg accccatgcc gaactcagaa gtgaaacgcc gtagcgccga                                                   | 3777 |
| tggtagtgtg gggtctcccc atgcgagagt agggaactgc caggcatcaa ataaaacgaa                                                   | 3837 |
| aggctcagtc gaaagactgg gcctttcgtt ttatctgttg tttgtcggtg aacgctctcc                                                   | 3897 |
| tgagtaggac aaatccgccg ggagcggatt tgaacgttgc gaagcaacgg cccggagggt                                                   | 3957 |
| ggcgggcagg acgcccgcca taaactgcca ggcatcaaat taagcagaag gccatcctga                                                   | 4017 |

```
cggatggcct ttttgcgttt ctacaaactc tttttgttta tttttctaaa tacattcaaa    4077
tatgtatccg ctcatgagac aataaccctg ataaatgctt caataatatt gaaaaaggaa    4137
gagtatgagt attcaacatt tccgtgtcgc ccttattccc tttttgcgg  cattttgcct    4197
tcctgttttt gctcacccag aaacgctggt gaaagtaaaa gatgctgaag atcagttggg    4257
tgcacgagtg ggttacatcg aactggatct caacagcggt aagatccttg agagttttcg    4317
ccccgaagaa cgttctccaa tgatgagcac ttttaaagtt ctgctatgtg gcgcggtatt    4377
atcccgtgtt gacgccgggc aagagcaact cggtcgccgc atacactatt ctcagaatga    4437
cttggttgag tactcaccag tcacagaaaa gcatcttacg gatggcatga cagtaagaga    4497
attatgcagt gctgccataa ccatgagtga taacactgcg ccaacttac  ttctgacaac    4557
gatcggagga ccgaaggagc taaccgcttt tttgcacaac atgggggatc atgtaactcg    4617
ccttgatcgt tgggaaccgg agctgaatga agccatacca aacgacgagc gtgacaccac    4677
gatgcctgta gcaatggcaa caacgttgcg caaactatta actggcgaac tacttactct    4737
agcttcccgg caacaattaa tagactggat ggaggcggat aaagttgcag gaccacttct    4797
gcgctcggcc cttccggctg gctggtttat tgctgataaa tctggagccg gtgagcgtgg    4857
gtctcgcggt atcattgcag cactgggggcc agatggtaag ccctcccgta tcgtagttat    4917
ctacacgacg gggagtcagg caactatgga tgaacgaaat agacagatcg ctgagatagg    4977
tgcctcactg attaagcatt ggtaactgtc agaccaagtt tactcatata ctttagat     5037
tgatttaccc cggttgataa tcagaaaagc cccaaaaaca ggaagattgt ataagcaaat    5097
atttaaattg taaacgttaa tattttgtta aaattcgcgt taaattttg  ttaaatcagc    5157
tcatttttta accataggc  cgaaatcggc aaaatccctt ataaatcaaa agaatagacc    5217
gagatagggt tgagtgttgt tccagtttgg aacaagagtc cactattaaa gaacgtggac    5277
tccaacgtca aagggcgaaa aaccgtctat cagggcgatg gcccactacg tgaaccatca    5337
cccaaatcaa gttttttggg gtcgaggtgc cgtaaagcac taaatcggaa ccctaaaggg    5397
agcccccgat ttagagcttg acggggaaag ccggcgaacg tggcgagaaa ggaagggaag    5457
aaagcgaaag gagcgggcgc tagggcgctg gcaagtgtag cggtcacgct gcgcgtaacc    5517
accacacccg ccgcgcttaa tgcgccgcta cagggcgcgt aaaaggatct aggtgaagat    5577
cctttttgat aatctcatga ccaaaatccc ttaacgtgag ttttcgttcc actgagcgtc    5637
agaccccgta gaaaagatca aaggatcttc ttgagatcct ttttttctgc gcgtaatctg    5697
ctgcttgcaa acaaaaaaac caccgctacc agcggtggtt tgtttgccgg atcaagagct    5757
accaactctt tttccgaagg taactggctt cagcagagcg cagataccaa atactgtcct    5817
tctagtgtag ccgtagttag gccaccactt caagaactct gtagcaccgc ctacatacct    5877
cgctctgcta atcctgttac cagtggctgc tgccagtggc gataagtcgt gtcttaccgg    5937
gttggactca agacgatagt taccggataa ggcgcagcgg tcgggctgaa cggggggttc    5997
gtgcacacag cccagcttgg agcgaacgac ctacaccgaa ctgagatacc tacagcgtga    6057
gctatgagaa agcgccacgc ttcccgaagg gagaaaggcg gacaggtatc cggtaagcgg    6117
cagggtcgga acaggagagc gcacgaggga gcttccaggg ggaaacgcct ggtatcttta    6177
tagtcctgtc gggtttcgcc acctctgact tgagcgtcga ttttttgtgat gctcgtcagg    6237
ggggcggagc ctatgaaaaa cgccagcaa  cgcggccttt ttacggttcc tggccttttg    6297
ctggcctttt gctcacatgt tctttcctgc gttatcccct gattctgtgg ataaccgtat    6357
```

-continued

```
taccgccttt gagtgagctg ataccgctcg ccgcagccga acgaccgagc gcagcgagtc    6417
agtgagcgag gaagcggaag agcgcctgat gcggtatttt ctccttacgc atctgtgcgg    6477
tatttcacac cgcatatatg gtgcactctc agtacaatct gctctgatgc cgcatagtta    6537
agccagtata cactccgcta tcgctacgtg actgggtcat ggctgcgccc cgacacccgc    6597
caacacccgc tgacgcgccc tgacgggctt gtctgctccc ggcatccgct tacagacaag    6657
ctgtgaccgt ctccgggagc tgcatgtgtc agaggttttc accgtcatca ccgaaacgcg    6717
cgaggcagct gcggtaaagc tcatcagcgt ggtcgtgcag cgattcacag atgtctgcct    6777
gttcatccgc gtccagctcg ttgagtttct ccagaagcgt taatgtctgg cttctgataa    6837
agcgggccat gttaagggcg ttttttcct gtttggtcac tgatgcctcc gtgtaagggg    6897
gatttctgtt catgggggta atgataccga tgaaacgaga gaggatgctc acgatacggg    6957
ttactgatga tgaacatgcc cggttactgg aacgttgtga gggtaaacaa ctggcggtat    7017
ggatgcggcg ggaccagaga aaaatcactc agggtcaatg ccagcgcttc gttaatacag    7077
atgtaggtgt tccacagggt agccagcagc atcctgcgat gcagatccgg aacataatgg    7137
tgcagggcgc tgacttccgc gtttccagac tttacgaaac acggaaaccg aagaccattc    7197
atgttgttgc tcaggtcgca gacgttttgc agcagcagtc gcttcacgtt cgctcgcgta    7257
tcggtgattc attctgctaa ccagtaaggc aaccccgcca gcctagccgg gtcctcaacg    7317
acaggagcac gatcatgcgc acccgtggcc aggacccaac gctgcccgaa att           7370
```

<210> SEQ ID NO 62
<211> LENGTH: 640
<212> TYPE: PRT
<213> ORGANISM: Toxoplasma gondii
<220> FEATURE:
<223> OTHER INFORMATION: pMBP-c2X-ToxoP30MIX1

<400> SEQUENCE: 62

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190
```

```
Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
        370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
            405                 410                 415

His Phe Thr Leu Lys Cys Pro Lys Thr Ala Leu Thr Glu Pro Pro Thr
            420                 425                 430

Leu Ala Tyr Ser Pro Asn Arg Gln Ile Cys Pro Ala Gly Thr Thr Ser
        435                 440                 445

Ser Cys Thr Ser Lys Ala Val Thr Leu Ser Ser Leu Ile Pro Glu Ala
450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
            485                 490                 495

Phe Val Val Gly Cys Ile Lys Gly Asp Asp Ala Gln Ser Cys Met Val
            500                 505                 510

Thr Val Thr Val Gln Ala Arg Ala Ser Ser Val Val Asn Asn Val Ala
        515                 520                 525

Arg Cys Ser Tyr Gly Ala Asp Ser Thr Leu Gly Pro Val Lys Leu Ser
        530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
            565                 570                 575

Gly Ala Asn Glu Lys Ser Phe Lys Asp Ile Leu Pro Lys Leu Thr Glu
            580                 585                 590

Asn Pro Trp Gln Gly Asn Ala Ser Ser Asp Lys Gly Ala Thr Leu Thr
        595                 600                 605
```

```
Ile Lys Lys Glu Ala Phe Pro Ala Glu Ser Lys Ser Val Ile Ile Gly
        610                 615                 620

Ala Thr Gly Gly Ser Pro Glu Lys His His Ala Thr Val Lys Leu Glu
625                 630                 635                 640

<210> SEQ ID NO 63
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX1

<400> SEQUENCE: 63 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct      96
Ala Val Ile Leu Thr Pro Thr Glu Asn His Phe Thr Leu Lys Cys Pro
             20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
     50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc     288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag     336
Glu Lys Phe Pro Val Thr Thr Gln Thr Phe Val Val Gly Cys Ile Lys
            100                 105                 110 gga gac gac gca cag agt tgt atg gtc acg gtg aca gta caa gcc aga     384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac     432
Ala Ser Ser Val Val Asn Asn Val Ala Arg Cys Ser Tyr Gly Ala Asp
    130                 135                 140 agc act ctt ggt cct gtc aag ttg tct gcg gaa gga ccc act aca atg     480
Ser Thr Leu Gly Pro Val Lys Leu Ser Ala Glu Gly Pro Thr Thr Met
145                 150                 155                 160 acc ctc gtg gct ggg aaa gat gga gtc aaa gtt cct caa gac aat aat     528
Thr Leu Val Ala Gly Lys Asp Gly Val Lys Val Pro Gln Asp Asn Asn
                165                 170                 175 cag tac gct tcc ggg acg acg ctg act ggt gct aac gag aaa tcg ttc     576
Gln Tyr Ala Ser Gly Thr Thr Leu Thr Gly Ala Asn Glu Lys Ser Phe
            180                 185                 190 aaa gat att ttg cca aaa tta act gag aac ccg tgg cag ggt aac gct     624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca     672
Ser Ser Asp Lys Gly Ala Thr Leu Thr Ile Lys Lys Glu Ala Phe Pro
    210                 215                 220 gcc gag tca aaa agc gtc att att gga gct aca ggg gga tcg cct gag     720
Ala Glu Ser Lys Ser Val Ile Ile Gly Ala Thr Gly Gly Ser Pro Glu
225                 230                 235                 240 aag cat cac gct acc gtg aaa ctg gag                                 747
Lys His His Ala Thr Val Lys Leu Glu
```

```
Lys His His Ala Thr Val Lys Leu Glu
            245

<210> SEQ ID NO 64
<211> LENGTH: 249
<212> TYPE: PRT
<213> ORGANISM: Toxoplasma gondii
<220> FEATURE:
<223> OTHER INFORMATION: ToxoP30MIX1

<400> SEQUENCE: 64

Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
                165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
            245

<210> SEQ ID NO 65
<211> LENGTH: 70
<212> TYPE: DNA
<213> ORGANISM: Artificial Sequence
<220> FEATURE:
<223> OTHER INFORMATION: P30.009Ala7 Primer

<400> SEQUENCE: 65
catcggtcgt caataatgtc gcaagggctt cctacggtgc agacagcact cttggtcctg    60
tcaagttgtc                                                          70

<210> SEQ ID NO 66
<211> LENGTH: 7370
<212> TYPE: DNA
```

<213> ORGANISM: Toxoplasma gondii
<220> FEATURE:
<221> NAME/KEY: CDS
<222> LOCATION: (1528)...(3447)
<223> OTHER INFORMATION: pMBP-c2X-ToxoP30MIX3

<400> SEQUENCE: 66

```
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc ggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatgcg ctgggcgcaa     840
tgcgcgccat taccgagtcc gggctgcgcg ttggtgcgga tatctcggta gtgggatacg     900
acgataccga agacagctca tgttatatcc gccgttaac caccatcaaa caggattttc     960
gcctgctggg gcaaaccagc gtggaccgct tgctgcaact ctctcagggc caggcggtga    1020
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcacttcacc aacaaggacc atagcat atg aaa atc gaa gaa ggt aaa ctg gta   1554
                               Met Lys Ile Glu Glu Gly Lys Leu Val
                                 1               5
atc tgg att aac ggc gat aaa ggc tat aac ggt ctc gct gaa gtc ggt      1602
Ile Trp Ile Asn Gly Asp Lys Gly Tyr Asn Gly Leu Ala Glu Val Gly
 10                  15                  20                  25
aag aaa ttc gag aaa gat acc gga att aaa gtc acc gtt gag cat ccg      1650
Lys Lys Phe Glu Lys Asp Thr Gly Ile Lys Val Thr Val Glu His Pro
                 30                  35                  40
gat aaa ctg gaa gag aaa ttc cca cag gtt gcg gca act ggc gat ggc      1698
Asp Lys Leu Glu Glu Lys Phe Pro Gln Val Ala Ala Thr Gly Asp Gly
             45                  50                  55
cct gac att atc ttc tgg gca cac gac cgc ttt ggt ggc tac gct caa      1746
Pro Asp Ile Ile Phe Trp Ala His Asp Arg Phe Gly Gly Tyr Ala Gln
         60                  65                  70
tct ggc ctg ttg gct gaa atc acc ccg gac aaa gcg ttc cag gac aag      1794
```

-continued

```
Ser Gly Leu Leu Ala Glu Ile Thr Pro Asp Lys Ala Phe Gln Asp Lys
    75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
                    110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
                125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
            140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
        155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
                    190                 195                 200 aac aaa cac atg aat gca gac acc gat tac tcc atc gca gaa gct gcc    2178
Asn Lys His Met Asn Ala Asp Thr Asp Tyr Ser Ile Ala Glu Ala Ala
                205                 210                 215 ttt aat aaa ggc gaa aca gcg atg acc atc aac ggc ccg tgg gca tgg    2226
Phe Asn Lys Gly Glu Thr Ala Met Thr Ile Asn Gly Pro Trp Ala Trp
            220                 225                 230 tcc aac atc gac acc agc aaa gtg aat tat ggt gta acg gta ctg ccg    2274
Ser Asn Ile Asp Thr Ser Lys Val Asn Tyr Gly Val Thr Val Leu Pro
        235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                    270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
                285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
            300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
        315                 320                 325 atc atg ccg aac atc ccg cag atg tcc gct ttc tgg tat gcc gtg cgt    2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                    350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
                365                 370                 375 aat aac aac aac ctc ggg atc gag gga agg att tca gaa ttc ctt gtt    2706
Asn Asn Asn Asn Leu Gly Ile Glu Gly Arg Ile Ser Glu Phe Leu Val
            380                 385                 390
```

```
gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
    395             400                 405 att ctc aca ccg acg gag aac cac ttc act ctc aag tgc cct aaa aca      2802
Ile Leu Thr Pro Thr Glu Asn His Phe Thr Leu Lys Cys Pro Lys Thr
410             415                 420                 425 gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475             480                 485 ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490             495                 500                 505 gac gca cag agt tgt atg gtc acg gtg aca gta caa gcc aga gcc tca      3090
Asp Ala Gln Ser Cys Met Val Thr Val Thr Val Gln Ala Arg Ala Ser
                510                 515                 520 tcg gtc gtc aat aat gtc gca agg gct tcc tac ggt gca gac agc act      3138
Ser Val Val Asn Asn Val Ala Arg Ala Ser Tyr Gly Ala Asp Ser Thr
            525                 530                 535 ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550 gtg gct ggg aaa gat gga gtc aaa gtt cct caa gac aac aat cag tac      3234
Val Ala Gly Lys Asp Gly Val Lys Val Pro Gln Asp Asn Asn Gln Tyr
    555             560                 565 gct tcc ggg acg acg ctg act ggt gct aac gag aaa tcg ttc aaa gat      3282
Ala Ser Gly Thr Thr Leu Thr Gly Ala Asn Glu Lys Ser Phe Lys Asp
570             575                 580                 585 att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615 tca aaa agc gtc att att gga gct aca ggg gga tcg cct gag aag cat      3426
Ser Lys Ser Val Ile Ile Gly Ala Thr Gly Gly Ser Pro Glu Lys His
        620                 625                 630 cac gct acc gtg aaa ctg gag tgaaagcttg gcactggccg tcgttttaca         3477
His Ala Thr Val Lys Leu Glu
    635             640 acgtcgtgac tgggaaaacc ctggcgttac ccaacttaat cgccttgcag cacatccccc    3537
tttcgccagc tggcgtaata gcgaagaggc ccgcaccgat cgcccttccc aacagttgcg    3597
cagcctgaat ggcgaatggc agcttggctg ttttggcgga tgagataaga ttttcagcct    3657
gatacagatt aaatcagaac gcagaagcgg tctgataaaa cagaatttgc ctggcggcag    3717
tagcgcggtg gtcccacctg accccatgcc gaactcagaa gtgaaagccg tagcgccga    3777 tggtagtgtg gggtctcccc atgcgagagt agggaactgc caggcatcaa ataaaacgaa    3837
aggctcagtc gaaagactgg gcctttcgtt ttatctgttg tttgtcggtg aacgctctcc    3897
tgagtaggac aaatccgccg ggagcggatt tgaacgttgc gaagcaacgg cccggagggt    3957
```

```
ggcgggcagg acgcccgcca taaactgcca ggcatcaaat taagcagaag gccatcctga   4017
cggatggcct ttttgcgttt ctacaaactc tttttgttta tttttctaaa tacattcaaa   4077
tatgtatccg ctcatgagac aataaccctg ataaatgctt caataatatt gaaaaaggaa   4137
gagtatgagt attcaacatt tccgtgtcgc ccttattccc ttttttgcgg cattttgcct   4197
tcctgttttt gctcacccag aaacgctggt gaaagtaaaa gatgctgaag atcagttggg   4257
tgcacgagtg ggttacatcg aactggatct caacagcggt aagatccttg agagttttcg   4317
ccccgaagaa cgttctccaa tgatgagcac ttttaaagtt ctgctatgtg gcgcggtatt   4377
atcccgtgtt gacgccgggc aagagcaact cggtcgccgc atacactatt ctcagaatga   4437
cttggttgag tactcaccag tcacagaaaa gcatcttacg gatggcatga cagtaagaga   4497
attatgcagt gctgccataa ccatgagtga taacactgcg gccaacttac ttctgacaac   4557
gatcggagga ccgaaggagc taaccgcttt tttgcacaac atgggggatc atgtaactcg   4617
ccttgatcgt tgggaaccgg agctgaatga agccatacca aacgacgagc gtgacaccac   4677
gatgcctgta gcaatggcaa caacgttgcg caaactatta actggcgaac tacttactct   4737
agcttcccgg caacaattaa tagactggat ggaggcggat aaagttgcag gaccacttct   4797
gcgctcggcc cttccggctg gctggtttat tgctgataaa tctggagccg gtgagcgtgg   4857
gtctcgcggt atcattgcag cactgggggcc agatggtaag ccctcccgta tcgtagttat   4917
ctacacgacg gggagtcagg caactatgga tgaacgaaat agacagatcg ctgagatagg   4977
tgcctcactg attaagcatt ggtaactgtc agaccaagtt tactcatata ctttagat     5037
tgatttaccc cggttgataa tcagaaaagc cccaaaaaca ggaagattgt ataagcaaat   5097
atttaaattg taaacgttaa tattttgtta aaattcgcgt taaattttg ttaaatcagc    5157
tcatttttta accataggc cgaaatcggc aaaatccctt ataaatcaaa agaatagacc    5217
gagatagggt tgagtgttgt tccagtttgg aacaagagtc cactattaaa gaacgtggac   5277
tccaacgtca aagggcgaaa aaccgtctat cagggcgatg gcccactacg tgaaccatca   5337
cccaaatcaa gttttttggg gtcgaggtgc cgtaaagcac taaatcggaa ccctaaaggg   5397
agcccccgat ttagagcttg acggggaaag ccggcgaacg tggcgagaaa ggaagggaag   5457
aaagcgaaag gagcgggcgc tagggcgctg gcaagtgtag cggtcacgct gcgcgtaacc   5517
accacacccg ccgcgcttaa tgcgccgcta cagggcgcgt aaaaggatct aggtgaagat   5577
cctttttgat aatctcatga ccaaaatccc ttaacgtgag ttttcgttcc actgagcgtc   5637
agaccccgta gaaaagatca aaggatcttc ttgagatcct ttttttctgc gcgtaatctg   5697
ctgcttgcaa acaaaaaaac caccgctacc agcggtggtt tgtttgccgg atcaagagct   5757
accaactctt tttccgaagg taactggctt cagcagagcg cagataccaa atactgtcct   5817
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga ttttgtgat gctcgtcagg    6237
ggggcggagc ctatggaaaa acgccagcaa cgcggccttt ttacggttcc tggccttttg   6297
```

-continued

```
ctggccttttt gctcacatgt tctttcctgc gttatcccct gattctgtgg ataaccgtat    6357
taccgccttt gagtgagctg ataccgctcg ccgcagccga acgaccgagc gcagcgagtc    6417
agtgagcgag gaagcggaag agcgcctgat gcggtatttt ctccttacgc atctgtgcgg    6477
tatttcacac cgcatatatg gtgcactctc agtacaatct gctctgatgc cgcatagtta    6537
agccagtata cactccgcta tcgctacgtg actgggtcat ggctgcgccc cgacacccgc    6597
caacacccgc tgacgcgccc tgacgggctt gtctgctccc ggcatccgct tacagacaag    6657
ctgtgaccgt ctccgggagc tgcatgtgtc agaggttttc accgtcatca ccgaaacgcg    6717
cgaggcagct gcggtaaagc tcatcagcgt ggtcgtgcag cgattcacag atgtctgcct    6777
gttcatccgc gtccagctcg ttgagtttct ccagaagcgt taatgtctgg cttctgataa    6837
agcgggccat gttaagggcg ttttttcct gtttggtcac tgatgcctcc gtgtaagggg    6897
gatttctgtt catgggggta atgataccga tgaaacgaga gaggatgctc acgatacggg    6957
ttactgatga tgaacatgcc cggttactgg aacgttgtga gggtaaacaa ctggcggtat    7017
ggatgcggcg ggaccagaga aaaatcactc agggtcaatg ccagcgcttc gttaatacag    7077
atgtaggtgt tccacagggt agccagcagc atcctgcgat gcagatccgg aacataatgg    7137
tgcagggcgc tgacttccgc gtttccagac tttacgaaac acggaaaccg aagaccattc    7197
atgttgttgc tcaggtcgca gacgttttgc agcagcagtc gcttcacgtt cgctcgcgta    7257
tcggtgattc attctgctaa ccagtaaggc aaccccgcca gcctagccgg gtcctcaacg    7317
acaggagcac gatcatgcgc acccgtggcc aggacccaac gctgcccgaa att           7370
```

<210> SEQ ID NO 67
<211> LENGTH: 640
<212> TYPE: PRT
<213> ORGANISM: Toxoplasma gondii
<220> FEATURE:
<223> OTHER INFORMATION: pMBP-c2X-ToxoP30MIX3

<400> SEQUENCE: 67

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
                 20                  25                  30

Gly Ile Lys Val Thr Val Glu His Pro Asp Lys Leu Glu Glu Lys Phe
             35                  40                  45

Pro Gln Val Ala Ala Thr Gly Asp Gly Pro Asp Ile Ile Phe Trp Ala
         50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175
```

-continued

```
Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
        260                 265                 270

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
        340                 345                 350

Ser Gly Arg Gln Thr Val Asp Glu Ala Leu Lys Asp Ala Gln Thr Asn
    355                 360                 365

Ser Ser Ser Asn Asn Asn Asn Asn Asn Asn Asn Asn Leu Gly Ile
    370                 375                 380

Glu Gly Arg Ile Ser Glu Phe Leu Val Ala Asn Gln Val Val Thr Cys
385                 390                 395                 400

Pro Asp Lys Lys Ser Thr Ala Ala Val Ile Leu Thr Pro Thr Glu Asn
            405                 410                 415

His Phe Thr Leu Lys Cys Pro Lys Thr Ala Leu Thr Glu Pro Pro Thr
        420                 425                 430

Leu Ala Tyr Ser Pro Asn Arg Gln Ile Cys Pro Ala Gly Thr Thr Ser
    435                 440                 445

Ser Cys Thr Ser Lys Ala Val Thr Leu Ser Ser Leu Ile Pro Glu Ala
    450                 455                 460

Glu Asp Ser Trp Trp Thr Gly Asp Ser Ala Ser Leu Asp Thr Ala Gly
465                 470                 475                 480

Ile Lys Leu Thr Val Pro Ile Glu Lys Phe Pro Val Thr Thr Gln Thr
            485                 490                 495

Phe Val Val Gly Cys Ile Lys Gly Asp Asp Ala Gln Ser Cys Met Val
        500                 505                 510

Thr Val Thr Val Gln Ala Arg Ala Ser Ser Val Val Asn Asn Val Ala
    515                 520                 525

Arg Ala Ser Tyr Gly Ala Asp Ser Thr Leu Gly Pro Val Lys Leu Ser
    530                 535                 540

Ala Glu Gly Pro Thr Thr Met Thr Leu Val Ala Gly Lys Asp Gly Val
545                 550                 555                 560

Lys Val Pro Gln Asp Asn Asn Gln Tyr Ala Ser Gly Thr Thr Leu Thr
            565                 570                 575

Gly Ala Asn Glu Lys Ser Phe Lys Asp Ile Leu Pro Lys Leu Thr Glu
        580                 585                 590

Asn Pro Trp Gln Gly Asn Ala Ser Ser Asp Lys Gly Ala Thr Leu Thr
```

```
                    595                 600                 605
Ile Lys Lys Glu Ala Phe Pro Ala Glu Ser Lys Ser Val Ile Ile Gly
    610                 615                 620

Ala Thr Gly Gly Ser Pro Glu Lys His His Ala Thr Val Lys Leu Glu
625                 630                 635                 640

<210> SEQ ID NO 68
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX3

<400> SEQUENCE: 68 ctt gtt gcc aat caa gtt gtc acc tgc cca gat aaa aaa tcg aca gcc    48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag tgc cct    96
Ala Val Ile Leu Thr Pro Thr Glu Asn His Phe Thr Leu Lys Cys Pro
             20                  25                  30 aaa aca gcg ctc aca gag cct ccc act ctt gcg tac tca ccc aac agg   144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta   192
Gln Ile Cys Pro Ala Gly Thr Thr Ser Ser Cys Thr Ser Lys Ala Val
     50                  55                  60 aca ttg agc tcc ttg att cct gaa gca gaa gat agc tgg tgg acg ggg   240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc   288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag   336
Glu Lys Phe Pro Val Thr Thr Gln Thr Phe Val Val Gly Cys Ile Lys
            100                 105                 110 gga gac gac gca cag agt tgt atg gtc acg gtg aca gta caa gcc aga   384
Gly Asp Asp Ala Gln Ser Cys Met Val Thr Val Thr Val Gln Ala Arg
        115                 120                 125 gcc tca tcg gtc gtc aat aat gtc gca agg gct tcc tac ggt gca gac   432
Ala Ser Ser Val Val Asn Asn Val Ala Arg Ala Ser Tyr Gly Ala Asp
    130                 135                 140 agc act ctt ggt cct gtc aag ttg tct gcg gaa gga ccc act aca atg   480
Ser Thr Leu Gly Pro Val Lys Leu Ser Ala Glu Gly Pro Thr Thr Met
145                 150                 155                 160 acc ctc gtg gct ggg aaa gat gga gtc aaa gtt cct caa gac aac aat   528
Thr Leu Val Ala Gly Lys Asp Gly Val Lys Val Pro Gln Asp Asn Asn
                165                 170                 175 cag tac gct tcc ggg acg acg ctg act ggt gct aac gag aaa tcg ttc   576
Gln Tyr Ala Ser Gly Thr Thr Leu Thr Gly Ala Asn Glu Lys Ser Phe
            180                 185                 190 aaa gat att ttg cca aaa tta act gag aac ccg tgg cag ggt aac gct   624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca   672
Ser Ser Asp Lys Gly Ala Thr Leu Thr Ile Lys Lys Glu Ala Phe Pro
    210                 215                 220 gcc gag tca aaa agc gtc att att gga gct aca ggg gga tcg cct gag   720
Ala Glu Ser Lys Ser Val Ile Ile Gly Ala Thr Gly Gly Ser Pro Glu
225                 230                 235                 240
```

```
aag cat cac gct acc gtg aaa ctg gag                                    747
Lys His His Ala Thr Val Lys Leu Glu
            245
```

<210> SEQ ID NO 69
<211> LENGTH: 249
<212> TYPE: PRT
<213> ORGANISM: Toxoplasma gondii
<220> FEATURE:
<223> OTHER INFORMATION: ToxoP30MIX3

<400> SEQUENCE: 69

```
Leu Val Ala Asn Gln Val Val Thr Cys Pro Asp Lys Lys Ser Thr Ala
 1               5                  10                  15

Ala Val Ile Leu Thr Pro Thr Glu Asn His Phe Thr Leu Lys Cys Pro
            20                  25                  30

Lys Thr Ala Leu Thr Glu Pro Pro Thr Leu Ala Tyr Ser Pro Asn Arg
        35                  40                  45

Gln Ile Cys Pro Ala Gly Thr Thr Ser Ser Cys Thr Ser Lys Ala Val
    50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Ala Ser Tyr Gly Ala Asp
    130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
                165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
    210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
            245
```

<210> SEQ ID NO 70
<211> LENGTH: 69
<212> TYPE: DNA
<213> ORGANISM: Artificial Sequence
<220> FEATURE:
<223> OTHER INFORMATION: P30.002Ala2 Primer

<400> SEQUENCE: 70

```
gaggctctgt gagcgctgtt ttaggagcct tgagagtgaa gtggttctcc gtcggtgtga    60
gaatgaccg                                                             69
```

<210> SEQ ID NO 71

-continued

```
<211> LENGTH: 7370
<212> TYPE: DNA
<213> ORGANISM: Toxoplasma gondii
<220> FEATURE:
<221> NAME/KEY: CDS
<222> LOCATION: (1528)...(3447)
<223> OTHER INFORMATION: pMBP-c2X-ToxoP30MIX5

<400> SEQUENCE: 71
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc ggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc gccgttaac caccatcaaa caggattttc     960
gcctgctggg gcaaaccagc gtggaccgct tgctgcaact ctctcagggc caggcggtga    1020
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgtttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcacttcacc aacaaggacc atagcat atg aaa atc gaa gaa ggt aaa ctg gta    1554
                               Met Lys Ile Glu Glu Gly Lys Leu Val
                                1               5 atc tgg att aac ggc gat aaa ggc tat aac ggt ctc gct gaa gtc ggt        1602
Ile Trp Ile Asn Gly Asp Lys Gly Tyr Asn Gly Leu Ala Glu Val Gly
 10              15                  20                  25 aag aaa ttc gag aaa gat acc gga att aaa gtc acc gtt gag cat ccg        1650
Lys Lys Phe Glu Lys Asp Thr Gly Ile Lys Val Thr Val Glu His Pro
             30                  35                  40 gat aaa ctg gaa gag aaa ttc cca cag gtt gcg gca act ggc gat ggc        1698
Asp Lys Leu Glu Glu Lys Phe Pro Gln Val Ala Ala Thr Gly Asp Gly
         45                  50                  55 cct gac att atc ttc tgg gca cac gac cgc ttt ggt ggc tac gct caa        1746
Pro Asp Ile Ile Phe Trp Ala His Asp Arg Phe Gly Gly Tyr Ala Gln
 60                  65                  70
```

```
tct ggc ctg ttg gct gaa atc acc ccg gac aaa gcg ttc cag gac aag    1794
Ser Gly Leu Leu Ala Glu Ile Thr Pro Asp Lys Ala Phe Gln Asp Lys
 75                  80                  85 ctg tat ccg ttt acc tgg gat gcc gta cgt tac aac ggc aag ctg att    1842
Leu Tyr Pro Phe Thr Trp Asp Ala Val Arg Tyr Asn Gly Lys Leu Ile
 90                  95                 100                 105 gct tac ccg atc gct gtt gaa gcg tta tcg ctg att tat aac aaa gat    1890
Ala Tyr Pro Ile Ala Val Glu Ala Leu Ser Leu Ile Tyr Asn Lys Asp
                110                 115                 120 ctg ctg ccg aac ccg cca aaa acc tgg gaa gag atc ccg gcg ctg gat    1938
Leu Leu Pro Asn Pro Pro Lys Thr Trp Glu Glu Ile Pro Ala Leu Asp
            125                 130                 135 aaa gaa ctg aaa gcg aaa ggt aag agc gcg ctg atg ttc aac ctg caa    1986
Lys Glu Leu Lys Ala Lys Gly Lys Ser Ala Leu Met Phe Asn Leu Gln
140                 145                 150 gaa ccg tac ttc acc tgg ccg ctg att gct gct gac ggg ggt tat gcg    2034
Glu Pro Tyr Phe Thr Trp Pro Leu Ile Ala Ala Asp Gly Gly Tyr Ala
        155                 160                 165 ttc aag tat gaa aac ggc aag tac gac att aaa gac gtg ggc gtg gat    2082
Phe Lys Tyr Glu Asn Gly Lys Tyr Asp Ile Lys Asp Val Gly Val Asp
170                 175                 180                 185 aac gct ggc gcg aaa gcg ggt ctg acc ttc ctg gtt gac ctg att aaa    2130
Asn Ala Gly Ala Lys Ala Gly Leu Thr Phe Leu Val Asp Leu Ile Lys
                190                 195                 200 aac aaa cac atg aat gca gac acc gat tac tcc atc gca gaa gct gcc    2178
Asn Lys His Met Asn Ala Asp Thr Asp Tyr Ser Ile Ala Glu Ala Ala
            205                 210                 215 ttt aat aaa ggc gaa aca gcg atg acc atc aac ggc ccg tgg gca tgg    2226
Phe Asn Lys Gly Glu Thr Ala Met Thr Ile Asn Gly Pro Trp Ala Trp
        220                 225                 230 tcc aac atc gac acc agc aaa gtg aat tat ggt gta acg gta ctg ccg    2274
Ser Asn Ile Asp Thr Ser Lys Val Asn Tyr Gly Val Thr Val Leu Pro
235                 240                 245 acc ttc aag ggt caa cca tcc aaa ccg ttc gtt ggc gtg ctg agc gca    2322
Thr Phe Lys Gly Gln Pro Ser Lys Pro Phe Val Gly Val Leu Ser Ala
250                 255                 260                 265 ggt att aac gcc gcc agt ccg aac aaa gag ctg gca aaa gag ttc ctc    2370
Gly Ile Asn Ala Ala Ser Pro Asn Lys Glu Leu Ala Lys Glu Phe Leu
                270                 275                 280 gaa aac tat ctg ctg act gat gaa ggt ctg gaa gcg gtt aat aaa gac    2418
Glu Asn Tyr Leu Leu Thr Asp Glu Gly Leu Glu Ala Val Asn Lys Asp
            285                 290                 295 aaa ccg ctg ggt gcc gta gcg ctg aag tct tac gag gaa gag ttg gcg    2466
Lys Pro Leu Gly Ala Val Ala Leu Lys Ser Tyr Glu Glu Glu Leu Ala
        300                 305                 310 aaa gat cca cgt att gcc gcc act atg gaa aac gcc cag aaa ggt gaa    2514
Lys Asp Pro Arg Ile Ala Ala Thr Met Glu Asn Ala Gln Lys Gly Glu
315                 320                 325 atc atg ccg aac atc ccg cag atg tcc gct ttc tgg tat gcc gtg cgt    2562
Ile Met Pro Asn Ile Pro Gln Met Ser Ala Phe Trp Tyr Ala Val Arg
330                 335                 340                 345 act gcg gtg atc aac gcc gcc agc ggt cgt cag act gtc gat gaa gcc    2610
Thr Ala Val Ile Asn Ala Ala Ser Gly Arg Gln Thr Val Asp Glu Ala
                350                 355                 360 ctg aaa gac gcg cag act aat tcg agc tcg aac aac aac aac aat aac    2658
Leu Lys Asp Ala Gln Thr Asn Ser Ser Ser Asn Asn Asn Asn Asn Asn
            365                 370                 375 aat aac aac aac ctc ggg atc gag gga agg att tca gaa ttc ctt gtt    2706
Asn Asn Asn Asn Leu Gly Ile Glu Gly Arg Ile Ser Glu Phe Leu Val
```

-continued

```
              380                 385                 390
gcc aat caa gtt gtc acc tgc cca gat aaa aaa tcg aca gcc gcg gtc      2754
Ala Asn Gln Val Val Thr Cys Pro Asp Lys Lys Ser Thr Ala Ala Val
        395                 400                 405 att ctc aca ccg acg gag aac cac ttc act ctc aag gct cct aaa aca      2802
Ile Leu Thr Pro Thr Glu Asn His Phe Thr Leu Lys Ala Pro Lys Thr
410                 415                 420                 425 gcg ctc aca gag cct ccc act ctt gcg tac tca ccc aac agg caa atc      2850
Ala Leu Thr Glu Pro Pro Thr Leu Ala Tyr Ser Pro Asn Arg Gln Ile
                430                 435                 440 tgc cca gcg ggt act aca agt agc tgt aca tca aag gct gta aca ttg      2898
Cys Pro Ala Gly Thr Thr Ser Ser Cys Thr Ser Lys Ala Val Thr Leu
            445                 450                 455 agc tcc ttg att cct gaa gca gaa gat agc tgg tgg acg ggg gat tct      2946
Ser Ser Leu Ile Pro Glu Ala Glu Asp Ser Trp Trp Thr Gly Asp Ser
        460                 465                 470 gct agt ctc gac acg gca ggc atc aaa ctc aca gtt cca atc gag aag      2994
Ala Ser Leu Asp Thr Ala Gly Ile Lys Leu Thr Val Pro Ile Glu Lys
    475                 480                 485 ttc ccc gtg aca acg cag acg ttt gtg gtc ggt tgc atc aag gga gac      3042
Phe Pro Val Thr Thr Gln Thr Phe Val Val Gly Cys Ile Lys Gly Asp
490                 495                 500                 505 gac gca cag agt tgt atg gtc acg gtg aca gta caa gcc aga gcc tca      3090
Asp Ala Gln Ser Cys Met Val Thr Val Thr Val Gln Ala Arg Ala Ser
                510                 515                 520 tcg gtc gtc aat aat gtc gca agg tgc tcc tac ggt gca gac agc act      3138
Ser Val Val Asn Asn Val Ala Arg Cys Ser Tyr Gly Ala Asp Ser Thr
            525                 530                 535 ctt ggt cct gtc aag ttg tct gcg gaa gga ccc act aca atg acc ctc      3186
Leu Gly Pro Val Lys Leu Ser Ala Glu Gly Pro Thr Thr Met Thr Leu
        540                 545                 550 gtg gct ggg aaa gat gga gtc aaa gtt cct caa gac aac aat cag tac      3234
Val Ala Gly Lys Asp Gly Val Lys Val Pro Gln Asp Asn Asn Gln Tyr
    555                 560                 565 gct tcc ggg acg acg ctg act ggt gct aac gag aaa tcg ttc aaa gat      3282
Ala Ser Gly Thr Thr Leu Thr Gly Ala Asn Glu Lys Ser Phe Lys Asp
570                 575                 580                 585 att ttg cca aaa tta act gag aac ccg tgg cag ggt aac gct tcg agt      3330
Ile Leu Pro Lys Leu Thr Glu Asn Pro Trp Gln Gly Asn Ala Ser Ser
                590                 595                 600 gat aag ggt gcc acg cta acg atc aag aag gaa gca ttt cca gcc gag      3378
Asp Lys Gly Ala Thr Leu Thr Ile Lys Lys Glu Ala Phe Pro Ala Glu
            605                 610                 615 tca aaa agc gtc att att gga gct aca ggg gga tcg cct gag aag cat      3426
Ser Lys Ser Val Ile Ile Gly Ala Thr Gly Gly Ser Pro Glu Lys His
        620                 625                 630 cac gct acc gtg aaa ctg gag tgaaagcttg gcactggccg tcgttttaca         3477
His Ala Thr Val Lys Leu Glu
    635                 640 acgtcgtgac tgggaaaacc ctggcgttac ccaacttaat cgccttgcag cacatccccc   3537
tttcgccagc tggcgtaata gcgaagaggc ccgcaccgat cgcccttccc aacagttgcg   3597
cagcctgaat ggcgaatggc agcttggctg ttttggcgga tgagataaga ttttcagcct   3657
gatacagatt aaatcagaac gcagaagcgg tctgataaaa cagaatttgc ctggcggcag   3717
tagcgcggtg gtcccacctg accccatgcc gaactcagaa gtgaaacgcc gtagcgccga   3777
tggtagtgtg gggtctcccc atgcgagagt agggaactgc caggcatcaa ataaaacgaa   3837
aggctcagtc gaaagactgg gcctttcgtt ttatctgttg tttgtcggtg aacgctctcc   3897
```

```
tgagtaggac aaatccgccg ggagcggatt tgaacgttgc gaagcaacgg cccggagggt   3957
ggcgggcagg acgcccgcca taaactgcca ggcatcaaat taagcagaag gccatcctga   4017
cggatggcct ttttgcgttt ctacaaactc tttttgttta tttttctaaa tacattcaaa   4077
tatgtatccg ctcatgagac aataaccctg ataaatgctt caataatatt gaaaaggaa   4137
gagtatgagt attcaacatt tccgtgtcgc ccttattccc ttttttgcgg cattttgcct   4197
tcctgttttt gctcacccag aaacgctggt gaaagtaaaa gatgctgaag atcagttggg   4257
tgcacgagtg ggttacatcg aactggatct caacagcggt aagatccttg agagttttcg   4317
ccccgaagaa cgttctccaa tgatgagcac ttttaaagtt ctgctatgtg gcgcggtatt   4377
atcccgtgtt gacgccgggc aagagcaact cggtcgccgc atacactatt ctcagaatga   4437
cttggttgag tactcaccag tcacagaaaa gcatcttacg gatggcatga cagtaagaga   4497
attatgcagt gctgccataa ccatgagtga ataacactgc gccaacttac ttctgacaac   4557
gatcggagga ccgaaggagc taaccgcttt tttgcacaac atgggggatc atgtaactcg   4617
ccttgatcgt tgggaaccgg agctgaatga agccatacca aacgacgagc gtgacaccac   4677
gatgcctgta gcaatggcaa caacgttgcg caaactatta actggcgaac tacttactct   4737
agcttcccgg caacaattaa tagactggat ggaggcggat aaagttgcag gaccacttct   4797
gcgctcggcc cttccggctg gctggtttat tgctgataaa tctggagccg gtgagcgtgg   4857
gtctcgcggt atcattgcag cactggggcc agatggtaag ccctcccgta tcgtagttat   4917
ctacacgacg gggagtcagg caactatgga tgaacgaaat agacagatcg ctgagatagg   4977
tgcctcactg attaagcatt ggtaactgtc agaccaagtt tactcatata ctttagat    5037
tgatttaccc cggttgataa tcagaaaagc cccaaaaaca ggaagattgt ataagcaaat   5097
atttaaattg taaacgttaa tattttgtta aaattcgcgt taaatttttg ttaaatcagc   5157
tcattttta accataggc cgaaatcggc aaaatccctt ataaatcaaa agaatagacc    5217
gagatagggt tgagtgttgt tccagtttgg aacaagagtc cactattaaa gaacgtggac   5277
tccaacgtca aagggcgaaa aaccgtctat cagggcgatg gcccactacg tgaaccatca   5337
cccaaatcaa gttttttggg gtcgaggtgc cgtaaagcac taaatcggaa ccctaaaggg   5397
agcccccgat ttagagcttg acggggaaag ccggcgaacg tggcgagaaa ggaagggaag   5457
aaagcgaaag gagcgggcgc tagggcgctg gcaagtgtag cggtcacgct gcgcgtaacc   5517
accacacccg ccgcgcttaa tgcgccgcta caggcgcgt aaaaggatct aggtgaagat   5577
ccttttttgat aatctcatga ccaaaatccc ttaacgtgag ttttcgttcc actgagcgtc   5637
agaccccgta gaaaagatca aaggatcttc ttgagatcct ttttttctgc gcgtaatctg   5697
ctgcttgcaa acaaaaaaac caccgctacc agcggtggtt tgtttgccgg atcaagagct   5757
accaactctt tttccgaagg taactggctt cagcagagcg cagataccaa atactgtcct   5817
tctagtgtag ccgtagttag gccaccactt caagaactct gtagcaccgc ctacatacct   5877
cgctctgcta atcctgttac cagtggctgc tgccagtggc gataagtcgt gtcttaccgg   5937
gttggactca agacgatagt taccggataa ggcgcagcgg tcgggctgaa cggggggttc   5997
gtgcacacag cccagcttgg agcgaacgac ctacaccgaa ctgagatacc tacagcgtga   6057
gctatgagaa agcgccacgc ttcccgaagg gagaaaggcg gacaggtatc cggtaagcgg   6117
cagggtcgga acaggagagc gcacgaggga gcttccaggg ggaaacgcct ggtatcttta   6177
tagtcctgtc gggtttcgcc acctctgact tgagcgtcga ttttgtgat gctcgtcagg   6237
```

-continued

```
ggggcggagc ctatggaaaa acgccagcaa cgcggccttt ttacggttcc tggccttttg    6297 ctggccttt  gctcacatgt tctttcctgc gttatcccct gattctgtgg ataaccgtat    6357
taccgccttt gagtgagctg ataccgctcg ccgcagccga acgaccgagc gcagcgagtc    6417
agtgagcgag gaagcggaag agcgcctgat gcggtatttt ctccttacgc atctgtgcgg    6477
tatttcacac cgcatatatg gtgcactctc agtacaatct gctctgatgc cgcatagtta    6537
agccagtata cactccgcta tcgctacgtg actgggtcat gctgcgccc cgacacccgc     6597 caacacccgc tgacgcgccc tgacgggctt gtctgctccc ggcatccgct tacagacaag    6657
ctgtgaccgt ctccgggagc tgcatgtgtc agaggttttc accgtcatca ccgaaacgcg    6717
cgaggcagct gcggtaaagc tcatcagcgt ggtcgtgcag cgattcacag atgtctgcct    6777
gttcatccgc gtccagctcg ttgagtttct ccagaagcgt taatgtctgg cttctgataa    6837
agcgggccat gttaagggcg gttttttcct gtttggtcac tgatgcctcc gtgtaagggg    6897
gatttctgtt catggggta atgataccga tgaaacgaga gaggatgctc acgatacggg     6957
ttactgatga tgaacatgcc cggttactgg aacgttgtga gggtaaacaa ctggcggtat    7017
ggatgcggcg ggaccagaga aaatcactc agggtcaatg ccagcgcttc gttaatacag     7077
atgtaggtgt tccacagggt agccagcagc atcctgcgat gcagatccgg aacataatgg    7137
tgcagggcgc tgacttccgc gtttccagac tttacgaaac acggaaaccg aagaccattc    7197
atgttgttgc tcaggtcgca gacgttttgc agcagcagtc gcttcacgtt cgctcgcgta    7257
tcggtgattc attctgctaa ccagtaaggc aaccccgcca gcctagccgg gtcctcaacg    7317
acaggagcac gatcatgcgc acccgtggcc aggacccaac gctgcccgaa att           7370
```

<210> SEQ ID NO 72
<211> LENGTH: 640
<212> TYPE: PRT
<213> ORGANISM: Toxoplasma gondii
<220> FEATURE:
<223> OTHER INFORMATION: pMBP-c2X-ToxoP30MIX5

<400> SEQUENCE: 72

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
```

```
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
    290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
        355                 360                 365
Ser Ser Ser Asn Asn Asn Asn Asn Asn Asn Asn Asn Leu Gly Ile
    370                 375                 380
Glu Gly Arg Ile Ser Glu Phe Leu Val Ala Asn Gln Val Val Thr Cys
385                 390                 395                 400
Pro Asp Lys Lys Ser Thr Ala Ala Val Ile Leu Thr Pro Thr Glu Asn
                405                 410                 415
His Phe Thr Leu Lys Ala Pro Lys Thr Ala Leu Thr Glu Pro Pro Thr
            420                 425                 430
Leu Ala Tyr Ser Pro Asn Arg Gln Ile Cys Pro Ala Gly Thr Thr Ser
        435                 440                 445
Ser Cys Thr Ser Lys Ala Val Thr Leu Ser Ser Leu Ile Pro Glu Ala
    450                 455                 460
Glu Asp Ser Trp Trp Thr Gly Asp Ser Ala Ser Leu Asp Thr Ala Gly
465                 470                 475                 480
Ile Lys Leu Thr Val Pro Ile Glu Lys Phe Pro Val Thr Thr Gln Thr
                485                 490                 495
Phe Val Val Gly Cys Ile Lys Gly Asp Asp Ala Gln Ser Cys Met Val
            500                 505                 510
Thr Val Thr Val Gln Ala Arg Ala Ser Ser Val Val Asn Asn Val Ala
        515                 520                 525
Arg Cys Ser Tyr Gly Ala Asp Ser Thr Leu Gly Pro Val Lys Leu Ser
    530                 535                 540
Ala Glu Gly Pro Thr Thr Met Thr Leu Val Ala Gly Lys Asp Gly Val
545                 550                 555                 560
Lys Val Pro Gln Asp Asn Asn Gln Tyr Ala Ser Gly Thr Thr Leu Thr
                565                 570                 575
Gly Ala Asn Glu Lys Ser Phe Lys Asp Ile Leu Pro Lys Leu Thr Glu
            580                 585                 590
```

```
Asn Pro Trp Gln Gly Asn Ala Ser Ser Asp Lys Gly Ala Thr Leu Thr
            595                 600                 605

Ile Lys Lys Glu Ala Phe Pro Ala Glu Ser Lys Ser Val Ile Ile Gly
        610                 615                 620

Ala Thr Gly Gly Ser Pro Glu Lys His His Ala Thr Val Lys Leu Glu
625                 630                 635                 640

<210> SEQ ID NO 73
<211> LENGTH: 747
<212> TYPE: DNA
<213> ORGANISM: Toxoplasma gondii
<220> FEATURE:
<221> NAME/KEY: CDS
<222> LOCATION: (1)...(747)
<223> OTHER INFORMATION: ToxoP30MIX5

<400> SEQUENCE: 73 ctt gtt gcc aat caa gtt gtc acc tgc cca gat aaa aaa tcg aca gcc      48
Leu Val Ala Asn Gln Val Val Thr Cys Pro Asp Lys Lys Ser Thr Ala
 1               5                  10                  15 gcg gtc att ctc aca ccg acg gag aac cac ttc act ctc aag gct cct      96
Ala Val Ile Leu Thr Pro Thr Glu Asn His Phe Thr Leu Lys Ala Pro
             20                  25                  30 aaa aca gcg ctc aca gag cct ccc act ctt gcg tac tca ccc aac agg     144
Lys Thr Ala Leu Thr Glu Pro Pro Thr Leu Ala Tyr Ser Pro Asn Arg
         35                  40                  45 caa atc tgc cca gcg ggt act aca agt agc tgt aca tca aag gct gta     192
Gln Ile Cys Pro Ala Gly Thr Thr Ser Ser Cys Thr Ser Lys Ala Val
     50                  55                  60 aca ttg agc tcc ttg att cct gaa gca gaa gat agc tgg tgg acg ggg     240
Thr Leu Ser Ser Leu Ile Pro Glu Ala Glu Asp Ser Trp Trp Thr Gly
 65                  70                  75                  80 gat tct gct agt ctc gac acg gca ggc atc aaa ctc aca gtt cca atc     288
Asp Ser Ala Ser Leu Asp Thr Ala Gly Ile Lys Leu Thr Val Pro Ile
                 85                  90                  95 gag aag ttc ccc gtg aca acg cag acg ttt gtg gtc ggt tgc atc aag     336
Glu Lys Phe Pro Val Thr Thr Gln Thr Phe Val Val Gly Cys Ile Lys
            100                 105                 110 gga gac gac gca cag agt tgt atg gtc acg gtg aca gta caa gcc aga     384
Gly Asp Asp Ala Gln Ser Cys Met Val Thr Val Thr Val Gln Ala Arg
        115                 120                 125 gcc tca tcg gtc gtc aat aat gtc gca agg tgc tcc tac ggt gca gac     432
Ala Ser Ser Val Val Asn Asn Val Ala Arg Cys Ser Tyr Gly Ala Asp
    130                 135                 140 agc act ctt ggt cct gtc aag ttg tct gcg gaa gga ccc act aca atg     480
Ser Thr Leu Gly Pro Val Lys Leu Ser Ala Glu Gly Pro Thr Thr Met
145                 150                 155                 160 acc ctc gtg gct ggg aaa gat gga gtc aaa gtt cct caa gac aac aat     528
Thr Leu Val Ala Gly Lys Asp Gly Val Lys Val Pro Gln Asp Asn Asn
                165                 170                 175 cag tac gct tcc ggg acg acg ctg act ggt gct aac gag aaa tcg ttc     576
Gln Tyr Ala Ser Gly Thr Thr Leu Thr Gly Ala Asn Glu Lys Ser Phe
            180                 185                 190 aaa gat att ttg cca aaa tta act gag aac ccg tgg cag ggt aac gct     624
Lys Asp Ile Leu Pro Lys Leu Thr Glu Asn Pro Trp Gln Gly Asn Ala
        195                 200                 205 tcg agt gat aag ggt gcc acg cta acg atc aag aag gaa gca ttt cca     672
Ser Ser Asp Lys Gly Ala Thr Leu Thr Ile Lys Lys Glu Ala Phe Pro
    210                 215                 220 gcc gag tca aaa agc gtc att att gga gct aca ggg gga tcg cct gag     720
```

-continued

```
Ala Glu Ser Lys Ser Val Ile Ile Gly Ala Thr Gly Gly Ser Pro Glu
225                 230                 235                 240 aag cat cac gct acc gtg aaa ctg gag                                    747
Lys His His Ala Thr Val Lys Leu Glu
                     245
```

<210> SEQ ID NO 74
<211> LENGTH: 249
<212> TYPE: PRT
<213> ORGANISM: Toxoplasma gondii
<220> FEATURE:
<223> OTHER INFORMATION: ToxoP30MIX5

<400> SEQUENCE: 74

```
Leu Val Ala Asn Gln Val Val Thr Cys Pro Asp Lys Lys Ser Thr Ala
1               5                   10                  15

Ala Val Ile Leu Thr Pro Thr Glu Asn His Phe Thr Leu Lys Ala Pro
                20                  25                  30

Lys Thr Ala Leu Thr Glu Pro Pro Thr Leu Ala Tyr Ser Pro Asn Arg
            35                  40                  45

Gln Ile Cys Pro Ala Gly Thr Thr Ser Ser Cys Thr Ser Lys Ala Val
50                  55                  60

Thr Leu Ser Ser Leu Ile Pro Glu Ala Glu Asp Ser Trp Trp Thr Gly
65                  70                  75                  80

Asp Ser Ala Ser Leu Asp Thr Ala Gly Ile Lys Leu Thr Val Pro Ile
                85                  90                  95

Glu Lys Phe Pro Val Thr Thr Gln Thr Phe Val Val Gly Cys Ile Lys
            100                 105                 110

Gly Asp Asp Ala Gln Ser Cys Met Val Thr Val Thr Val Gln Ala Arg
        115                 120                 125

Ala Ser Ser Val Val Asn Asn Val Ala Arg Cys Ser Tyr Gly Ala Asp
130                 135                 140

Ser Thr Leu Gly Pro Val Lys Leu Ser Ala Glu Gly Pro Thr Thr Met
145                 150                 155                 160

Thr Leu Val Ala Gly Lys Asp Gly Val Lys Val Pro Gln Asp Asn Asn
                165                 170                 175

Gln Tyr Ala Ser Gly Thr Thr Leu Thr Gly Ala Asn Glu Lys Ser Phe
            180                 185                 190

Lys Asp Ile Leu Pro Lys Leu Thr Glu Asn Pro Trp Gln Gly Asn Ala
        195                 200                 205

Ser Ser Asp Lys Gly Ala Thr Leu Thr Ile Lys Lys Glu Ala Phe Pro
210                 215                 220

Ala Glu Ser Lys Ser Val Ile Ile Gly Ala Thr Gly Gly Ser Pro Glu
225                 230                 235                 240

Lys His His Ala Thr Val Lys Leu Glu
                    245
```